(12) United States Patent
Li et al.

(10) Patent No.: US 10,780,108 B2
(45) Date of Patent: Sep. 22, 2020

(54) RNAI AGENTS FOR HEPATITIS B VIRUS INFECTION

(71) Applicant: Arrowhead Pharmaceuticals, Inc., Pasadena, CA (US)

(72) Inventors: Zhen Li, Madison, WI (US); Rui Zhu, Madison, WI (US); Christine Wooddell, Madison, WI (US); Bruce D. Given, Madison, WI (US); Tao Pei, Madison, WI (US); David L. Lewis, Madison, WI (US); Lauren J. Almeida, Madison, WI (US); David B. Rozema, Cross Plains, WI (US); Darren H. Wakefield, Fitchburg, WI (US)

(73) Assignee: ARROWHEAD PHARMACEUTICALS, INC., Pasadena, CA (US)

( * ) Notice: Subject to any disclaimer, the term of this patent is extended or adjusted under 35 U.S.C. 154(b) by 0 days.

(21) Appl. No.: 15/766,036

(22) PCT Filed: Aug. 4, 2017

(86) PCT No.: PCT/US2017/045446
§ 371 (c)(1),
(2) Date: Apr. 5, 2018

(87) PCT Pub. No.: WO2018/027106
PCT Pub. Date: Feb. 8, 2018

(65) Prior Publication Data
US 2019/0292547 A1  Sep. 26, 2019

Related U.S. Application Data

(60) Provisional application No. 62/370,754, filed on Aug. 4, 2016, provisional application No. 62/534,733, filed on Jul. 20, 2017, provisional application No. 62/540,639, filed on Aug. 3, 2017.

(51) Int. Cl.
| | | |
|---|---|---|
| C12N 15/113 | (2010.01) | |
| A61K 31/7105 | (2006.01) | |
| A61P 31/14 | (2006.01) | |
| A61K 9/00 | (2006.01) | |
| A61K 31/675 | (2006.01) | |
| A61P 31/20 | (2006.01) | |
| A61K 31/7088 | (2006.01) | |

(52) U.S. Cl.
CPC ........ *A61K 31/7105* (2013.01); *A61K 9/0019* (2013.01); *A61K 31/675* (2013.01); *A61K 31/7088* (2013.01); *A61P 31/14* (2018.01); *A61P 31/20* (2018.01); *C12N 15/113* (2013.01); *C12N 15/1131* (2013.01); *C12N 2310/11* (2013.01); *C12N 2310/14* (2013.01); *C12N 2310/314* (2013.01); *C12N 2310/315* (2013.01); *C12N 2310/321* (2013.01); *C12N 2310/322* (2013.01); *C12N 2310/3515* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 5,885,968 | A | 3/1999 | Biessen |
| 8,232,383 | B2 | 7/2012 | Mcswiggen |
| 8,242,257 | B2 | 8/2012 | Beigelman |
| 8,273,866 | B2 | 9/2012 | Mcswiggen |
| 8,618,277 | B2 | 12/2013 | Beigelman |
| 8,648,185 | B2 | 2/2014 | Mcswigen |
| 8,809,293 | B2 | 8/2014 | Chin |
| 8,828,956 | B2 | 9/2014 | Manoharan |
| 9,181,551 | B2 | 11/2015 | Mcswiggen |
| 9,222,092 | B2 | 12/2015 | Giese |
| 9,260,471 | B2 | 2/2016 | Cancilla |
| 9,290,760 | B2 | 3/2016 | Rajeev |
| 9,352,048 | B2 | 5/2016 | Manoharan |
| 9,566,340 | B2 | 2/2017 | Manoharan |
| 9,695,423 | B2 | 7/2017 | Giese |
| 9,771,588 | B2 | 9/2017 | Mcswiggen |

(Continued)

FOREIGN PATENT DOCUMENTS

| | | |
|---|---|---|
| EP | 1560840 B1 | 5/2015 |
| EP | 1931781 B1 | 7/2016 |

(Continued)

OTHER PUBLICATIONS

Baenziger, J. et al. (Nov. 1980). "Galactose and N-Acetylgalactosamine-Specific Endocytosis of Glycopeptides by Isolated Rat Hepatocytes," Cell 22(2):611-620.

(Continued)

*Primary Examiner* — J. E Angell
(74) *Attorney, Agent, or Firm* — Morrison & Foerster LLP

(57) ABSTRACT

Described are compositions and methods for inhibition of Hepatitis B virus gene expression. RNA interference (RNAi) agents for inhibiting the expression of Hepatitis B virus gene are described. The HBV RNAi agents disclosed herein may be targeted to cells, such as hepatocytes, for example, by using conjugated targeting ligands. Pharmaceutical compositions comprising one or more HBV RNAi agents optionally with one or more additional therapeutics are also described. Delivery of the described HBV RNAi agents to infected liver in vivo provides for inhibition of HBV gene expression and treatment of diseases and conditions associated with HBV infection.

67 Claims, No Drawings
Specification includes a Sequence Listing.

(56) References Cited

U.S. PATENT DOCUMENTS

| | | |
|---|---|---|
| 9,790,505 B2 | 10/2017 | Giese |
| 9,943,604 B2 | 4/2018 | Seth |
| 9,970,005 B2 | 5/2018 | Cancilla |
| 10,098,959 B2 | 10/2018 | Migawa |
| 10,130,651 B2 | 11/2018 | Wooddell |
| 10,131,907 B2 | 11/2018 | Forst |
| 10,246,709 B2 | 4/2019 | Rozema |
| 10,294,474 B2 | 5/2019 | Li |
| 10,351,852 B2 | 7/2019 | Mcswiggen |
| 10,590,418 B2 | 3/2020 | Kay |
| 2003/0206887 A1 | 11/2003 | Morrissey |
| 2012/0165393 A1 | 6/2012 | Rozema |
| 2013/0005793 A1 | 1/2013 | Chin |
| 2013/0150433 A1 | 6/2013 | Bartz |
| 2016/0152973 A1 | 6/2016 | Jadhav |
| 2017/0035796 A1 | 2/2017 | Wooddell |
| 2017/0137821 A1 | 5/2017 | Limphong |
| 2017/0369883 A1 | 12/2017 | Swayze |
| 2018/0064819 A1 | 3/2018 | Li |
| 2018/0371463 A1 | 12/2018 | Limphong |
| 2019/0022123 A1 | 1/2019 | Wooddell |
| 2019/0160176 A1 | 5/2019 | Heyes |
| 2019/0255091 A1 | 8/2019 | Li |
| 2019/0256849 A1 | 8/2019 | Li |

FOREIGN PATENT DOCUMENTS

| | | |
|---|---|---|
| EP | 3218487 A1 | 9/2017 |
| WO | WO0053722 A2 | 9/2000 |
| WO | WO0053722 A3 | 7/2001 |
| WO | WO02081494 A1 | 10/2002 |
| WO | WO2008022309 A2 | 2/2008 |
| WO | WO2008022309 A3 | 11/2008 |
| WO | WO2011104169 A1 | 9/2011 |
| WO | WO2011148193 A1 | 12/2011 |
| WO | WO2012083185 A2 | 6/2012 |
| WO | WO2013003520 A1 | 1/2013 |
| WO | WO2013032829 A1 | 3/2013 |
| WO | WO2013075035 A1 | 5/2013 |
| WO | WO2012083185 A8 | 6/2013 |
| WO | WO2012083185 A3 | 10/2013 |
| WO | WO2013158141 A1 | 10/2013 |
| WO | WO2013159109 A1 | 10/2013 |
| WO | WO2013176772 A1 | 11/2013 |
| WO | WO2014037377 A1 | 3/2014 |
| WO | WO2015050871 A2 | 4/2015 |
| WO | WO2016057893 A9 | 5/2016 |
| WO | WO2016077321 A1 | 5/2016 |
| WO | WO2016077349 A1 | 5/2016 |
| WO | WO2017015175 A1 | 1/2017 |
| WO | WO2017027350 A2 | 2/2017 |

OTHER PUBLICATIONS

Biessen, E.A.L. et al. (1995). "Synthesis of Cluster Galactosides with High Affinity for the Hepatic Asialoglycoprotein Receptor," J. Med. Chem. 38(9):1538-1546.

Connolly, D.T. et al. (Jan. 25, 1982). "Binding and Endocytosis of Cluster Glycosides by Rabbit Hepatocytes. Evidence for a Short-Circuit Pathway That Does Not Lead to Degradation," J. Biol. Chem. 257(2):939-945.

Guidotti, L.G. et al. (Oct. 1885). "High-Level Hepatitis B Virus Replication in Transgenic Mice," J Virol 69(10):6158-6169.

International Preliminary Report on Patentability dated Feb. 14, 2019 for PCT Application No. PCT/US2017/045446 filed on Aug. 4, 2017, 7 pages.

International Search Report and Written Opinion dated Jan. 18, 2018 for PCT Application No. PCT/US2017/045446 filed on Aug. 4, 2017, 11 pages.

Iobst, S.T. et al. (Mar. 22, 1996). "Selective Sugar Binding to the Carbohydrate Recognition Domains of the Rat Hepatic and Macrophage Asialoglycoprotein Receptors," Journal of Biological Chemistry 271(12):6686-6693.

U.S. Appl. No. 16/267,194, filed Feb. 4, 2019 by Li et al.

Wooddell, C.I. et al. (Aug. 19, 2005; e-pub. Jun. 24, 2005). "Long-Term RNA Interference From Optimized siRNA Expression Constructs in Adult Mice." Biochemical and Biophysical Research Communications 334(1):117-127.

Yang, P.L. et al. (Oct. 15, 2002). "Hydrodynamic Injection of Viral DNA: A Mouse Model of Acute Hepatitis B Virus Infection," PNAS USA 99(21):13825-13830.

Zhang, G. et al. (Jul. 1999). "High Levels of Foreign Gene Expression in Hepatocvtes After Tail Vein Injection of Naked Plasmid DNA," Human Gene Therapy 10(10):1735-1737.

European Search Report dated Feb. 21, 2020, for European Patent Application No. 17837738.8, filed Mar. 1, 2019, 15 pages.

U.S. Appl. No. 15/241,733, filed on Aug. 19, 2016, by Chin et al.(Copy not submitted herewith pursuant to the waiver of 37 C.F.R. §1 .98(a)(2)(iii) issued by the Office on Sep. 21, 2004).

Database Geneseq. (Jul. 13, 2017). "Hepatitis B Virus Targeted Sense Strand, SEQ ID 323," XP055705029, retrieved from EBI Accession No. GSN:BDW71266, Database Accession No. BDW71266, 1 page.

Database Geneseq. (Jul. 28, 2016). "Hepatitis B virus (HBV) Multifunctional siNA, SEQ ID 100," XP055705026, retrieved from EBI Accession No. GSN:BCR34400 Database Accession No. BCR34400, 1 page.

Database Geneseq. (Jul. 28, 2016). "Hepatitis B virus (HBV) Multifunctional siNA, SEQ ID 62," XP055705020, retrieved from EBI Accession No. GSN:BCR34362 Database Accession No. BCR34362, 2 pages.

Database Geneseq. (Jun. 30, 2016). "Hepatitis B Virus Genome Targeted siRNA Sense Strand, SEQ ID 1707," KP055705036, retrieved from EBI Accession No. GSN:BDA34061 Database Accession No. BDA34061, 1 page.

Database Geneseq. (Jun. 30, 2016). HBV X Gene-Targeted Modified siRNA Sense Strand, SEQ 1169, KP055705062, retrieved from EBI, Accession No. GSN:BDA28856, Database Accession No. BDA28856, 1 page.

Extended European Search Report dated Jun. 23, 2020, for EP Application No. 17837738.8, 19 pages.

RNAI AGENTS FOR HEPATITIS B VIRUS INFECTION

CROSS REFERENCE TO RELATED APPLICATIONS

This application is a U.S. National Phase Application under 35 U.S.C. § 371 of International Patent Application No. PCT/US2017/045446, filed on Aug. 4, 2017, which claims priority from U.S. Provisional Patent Application Ser. No. 62/540,639, filed on Aug. 3, 2017, U.S. Provisional Patent Application Ser. No. 62/534,733, filed on Jul. 20, 2017, and U.S. Provisional Patent Application Ser. No. 62/370,754, filed on Aug. 4, 2016, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165002000400seqlist.txt, date recorded: Apr. 24, 2019, size: 78 KB).

FIELD OF THE INVENTION

Disclosed herein are RNA interference (RNAi) agents for inhibition of Hepatitis B Virus gene expression, compositions that include HBV RNAi agents, and methods of use thereof.

BACKGROUND

The Hepatitis B Virus (HBV) is a strict hepatotrophic, double-stranded DNA containing virus. Although DNA is the genetic material, the replication cycle involves a reverse transcription step to copy a pregenomic RNA into DNA. Hepatitis B Virus is classified as one member of the Hepadnaviruses and belongs to the family of Hepadnaviridae. The primary infection of adult humans with Hepatitis B Virus causes an acute hepatitis with symptoms of organ inflammation, fever, jaundice and increased liver transaminases in blood. Those patients that are not able to overcome the virus infection suffer a chronic disease progression over many years with increased risk of developing cirrhotic liver or liver cancer. Perinatal transmission from Hepatitis B Virus-infected mothers to newborns also leads to chronic hepatitis.

Upon uptake by hepatocytes, the nucleocapsid is transferred to the nucleus and DNA is released. There, the DNA strand synthesis is completed and gaps repaired to give the covalently closed circular (ccc) supercoiled DNA of 3.2 kb. The cccDNA serves as a template for transcription of five major viral mRNAs, which are 3.5, 3.5, 2.4, 2.1 and 0.7 kb long. All mRNAs are 5'-capped and polyadenylated at the 3'-end. There is sequence overlap at the 3'-end between all five mRNAs.

One 3.5 kb mRNA serves as template for core protein and polymerase production. In addition, the same transcript serves as a pre-genomic replication intermediate and allows the viral polymerase to initiate the reverse transcription into DNA. Core protein is needed for nucleocapsid formation. The other 3.5 kb mRNA encodes pre-core, the secretable e-antigen (HBeAg). In the absence of replication inhibitors, the abundance of e-antigen in blood correlates with Hepatitis B Virus replication in liver and serves as an important diagnostic marker for monitoring the disease progression.

The 2.4 and 2.1 kb mRNAs carry the open reading frames ("ORF") pre-S1, pre-S2 and S for expression of viral large, medium and small surface antigen. The s-antigen is associated with infectious, complete particles. In addition, blood of infected patients also contain non-infectious particles derived from s-antigen alone, free of genomic DNA or polymerase. The function of these particles is not fully understood. The complete and lasting depletion of detectable s-antigen in blood is considered as a reliable indicator for Hepatitis B Virus clearance.

The 0.7 kb mRNA encodes the X protein. This gene product is important for efficient transcription of viral genes and also acts as a transactivator on host gene expression. The latter activity seems to be important for hepatocyte transformation during development of liver cancer.

Patients with detectable s-antigen, e-antigen, and/or viral DNA in the blood for more than 6 months are considered chronically infected. Nucleoside analogs as inhibitors of reverse transcriptase activity are typically the first treatment option for many patients. Administration of lamivudine, tenofovir, and/or entecavir has been shown to suppress Hepatitis B Virus replication, sometimes to undetectable levels, with improvement of liver function and reduction of liver inflammation typically seen as the most important benefits. However, only few patients achieve complete and lasting remission after the end of treatment. Furthermore, the Hepatitis B Virus develops drug resistance with increasing duration of treatment. This is especially difficult for patients co-infected with Hepatitis B and Human Immunodeficiency Virus (HIV). Both viruses are susceptible to nucleoside analogue drugs and may co-develop resistance.

A second treatment option is the administration of interferon-alpha. Here, patients receive high doses of interferon-alpha over a period of 6 months. The Asian genotype B gives very poor response rates. Co-infection with Hepatitis D Virus (HDV) or Human Immunodeficiency Virus has been shown to render interferon-alpha therapy completely ineffective. Patients with strong liver damage and heavy fibrotic conditions are not qualified for interferon-alpha therapy.

Certain Hepatitis B Virus-specific RNA interference (RNAi) agents have been previously shown to inhibit expression of HBV gene expression. For example, U.S. Patent Application Publication No. 201310005793, to Chin et al., which is incorporated herein by reference in its entirety, discloses certain double-stranded ribonucleic acid (dsRNA) molecules for inhibiting the expression of Hepatitis B Virus gene.

SUMMARY

There exists a need for novel Hepatitis B Virus (HBV)-specific RNA interference (RNAi) agents (also herein termed RNAi agent, RNAi trigger, or trigger) that are able to selectively and efficiently inhibit the expression of an Hepatitis B Virus (HBV) gene. Further, there exists a need for combinations of novel HBV-specific RNAi agents for the treatment of HBV infection and prevention of diseases associated with HBV.

Described herein are HBV gene-specific RNAi agents able to selectively and efficiently decrease expression of an HBV gene. The described HBV RNAi agents can be used in methods for therapeutic treatment and/or prevention of symptoms and diseases associated with HBV infection, including but not limited to chronic liver diseases/disorders, inflammations, fibrotic conditions, proliferative disorders (including cancers, such as hepatocellular carcinoma), Hepatitis D Virus (HDV) infection, and acute HBV infection. In some embodiments, the HBV RNAi agents can be used in methods for therapeutic treatment and/or prevention of symptoms and diseases associated with chronic HBV infection and/or HDV infection. Such methods comprise administration of one or more HBV RNAi agents as described herein to a subject, e.g., a human or animal subject.

Additionally, described herein are compositions comprising one or more of the disclosed HBV RNAi agents that are able to selectively and efficiently decrease expression of an HBV gene. The compositions comprising one or more HBV RNAi agents can be administered to a subject, such as a human or animal subject, for the treatment and/or prevention of symptoms and diseases associated with HBV infection.

Each HBV RNAi agent disclosed herein includes at least a sense strand and an antisense strand. The sense strand and the antisense strand can be partially, substantially, or fully complementary to each other. The length of the RNAi agent sense and antisense strands described herein each can be 16 to 30 nucleotides in length. In some embodiments, the sense and antisense strands are independently 17 to 26 nucleotides in length. In some embodiments, the sense and antisense strands are independently 19 to 26 nucleotides in length. In some embodiments, the sense and antisense strands are independently 21 to 26 nucleotides in length. In some embodiments, the sense and antisense strands are independently 21 to 24 nucleotides in length. The sense and antisense strands can be either the same length or different lengths. The HBV RNAi agents disclosed herein have been designed to include antisense strand sequences that are at least partially complementary to a sequence in the HBV genome that is conserved across the majority of known serotypes of HBV. The RNAi agents described herein, upon delivery to a cell expressing HBV, inhibit the expression of one or more HBV genes in vivo or in vitro.

An HBV RNAi agent includes a sense strand (also referred to as a passenger strand) that includes a first sequence, and an antisense strand (also referred to as a guide strand) that includes a second sequence. A sense strand of the HBV RNAi agents described herein includes a core stretch having at least about 85% identity to a nucleotide sequence of at least 16 consecutive nucleotides in an HBV mRNA. In some embodiments, the sense strand core nucleotide stretch having at least about 85% identity to a sequence in an HBV mRNA is 16, 17, 18, 19, 20, 21, 22, or 23 nucleotides in length. An antisense strand of an HBV RNAi agent comprises a nucleotide sequence having at least about 85% complementary over a core stretch of at least 16 consecutive nucleotides to a sequence in an HBV mRNA and the corresponding sense strand. In some embodiments, the antisense strand core nucleotide sequence having at least about 85% complementarity to a sequence in an HBV mRNA or the corresponding sense strand is 16, 17, 18, 19, 20, 21, 22, or 23 nucleotides in length.

Examples of HBV RNAi agent sense strands and antisense strands that can be used in HBV RNAi agents are provided in Tables 3 and 4. Examples of HBV RNAi agent duplexes are provided in Table 5. Examples of 19-nucleotide core stretch sequences that consist of or are included in the sense strands and antisense strands of HBV RNAi agents disclosed herein, are provided in Table 2.

In some embodiments, one or more HBV RNAi agents are delivered to target cells or tissues using any oligonucleotide delivery technology known in the art. Nucleic acid delivery methods include, but are not limited to, by encapsulation in liposomes, by iontophoresis, or by incorporation into other vehicles, such as hydrogels, cyclodextrins, biodegradable nanocapsules, and bioadhesive microspheres, proteinaceous vectors or Dynamic Polyconjugates (DPCs) (see, for example WO 2000/053722, WO 2008/0022309, WO 2011/104169, and WO 2012/083185, each of which is incorporated herein by reference). In some embodiments, an HBV RNAi agent is delivered to target cells or tissues by covalently linking the RNAi agent to a targeting group. In some embodiments, the targeting group can include a cell receptor ligand, such as an asialoglycoprotein receptor (ASGPr) ligand. In some embodiments, an ASGPr ligand includes or consists of a galactose derivative cluster. In some embodiments, a galactose derivative cluster includes an N-acetyl-galactosamine trimer or an N-acetyl-galactosamine tetramer. In some embodiments, a galactose derivative cluster is an N-acetyl-galactosamine trimer or an N-acetyl-galactosamine tetramer.

A targeting group can be linked to the 3' or 5' end of a sense strand or an antisense strand of an HBV RNAi agent. In some embodiments, a targeting group is linked to the 3' or 5' end of the sense strand. In some embodiments, a targeting group is linked to the 5' end of the sense strand. In some embodiments, a targeting group is linked to the RNAi agent via a linker.

A targeting group, with or without a linker, can be linked to the 5' or 3' end of any of the sense and/or antisense strands disclosed in Tables 2, 3, and 4. A linker, with or without a targeting group, can be attached to the 5' or 3' end of any of the sense and/or antisense strands disclosed in Tables 2, 3, and 4.

In some embodiments, described herein are compositions that include one or more HBV RNAi agents having the duplex sequences disclosed in Table 5.

In some embodiments, described herein are compositions that include a combination or cocktail of at least two HBV RNAi agents having different nucleotide sequences. In some embodiments, the two or more different HBV RNAi agents are each separately and independently linked to targeting groups. In some embodiments, the two or more different HBV RNAi agents are each linked to targeting groups comprised of N-acetyl-galactosamines. In some embodiments, when two or more RNAi agents are included in a composition, each of the RNAi agents is linked to the same targeting group. In some embodiments, when two or more RNAi agents are included in a composition, each of the RNAi agents is linked to different targeting groups, such as targeting groups having different chemical structures.

In some embodiments, targeting groups are linked to the HBV RNAi agents without the use of an additional linker. In some embodiments, the targeting group is designed having a linker readily present to facilitate the linkage to an HBV RNAi agent. In some embodiments, when two or more RNAi agents are included in a composition, the two or more RNAi agents may be linked to the targeting groups using the same linkers. In some embodiments, when two or more RNAi agents are included in a composition, the two or more RNAi agents are linked to the targeting groups using different linkers.

In some embodiments, described herein are compositions that include a combination of at least two HBV RNAi agents having different sequences, wherein each HBV RNAi agent targets a different location or different region of an HBV gene. In some embodiments, described herein are compositions that include a combination of at least two HBV RNAi agents, wherein each HBV RNAi agent is designed to target a different HBV transcript (for example, a composition that includes two HBV RNAi agents, wherein the first HBV RNAi agent includes an antisense strand that is at least partially complementary to a nucleotide sequence located in the S ORF of an HBV gene, while the second HBV RNAi agent includes an antisense strand that is at least partially complementary to a nucleotide sequence located in the X ORF of an HBV gene). As used herein, an RNAi agent that includes an antisense strand at least partially complementary to a nucleotide sequence located in the S ORF targets a portion of the HBV genome of SEQ ID NO:1 between positions 1-1307 and 3185-3221. As used herein, an RNAi agent that includes an antisense strand at least partially complementary to a nucleotide sequence located in the X ORF targets a portion of the HBV genome of SEQ ID NO:1 between positions 1308-1930.

HBV mRNA is known to be polycistronic, resulting in the translation of multiple polypeptides, and separate mRNAs overlap in RNA sequence, therefore a single RNAi agent targeting an HBV gene may result in inhibition of most or all HBV transcripts. However, while not wishing to be bound to any theory, it is hypothesized that a composition that includes two or more HBV RNAi agents targeting different locations or regions of an HBV gene (and, in particular, two or more HBV RNAi agents wherein one HBV RNAi agent targets the S ORF and a second HBV RNAi agent targets the X ORF) may provide for additional advantages over a composition that includes only a single HBV RNAi agent, such as (a) ensuring that all HBV viral transcripts are targeted (i.e., 3.5 kb pre-genomic RNA; 3.5 kb pre-core mRNA; 2.4 kb pre-S1 mRNA; 2.1 kb pre-S2/S mRNA; 0.7 kb X mRNA; as well as any S-antigen expressing mRNAs produced from integrated HBV DNA); (b) serving to expand the genotype coverage to potentially address a larger patient population; and/or (c) potentially decreasing the viral resistance due to mutations in the siRNA binding site.

In some embodiments, described herein are compositions that include a combination of one HBV RNAi agent that targets the S ORF of an HBV RNA (i.e., having an antisense strand that targets the S transcripts (S, pre-S1, and pre-S2), the pregenomic RNA (core and polymerase), and the pre-core transcripts (HBeAg) of an HBV genome), and one HBV RNAi agent that targets the X ORF of an HBV RNA (i.e., having an antisense strand that targets the X transcript of an HBV genome, the S transcripts (S, pre-S1, and pre-S2), the pregenomic RNA (core and polymerase), and the pre-core transcripts (HBeAg) of an HBV genome). In some embodiments, the compositions described herein include at least one HBV RNAi agent that contains a sequence that targets the S ORF of an HBV gene, and a second HBV RNAi agent that contains a sequence that targets the X ORF of an HBV gene.

Disclosed herein are methods for inhibiting expression of an HBV gene, the method comprising administering one or more HBV RNAi agents having an antisense strand comprising the sequence of any of the sequences in Table 3.

Disclosed herein are methods for inhibiting expression of an HBV gene, the method comprising administering one or more HBV RNAi agents having a sense strand comprising the sequence of any of the sequences in Table 4.

Disclosed herein are methods for inhibiting expression of an HBV gene, the method comprising administering one or more HBV RNAi agents having an antisense strand comprising the sequence of any of the sequences in Table 3, and a sense strand comprising the sequence of any of the sequences in Table 4 that is at least partially complementary to the antisense strand.

Disclosed herein are methods for inhibiting expression of an HBV gene, the method comprising administering one or more HBV RNAi agents having an antisense strand that consists of the sequence of any of the sequences in Table 3, and a sense strand that consists of the sequence of any of the sequences in Table 4 that is at least partially complementary to the antisense strand.

Disclosed herein are methods for inhibiting expression of an HBV gene in a cell, the method comprising administering one or more HBV RNAi agents having the duplex structure of Table 5.

Disclosed herein are methods of treatment of an HBV infection or prevention of disease or symptoms caused by an HBV infection, the method comprising administering one or more HBV RNAi agents having an antisense strand comprising the sequence of any of the sequences in Table 3.

Disclosed herein are methods of treatment of an HBV infection or prevention of disease or symptoms caused by an HBV infection, the method comprising administering one or more HBV RNAi agents having a sense strand comprising the sequence of any of the sequences in Table 4.

Disclosed herein are methods of treatment of an HBV infection or prevention of disease or symptoms caused by an HBV infection, the method comprising administering one or more HBV RNAi agents having an antisense strand comprising the sequence of any of the sequences in Table 3, and a sense strand comprising the sequence of any of the sequences in Table 4 that is at least partially complementary to the antisense strand.

Disclosed herein are methods of treatment of an HBV infection or prevention of disease or symptoms caused by an HBV infection, the method comprising administering one or more HBV RNAi agents having an antisense strand that consists of the sequence of any of the sequences in Table 3, and a sense strand that consists of the sequence of any of the sequences in Table 4 that is at least partially complementary to the antisense strand.

Disclosed herein are methods of treatment of an HBV infection or prevention of disease or symptoms caused by an HBV infection, the method comprising administering one or more HBV RNAi agents having the duplex structure of Table 5.

Disclosed herein are methods for inhibiting expression of an HBV gene, the method comprising administering (i) an HBV RNAi agent having an antisense strand comprising or consisting of the sequence of any of the sequences in Table 2 or Table 3, and (ii) a second HBV RNAi agent having an antisense strand comprising or consisting of the sequence of any of the sequences in Table 2 or Table 3.

Disclosed herein are methods of treatment of an HBV infection or prevention of disease or symptoms caused by an HBV infection, the method comprising administering (i) an HBV RNAi agent having an antisense strand comprising or consisting of the sequence of any of the sequences in Table 2 or Table 3, and (ii) a second HBV RNAi agent having an antisense strand comprising or consisting of the sequence of any of the sequences in Table 2 or Table 3.

Disclosed herein are methods for inhibiting expression of an HBV gene, the method comprising administering (i) a first HBV RNAi agent having an antisense strand comprising or consisting of the sequence of any of the sequences in Table 2 or Table 3 and a sense strand comprising or consisting of the sequence of any of the sequences in Table 2 or Table 4 that is at least partially complementary to the antisense strand of the first HBV RNAi agent, and (ii) a second HBV RNAi agent having an antisense strand comprising or consisting of the sequence of any of the sequences in Table 2 or Table 3 and a sense strand comprising or consisting of the sequence of any of the sequences in Table 2 or Table 4 that is at least partially complementary to the antisense strand of the second HBV RNAi agent.

Disclosed herein are methods of treatment of an HBV infection or prevention of disease or symptoms caused by an HBV infection, the method comprising administering (i) a first HBV RNAi agent having an antisense strand comprising or consisting of the sequence of any of the sequences in Table 2 or Table 3 and a sense strand comprising or consisting of the sequence of any of the sequences in Table 2 or Table 4 that is at least partially complementary to the antisense strand of the first HBV RNAi agent, and (ii) a second HBV RNAi agent having an antisense strand comprising or consisting of the sequence of any of the sequences in Table 2 or Table 3 and a sense strand comprising or consisting of the sequence of any of the sequences in Table 2 or Table 4 that is at least partially complementary to the antisense strand of the second HBV RNAi agent.

In some embodiments, an HBV RNAi agent disclosed herein comprises:

a. an antisense strand that comprises the nucleobase sequence differing by 0, 1, 2 or 3 nucleobases from the sequence (5'→3') AUUGAGAGAAGUCCACCAC (SEQ ID NO: 7), and a sense strand that comprises the nucleobase sequence differing by 0, 1, 2 or 3 nucleobases from the sequence (5'→3') GUGGUGGACUUCUCUCAAU (SEQ ID NO: 34); or b. an antisense strand that comprises the nucleobase sequence differing by 0, 1, 2 or 3 nucleobases from the sequence (5'→3') UUUGAGAGAAGUCCACCAC (SEQ ID NO: 8), and a sense strand that comprises the nucleobase sequence differing by 0, 1, 2 or 3 nucleobases from the sequence (5'→3') GUGGUGGACUUCUCUCAAA (SEQ ID NO: 35); or c. an antisense strand that comprises the nucleobase sequence differing by 0, 1, 2 or 3 nucleobases from the sequence (5'→3') AAUUGAGAGAAGUCCACCA (SEQ ID NO: 12), and a sense strand that comprises the nucleobase sequence differing by 0, 1, 2 or 3 nucleobases from the sequence (5'→3') UGGUGGACUUCUCUCAAUU (SEQ ID NO: 39); or d. an antisense strand that comprises the nucleobase sequence differing by 0, 1, 2 or 3 nucleobases from the sequence (5'→3') UAUUGAGAGAAGUCCACCA (SEQ ID NO: 13), and a sense strand that comprises the nucleobase sequence differing by 0, 1, 2 or 3 nucleobases from the sequence (5'→3') UGGUGGACUUCUCUCAAUA (SEQ ID NO: 40); or e. an antisense strand that comprises the nucleobase sequence differing by 0, 1, 2 or 3 nucleobases from the sequence (5'→3') AGAAAAUUGAGAGAAGUCC (SEQ ID NO: 17), and a sense strand that comprises the nucleobase sequence differing by 0, 1, 2 or 3 nucleobases from the sequence (5'→3') GGACUUCUCUCAAUUUUCU (SEQ ID NO: 44); or f. an antisense strand that comprises the nucleobase sequence differing by 0, 1, 2 or 3 nucleobases from the sequence (5'→3') UGAAAAUUGAGAGAAGUCC (SEQ ID NO: 18), and a sense strand that comprises the nucleobase sequence differing by 0, 1, 2 or 3 nucleobases from the sequence (5'→3') GGACUUCUCUCAAUUUUCA (SEQ ID NO: 45); or g. an antisense strand that comprises the nucleobase sequence differing by 0, 1, 2 or 3 nucleobases from the sequence (5'→3') ACCAAUUUAUGCCUACAGC (SEQ ID NO: 22), and a sense strand that comprises the nucleobase sequence differing by 0, 1, 2 or 3 nucleobases from the sequence (5'→3') GCUGUAGGCAUAAAUUGGU (SEQ ID NO: 49); or h. an antisense strand that comprises the nucleobase sequence differing by 0, 1, 2 or 3 nucleobases from the sequence (5'→3') UCCAAUUUAUGCCUACAGC (SEQ ID NO: 23), and a sense strand that comprises the nucleobase sequence differing by 0, 1, 2 or 3 nucleobases from the sequence (5'→3') GCUGUAGGCAUAAAUUGGA (SEQ ID NO: 50); or i. an antisense strand that comprises the nucleobase sequence differing by 0, 1, 2 or 3 nucleobases from the sequence (5'→3') GACCAAUUUAUGCCUACAG (SEQ ID NO: 27), and a sense strand that comprises the nucleobase sequence differing by 0, 1, 2 or 3 nucleobases from the sequence (5'→3') CUGUAGGCAUAAAUUGGUC (SEQ ID NO: 54); or j. an antisense strand that comprises the nucleobase sequence differing by 0, 1, 2 or 3 nucleobases from the sequence (5'→3') AACCAAUUUAUGCCUACAG (SEQ ID NO: 28), and a sense strand that comprises the nucleobase sequence differing by 0, 1, 2 or 3 nucleobases from the sequence (5'→3') CUGUAGGCAUAAAUUGGUU (SEQ ID NO: 55); or k. an antisense strand that comprises the nucleobase sequence differing by 0, 1, 2 or 3 nucleobases from the sequence (5'→3') UACCAAUUUAUGCCUACAG (SEQ ID NO: 29), and a sense strand that comprises the nucleobase sequence differing by 0, 1, 2 or 3 nucleobases from the sequence (5'→3') CUGUAGGCAUAAAUUGGUA (SEQ ID NO: 56).

In some embodiments, disclosed herein are compositions for inhibiting expression of an HBV gene in a cell, the composition comprising an HBV RNAi agent.

In some embodiments, disclosed herein are compositions for inhibiting expression of an HBV gene in a cell, the composition comprising two or more HBV RNAi agents, wherein a first HBV RNAi agent comprises:

i) an antisense strand that comprises the nucleobase sequence differing by 0, 1, 2 or 3 nucleobases from the sequence (5'→3') AAUUGAGAGAAGUCCACCA (SEQ ID NO: 12), and a sense strand that comprises the nucleobase sequence differing by 0, 1, 2 or 3 nucleobases from the sequence (5'→3') UGGUGGACUUCUCUCAAUU (SEQ ID NO: 39); or ii) an antisense strand that comprises the nucleobase sequence differing by 0, 1, 2 or 3 nucleobases from the sequence (5'→3') UAUUGAGAGAAGUCCACCA (SEQ ID NO: 13), and a sense strand that comprises the nucleobase sequence differing by 0, 1, 2 or 3 nucleobases from the sequence (5'→3') UGGUGGACUUCUCUCAAUA (SEQ ID NO: 40);

and wherein a second HBV RNAi agent comprises:

i) an antisense strand that comprises the nucleobase sequence differing by 0, 1, 2 or 3 nucleobases from the sequence (5'→3') GACCAAUUUAUGCCUACAG (SEQ ID NO: 27), and a sense strand that comprises the nucleobase sequence differing by 0, 1, 2 or 3 nucleobases from the sequence (5'→3') CUGUAGGCAUAAAUUGGUC (SEQ ID NO: 54); or ii) an antisense strand that comprises the nucleobase sequence differing by 0, 1, 2 or 3 nucleobases from the sequence (5'→3') AACCAAUUUAUGCCUACAG (SEQ ID NO: 28), and a sense strand that comprises the nucleobase sequence differing by 0, 1, 2 or 3 nucleobases from the sequence (5'→3') CUGUAGGCAUAAAUUGGUU (SEQ ID NO: 55); or iii) an antisense strand that comprises the nucleobase sequence differing by 0, 1, 2 or 3 nucleobases from the sequence (5'→3') UACCAAUUUAUGCCUACAG (SEQ ID NO: 29), and a sense strand that comprises the nucleobase sequence differing by 0, 1, 2 or 3 nucleobases from the sequence (5'→3') CUGUAGGCAUAAAUUGGUA (SEQ ID NO: 56).

In some embodiments, disclosed herein are compositions for inhibiting expression of an HBV gene in a cell, the composition comprising two or more HBV RNAi agents, wherein a first HBV RNAi agent comprises:
  i) an antisense strand that comprises the nucleobase sequence differing by 0, 1, 2 or 3 nucleobases from the sequence (5'→3') AGAAAAUUGAGAGAAGUCC (SEQ ID NO: 17), and a sense strand that comprises the nucleobase sequence differing by 0, 1, 2 or 3 nucleobases from the sequence (5'→3') GGACUUCUCUCAAUUUUCU (SEQ ID NO: 44); or
  ii) an antisense strand that comprises the nucleobase sequence differing by 0, 1, 2 or 3 nucleobases from the sequence (5'→3') UGAAAAUUGAGAGAAGUCC (SEQ ID NO: 18), and a sense strand that comprises the nucleobase sequence differing by 0, 1, 2 or 3 nucleobases from the sequence (5'3') GGACUUCUCUCAAUUUUCA (SEQ ID NO: 45);
and wherein a second HBV RNAi agent comprises:
  i) an antisense strand that comprises the nucleobase sequence differing by 0, 1, 2 or 3 nucleobases from the sequence (5'→3') GACCAAUUUAUGCCUACAG (SEQ ID NO: 27), and a sense strand that comprises the nucleobase sequence differing by 0, 1, 2 or 3 nucleobases from the sequence (5'→3') CUGUAGGCAUAAAUUGGUC (SEQ ID NO: 54); or
  ii) an antisense strand that comprises the nucleobase sequence differing by 0, 1, 2 or 3 nucleobases from the sequence (5'→3') AACCAAUUUAUGCCUACAG (SEQ ID NO: 28), and a sense strand that comprises the nucleobase sequence differing by 0, 1, 2 or 3 nucleobases from the sequence (5'→3') CUGUAGGCAUAAAUUGGUU (SEQ ID NO: 55); or
  iii) an antisense strand that comprises the nucleobase sequence differing by 0, 1, 2 or 3 nucleobases from the sequence (5'→3') UACCAAUUUAUGCCUACAG (SEQ ID NO: 29), and a sense strand that comprises the nucleobase sequence differing by 0, 1, 2 or 3 nucleobases from the sequence (5'→3') CUGUAGGCAUAAAUUGGUA (SEQ ID NO: 56).

In some embodiments, disclosed herein are compositions for inhibiting expression of an HBV gene in a cell, the composition comprising two or more HBV RNAi agents, wherein a first HBV RNAi agent comprises:
  i) an antisense strand that comprises the nucleobase sequence differing by 0, 1, 2 or 3 nucleobases from the sequence (5'→3') AAUUGAGAGAAGUCCACCA (SEQ ID NO: 12), and a sense strand that comprises the nucleobase sequence differing by 0, 1, 2 or 3 nucleobases from the sequence (5'→3') UGGUGGACUUCUCUCAAUU (SEQ ID NO: 39); or
  ii) an antisense strand that comprises the nucleobase sequence differing by 0, 1, 2 or 3 nucleobases from the sequence (5'→3') UAUUGAGAGAAGUCCACCA (SEQ ID NO: 13), and a sense strand that comprises the nucleobase sequence differing by 0, 1, 2 or 3 nucleobases from the sequence (5'→3') UGGUGGACUUCUCUCAAUA (SEQ ID NO: 40);

and wherein a second HBV RNAi agent comprises an antisense strand having a sequence that is at least partially complementary to a portion of the X ORF of an HBV mRNA.

In some embodiments, disclosed herein are compositions for inhibiting expression of an HBV gene in a cell, the composition comprising two or more HBV RNAi agents, wherein a first HBV RNAi agent comprises:
  i) an antisense strand that comprises the nucleobase sequence differing by 0, 1, 2 or 3 nucleobases from the sequence (5'→3') AGAAAAUUGAGAGAAGUCC (SEQ ID NO: 17), and a sense strand that comprises the nucleobase sequence differing by 0, 1, 2 or 3 nucleobases from the sequence (5'→3') GGACUUCUCUCAAUUUUCU (SEQ ID NO: 44); or
  ii) an antisense strand that comprises the nucleobase sequence differing by 0, 1, 2 or 3 nucleobases from the sequence (5'→3') UGAAAAUUGAGAGAAGUCC (SEQ ID NO: 18), and a sense strand that comprises the nucleobase sequence differing by 0, 1, 2 or 3 nucleobases from the sequence (5'→3') GGACUUCUCUCAAUUUUCA (SEQ ID NO: 45);
and wherein a second HBV RNAi agent comprises an antisense strand having a sequence that is at least partially complementary to a portion of the X ORF of an HBV mRNA:

In some embodiments, disclosed herein are compositions for inhibiting expression of an HBV gene in a cell, the composition comprising two or more HBV RNAi agents, wherein a first HBV RNAi agent comprises an antisense strand having a sequence that is at least partially complementary to a portion of the S ORF of an HBV mRNA, and wherein a second HBV RNAi agent comprises:
  i) an antisense strand that comprises the nucleobase sequence differing by 0, 1, 2 or 3 nucleobases from the sequence (5'→3') GACCAAUUUAUGCCUACAG (SEQ ID NO: 27), and a sense strand that comprises the nucleobase sequence differing by 0, 1, 2 or 3 nucleobases from the sequence (5'→3') CUGUAGGCAUAAAUUGGUC (SEQ ID NO: 54); or
  ii) an antisense strand that comprises the nucleobase sequence differing by 0, 1, 2 or 3 nucleobases from the sequence (5'→3') AACCAAUUUAUGCCUACAG (SEQ ID NO: 28), and a sense strand that comprises the nucleobase sequence differing by 0, 1, 2 or 3 nucleobases from the sequence (5'→3') CUGUAGGCAUAAAUUGGUU (SEQ ID NO: 55); or
  iii) an antisense strand that comprises the nucleobase sequence differing by 0, 1, 2 or 3 nucleobases from the sequence (5'→3') UACCAAUUUAUGCCUACAG (SEQ ID NO: 29), and a sense strand that comprises the nucleobase sequence differing by 0, 1, 2 or 3 nucleobases from the sequence (5'→3') CUGUAGGCAUAAAUUGGUA (SEQ ID NO: 56).

In some embodiments, an HBV RNAi agent disclosed herein comprises:
  a. an antisense strand that comprises the nucleobase sequence differing by 0, 1, 2 or 3 nucleobases from the sequence (5'→3') UACCAAUUUAUGCCUACAGGCCUUAU (SEQ ID NO: 149); or
  b. an antisense strand that comprises the nucleobase sequence differing by 0, 1, 2 or 3 nucleobases from the sequence (5'→3') UACCAAUUUAUGCCUACAGGCCU (SEQ ID NO: 150); or c. an antisense strand that comprises the nucleobase sequence differing by 0, 1, 2 or 3 nucleobases from the sequence (5'→3') UACCAAUUUAUGCCUACAGGC (SEQ ID NO: 151); or
d. an antisense strand that comprises the nucleobase sequence differing by 0, 1, 2 or 3 nucleobases from the sequence (5'→3') UGAAAAUUGAGAGAAGUC-CUU (SEQ ID NO: 152); or
e. an antisense strand that comprises the nucleobase sequence differing by 0, 1, 2 or 3 nucleobases from the sequence (5'→3') UACCAAUUUAUGCCUACAGUU (SEQ ID NO: 154); or
f. an antisense strand that comprises the nucleobase sequence differing by 0, 1, 2 or 3 nucleobases from the sequence (5'→3') UAUUGAGAGAAGUCCACCACG (SEQ ID NO: 160); or
g. an antisense strand that comprises the nucleobase sequence differing by 0, 1, 2 or 3 nucleobases from the sequence (5'→3') UACCAAUUUAUGCCUACAGCC (SEQ ID NO: 162); or
h. an antisense strand that comprises the nucleobase sequence differing by 0, 1, 2 or 3 nucleobases from the sequence (5'→3') UACCAAUUUAUGCCUACAGC-CUU (SEQ ID NO: 163); or
i. an antisense strand that comprises the nucleobase sequence differing by 0, 1, 2 or 3 nucleobases from the sequence (5'→3') UAUUGAGAGAAGUCCAC-CACGA (SEQ ID NO: 170); or
j. an antisense strand that comprises the nucleobase sequence differing by 0, 1, 2 or 3 nucleobases from the sequence (5'→3') AGAAAAUUGAGAGAAGUC-CAC (SEQ ID NO: 171); or
k. an antisense strand that comprises the nucleobase sequence differing by 0, 1, 2 or 3 nucleobases from the sequence (5'→3') UACCAAUUUAUGCCUACA-GCUU (SEQ ID NO: 172); or
l. an antisense strand that comprises the nucleobase sequence differing by 0, 1, 2 or 3 nucleobases from the sequence (5'→3') UACCAAUUUAUGCCUACA-GCCU (SEQ ID NO: 173); or
m. an antisense strand that comprises the nucleobase sequence differing by 0, 1, 2 or 3 nucleobases from the sequence (5'→3') UAUUGAGAGAAGUCCAC-CAUU (SEQ ID NO: 174); or
n. an antisense strand that comprises the nucleobase sequence differing by 0, 1, 2 or 3 nucleobases from the sequence (5'→3') UAUUGAGAGAAGUCCACCA-CUU (SEQ ID NO: 175); or
o. an antisense strand that comprises the nucleobase sequence differing by 0, 1, 2 or 3 nucleobases from the sequence (5'→3') AGAAAAUUGAGAGAAGUC-CUU (SEQ ID NO: 178); or
p. an antisense strand that comprises the nucleobase sequence differing by 0, 1, 2 or 3 nucleobases from the sequence (5'→3') AGAAAAUUGAGAGAAGUCCA-CUU (SEQ ID NO: 179); or
q. an antisense strand that comprises the nucleobase sequence differing by 0, 1, 2 or 3 nucleobases from the sequence (5'→3') AGAAAAUUGAGAGAAGUC-CACC (SEQ ID NO: 180); or
r. an antisense strand that comprises the nucleobase sequence differing by 0, 1, 2 or 3 nucleobases from the sequence (5'→3') UGAAAAUUGAGAGAAGUC-CAC (SEQ ID NO: 181); or
s. an antisense strand that comprises the nucleobase sequence differing by 0, 1, 2 or 3 nucleobases from the sequence (5'→3') ACCAAUUUAUGCCUACAGCUU (SEQ ID NO: 182); or
t. an antisense strand that comprises the nucleobase sequence differing by 0, 1, 2 or 3 nucleobases from the sequence (5'→3') ACCAAUUUAUGCCUACAGC-CUU (SEQ ID NO: 183); or
u. an antisense strand that comprises the nucleobase sequence differing by 0, 1, 2 or 3 nucleobases from the sequence (5'→3') ACCAAUUUAUGCCUACAGC-CUC (SEQ ID NO: 184); or
v. an antisense strand that comprises the nucleobase sequence differing by 0, 1, 2 or 3 nucleobases from the sequence (5'→3') UCCAAUUUAUGCCUACAGCUU (SEQ ID NO: 185); or
w. an antisense strand that comprises the nucleobase sequence differing by 0, 1, 2 or 3 nucleobases from the sequence (5'→3') UCCAAUUUAUGCCUACAGC-CUU (SEQ ID NO: 186); or
x. an antisense strand that comprises the nucleobase sequence differing by 0, 1, 2 or 3 nucleobases from the sequence (5'→3') UACCAAUUUAUGCCUACAGCU (SEQ ID NO: 187); or
y. an antisense strand that comprises the nucleobase sequence differing by 0, 1, 2 or 3 nucleobases from the sequence (5'→3') UACCAAUUUAUGCCUACAGCG (SEQ ID NO: 188); or
z. an antisense strand that comprises the nucleobase sequence differing by 0, 1, 2 or 3 nucleobases from the sequence (5'→3') AACCAAUUUAUGCCUACAGCC (SEQ ID NO: 189); or
aa. an antisense strand that comprises the nucleobase sequence differing by 0, 1, 2 or 3 nucleobases from the sequence (5'→3') ACCAAUUUAUGCCUACAGCCU (SEQ ID NO: 190); or
bb. an antisense strand that comprises the nucleobase sequence differing by 0, 1, 2 or 3 nucleobases from the sequence (5'→3') UCCAAUUUAUGCCUACAGCCU (SEQ ID NO: 191); or
cc. an antisense strand that comprises the nucleobase sequence differing by 0, 1, 2 or 3 nucleobases from the sequence (5'→3') ACCAAUUUAUGCCUACAGCCG (SEQ ID NO: 192); or
dd. an antisense strand that comprises the nucleobase sequence differing by 0, 1, 2 or 3 nucleobases from the sequence (5'→3') UCCAAUUUAUGCCUACAGCCG (SEQ ID NO: 193); or
ee. an antisense strand that comprises the nucleobase sequence differing by 0, 1, 2 or 3 nucleobases from the sequence (5'→3') UACCAAUUUAUGCCUACAGGG (SEQ ID NO: 194);

and wherein the HBV RNAi agent further comprises a sense strand at least partially complementary to the respective antisense strand.

In some embodiments, an HBV RNAi agent disclosed herein comprises:
a. an antisense strand that consists of the nucleobase sequence differing by 0, 1, 2 or 3 nucleobases from the sequence (5'→3') UACCAAUUUAUGCCUACAG-GCCUUAU (SEQ ID NO: 149); or
b. an antisense strand that consists of the nucleobase sequence differing by 0, 1, 2 or 3 nucleobases from the sequence (5'→3') UACCAAUUUAUGCCUACAG-GCCU (SEQ ID NO: 150); or c. an antisense strand that consists of the nucleobase sequence differing by 0, 1, 2 or 3 nucleobases from the sequence (5'→3') UACCAAUUUAUGCCUACAGGC (SEQ ID NO: 151); or d. an antisense strand that consists of the nucleobase sequence differing by 0, 1, 2 or 3 nucleobases from the sequence (5'→3') UGAAAAUUGAGAGAAGUCCUU (SEQ ID NO: 152); or e. an antisense strand that consists of the nucleobase sequence differing by 0, 1, 2 or 3 nucleobases from the sequence (5'→3') UACCAAUUUAUGCCUACAGUU (SEQ ID NO: 154); or f. an antisense strand that consists of the nucleobase sequence differing by 0, 1, 2 or 3 nucleobases from the sequence (5'→3') UAUUGAGAGAAGUCCACCACG (SEQ ID NO: 160); or g. an antisense strand that consists of the nucleobase sequence differing by 0, 1, 2 or 3 nucleobases from the sequence (5'→3') UACCAAUUUAUGCCUACAGCC (SEQ ID NO: 162); or h. an antisense strand that consists of the nucleobase sequence differing by 0, 1, 2 or 3 nucleobases from the sequence (5'→3') UACCAAUUUAUGCCUACAGCCUU (SEQ ID NO: 163); or i. an antisense strand that consists of the nucleobase sequence differing by 0, 1, 2 or 3 nucleobases from the sequence (5'→3') UAUUGAGAGAAGUCCACCACGA (SEQ ID NO: 170); or j. an antisense strand that consists of the nucleobase sequence differing by 0, 1, 2 or 3 nucleobases from the sequence (5'→3') AGAAAAUUGAGAGAAGUCCAC (SEQ ID NO: 171); or k. an antisense strand that consists of the nucleobase sequence differing by 0, 1, 2 or 3 nucleobases from the sequence (5'→3') UACCAAUUUAUGCCUACAGCUU (SEQ ID NO: 172); or l. an antisense strand that consists of the nucleobase sequence differing by 0, 1, 2 or 3 nucleobases from the sequence (5'→3') UACCAAUUUAUGCCUACAGCCU (SEQ ID NO: 173); or m. an antisense strand that consists of the nucleobase sequence differing by 0, 1, 2 or 3 nucleobases from the sequence (5'→3') UAUUGAGAGAAGUCCACCAUU (SEQ ID NO: 174); or n. an antisense strand that consists of the nucleobase sequence differing by 0, 1, 2 or 3 nucleobases from the sequence (5'→3') UAUUGAGAGAAGUCCACCACUU (SEQ ID NO: 175); or o. an antisense strand that consists of the nucleobase sequence differing by 0, 1, 2 or 3 nucleobases from the sequence (5'→3') AGAAAAUUGAGAGAAGUCCUU (SEQ ID NO: 178); or p. an antisense strand that consists of the nucleobase sequence differing by 0, 1, 2 or 3 nucleobases from the sequence (5'→3') AGAAAAUUGAGAGAAGUCCACUU (SEQ ID NO: 179); or q. an antisense strand that consists of the nucleobase sequence differing by 0, 1, 2 or 3 nucleobases from the sequence (5'→3') AGAAAAUUGAGAGAAGUCCACC (SEQ ID NO: 180); or r. an antisense strand that consists of the nucleobase sequence differing by 0, 1, 2 or 3 nucleobases from the sequence (5'→3') UGAAAAUUGAGAGAAGUCCAC (SEQ ID NO: 181); or s. an antisense strand that consists of the nucleobase sequence differing by 0, 1, 2 or 3 nucleobases from the sequence (5'→3') ACCAAUUUAUGCCUACAGCUU (SEQ ID NO: 182); or t. an antisense strand that consists of the nucleobase sequence differing by 0, 1, 2 or 3 nucleobases from the sequence (5'→3) ACCAAUUUAUGCCUACAGCCUU (SEQ ID NO: 183); or u. an antisense strand that comprises the nucleobase sequence differing by 0, 1, 2 or 3 nucleobases from the sequence (5'→3') ACCAAUUUAUGCCUACAGCCUC (SEQ ID NO: 184); or v. an antisense strand that consists of the nucleobase sequence differing by 0, 1, 2 or 3 nucleobases from the sequence (5'→3') UCCAAUUUAUGCCUACAGCUU (SEQ ID NO: 185); or w. an antisense strand that consists of the nucleobase sequence differing by 0, 1, 2 or 3 nucleobases from the sequence (5'→3') UCCAAUUUAUGCCUACAGCCUU (SEQ ID NO: 186); or x. an antisense strand that consists of the nucleobase sequence differing by 0, 1, 2 or 3 nucleobases from the sequence (5'→3') UACCAAUUUAUGCCUACAGCU (SEQ ID NO: 187); or y. an antisense strand that comprises the nucleobase sequence differing by 0, 1, 2 or 3 nucleobases from the sequence (5'→3') UACCAAUUUAUGCCUACAGCG (SEQ ID NO: 188); or z. an antisense strand that consists of the nucleobase sequence differing by 0, 1, 2 or 3 nucleobases from the sequence (5'→3') AACCAAUUUAUGCCUACAGCC (SEQ ID NO: 189); or aa. an antisense strand that consists of the nucleobase sequence differing by 0, 1, 2 or 3 nucleobases from the sequence (5'→3') ACCAAUUUAUGCCUACAGCCU (SEQ ID NO: 190); or bb. an antisense strand that consists of the nucleobase sequence differing by 0, 1, 2 or 3 nucleobases from the sequence (5'→3') UCCAAUUUAUGCCUACAGCCU (SEQ ID NO: 191); or cc. an antisense strand that consists of the nucleobase sequence differing by 0, 1, 2 or 3 nucleobases from the sequence (5'→3') ACCAAUUUAUGCCUACAGCCG (SEQ ID NO: 192); or dd. an antisense strand that comprises the nucleobase sequence differing by 0, 1, 2 or 3 nucleobases from the sequence (5'→3') UCCAAUUUAUGCCUACAGCCG (SEQ ID NO: 193); or.

ee. an antisense strand that consists of the nucleobase sequence differing by 0, 1, 2 or 3 nucleobases from the sequence (5'→3') UACCAAUUUAUGCCUACAGGG (SEQ ID NO: 194);

and wherein the HBV RNAi agent further comprises a sense strand at least partially complementary to the respective antisense strand.

In some embodiments, an HBV RNAi agent disclosed herein comprises:

i. an antisense strand that comprises the sequence differing by 0, 1, 2 or 3 nucleotides from the sequence (5'→3') usAfscCfaAfuUfuAfuGfcCfuAfcAfgGfccsusuAu (SEQ ID NO: 61); or ii. an antisense strand that comprises the sequence differing by 0, 1, 2 or 3 nucleotides from the sequence (5'→3') usAfscCfaAfuUfuAfuGfcCfuAfcAfgGfcscsu (SEQ ID NO: 62); or iii. an antisense strand that comprises the sequence differing by 0, 1, 2 or 3 nucleotides from the sequence (5'→3') usAfscsCfaAfuUfuAfuGfcCfuAfcAfgGfccsu (SEQ ID NO: 63); or iv. an antisense strand that comprises the sequence differing by 0, 1, 2 or 3 nucleotides from the sequence (5'→3') usAfscsCfaAfuUfuAfuGfcCfuAfcAfgGfsc (SEQ ID NO: 64); or v. an antisense strand that comprises the sequence differing by 0, 1, 2 or 3 nucleotides from the sequence (5'→3') usAfscsCfaAfuUfuAfuGfcCfuAfcAfgusu (SEQ ID NO: 68); or vi. an antisense strand that comprises the sequence differing by 0, 1, 2 or 3 nucleotides from the sequence (5'→3') usAfscscaauUfuAfuGfcCfuacagcsc (SEQ ID NO: 85); or vii. an antisense strand that comprises the sequence differing by 0, 1, 2 or 3 nucleotides from the sequence (5'→3') usAfsusugagAfgAfaGfuCfcaccacsg (SEQ ID NO: 94); or viii. an antisense strand that comprises the sequence differing by 0, 1, 2 or 3 nucleotides from the sequence (5'→3') usAfsusUfgAfgAfgAfaGfuCfcAfcCfaCfgsa (SEQ ID NO: 98); or ix. an antisense strand that comprises the sequence differing by 0, 1, 2 or 3 nucleotides from the sequence (5'→3') usAfscsCfaAfuuuauGfcCfuAfcAfgcsc (SEQ ID NO: 102); or x. an antisense strand that comprises the sequence differing by 0, 1, 2 or 3 nucleotides from the sequence (5'→3') usAfscsCfaAfuuuauGfcCfuAfcAfgcusu (SEQ ID NO: 103); or xi. an antisense strand that comprises the sequence differing by 0, 1, 2 or 3 nucleotides from the sequence (5'→3') usAfscsCfaAfuuuauGfcCfuAfcAfgccsu (SEQ ID NO: 104); or xii. an antisense strand that comprises the sequence differing by 0, 1, 2 or 3 nucleotides from the sequence (5'→3') usAfscsCfaAfuuuauGfcCfuAfcAfgccusu (SEQ ID NO: 105); or xiii. an antisense strand that comprises the sequence differing by 0, 1, 2 or 3 nucleotides from the sequence (5'→3') cPrpusAfscsCfaAfuUfuAfuGfcCfuAfcAfgusu (SEQ ID NO: 107); or xiv. an antisense strand that comprises the sequence differing by 0, 1, 2 or 3 nucleotides from the sequence (5'→3') cPrpusAfsusUfgAfgAfgAfaGfuCfcAfcCfaCfsg (SEQ ID NO: 108); or xv. an antisense strand that comprises the sequence differing by 0, 1, 2 or 3 nucleotides from the sequence (5'→3') usAfsusUfgAfgagaaGfuCfcAfcCfausu (SEQ ID NO: 109); or xvi. an antisense strand that comprises the sequence differing by 0, 1, 2 or 3 nucleotides from the sequence (5'→3') usAfsusUfgAfgagaaGfuCfcAfcCfacsg (SEQ ID NO: 110); or xvii. an antisense strand that comprises the sequence differing by 0, 1, 2 or 3 nucleotides from the sequence (5'→3') usAfsusUfgAfgagaaGfuCfcAfcCfacsusu (SEQ ID NO: 111); or xviii. an antisense strand that comprises the sequence differing by 0, 1, 2 or 3 nucleotides from the sequence (5'→3') usAfsusUfgAfgagaaGfuCfcAfcCfacsgsa (SEQ ID NO: 112); or xix. an antisense strand that comprises the sequence differing by 0, 1, 2 or 3 nucleotides from the sequence (5'→3') usAfsusUfgAfgagaaGfuCfcAfcCfacusu (SEQ ID NO: 120); or xx. an antisense strand that comprises the sequence differing by 0, 1, 2 or 3 nucleotides from the sequence (5'→3') asGfsasAfaAfuUfgAfgAfgAfaGfuCfcusu (SEQ ID NO: 125);

xxi. an antisense strand that comprises the sequence differing by 0, 1, 2 or 3 nucleotides from the sequence (5'→3') asGfsasAfaAfuUfgAfgAfgAfaGfuCfcasc (SEQ ID NO: 126); or xxii. an antisense strand that comprises the sequence differing by 0, 1, 2 or 3 nucleotides from the sequence (5'→3') asGfsasAfaAfuUfgAfgAfgAfaGfuCfcacusu (SEQ ID NO: 127); or xxiii. an antisense strand that comprises the sequence differing by 0, 1, 2 or 3 nucleotides from the sequence (5'→3') asGfsasAfaAfuUfgAfgAfgAfaGfuCfcacsc (SEQ ID NO: 128); or xxiv. an antisense strand that comprises the sequence differing by 0, 1, 2 or 3 nucleotides from the sequence (5'→3') usGfsasAfaAfuUfgAfgAfgAfaGfuCfcusu (SEQ ID NO: 129); or xxv. an antisense strand that comprises the sequence differing by 0, 1, 2 or 3 nucleotides from the sequence (5'→3') usGfsasAfaAfuUfgAfgAfgAfaGfuCfcasc (SEQ ID NO: 130); or xxvi. an antisense strand that comprises the sequence differing by 0, 1, 2 or 3 nucleotides from the sequence (5'→3') asCfscsAfaUfuUfaUfgCfcUfaCfaGfcusu (SEQ ID NO: 131); or xxvii. an antisense strand that comprises the sequence differing by 0, 1, 2 or 3 nucleotides from the sequence (5'→3') asCfscsAfaUfuUfaUfgCfcUfaCfaGfccusu (SEQ ID NO: 132); or xxviii. an antisense strand that comprises the sequence differing by 0, 1, 2 or 3 nucleotides from the sequence (5'→3') asCfscsAfaUfuUfaUfgCfcUfaCfaGfccusc (SEQ ID NO: 133); or xxix. an antisense strand that comprises the sequence differing by 0, 1, 2 or 3 nucleotides from the sequence (5'→3') usCfscsAfaUfuUfaUfgCfcUfaCfaGfcusu (SEQ ID NO: 134); or xxx. an antisense strand that comprises the sequence differing by 0, 1, 2 or 3 nucleotides from the sequence (5'→3') usCfscsAfaUfuUfaUfgCfcUfaCfaGfccusu (SEQ ID NO: 135); or xxxi. an antisense strand that comprises the sequence differing by 0, 1, 2 or 3 nucleotides from the sequence (5'→3') cPrpusAfscsCfaAfuUfuAfuGfcCfuAfcAfgcsc (SEQ ID NO: 136); or xxxii. an antisense strand that comprises the sequence differing by 0, 1, 2 or 3 nucleotides from the sequence (5'→3') usAfscsCfaAfuUfuAfuGfcCfuAfcAfgscsc (SEQ ID NO: 137); or xxxiii. an antisense strand that comprises the sequence differing by 0, 1, 2 or 3 nucleotides from the sequence (5'→3') cPrpusAfscsCfaAfuUfuAfuGfcCfuAfcAfgscsc (SEQ ID NO: 138); or xxxiv. an antisense strand that comprises the sequence differing by 0, 1, 2 or 3 nucleotides from the sequence (5'→3') usAfscsCfaAfuUfuAfuGfcCfuAfcAfgcsu (SEQ ID NO: 139); or xxxv. an antisense strand that comprises the sequence differing by 0, 1, 2 or 3 nucleotides from the sequence (5'→3') usAfscsCfaAfuUfuAfuGfcCfuAfcAfgcsg (SEQ ID NO: 140); or
xxxvi. an antisense strand that comprises the sequence differing by 0, 1, 2 or 3 nucleotides from the sequence (5'→3') asAfscsCfaAfuUfuAfuGfcCfuAfcAfgcsc (SEQ ID NO: 141); or
xxxvii. an antisense strand that comprises the sequence differing by 0, 1, 2 or 3 nucleotides from the sequence (5'→3') usAfscsCfaAfuUfUJfAfuGfcCfuAfcAfgusu (SEQ ID NO: 142); or
xxxviii. an antisense strand that comprises the sequence differing by 0, 1, 2 or 3 nucleotides from the sequence (5'→3') usAfscsCfaAfuUfuAfuGfcCfuAfcAfgCfsc (SEQ ID NO: 143); or
xxxix. an antisense strand that comprises the sequence differing by 0, 1, 2 or 3 nucleotides from the sequence (5'→3') asCfscAfaUfuUfaUfgCfcUfaCfaGfcCfsu (SEQ ID NO: 144); or
xl. an antisense strand that comprises the sequence differing by 0, 1, 2 or 3 nucleotides from the sequence (5'→3') usCfscAfaUfuUfaUfgCfcUfaCfaGfcCfsu (SEQ ID NO: 145); or
xli. an antisense strand that comprises the sequence differing by 0, 1, 2 or 3 nucleotides from the sequence (5'→3') asCfscAfaUfuUfaUfgCfcUfaCfaGfccsg (SEQ ID NO: 146); or
xlii. an antisense strand that comprises the sequence differing by 0, 1, 2 or 3 nucleotides from the sequence (5'→3') usCfscAfaUfuUfaUfgCfcUfaCfaGfccsg (SEQ ID NO: 147); or
xliii. an antisense strand that comprises the sequence differing by 0, 1, 2 or 3 nucleotides from the sequence (5'→3') usAfscsCfaAfuUfuAfuGfcCfuAfcAfggsg (SEQ ID NO: 148);

wherein a, g, c and u are 2'-O-methyl (2'-OMe) modified nucleotides; Af, Cf, Gf, and Uf are 2'-fluoro modified nucleotides; s is a phosphorothioate internucleoside linkage and the remaining nucleotide monomers are linked by phosphodiester bonds; and cPrpu is 5'-cyclopropyl phosphonate-2'-O-methyl modified nucleotide; and wherein the HBV RNAi agent further comprises a sense strand at least partially complementary to the respective antisense strand.

In some embodiments, an HBV RNAi agent disclosed herein comprises:
i. an antisense strand that consists of the sequence (5'→3') usAfscCfaAfuUfuAfuGfcCfuAfcAfgGfccsusuAu (SEQ ID NO: 61); or
ii. an antisense strand that consists of the sequence (5'→3') usAfscCfaAfuUfuAfuGfcCfuAfcAfgGfcscsu (SEQ ID NO: 62); or
iii. an antisense strand that consists of the sequence (5'→3') usAfscsCfaAfuUfuAfuGfcCfuAfcAfgGfccsu (SEQ ID NO: 63); or
iv. an antisense strand that consists of the sequence (5'→3') usAfscsCfaAfuUfuAfuGfcCfuAfcAfgGfsc (SEQ ID NO: 64); or
v. an antisense strand that consists of the sequence (5'→3') usAfscsCfaAfuUfuAfuGfcCfuAfcAfgusu (SEQ ID NO: 68); or
vi. an antisense strand that consists of the sequence (5'→3') usAfscscaauUfuAfuGfcCfuacagcsc (SEQ ID NO: 85); or
vii. an antisense strand that consists of the sequence (5'→3') usAfsusugagAfgAfaGfuCfcaccacsg (SEQ ID NO: 94); or
viii. an antisense strand that consists of the sequence (5'→3') usAfsusUfgAfgAfgAfaGfuCfcAfcCfaCfgsa (SEQ ID NO: 98); or
ix. an antisense strand that consists of the sequence (5'→3') usAfscsCfaAfuuuauGfcCfuAfcAfgcsc (SEQ ID NO: 102); or
x. an antisense strand that consists of the sequence (5'→3') usAfscsCfaAfuuuauGfcCfuAfcAfgcusu (SEQ ID NO: 103); or
xi. an antisense strand that consists of the sequence (5'→3') usAfscsCfaAfuuuauGfcCfuAfcAfgccsu (SEQ ID NO: 104); or
xii. an antisense strand that consists of the sequence (5'→3') usAfscsCfaAfuuuauGfcCfuAfcAfgccusu (SEQ ID NO: 105); or
xiii. an antisense strand that consists of the sequence (5'→3') cPrpusAfscsCfaAfuUfuAfuGfcCfuAfcAfgusu (SEQ ID NO: 107); or
xiv. an antisense strand that consists of the sequence (5'→3') cPrpusAfsusUfgAfgAfgAfaGfuCfcAfcCfaCfsg (SEQ ID NO: 108); or
xv. an antisense strand that consists of the sequence (5'→3') usAfsusUfgAfgagaaGfuCfcAfcCfausu (SEQ ID NO: 109); or
xvi. an antisense strand that consists of the sequence (5'→3') usAfsusUfgAfgagaaGfuCfcAfcCfacsg (SEQ ID NO: 110); or
xvii. an antisense strand that consists of the sequence (5'→3') usAfsusUfgAfgagaaGfuCfcAfcCfacsusu (SEQ ID NO: 111); or
xviii. an antisense strand that consists of the sequence (5'→3') usAfsusUfgAfgagaaGfuCfcAfcCfacsgsa (SEQ ID NO: 112); or
xix. an antisense strand that consists of the sequence (5'→3') usAfsusUfgAfgagaaGfuCfcAfcCfacusu (SEQ ID NO: 120); or
xx. an antisense strand that consists of the sequence (5'→3') asGfsasAfaAfuUfgAfgAfgAfaGfuCfcusu (SEQ ID NO: 125);
xxi. an antisense strand that consists of the sequence (5'→3') asGfsasAfaAfuUfgAfgAfgAfaGfuCfcasc (SEQ ID NO: 126); or
xxii. an antisense strand that consists of the sequence (5'→3') asGfsasAfaAfuUfgAfgAfgAfaGfuCfcacusu (SEQ ID NO: 127); or
xxiii. an antisense strand that consists of the sequence (5'→3') asGfsasAfaAfuUfgAfgAfgAfaGfuCfcacsc (SEQ ID NO: 128); or
xxiv. an antisense strand that consists of the sequence (5'→3') usGfsasAfaAfuUfgAfgAfgAfaGfuCfcusu (SEQ ID NO: 129); or
xxv. an antisense strand that consists of the sequence (5'→3') usGfsasAfaAfuUfgAfgAfgAfaGfuCfcasc (SEQ ID NO: 130); or
xxvi. an antisense strand that consists of the sequence (5'→3') asCfscsAfaUfuUfaUfgCfcUfaCfaGfcusu (SEQ ID NO: 131); or
xxvii. an antisense strand that consists of the sequence (5'→3') asCfscsAfaUfuUfaUfgCfcUfaCfaGfccusu (SEQ ID NO: 132); or
xxviii. an antisense strand that consists of the sequence (5'→3') asCfscsAfaUfuUfaUfgCfcUfaCfaGfccusc (SEQ ID NO: 133); or
xxix. an antisense strand that consists of the sequence (5'→3') usCfscsAfaUfuUfaUfgCfcUfaCfaGfcusu (SEQ ID NO: 134); or xxx. an antisense strand that consists of the sequence (5'→3') usCfscsAfaUfuUfaUfgCfcUfaCfaGfccusu (SEQ ID NO: 135); or xxxi. an antisense strand that consists of the sequence (5'→3') cPrpusAfscsCfaAfuUfuAfuGfcCfuAfcAfgcsc (SEQ ID NO: 136); or xxxii. an antisense strand that consists of the sequence (5'→3') usAfscsCfaAfuUfuAfuGfcCfuAfcAfgscsc (SEQ ID NO: 137); or xxxiii. an antisense strand that consists of the sequence (5'→3') cPrpusAfscsCfaAfuUfuAfuGfcCfuAfcAfgscsc (SEQ ID NO: 138); or xxxiv. an antisense strand that consists of the sequence (5'→3') usAfscsCfaAfuUfuAfuGfcCfuAfcAfgcsu (SEQ ID NO: 139); or xxxv. an antisense strand that consists of the sequence (5'→3') usAfscsCfaAfuUfuAfuGfcCfuAfcAfgcsg (SEQ ID NO: 140); or xxxvi. an antisense strand that consists of the sequence (5'→3') asAfscsCfaAfuUfuAfuGfcCfuAfcAfgcsc (SEQ ID NO: 141); or xxxvii. an antisense strand that consists of the sequence (5'→3') usAfscsCfaAfuUfUJfAfuGfcCfuAfcAfgusu (SEQ ID NO: 142); or xxxviii. an antisense strand that consists of the sequence (5'→3') usAfscsCfaAfuUfuAfuGfcCfuAfcAfgCfsc (SEQ ID NO: 143); or xxxix. an antisense strand that consists of the sequence (5'→3') asCfscAfaUfuUfaUfgCfcUfaCfaGfcCfsu (SEQ ID NO: 144); or xl. an antisense strand that consists of the sequence (5'→3') usCfscAfaUfuUfaUfgCfcUfaCfaGfcCfsu (SEQ ID NO: 145); or xli. an antisense strand that consists of the sequence (5'→3') asCfscAfaUfuUfaUfgCfcUfaCfaGfccsg (SEQ ID NO: 146); or xlii. an antisense strand that consists of the sequence (5'→3') usCfscAfaUfuUfaUfgCfcUfaCfaGfccsg (SEQ ID NO: 147); or xliii. an antisense strand that consists of the sequence (5'→3') usAfscsCfaAfuUfuAfuGfcCfuAfcAfggsg (SEQ ID NO: 148);

wherein a, g, c and u are 2'-O-methyl (2'-OMe) modified nucleotides; Af, Cf, Gf, and Uf are 2'-fluoro modified nucleotides; s is a phosphorothioate internucleoside linkage and the remaining nucleotide monomers are linked by phosphodiester bonds; and cPrpu is 5'-cyclopropyl phosphonate-2'-O-methyl modified nucleotide; and wherein the HBV RNAi agent further comprises a sense strand at least partially complementary to the respective antisense strand.

In some embodiments, an HBV RNAi agent disclosed herein comprises:

a. a sense strand that comprises the nucleobase sequence differing by 0, 1, 2 or 3 nucleobases from the sequence (5'→3') UUGCCUGUAGGCAUAAAUUGGUAUT (SEQ ID NO: 275); or b. a sense strand that comprises the nucleobase sequence differing by 0, 1, 2 or 3 nucleobases from the sequence (5'→3') UAUAUGCCUGUAGGCAUAAAUUGGUA (SEQ ID NO: 276); or c. a sense strand that comprises the nucleobase sequence differing by 0, 1, 2 or 3 nucleobases from the sequence (5'→3') CUGUAGGCAUAAAUUGGUAUU (SEQ ID NO: 278); or d. a sense strand that comprises the nucleobase sequence differing by 0, 1, 2 or 3 nucleobases from the sequence (5'→3') CGUGGUGGACUUCUCUCAAUU (SEQ ID NO: 285); or e. a sense strand that comprises the nucleobase sequence differing by 0, 1, 2 or 3 nucleobases from the sequence (5'→3') CGUGGUGGACUUCUCUCAAUA (SEQ ID NO: 289); or f. a sense strand that comprises the nucleobase sequence differing by 0, 1, 2 or 3 nucleobases from the sequence (5'→3') CUGUAGGCAUAAAUUGGUA (SEQ ID NO: 292); or g. a sense strand that comprises the nucleobase sequence differing by 0, 1, 2 or 3 nucleobases from the sequence (5'→3') GGCUGUAGGCAUAAAUUGGUA (SEQ ID NO: 294); or h. a sense strand that comprises the nucleobase sequence differing by 0, 1, 2 or 3 nucleobases from the sequence (5'→3') UCGUGGUGGACUUCUCUCAAUU (SEQ ID NO: 300); or i. a sense strand that comprises the nucleobase sequence differing by 0, 1, 2 or 3 nucleobases from the sequence (5'→3') GUGGACUUCUCUCAAUUUUCU (SEQ ID NO: 302); or j. a sense strand that comprises the nucleobase sequence differing by 0, 1, 2 or 3 nucleobases from the sequence (5'→3') GCUGUAGGCAUAAAUUGGUAUU (SEQ ID NO: 303); or k. a sense strand that comprises the nucleobase sequence differing by 0, 1, 2 or 3 nucleobases from the sequence (5'→3') GGCUGUAGGCAUAAAUUGGUAUU (SEQ ID NO: 304); or l. a sense strand that comprises the nucleobase sequence differing by 0, 1, 2 or 3 nucleobases from the sequence (5'→3') UGGUGGACUUCUCUCAAUAUU (SEQ ID NO: 306); or m. a sense strand that comprises the nucleobase sequence differing by 0, 1, 2 or 3 nucleobases from the sequence (5'→3') GUGGUGGACUUCUCUCAAUAUU (SEQ ID NO: 307); or n. a sense strand that comprises the nucleobase sequence differing by 0, 1, 2 or 3 nucleobases from the sequence (5'→3') AAUGGUGGACUUCUCUCAAUAUU (SEQ ID NO: 308); or o. a sense strand that comprises the nucleobase sequence differing by 0, 1, 2 or 3 nucleobases from the sequence (5'→3') GGACUUCUCUCAAUUUUCU (SEQ ID NO: 318); or p. a sense strand that comprises the nucleobase sequence differing by 0, 1, 2 or 3 nucleobases from the sequence (5'→3') GGUGGACUUCUCUCAAUUUUCU (SEQ ID NO: 319); or q. a sense strand that comprises the nucleobase sequence differing by 0, 1, 2 or 3 nucleobases from the sequence (5'→3') GGACUUCUCUCAAUUUUCA (SEQ ID NO: 320); or r. a sense strand that comprises the nucleobase sequence differing by 0, 1, 2 or 3 nucleobases from the sequence (5'→3') GUGGACUUCUCUCAAUUUUCA (SEQ ID NO: 321); or s. a sense strand that comprises the nucleobase sequence differing by 0, 1, 2 or 3 nucleobases from the sequence (5'→3') GCUGUAGGCAUAAAUUGGU (SEQ ID NO: 322); or t. a sense strand that comprises the nucleobase sequence differing by 0, 1, 2 or 3 nucleobases from the sequence (5'→3') GGCUGUAGGCAUAAAUUGGU (SEQ ID NO: 323); or u. a sense strand that comprises the nucleobase sequence differing by 0, 1, 2 or 3 nucleobases from the sequence (5'→3') GAGGCUGUAGGCAUAAAUUGGU (SEQ ID NO: 324); or v. a sense strand that comprises the nucleobase sequence differing by 0, 1, 2 or 3 nucleobases from the sequence (5'→3') GCUGUAGGCAUAAAUUGGA (SEQ ID NO: 325); or w. a sense strand that comprises the nucleobase sequence differing by 0, 1, 2 or 3 nucleobases from the sequence (5'→3') GGCUGUAGGCAUAAAUUGGA (SEQ ID NO: 326); or x. a sense strand that comprises the nucleobase sequence differing by 0, 1, 2 or 3 nucleobases from the sequence (5'→3') AGCUGUAGGCAUAAAUUGGUA (SEQ ID NO: 327); or y. a sense strand that comprises the nucleobase sequence differing by 0, 1, 2 or 3 nucleobases from the sequence (5'→3') CGCUGUAGGCAUAAAUUGGUA (SEQ ID NO: 328); or z. a sense strand that comprises the nucleobase sequence differing by 0, 1, 2 or 3 nucleobases from the sequence (5'→3') GGCUGUAGGCAUAAAUUGGUU (SEQ ID NO: 329); or aa. an antisense strand that comprises the nucleobase sequence differing by 0, 1, 2 or 3 nucleobases from the sequence (5'→3') AGGCUGUAG-GCAUAAAUUGGU (SEQ ID NO: 330); or bb. a sense strand that comprises the nucleobase sequence differing by 0, 1, 2 or 3 nucleobases from the sequence (5'→3') AGGCUGUAGGCAUAAAUUGGA (SEQ ID NO: 331); or cc. a sense strand that comprises the nucleobase sequence differing by 0, 1, 2 or 3 nucleobases from the sequence (5'→3') CGGCUGUAGGCAUAAAUUGGU (SEQ ID NO: 332); or dd. a sense strand that comprises the nucleobase sequence differing by 0, 1, 2 or 3 nucleobases from the sequence (5'→3') CGGCUGUAGGCAUAAAUUGGA (SEQ ID NO: 333); or ee. a sense strand that comprises the nucleobase sequence differing by 0, 1, 2 or 3 nucleobases from the sequence (5'→3') CCCUGUAGGCAUAAAUUGGUA (SEQ ID NO: 334);

and wherein the HBV RNAi agent further comprises an antisense strand at least partially complementary to the respective antisense strand.

In some embodiments, an HBV RNAi agent disclosed herein comprises:

a. a sense strand that consists of the nucleobase sequence (5'→3') UUGCCUGUAGGCAUAAAUUGGUAUT (SEQ ID NO: 275); or b. a sense strand that consists of the nucleobase sequence (5'→3') UAUAUGCCUGUAGGCAUAAAUUGGUA (SEQ ID NO: 276); or c. a sense strand that consists of the nucleobase sequence (5'→3') CUGUAGGCAUAAAUUGGUAUU (SEQ ID NO: 278); or d. a sense strand that consists of the nucleobase sequence (5'→3') CGUGGUGGACUUCUCUCAAUU (SEQ ID NO: 285); or e. a sense strand that consists of the nucleobase sequence (5'→3') CGUGGUGGACUUCUCUCAAUA (SEQ ID NO: 289); or f. a sense strand that consists of the nucleobase sequence (5'→3') CUGUAGGCAUAAAUUGGUA (SEQ ID NO: 292); or g. a sense strand that consists of the nucleobase sequence (5'→3') GGCUGUAGGCAUAAAUUGGUA (SEQ ID NO: 294); or h. a sense strand that consists of the nucleobase sequence (5'→3') UCGUGGUGGACUUCUCUCAAUU (SEQ ID NO: 300); or i. a sense strand that consists of the nucleobase sequence (5'→3') GUGGACUUCUCUCAAUUUCU (SEQ ID NO: 302); or j. a sense strand that consists of the nucleobase sequence (5'→3') GCUGUAGGCAUAAAUUGGUAUU (SEQ ID NO: 303); or k. a sense strand that consists of the nucleobase sequence (5'→3') GGCUGUAGGCAUAAAUUGGUAUU (SEQ ID NO: 304); or l. a sense strand that consists of the nucleobase sequence (5'→3') UGGUGGACUUCUCUCAAUAUU (SEQ ID NO: 306); or m. a sense strand that consists of the nucleobase sequence (5'→3') GUGGUGGACUUCUCUCAAUAUU (SEQ ID NO: 307); or n. a sense strand that consists of the nucleobase sequence (5'→3') AAUGGUGGACUUCUCUCAAUAUU (SEQ ID NO: 308); or o. a sense strand that comprises the nucleobase sequence (5'→3') GGACUUCUCUCAAUUUUCU (SEQ ID NO: 318); or p. a sense strand that consists of the nucleobase sequence (5'→3') GGUGGACUUCUCUCAAUUUUCU (SEQ ID NO: 319); or q. a sense strand that consists of the nucleobase sequence (5'→3') GGACUUCUCUCAAUUUUCA (SEQ ID NO: 320); or r. a sense strand that consists of the nucleobase sequence (5'→3') GUGGACUUCUCUCAAUUUUCA (SEQ ID NO: 321); or s. a sense strand that consists of the nucleobase sequence (5'→3') GCUGUAGGCAUAAAUUGGU (SEQ ID NO: 322); or t. a sense strand that consists of the nucleobase sequence (5'→3') GGCUGUAGGCAUAAAUUGGU (SEQ ID NO: 323); or u. a sense strand that consists of the nucleobase sequence (5'→3') GAGGCUGUAGGCAUAAAUUGGU (SEQ ID NO: 324); or v. a sense strand that consists of the nucleobase sequence (5'→3') GCUGUAGGCAUAAAUUGGA (SEQ ID NO: 325); or w. a sense strand that consists of the nucleobase sequence (5'→3') GGCUGUAGGCAUAAAUUGGA (SEQ ID NO: 326); or x. a sense strand that consists of the nucleobase sequence (5'→3') AGCUGUAGGCAUAAAUUGGUA (SEQ ID NO: 327); or y. a sense strand that consists of the nucleobase sequence (5'→3') CGCUGUAGGCAUAAAUUGGUA (SEQ ID NO: 328); or z. a sense strand that consists of the nucleobase sequence (5'→3') GGCUGUAGGCAUAAAUUGGUU (SEQ ID NO: 329); or aa. an antisense strand that comprises the nucleobase sequence (5'→3') AGGCUGUAGGCAUAAAUUGGU (SEQ ID NO: 330); or
bb. a sense strand that consists of the nucleobase sequence (5'→3') AGGCUGUAGGCAUAAAUUGGA (SEQ ID NO: 331); or
cc. a sense strand that consists of the nucleobase sequence (5'→3') CGGCUGUAGGCAUAAAUUGGU (SEQ ID NO: 332); or
dd. a sense strand that consists of the nucleobase sequence (5'→3') CGGCUGUAGGCAUAAAUUGGA (SEQ ID NO: 333); or
ee. a sense strand that consists of the nucleobase sequence (5'→3') CCCUGUAGGCAUAAAUUGGUA (SEQ ID NO: 334);

and wherein the HBV RNAi agent further comprises an antisense strand at least partially complementary to the respective antisense strand.

In some embodiments, disclosed herein are compositions for inhibiting expression of an HBV gene in a cell, the composition comprising two HBV RNAi agents, wherein a first HBV RNAi agent comprises an antisense strand that comprises the nucleobase sequence differing by 0, 1, 2 or 3 nucleobases from the sequence (5'→3') UAUUGAGAGAAGUCCACCACUU (SEQ ID NO: 175), and a sense strand that comprises the nucleobase sequence differing by 0, 1, 2 or 3 nucleobases from the sequence (5'→3') GUGGUGGACUUCUCUCAAUAUU (SEQ ID NO: 307); and wherein a second HBV RNAi agent comprises an antisense strand that comprises the nucleobase sequence differing by 0, 1, 2 or 3 nucleobases from the sequence (5'→3') UACCAAUUUAUGCCUACAGUU (SEQ ID NO: 154), and a sense strand that comprises the nucleobase sequence differing by 0, 1, 2 or 3 nucleobases from the sequence (5'→3') CUGUAGGCAUAAAUUGGUA (SEQ ID NO: 292).

In some embodiments, disclosed herein are compositions for inhibiting expression of an HBV gene in a cell, the composition comprising two HBV RNAi agents, wherein a first HBV RNAi agent comprises an antisense strand that consists of the nucleobase sequence (5'→3') UAUUGAGAGAAGUCCACCACUU (SEQ ID NO: 175), and a sense strand that consists of the nucleobase sequence (5'→3') GUGGUGGACUUCUCUCAAUAUU (SEQ ID NO: 307); and wherein a second HBV RNAi agent comprises an antisense strand that consists of the nucleobase sequence (5'→3') UACCAAUUUAUGCCUACAGUU (SEQ ID NO: 154), and a sense strand that consists of the nucleobase sequence (5'→3') CUGUAGGCAUAAAUUGGUA (SEQ ID NO: 292).

In some embodiments, disclosed herein are compositions for inhibiting expression of an HBV gene in a cell, the composition comprising two HBV RNAi agents, wherein a first HBV RNAi agent comprises an antisense strand that comprises the nucleobase sequence differing by 0, 1, 2 or 3 nucleobases from the sequence (5'→3') AGAAAAUUGAGAGAAGUCCAC (SEQ ID NO: 171), and a sense strand that comprises the nucleobase sequence differing by 0, 1, 2 or 3 nucleobases from the sequence (5'→3') GUGGACUUCUCUCAAUUUUCU (SEQ ID NO: 302); and wherein a second HBV RNAi agent comprises an antisense strand that comprises the nucleobase sequence differing by 0, 1, 2 or 3 nucleobases from the sequence (5'→3') UACCAAUUUAUGCCUACAGCG (SEQ ID NO: 188), and a sense strand that comprises the nucleobase sequence differing by 0, 1, 2 or 3 nucleobases from the sequence (5'→3') CGCUGUAGGCAUAAAUUGGUA (SEQ ID NO: 328).

In some embodiments, disclosed herein are compositions for inhibiting expression of an HBV gene in a cell, the composition comprising two HBV RNAi agents, wherein a first HBV RNAi agent comprises an antisense strand that consists of the nucleobase sequence (5'→3') AGAAAAUUGAGAGAAGUCCAC (SEQ ID NO: 171), and a sense strand that consists of the nucleobase sequence (5'→3') GUGGACUUCUCUCAAUUUUCU (SEQ ID NO: 302); and wherein a second HBV RNAi agent comprises an antisense strand that consists of the nucleobase sequence (5'→3') UACCAAUUUAUGCCUACAGCG (SEQ ID NO: 188), and a sense strand that consists of the nucleobase sequence (5'→3') CGCUGUAGGCAUAAAUUGGUA (SEQ ID NO: 328).

In some embodiments, disclosed herein are compositions for inhibiting expression of an HBV gene in a cell, the composition comprising two HBV RNAi agents, wherein a first HBV RNAi agent comprises an antisense strand that comprises the nucleobase sequence differing by 0, 1, 2 or 3 nucleobases from the sequence (5'→3') AGAAAAUUGAGAGAAGUCCAC (SEQ ID NO: 171), and a sense strand that comprises the nucleobase sequence differing by 0, 1, 2 or 3 nucleobases from the sequence (5'→3') GUGGACUUCUCUCAAUUUUCU (SEQ ID NO: 302); and wherein a second HBV RNAi agent comprises an antisense strand that comprises the nucleobase sequence differing by 0, 1, 2 or 3 nucleobases from the sequence (5'→3') UACCAAUUUAUGCCUACAGCC (SEQ ID NO: 162), and a sense strand that comprises the nucleobase sequence differing by 0, 1, 2 or 3 nucleobases from the sequence (5'→3') GGCUGUAGGCAUAAAUUGGUA (SEQ ID NO: 294).

In some embodiments, disclosed herein are compositions for inhibiting expression of an HBV gene in a cell, the composition comprising two HBV RNAi agents, wherein a first HBV RNAi agent comprises an antisense strand that consists of the nucleobase sequence (5'→3') AGAAAAUUGAGAGAAGUCCAC (SEQ ID NO: 171), and a sense strand that consists of the nucleobase sequence (5'→3) GUGGACUUCUCUCAAUUUUCU (SEQ ID NO: 302); and wherein a second HBV RNAi agent comprises an antisense strand that consists of the nucleobase sequence (5'→3') UACCAAUUUAUGCCUACAGCC (SEQ ID NO: 162), and a sense strand that consists of the nucleobase sequence (5'→3') GGCUGUAGGCAUAAAUUGGUA (SEQ ID NO: 294).

In some embodiments, disclosed herein are compositions for inhibiting expression of an HBV gene in a cell, the composition comprising two HBV RNAi agents, wherein a first HBV RNAi agent comprises an antisense strand that comprises the nucleobase sequence differing by 0, 1, 2 or 3 nucleobases from the sequence (5'→3') AGAAAAUUGAGAGAAGUCCAC (SEQ ID NO: 171), and a sense strand that comprises the nucleobase sequence differing by 0, 1, 2 or 3 nucleobases from the sequence (5'→3') GUGGACUUCUCUCAAUUUUCU (SEQ ID NO: 302); and wherein a second HBV RNAi agent comprises an antisense strand that comprises the nucleobase sequence differing by 0, 1, 2 or 3 nucleobases from the sequence (5'→3') UACCAAUUUAUGCCUACAGCC (SEQ ID NO: 162), and a sense strand that comprises the nucleobase sequence differing by 0, 1, 2 or 3 nucleobases from the sequence (5'→3') GUGGUGGACUUCUCUCAAUAUU (SEQ ID NO: 307).

In some embodiments, disclosed herein are compositions for inhibiting expression of an HBV gene in a cell, the composition comprising two HBV RNAi agents, wherein a first HBV RNAi agent comprises an antisense strand that consists of the nucleobase sequence (5'→3')

AGAAAAUUGAGAGAAGUCCAC (SEQ ID NO: 171), and a sense strand that consists of the nucleobase sequence (5'→3') GUGGACUUCUCUCAAUUUUCU (SEQ ID NO: 302); and wherein a second HBV RNAi agent comprises an antisense strand that consists of the nucleobase sequence (5'→3') UACCAAUUUAUGCCUACAGCC (SEQ ID NO: 162), and a sense strand that consists of the nucleobase sequence (5'→3') GUGGUGGACUUCUCUCAAUAUU (SEQ ID NO: 307).

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'→3') UAUUGAGAGAAGUCCAC-CACUU (SEQ ID NO: 175), and a sense strand that comprises the nucleobase sequence differing by 0, 1, 2 or 3 nucleobases from the sequence (5'→3') GUGGUGGACUU-CUCUCAAUAUU (SEQ ID NO: 307); and wherein the second HBV RNAi agent comprises an antisense strand that comprises the nucleobase sequence differing by 0, 1, 2 or 3 nucleobases from the sequence (5'→3') UAC-CAAUUUAUGCCUACAGUU (SEQ ID NO: 154), and a sense strand that comprises the nucleobase sequence differing by 0, 1, 2 or 3 nucleobases from the sequence (5'→3') CUGUAGGCAUAAAUUGGUA (SEQ ID NO: 292).

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'→3') AGAAAAUUGAGAGAAGU-CCAC (SEQ ID NO: 171), and a sense strand that comprises the nucleobase sequence differing by 0, 1, 2 or 3 nucleobases from the sequence (5'→3') GUGGACUUCUCU-CAAUUUUCU (SEQ ID NO: 302); and wherein the second HBV RNAi agent comprises an antisense strand that comprises the nucleobase sequence differing by 0, 1, 2 or 3 nucleobases from the sequence (5'→3') UAC-CAAUUUAUGCCUACAGCG (SEQ ID NO: 188), and a sense strand that comprises the nucleobase sequence differing by 0, 1, 2 or 3 nucleobases from the sequence (5'→3') CGCUGUAGGCAUAAAUUGGUA (SEQ ID NO: 328).

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'9-3') AGAAAAUUGAGAGAAGU-CCAC (SEQ ID NO: 171), and a sense strand that comprises the nucleobase sequence differing by 0, 1, 2 or 3 nucleobases from the sequence (5'9-3') GUGGACUUCUCU-CAAUUUUCU (SEQ ID NO: 302); and wherein the second HBV RNAi agent comprises an antisense strand that comprises the nucleobase sequence differing by 0, 1, 2 or 3 nucleobases from the sequence (5'→3') UAC-CAAUUUAUGCCUACAGCC (SEQ ID NO: 162), and a sense strand that comprises the nucleobase sequence differing by 0, 1, 2 or 3 nucleobases from the sequence (5'→3') GGCUGUAGGCAUAAAUUGGUA (SEQ ID NO: 294).

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'→3') AGAAAAUUGAGAGAAGU-CCAC (SEQ ID NO: 171), and a sense strand that comprises the nucleobase sequence differing by 0, 1, 2 or 3 nucleobases from the sequence (5'→3') GUGGACUUCUCU-CAAUUUUCU (SEQ ID NO: 302); and wherein the second HBV RNAi agent comprises an antisense strand that comprises the nucleobase sequence differing by 0, 1, 2 or 3 nucleobases from the sequence (5'→3') UAC-CAAUUUAUGCCUACAGCC (SEQ ID NO: 162), and a sense strand that comprises the nucleobase sequence differing by 0, 1, 2 or 3 nucleobases from the sequence (5'→3') GUGGUGGACUUCUCUCAAUAUU (SEQ ID NO: 307).

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'→3') UAUUGAGAGAAGUCCAC-CACUU (SEQ ID NO: 175), and a sense strand that comprises the nucleobase sequence differing by 0, 1, 2 or 3 nucleobases from the sequence (5'→3') GUGGUGGACUU-CUCUCAAUAUU (SEQ ID NO: 307); and wherein the second HBV RNAi agent comprises an antisense strand that comprises the nucleobase sequence differing by 0, 1, 2 or 3 nucleobases from the sequence (5'→3') UAC-CAAUUUAUGCCUACAGUU (SEQ ID NO: 154), and a sense strand that comprises the nucleobase sequence differing by 0, 1, 2 or 3 nucleobases from the sequence (5'→3') CUGUAGGCAUAAAUUGGUA (SEQ ID NO: 292), and wherein the sense strand of the first HBV RNAi agent and the second HBV RNAi agent are conjugated to a targeting ligand comprising N-acetyl-galactosamine.

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'→3') AGAAAAUUGAGAGAAGU-CCAC (SEQ ID NO: 171), and a sense strand that comprises the nucleobase sequence differing by 0, 1, 2 or 3 nucleobases from the sequence (5'→3') GUGGACUUCUCU-CAAUUUUCU (SEQ ID NO: 302); and wherein the second HBV RNAi agent comprises an antisense strand that comprises the nucleobase sequence differing by 0, 1, 2 or 3 nucleobases from the sequence (5'→3') UAC- CAAUUUAUGCCUACAGCG (SEQ ID NO: 188), and a sense strand that comprises the nucleobase sequence differing by 0, 1, 2 or 3 nucleobases from the sequence (5'→3') CGCUGUAGGCAUAAAUUGGUA (SEQ ID NO: 328), and wherein the sense strand of the first HBV RNAi agent and the second HBV RNAi agent are conjugated to a targeting ligand comprising N-acetyl-galactosamine.

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'→3') AGAAAAUUGAGAGAAGU-CCAC (SEQ ID NO: 171), and a sense strand that comprises the nucleobase sequence differing by 0, 1, 2 or 3 nucleobases from the sequence (5'→3') GUGGACUUCUCU-CAAUUUUCU (SEQ ID NO: 302); and wherein the second HBV RNAi agent comprises an antisense strand that comprises the nucleobase sequence differing by 0, 1, 2 or 3 nucleobases from the sequence (5'→3') UAC-CAAUUUAUGCCUACAGCC (SEQ ID NO: 162), and a sense strand that comprises the nucleobase sequence differing by 0, 1, 2 or 3 nucleobases from the sequence (5'→3') GGCUGUAGGCAUAAAUUGGUA (SEQ ID NO: 294), and wherein the sense strand of the first HBV RNAi agent and the second HBV RNAi agent are conjugated to a targeting ligand comprising N-acetyl-galactosamine.

In some embodiments, disclosed herein are compositions for inhibiting expression of an HBV gene in a cell, the composition comprising two HBV RNAi agents, wherein all or substantially all of the nucleotides in the sense strand are modified and/or all or substantially all of the nucleotides in the antisense strand in the first and/or second HBV RNAi agent are modified nucleotides, and wherein the first HBV RNAi agent comprises an antisense strand that comprises the nucleobase sequence differing by 0, 1, 2 or 3 nucleobases from the sequence (5'→3') AGAAAAUUGAGAGAAGU-CCAC (SEQ ID NO: 171), and a sense strand that comprises the nucleobase sequence differing by 0, 1, 2 or 3 nucleobases from the sequence (5'→3') GUGGACUUCUCU-CAAUUUUCU (SEQ ID NO: 302); and wherein the second HBV RNAi agent comprises an antisense strand that comprises the nucleobase sequence differing by 0, 1, 2 or 3 nucleobases from the sequence (5'→3') UAC-CAAUUUAUGCCUACAGCC (SEQ ID NO: 162), and a sense strand that comprises the nucleobase sequence differing by 0, 1, 2 or 3 nucleobases from the sequence (5'→3') GUGGUGGACUUCUCUCAAUAUU (SEQ ID NO: 307), and wherein the sense strand of the first HBV RNAi agent and the second HBV RNAi agent are conjugated to a targeting ligand comprising N-acetyl-galactosamine.

In some embodiments, disclosed herein are methods of treatment of an HBV infection or prevention of disease or symptoms caused by an HBV infection comprising administering to a subject in need thereof an effective amount of AD04872 and an effective amount of AD05070. In some embodiments, the ratio of AD04872 to AD05070 administered to a subject in need thereof is about 2:1. In some embodiments, the ratio of AD04872 to AD05070 administered to a subject in need thereof is about 3:1. In some embodiments, the ratio of AD04872 to AD05070 administered to a subject in need thereof is about 1:1. In some embodiments, the ratio of AD04872 to AD05070 administered to a subject in need thereof is about 4:1. In some embodiments, the ratio of AD04872 to AD05070 administered to a subject in need thereof is about 5:1. In some embodiments, the ratio of AD04872 to AD05070 administered to a subject in need thereof is about 1:2.

In some embodiments, about 1 mg/kg (mpk) of AD04872 and about 1 mg/kg of AD05070 are administered to a subject in need thereof. In some embodiments, about 1.5 mg/kg of AD04872 and about 1.5 mg/kg of AD05070 are administered to a subject in need thereof. In some embodiments, about 2.0 mg/kg of AD04872 and about 1.0 mg/kg of AD05070 are administered to a subject in need thereof. In some embodiments, about 3.0 mg/kg of AD04872 and about 1.0 mg/kg of AD05070 are administered to a subject in need thereof. In some embodiments, about 3.2 mg/kg of AD04872 and about 0.8 mg/kg of AD05070 are administered to a subject in need thereof. In some embodiments, about 2.7 mg/kg of AD04872 and about 1.3 mg/kg of AD05070 are administered to a subject in need thereof. In some embodiments, about 4.0 mg/kg of AD04872 and about 1.0 mg/kg of AD05070 are administered to a subject in need thereof. In some embodiments, about 3.3 mg/kg of AD04872 and about 1.7 mg/kg of AD05070 are administered to a subject in need thereof. In some embodiments, between about 0.05 and about 5 mg/kg of AD04872 and between about 0.05 and about 5 mg/kg of AD05070 are administered to a subject in need thereof. In some embodiments, about AD04872 and about AD05070 are administered separately (e.g., in separate injections). In some embodiments, the respective dose of AD04872 and the respective dose of AD05070 are administered together (e.g., in the same injection). In some embodiments, the respective dose of AD04872 and the respective dose of AD05070 are prepared in a single pharmaceutical composition.

In some embodiments, disclosed herein are methods of treatment of an HBV infection or prevention of diseases or symptoms caused by an HBV infection comprising administering to a subject in need thereof an effective amount of AD04872 and an effective amount of AD04776. In some embodiments, the ratio of AD04872 to AD04776 administered to a subject in need thereof is about 2:1. In some embodiments, the ratio of AD04872 to AD04776 administered to a subject in need thereof is about 3:1. In some embodiments, the ratio of AD04872 to AD04776 administered to a subject in need thereof is about 4:1. In some embodiments, the ratio of AD04872 to AD04776 administered to a subject in need thereof is about 1:1. In some embodiments, the ratio of AD04872 to AD04776 administered to a subject in need thereof is 5:1. In some embodiments, the ratio of AD04872 to AD04776 administered to a subject in need thereof is 1:2.

In some embodiments, about 1 mg/kg (mpk) of AD04872 and about 1 mg/kg of AD04776 are administered to a subject in need thereof. In some embodiments, about 1.5 mg/kg of AD04872 and about 1.5 mg/kg of AD04776 are administered to a subject in need thereof. In some embodiments, about 2.0 mg/kg of AD04872 and about 1.0 mg/kg of AD04776 are administered to a subject in need thereof. In some embodiments, about 3.0 mg/kg of AD04872 and about 1.0 mg/kg of AD04776 are administered to a subject in need thereof. In some embodiments, about 3.2 mg/kg of AD04872 and about 0.8 mg/kg of AD04776 are administered to a subject in need thereof. In some embodiments, about 2.7 mg/kg of AD04872 and about 1.3 mg/kg of AD04776 are administered to a subject in need thereof. In some embodiments, about 4.0 mg/kg of AD04872 and about 1.0 mg/kg of AD04776 are administered to a subject in need thereof. In some embodiments, about 3.3 mg/kg of AD04872 and about 1.7 mg/kg of AD04776 are administered to a subject in need thereof. In some embodiments, between about 0.05 and about 5 mg/kg of AD04872 and between about 0.05 and about 5 mg/kg of AD04776 are administered to a subject in need thereof. In some embodiments, the respective doses of AD04872 and AD04776 are administered separately (e.g., in separate injections). In some embodiments, the respective doses of AD04872 and AD04776 are administered together (e.g., in the same injection). In some embodiments, the respective doses of AD04872 and AD04776 are prepared in a single pharmaceutical composition.

In some embodiments, disclosed herein are methods of treatment of an HBV infection or prevention of disease or symptoms caused by an HBV infection comprising administering to a subject in need thereof an effective amount of AD04872 and an effective amount of AD04982.

In some embodiments, the ratio of AD04872 to AD04982 administered to a subject in need thereof is about 2:1. In some embodiments, the ratio of AD04872 to AD04982 administered to a subject in need thereof is about 3:1. In some embodiments, the ratio of AD04872 to AD04982 administered to a subject in need thereof is about 4:1. In some embodiments, the ratio of AD04872 to AD04982 administered to a subject in need thereof is about 1:1. In some embodiments, the ratio of AD04872 to AD04982 administered to a subject in need thereof is about 5:1. In some embodiments, the ratio of AD04872 to AD04982 administered to a subject in need thereof is 1:2.

In some embodiments, about 1 mg/kg (mpk) of AD04872 and about 1 mg/kg of AD04982 are administered to a subject in need thereof. In some embodiments, about 1.5 mg/kg of AD04872 and about 1.5 mg/kg of AD04982 are administered to a subject in need thereof. In some embodiments, about 2.0 mg/kg of AD04872 and about 1.0 mg/kg of AD04982 are administered to a subject in need thereof. In some embodiments, about 3.0 mg/kg of AD04872 and about 1.0 mg/kg of AD04982 are administered to a subject in need thereof. In some embodiments, about 3.2 mg/kg of AD04872 and about 0.8 mg/kg of AD04982 are administered to a subject in need thereof. In some embodiments, about 2.7 mg/kg of AD04872 and about 1.3 mg/kg of AD04982 are administered to a subject in need thereof. In some embodiments, about 4.0 mg/kg of AD04872 and about 1.0 mg/kg of AD04982 are administered to a subject in need thereof. In some embodiments, about 3.3 mg/kg of AD04872 and about 1.7 mg/kg of AD04982 are administered to a subject in need thereof. In some embodiments, between about 0.05 and about 5 mg/kg of AD04872 and between about 0.05 and about 5 mg/kg of AD04982 are administered to a subject in need thereof. In some embodiments, the respective doses of AD04872 and AD04982 are administered separately (e.g., in separate injections). In some embodiments, the respective doses of AD04872 and AD04982 are administered together (e.g., in the same injection). In some embodiments, the respective doses of AD04872 and AD04982 are prepared in a single pharmaceutical composition.

In some embodiments, disclosed herein are methods of treatment of an HBV infection or prevention of disease or symptoms caused by an HBV infection comprising administering to a subject in need thereof an effective amount of AD04580 and an effective amount of AD04585. In some embodiments, the ratio of AD04580 to AD04585 administered to a subject in need thereof is about 2:1. In some embodiments, the ratio of AD04580 to AD04585 administered to a subject in need thereof is about 3:1. In some embodiments, the ratio of AD04580 to AD04585 administered to a subject in need thereof is about 4:1. In some embodiments, the ratio of AD04580 to AD04585 administered to a subject in need thereof is about 5:1. In some embodiments, the ratio of AD04580 to AD04585 administered to a subject in need thereof is about 1:1. In some embodiments, the ratio of AD04580 to AD04585 administered to a subject in need thereof is about 1:2. In some embodiments, about 1 mg/kg (mpk) of AD04580 and about 1 mg/kg of AD04585 are administered to a subject in need thereof. In some embodiments, about 1.5 mg/kg of AD04580 and about 1.5 mg/kg of AD04585 are administered to a subject in need thereof. In some embodiments, between about 0.05 and about 5 mg/kg of AD04580 and between about 0.05 and about 5 mg/kg of AD04585 are administered to a subject in need thereof.

In some embodiments, an HBV RNAi agent disclosed herein consists of or comprises AD05070 linked to (NAG37)s shown as a sodium salt having the structure represented by the following:

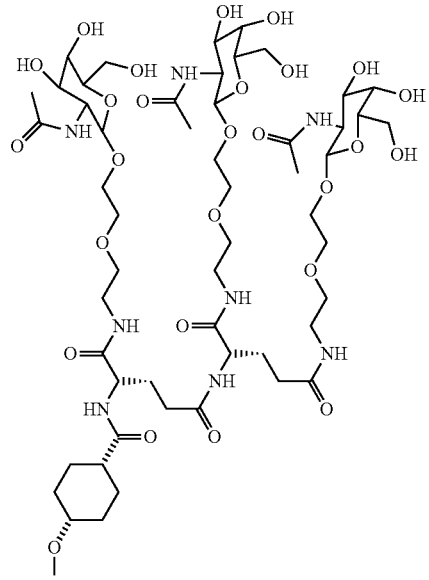

31
-continued
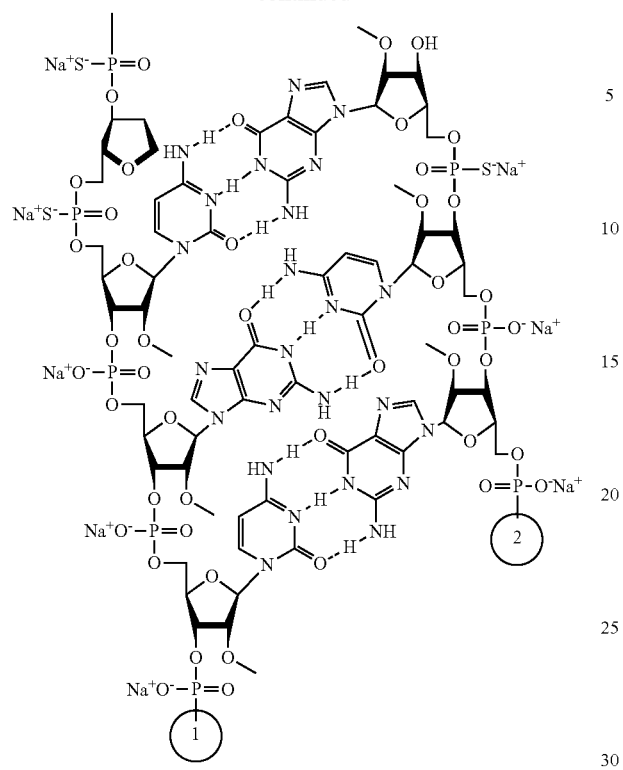
32
-continued
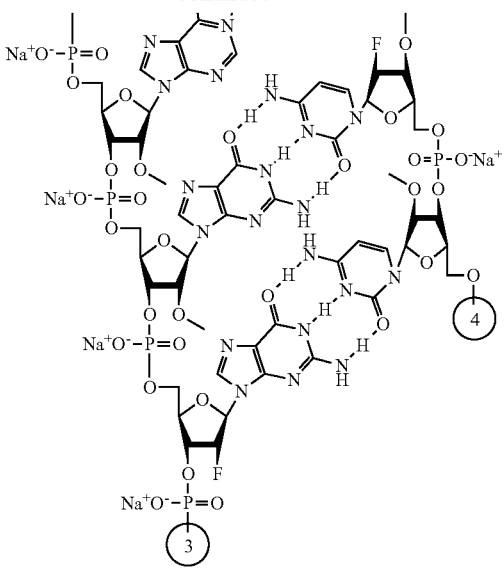
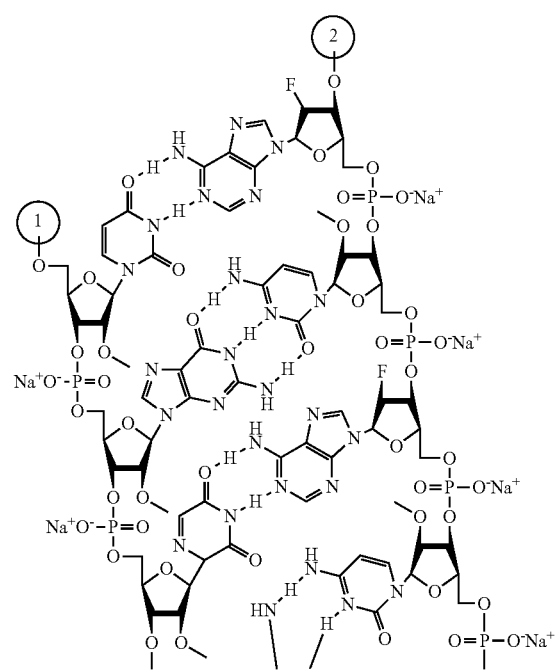
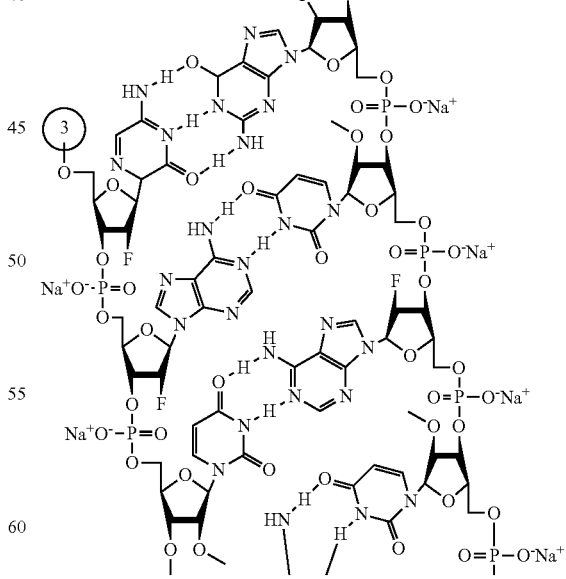

33
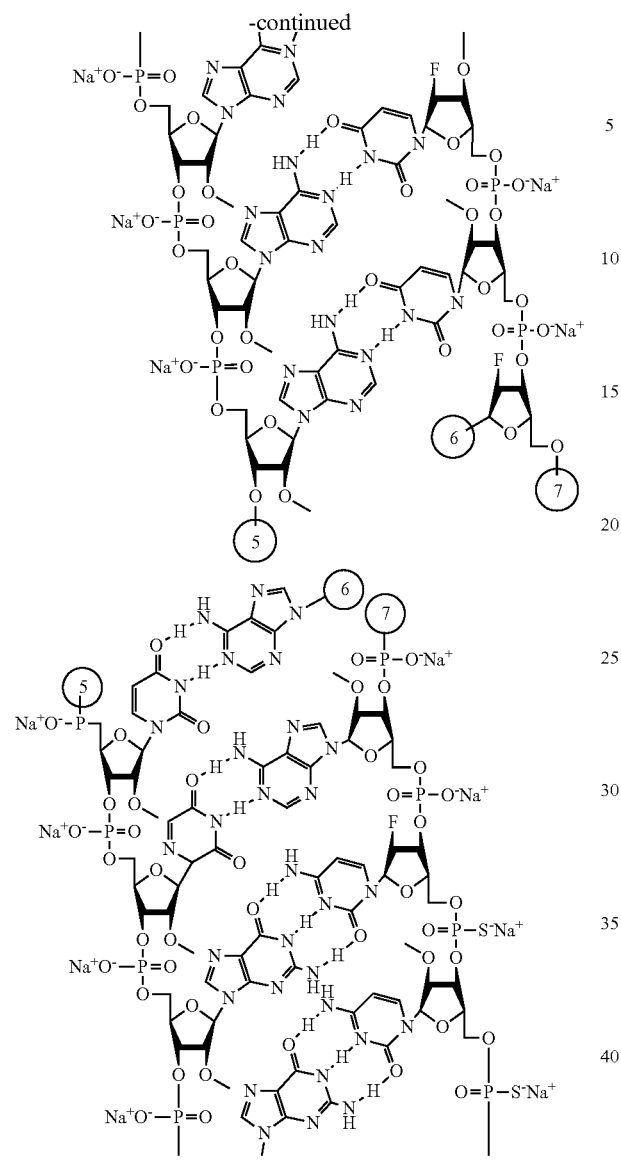
34
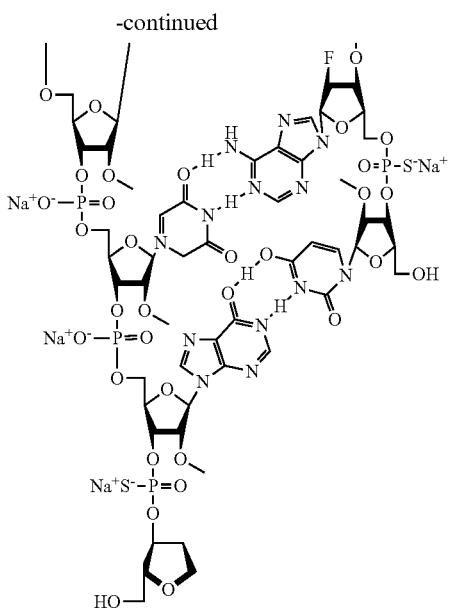
In some embodiments, an HBV RNAi agent disclosed herein consists of or comprises AD05070 linked to (NAG25)s shown as a sodium salt having the structure represented by the following:
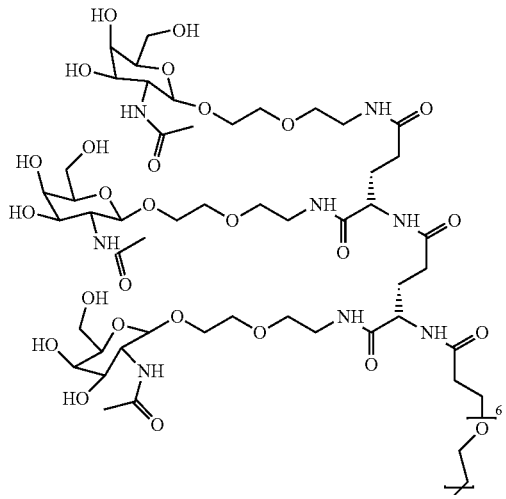

-continued
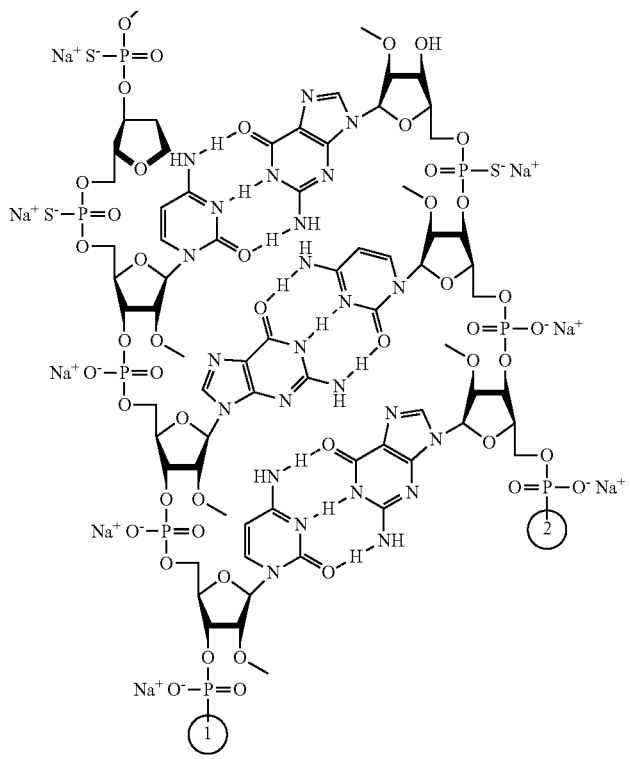
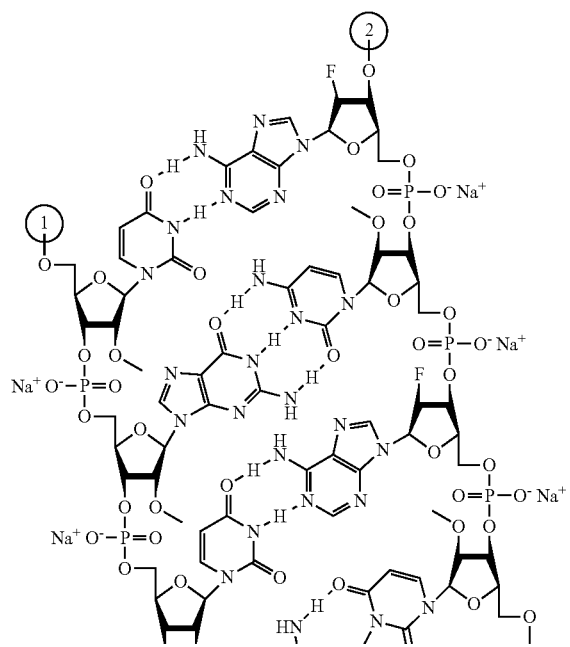

-continued
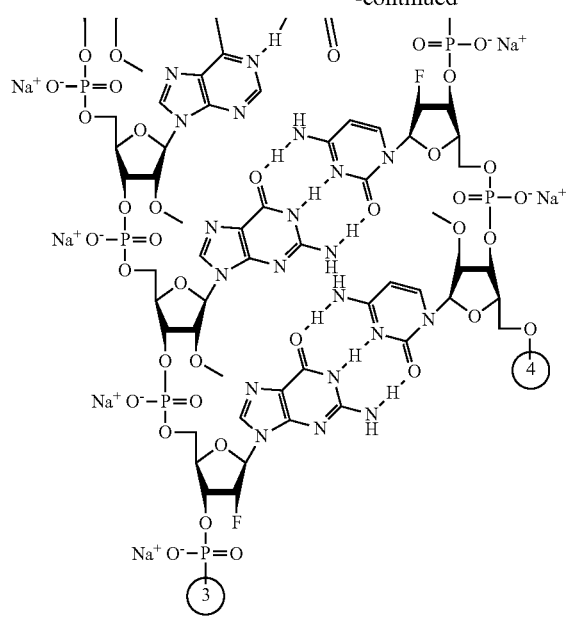
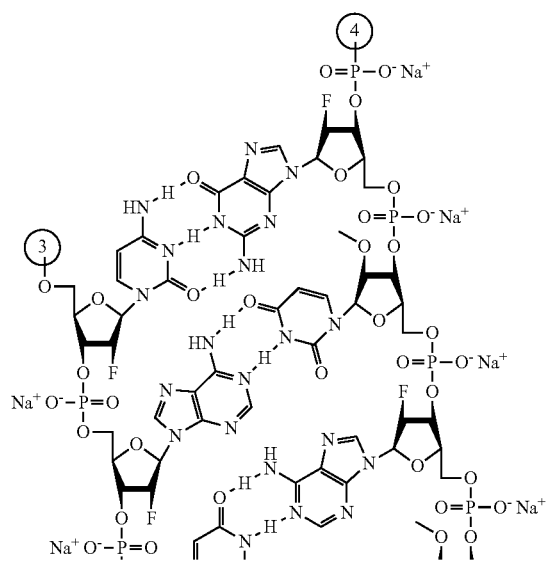

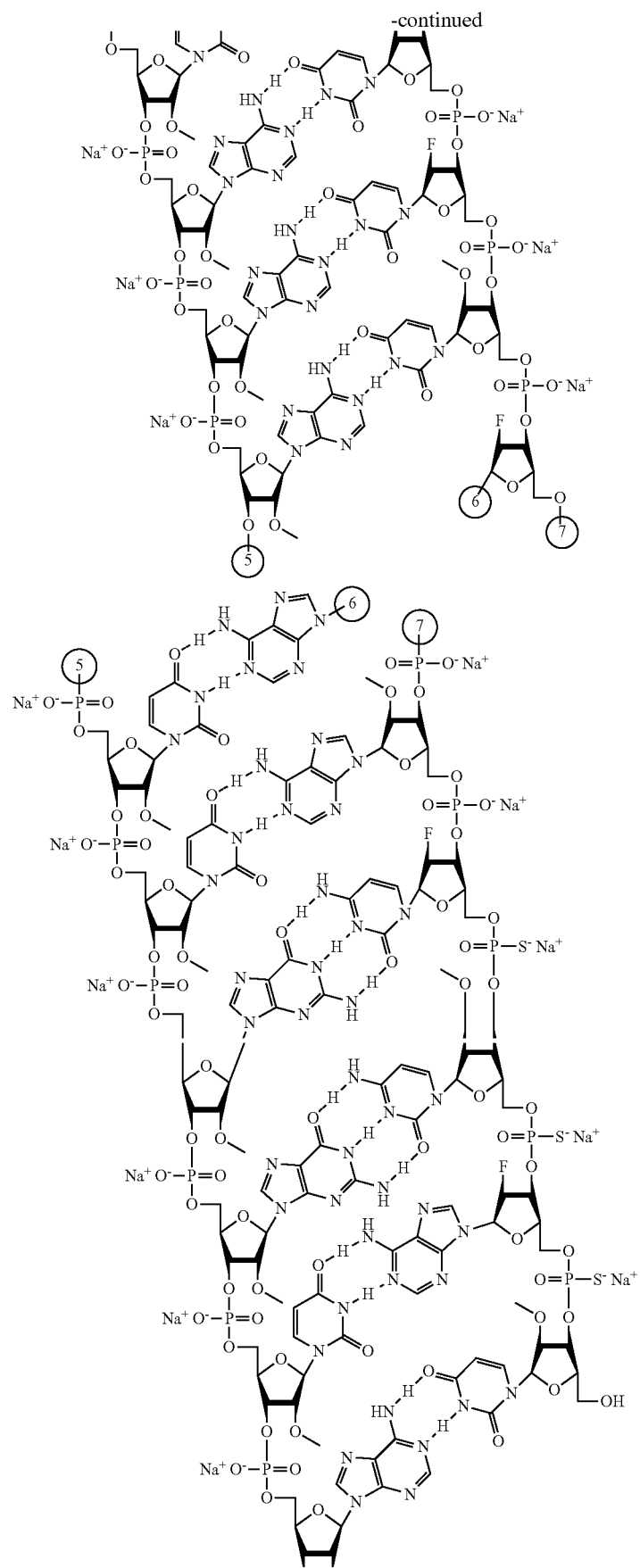

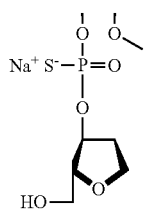
In some embodiments, an HBV RNAi agent disclosed herein consists of or comprises AD05070 linked to (NAG37)s shown as a free acid having the structure represented by the following:
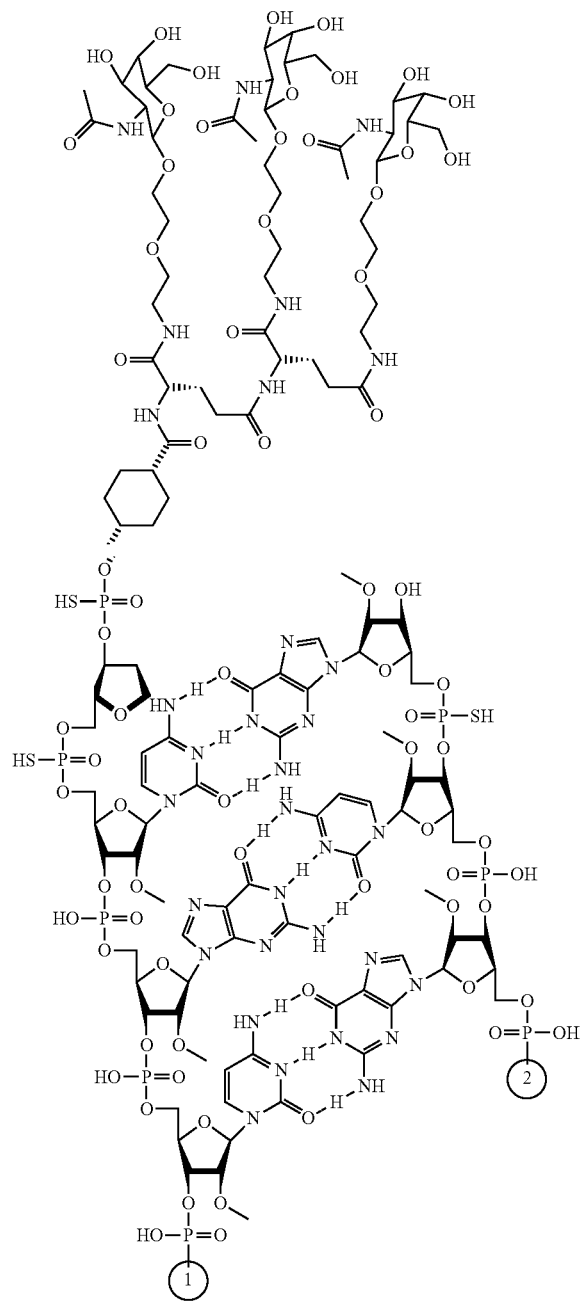

-continued
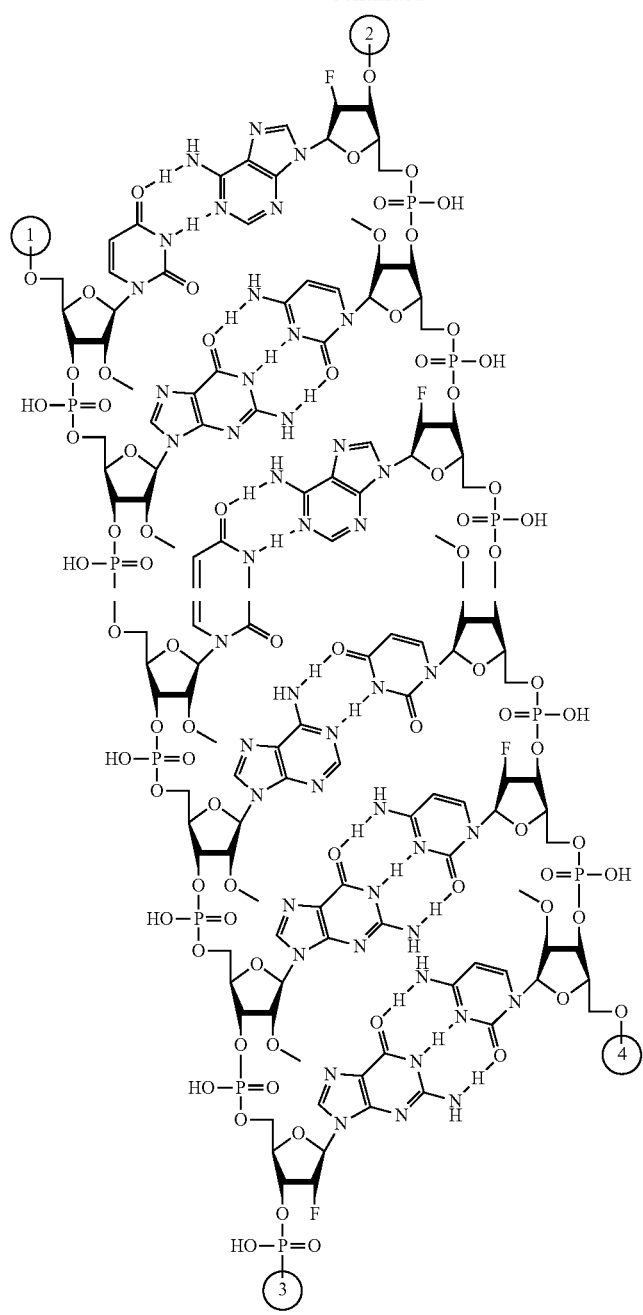

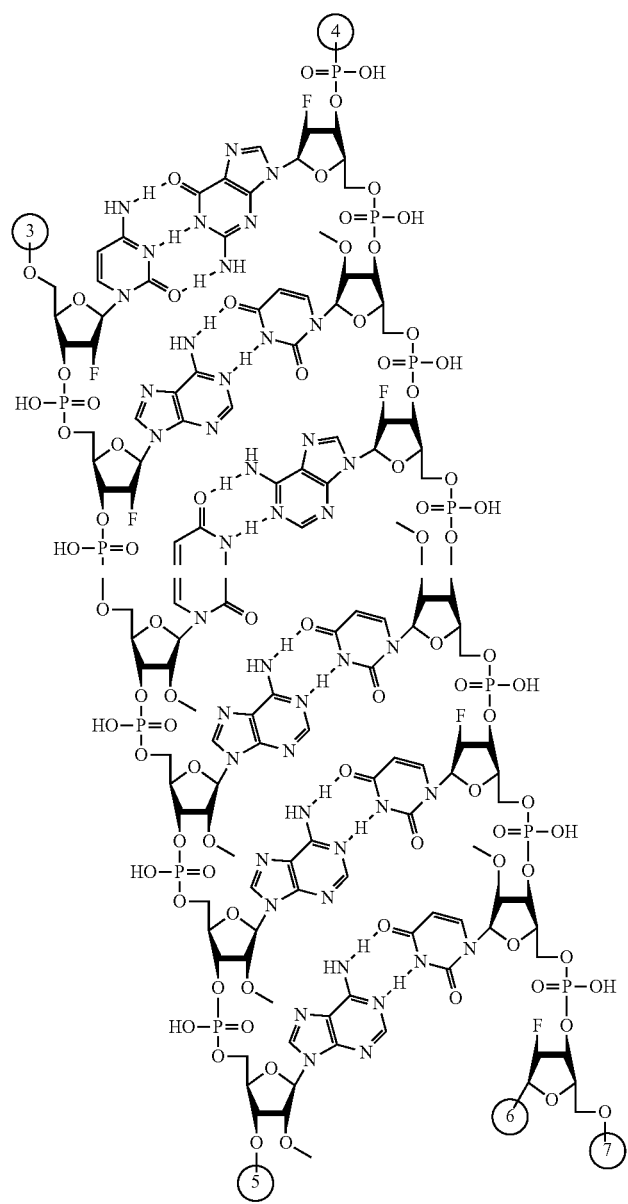

-continued
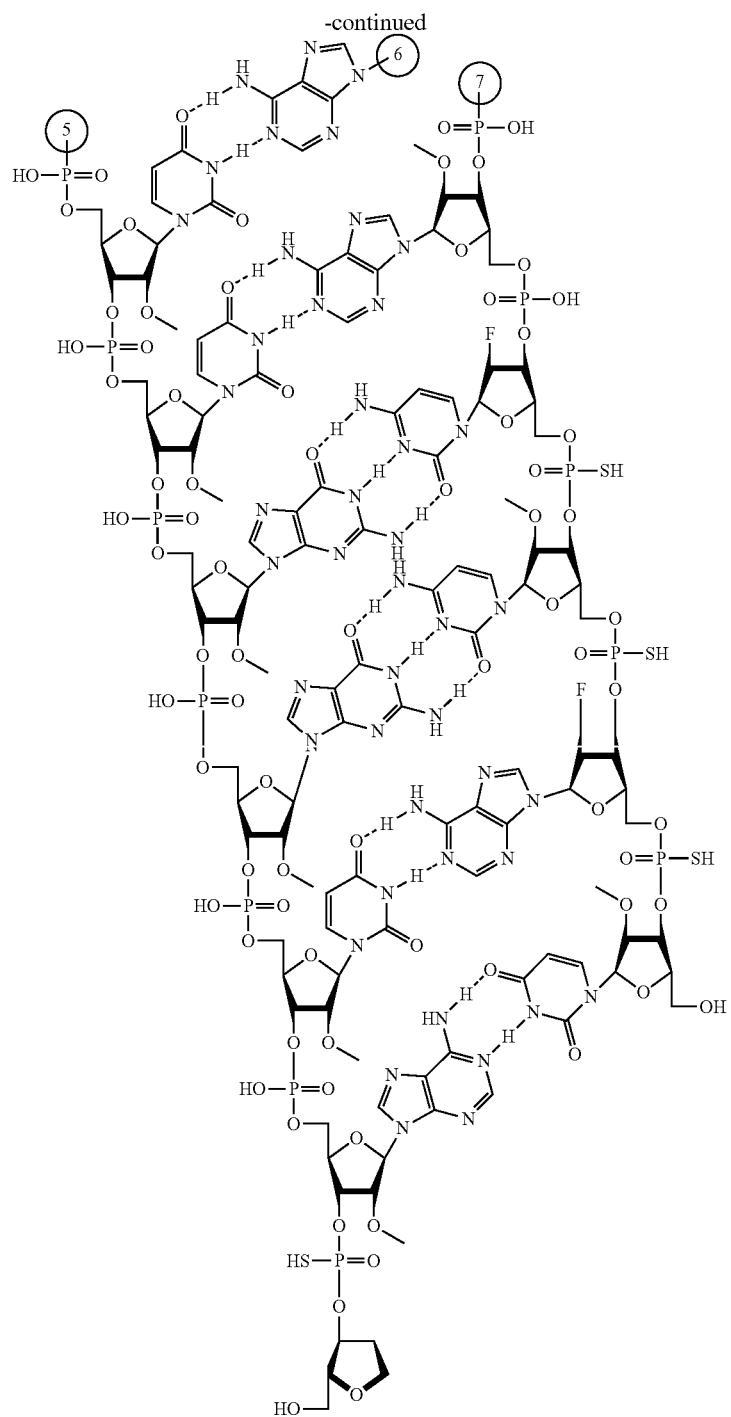
In some embodiments, an HBV RNAi agent disclosed herein consists of or comprises AD04580 linked to (NAG31)s shown as a sodium salt having the structure represented by the following:

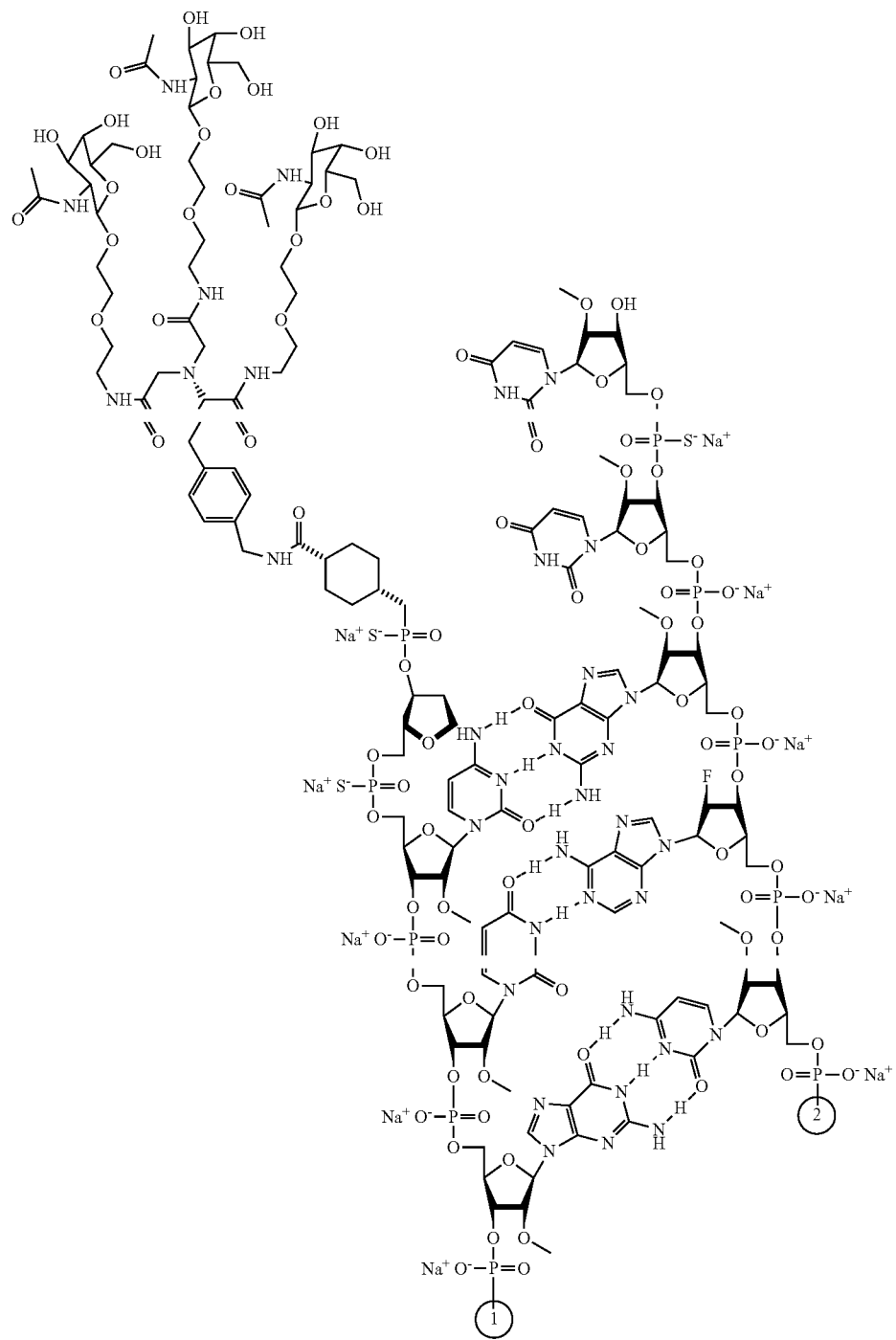

-continued
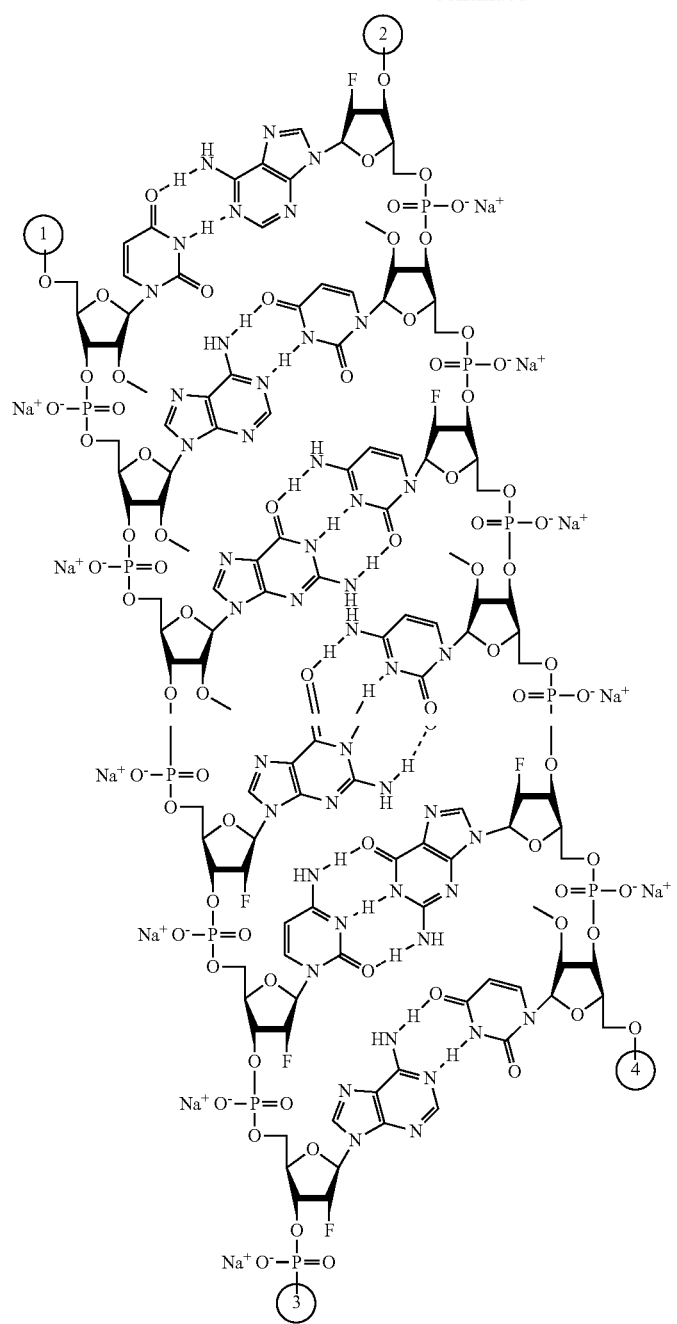

-continued
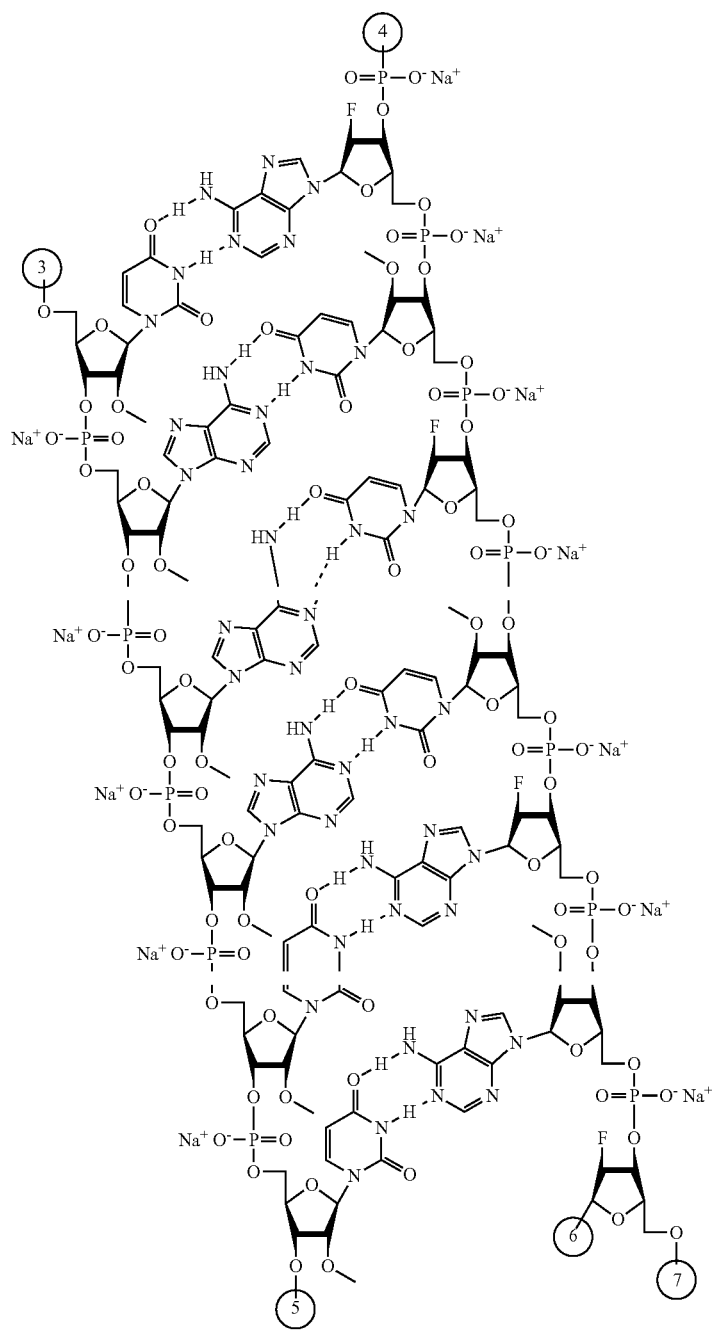

-continued
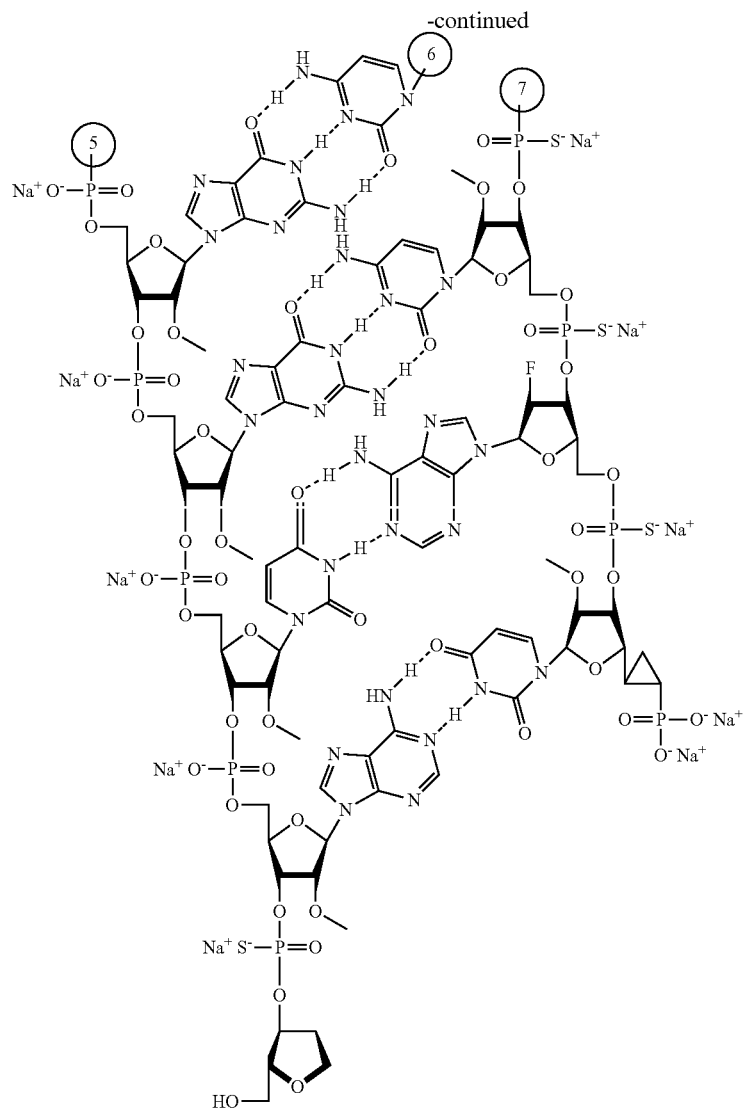
In some embodiments, an HBV RNAi agent disclosed herein consists of or comprises AD04585 linked to (NAG25)s shown as a sodium salt having the structure represented by the following:
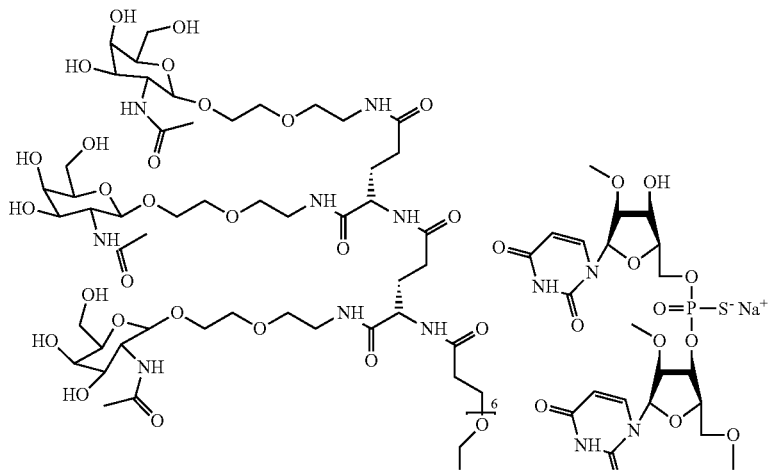

-continued
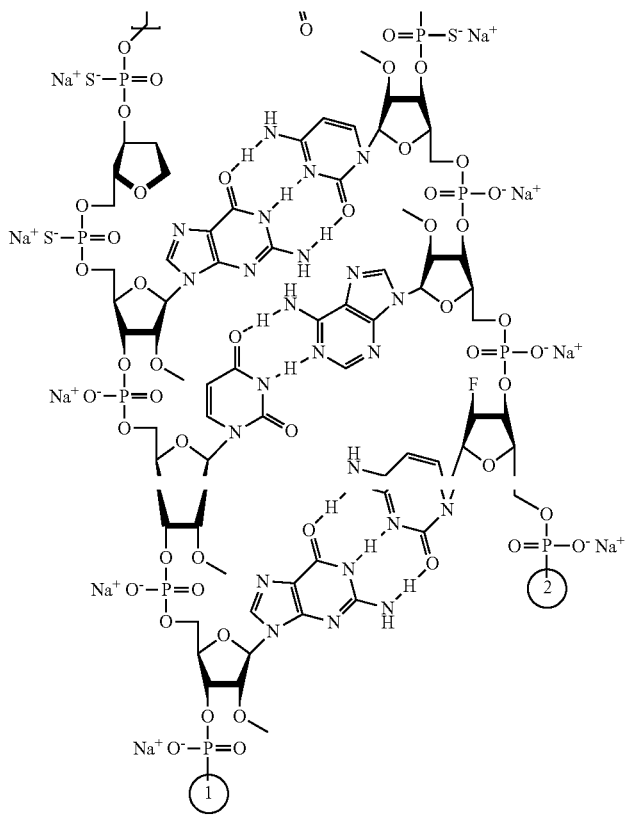
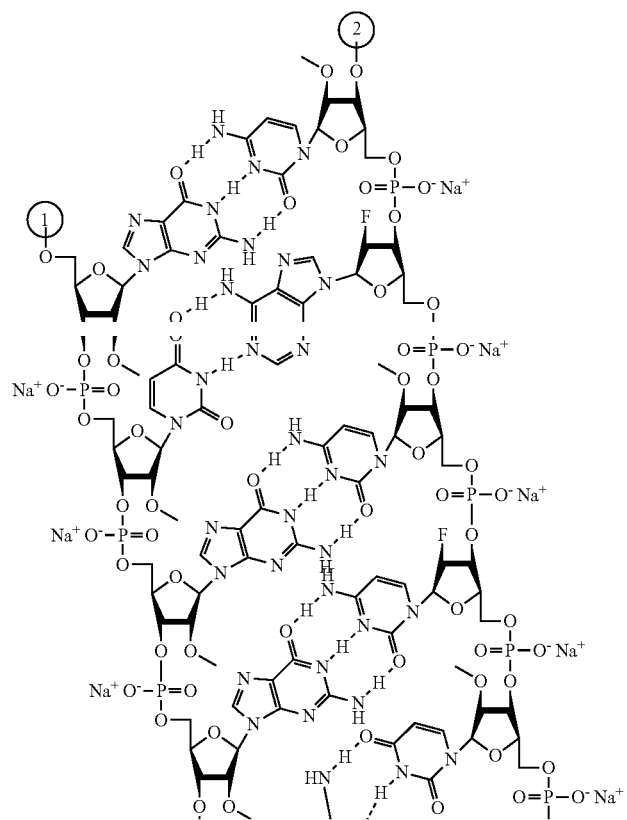

-continued
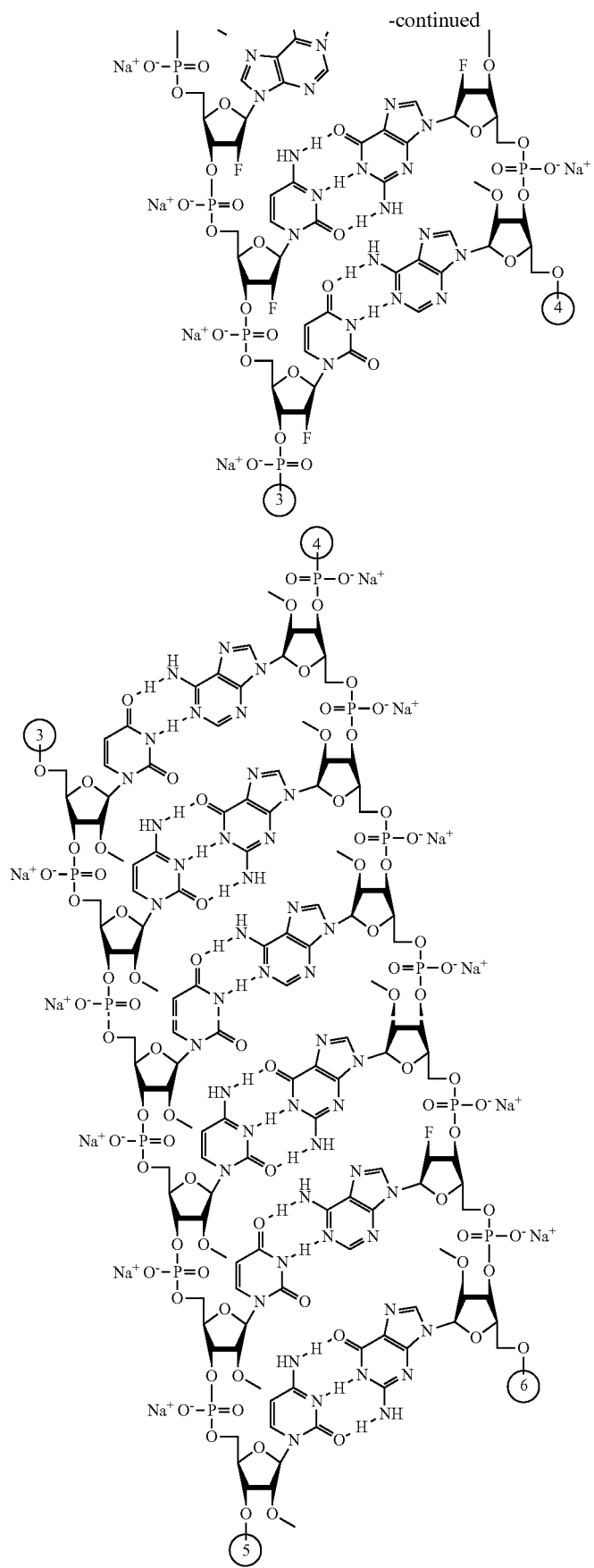

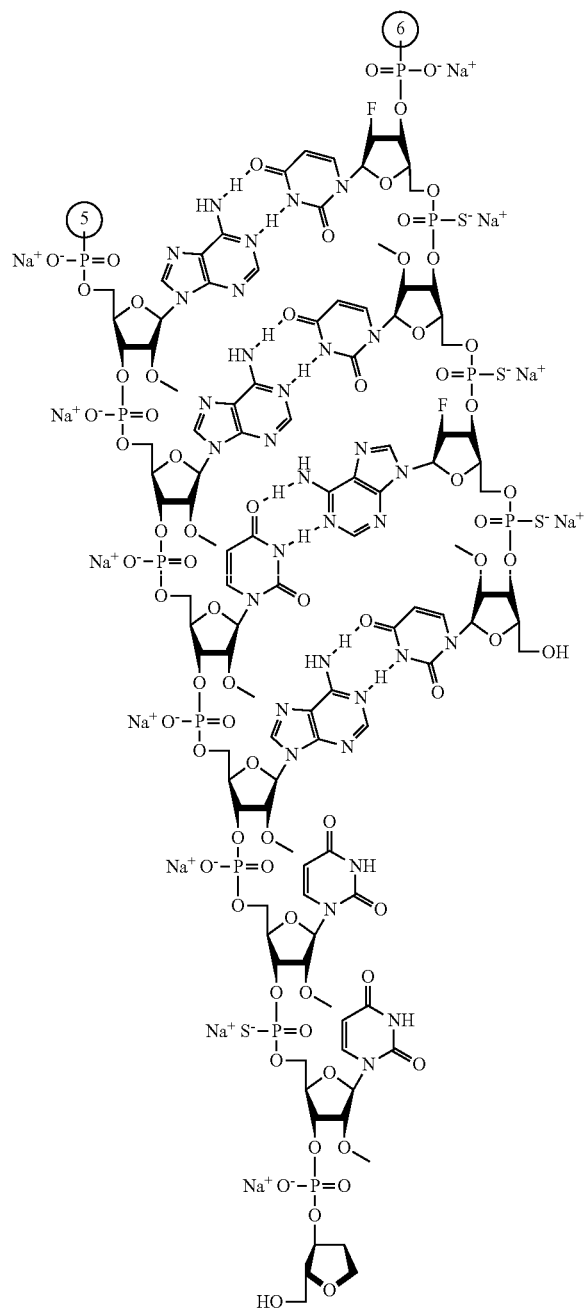
In some embodiments, an HBV RNAi agent disclosed herein consists of or comprises AD04872 linked to (NAG37)s shown as a sodium salt having the structure represented by the following:

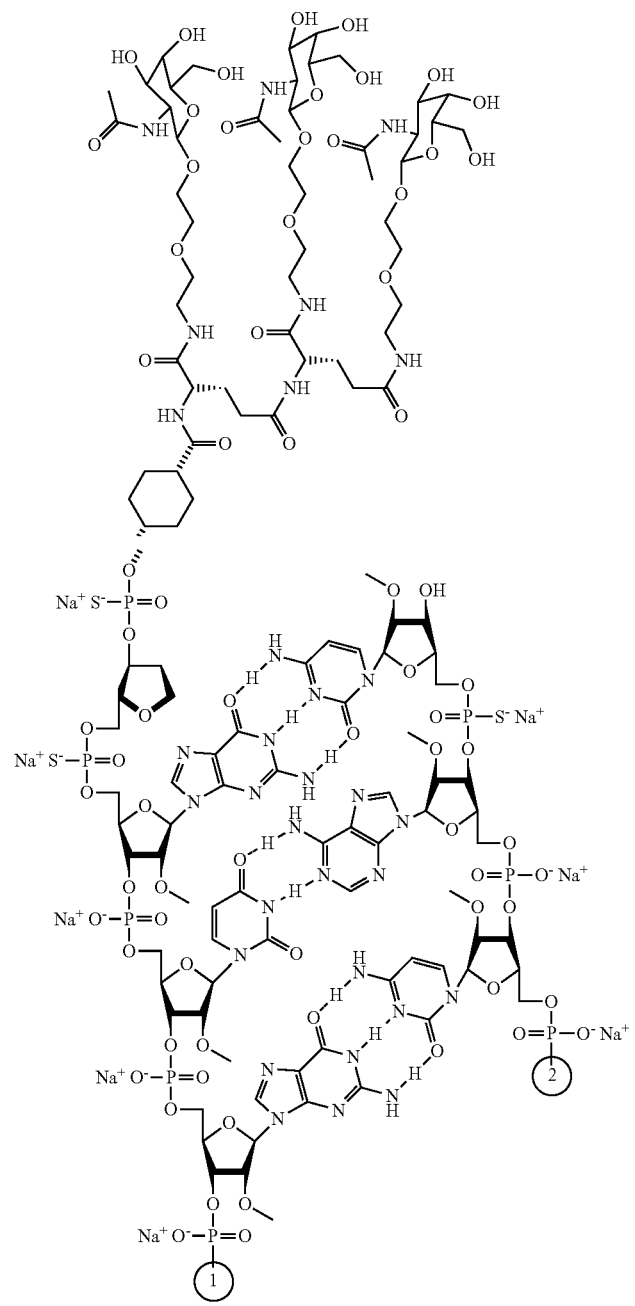

-continued
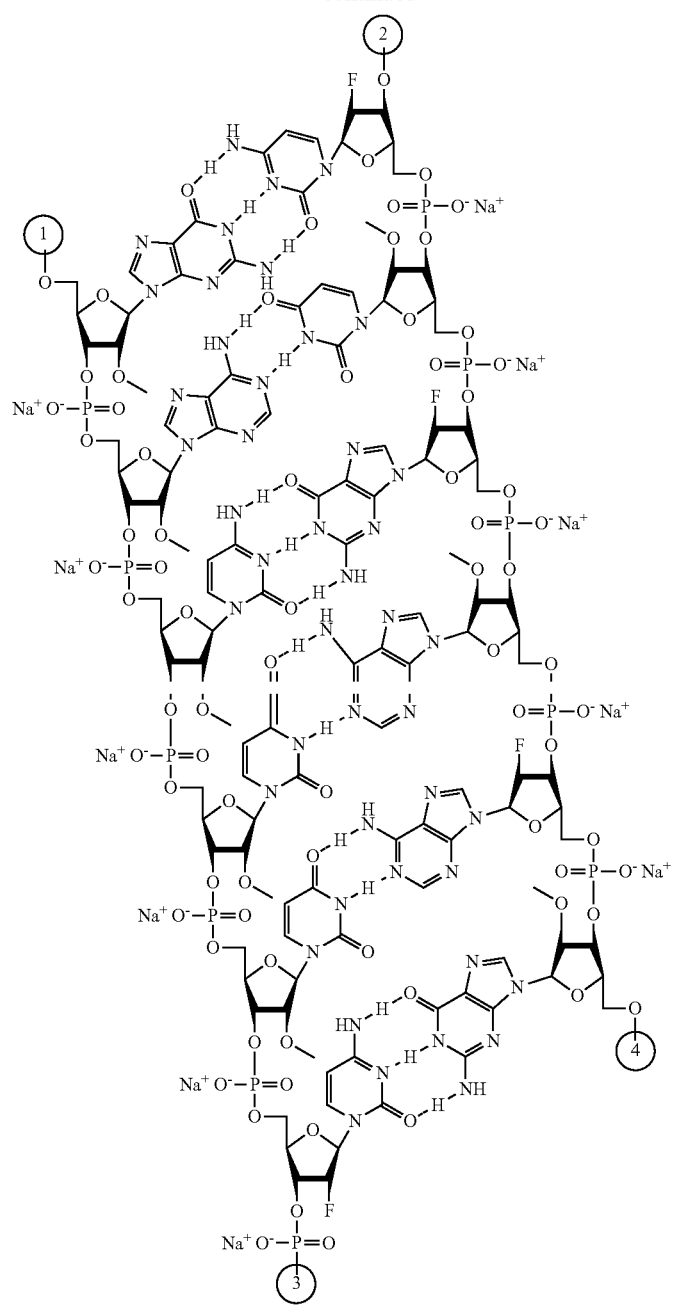

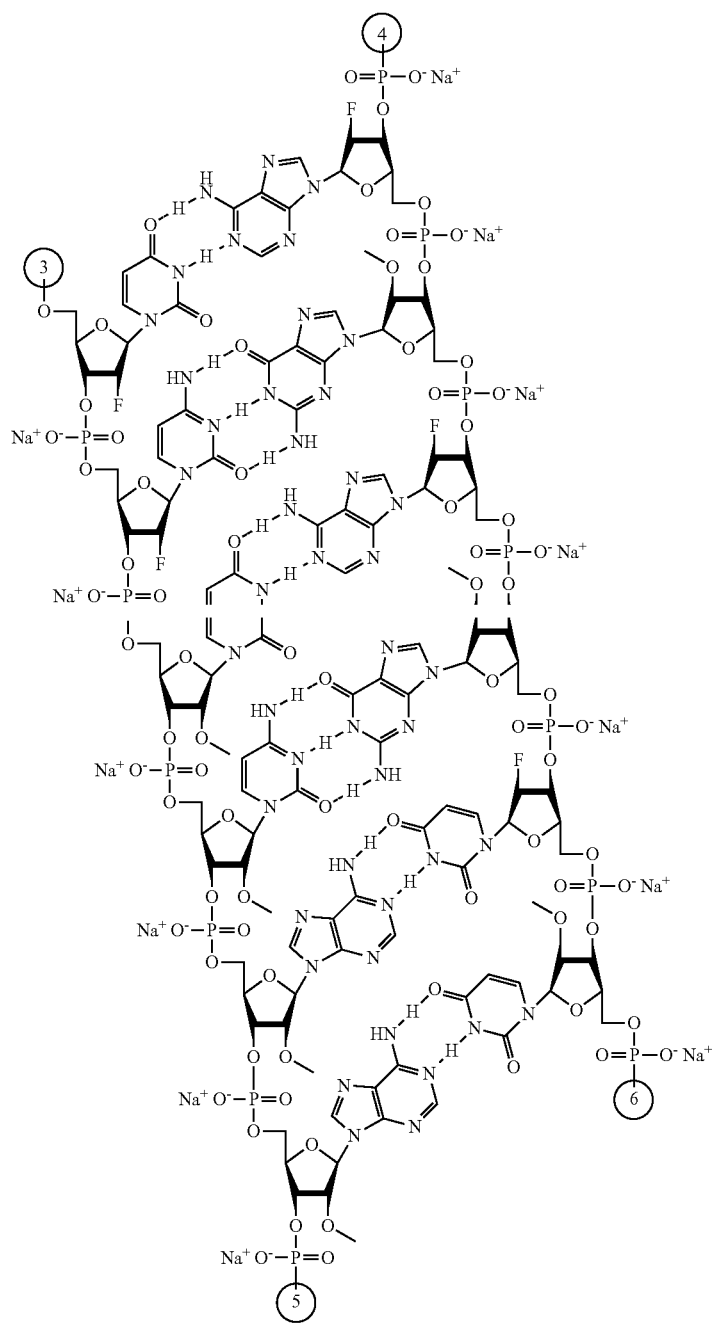

-continued
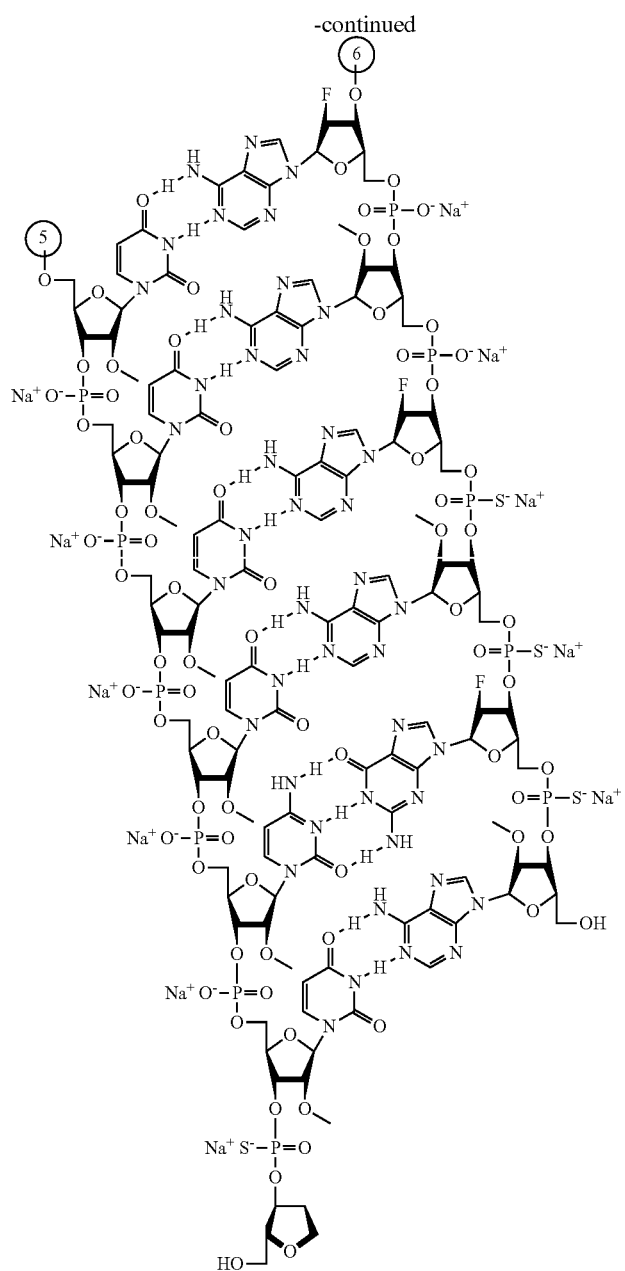
In some embodiments, an HBV RNAi agent disclosed herein consists of or comprises AD04872 linked to (NAG25)s shown as a sodium salt having the structure represented by the following:

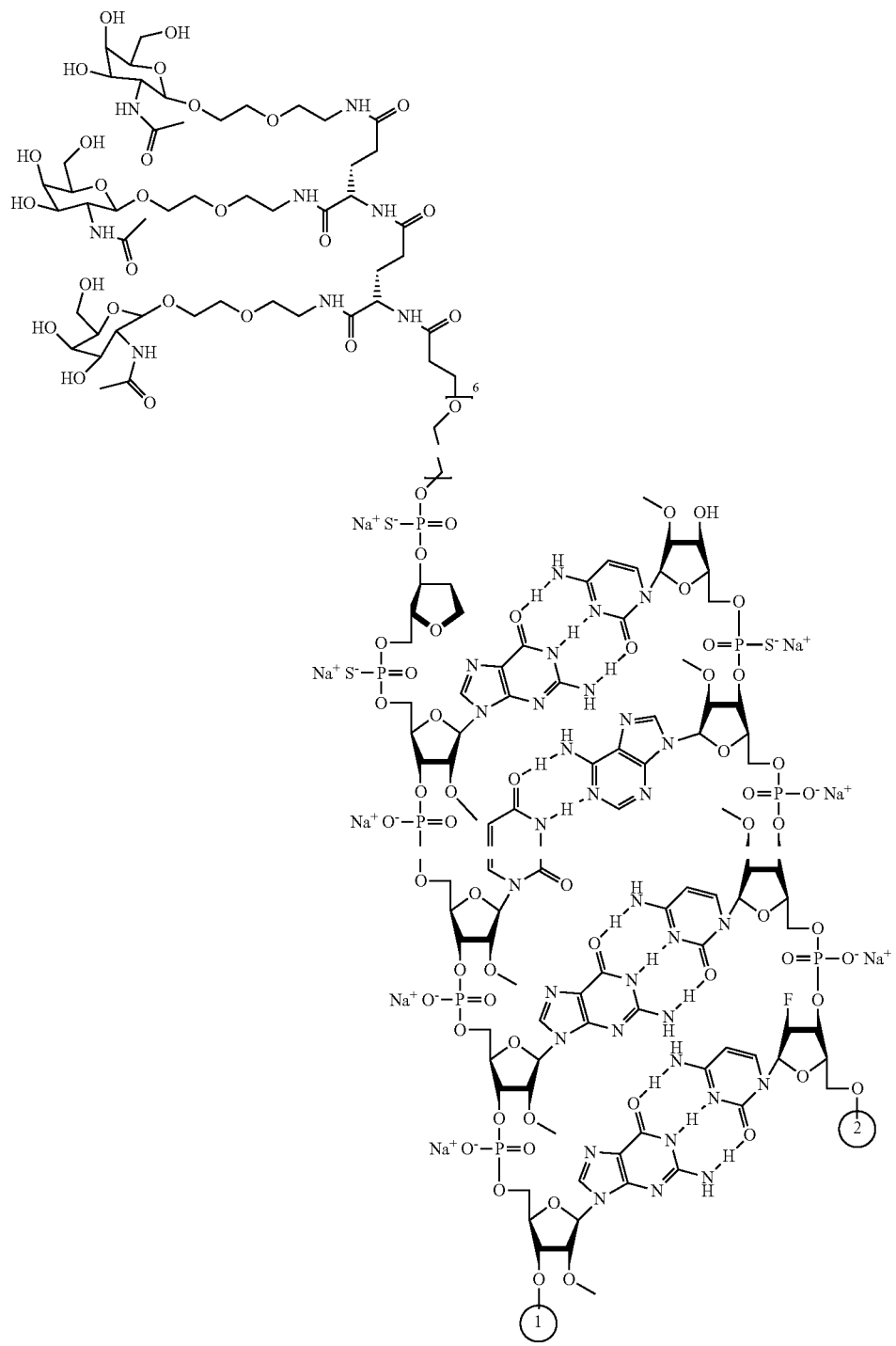

-continued
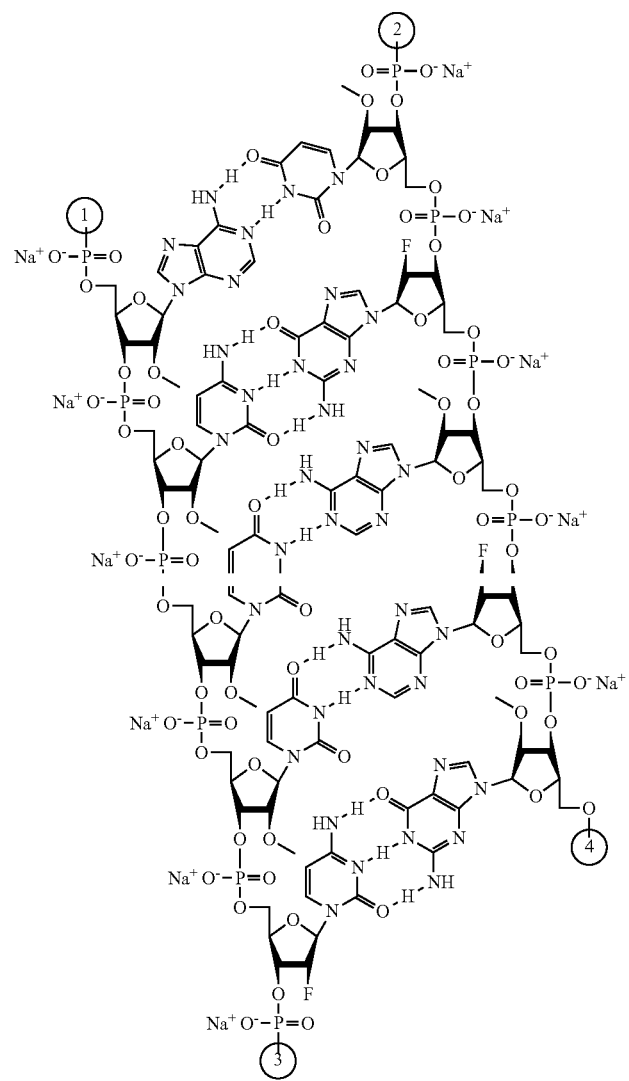
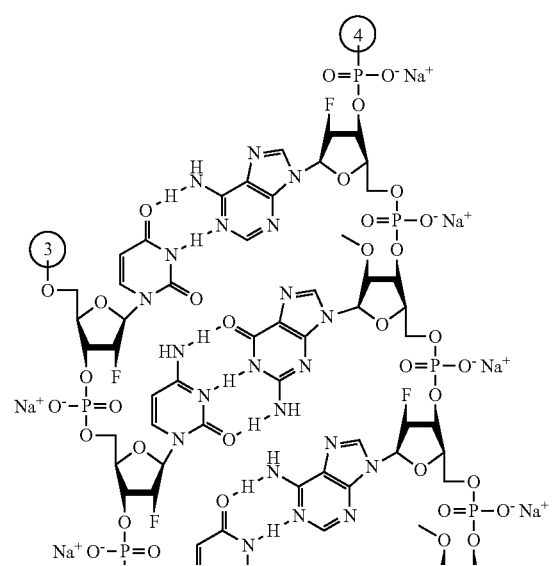

-continued
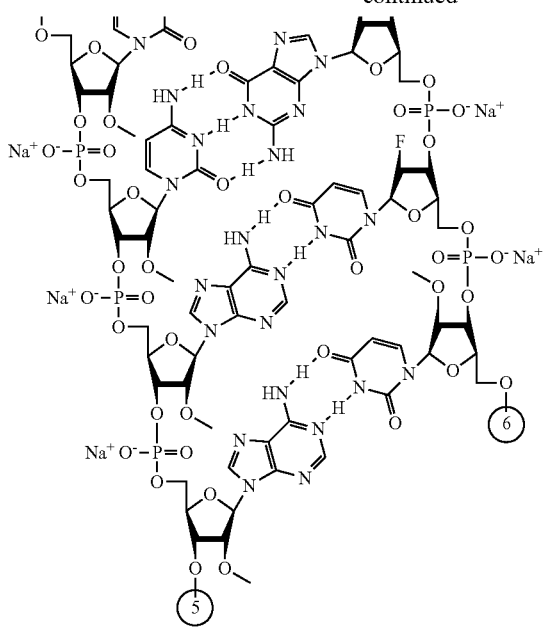
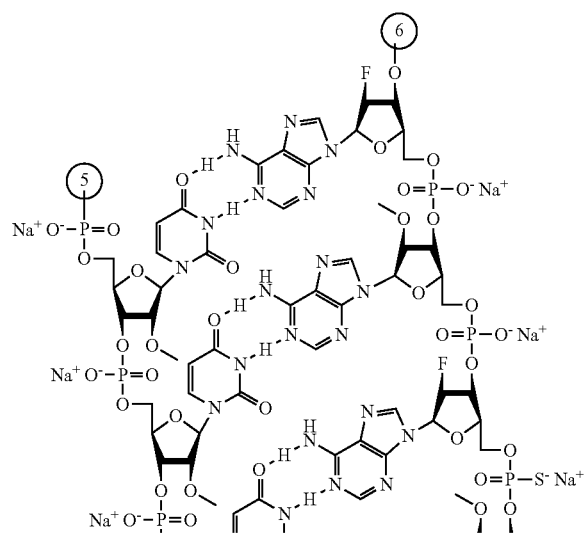

-continued
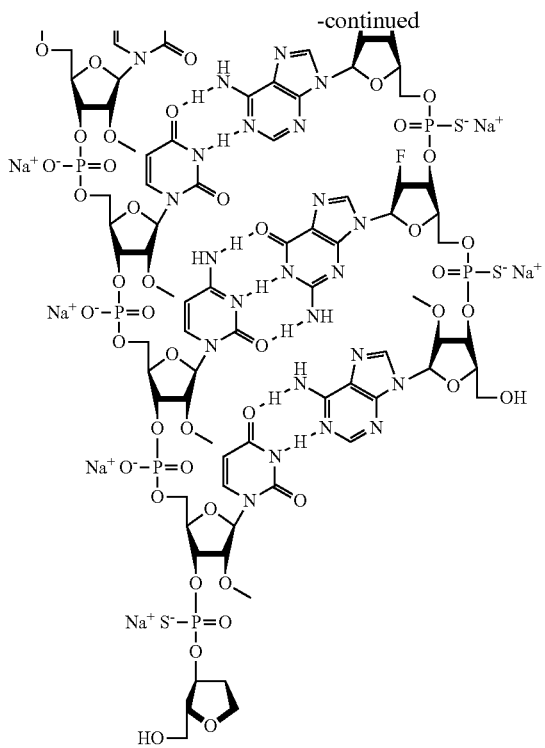
In some embodiments, an HBV RNAi agent disclosed herein consists of or comprises AD04872 linked to (NAG37)s shown as a free acid having the structure represented by the following:
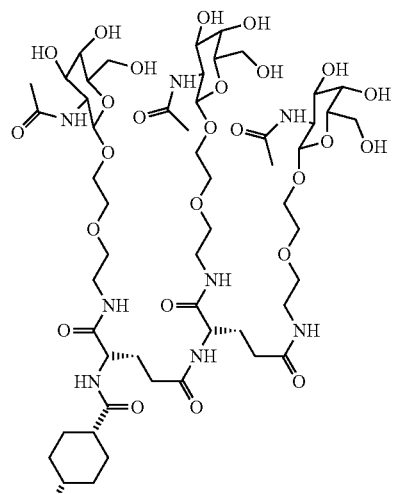

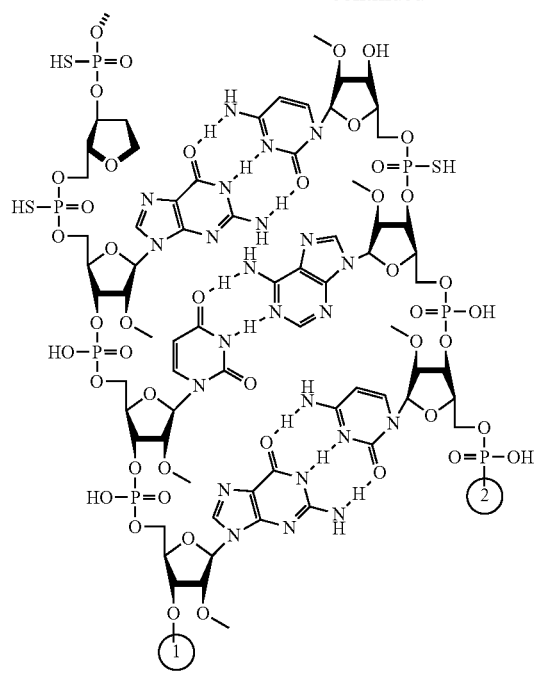
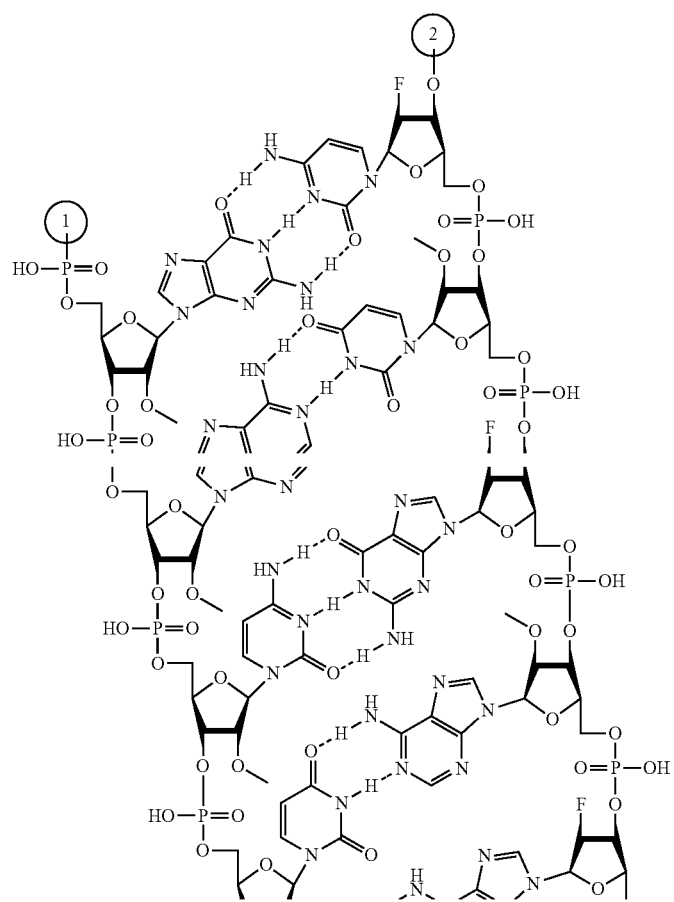

-continued
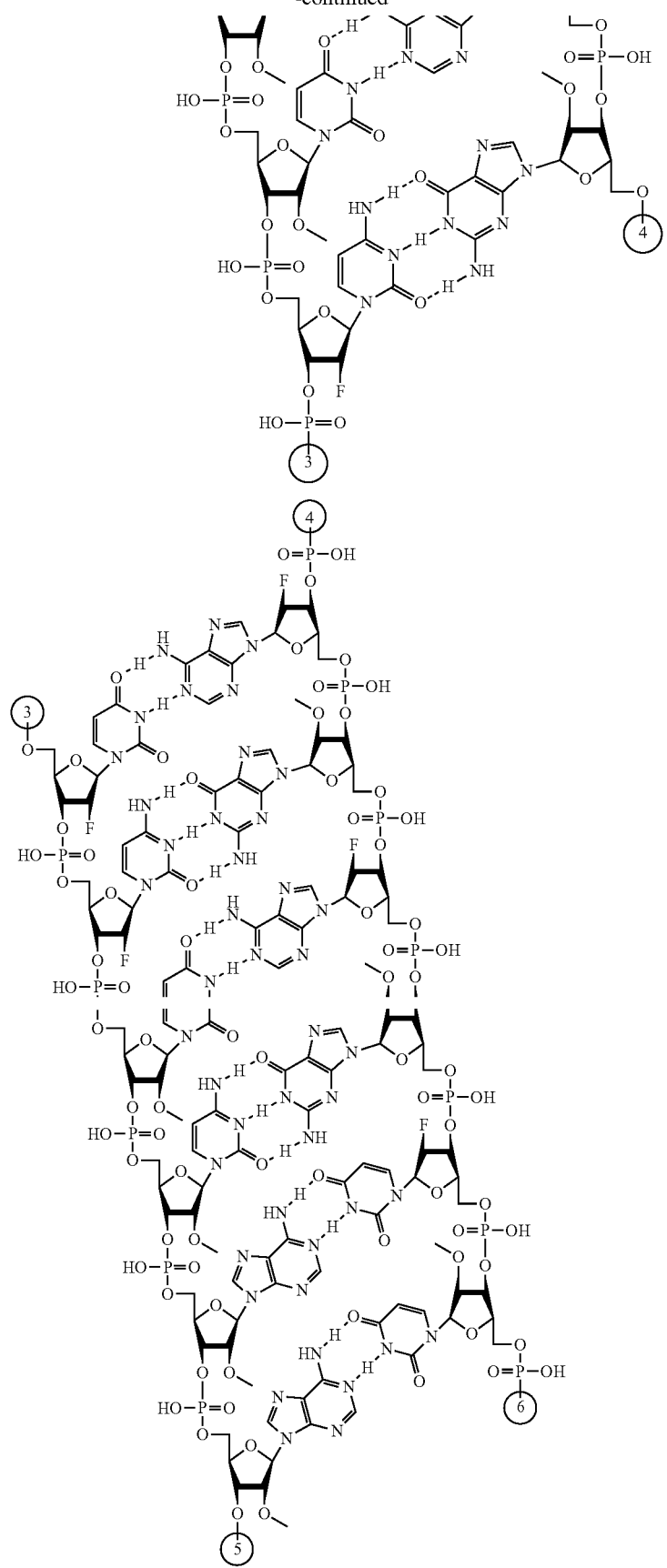

-continued

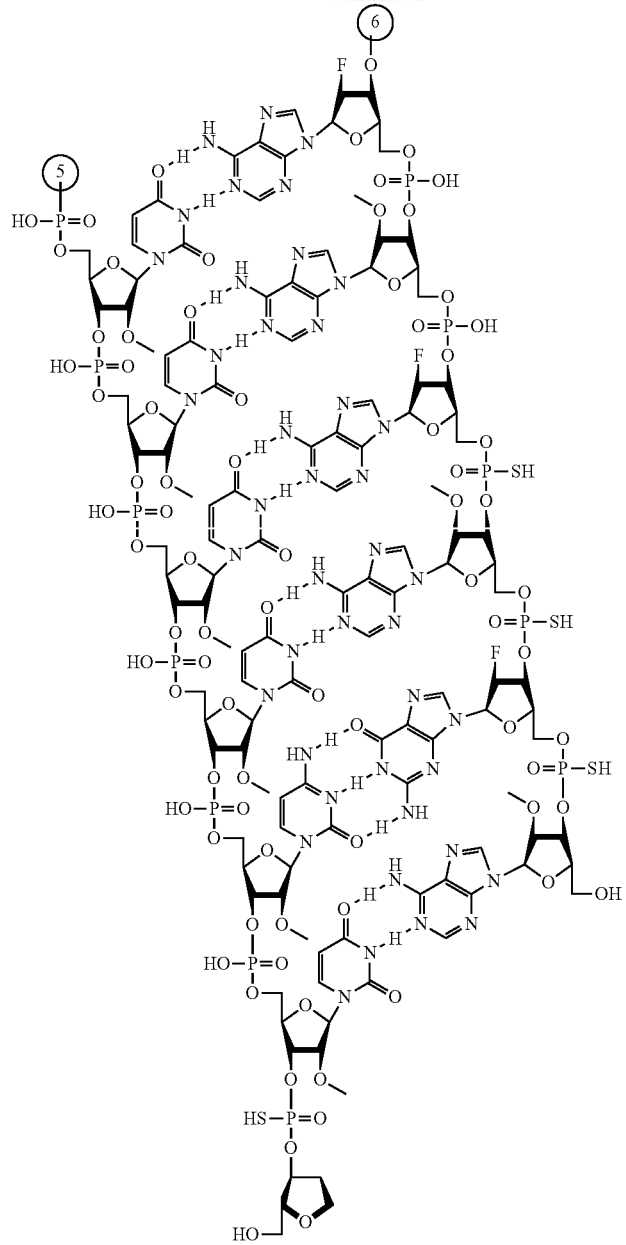

In some embodiments, the described HBV RNAi agent(s) are optionally combined with one or more additional (i.e., second, third, etc.) therapeutics. A second therapeutic can be another HBV RNAi agent (e.g., a HBV RNAi agent which targets a different sequence within an HBV genome). An additional therapeutic can also be a small molecule drug, antibody, antibody fragment, and/or vaccine. The HBV RNAi agents, with or without the one or more additional therapeutics, can be combined with one or more excipients to form pharmaceutical compositions.

In some embodiments, the described HBV RNAi agent(s) are optionally combined with one or more additional therapeutics, wherein the additional therapeutic is a nucleoside inhibitor or nucleotide inhibitor. In some embodiments, the described HBV RNAi agent(s) are optionally combined with one or more additional therapeutics, wherein the additional therapeutic entecavir, tenofovir, tenofovir alafenamide, tenofovir disoproxil, lamivudine, or another antiviral therapeutic. In some embodiments, the described HBV RNAi agent(s) are optionally combined with one or more additional therapeutics, wherein the additional therapeutic is an interferon. In some embodiments, the described HBV RNAi agent(s) are optionally combined with one or more additional therapeutics, wherein the additional therapeutic is interferon-alpha. In some embodiments, the described HBV RNAi agent(s) are optionally combined with one or more HBV additional therapeutics, wherein the additional therapeutic is an HBV vaccine.

In some embodiments, the described HBV RNAi agent(s) are optionally combined with one or more additional therapeutics in a single dosage form (i.e., a cocktail included in a single injection). In some embodiments, the described HBV RNAi agent(s) may be administered separately from one or more optional additional therapeutics. In some embodiments, the described HBV RNAi agent(s) are administered to a subject in need thereof via subcutaneous injection, and the one or more optional additional therapeutics are administered orally, which together provide for a treatment regimen for diseases and conditions associated with HBV infection. In some embodiments, the described HBV RNAi agent(s) are administered to a subject in need thereof via subcutaneous injection, and the one or more optional additional therapeutics are administered via a separate subcutaneous injection.

In some embodiments, disclosed herein are compositions for delivering an HBV RNAi agent to a liver cell in vivo, the composition including an HBV RNAi agent conjugated or linked to a targeting group. In some embodiments, the targeting group is an asialoglycoprotein receptor ligand. In some embodiments, compositions for delivering an HBV RNAi agent to a liver cell in vivo are described, the composition including an HBV RNAi agent linked to an N-acetyl-galactosamine targeting ligand.

In some embodiments, one or more of the described HBV RNAi agents are administered to a mammal in a pharmaceutically acceptable carrier or diluent. In some embodiments, the mammal is a human.

The use of Hepatitis B Virus RNAi agent(s) provides methods for therapeutic and/or prophylactic treatment of diseases/disorders which are associated with HBV infection. The described HBV RNAi agents mediate RNA interference to inhibit the expression of one or more genes necessary for replication and/or pathogenesis of Hepatitis B Virus. In particular, for example, HBV RNAi agents may inhibit viral polymerase, core protein, surface antigen, e-antigen and/or the X protein, in a cell, tissue or mammal. HBV RNAi agents can be used to treat HBV infection. HBV RNAi agents can also be used to treat or prevent chronic liver diseases/disorders, inflammations, fibrotic conditions and proliferative disorders, like cancers, associated with HBV infection. In some embodiments, the methods further comprise treatment of Hepatitis D Virus (HDV) in the subject. Such methods comprise administration of HBV RNAi agent to a human being or animal infected with HBV. Further, compositions for delivery of HBV RNAi agents to liver cells in vivo are described.

The pharmaceutical compositions comprising one or more HBV RNAi agents can be administered in a number of ways depending upon whether local or systemic treatment is desired. Administration can be, but is not limited to, intravenous, intraarterial, subcutaneous, intraperitoneal, subdermal (e.g., via an implanted device), and intraparenchymal administration. In some embodiments, the pharmaceutical compositions described herein are administered by subcutaneous injection.

The described HBV RNAi agents and/or compositions can be used in methods for therapeutic treatment of HBV infection or disease or conditions caused by HBV infection. Such methods include administration of an HBV RNAi agent as described herein to a subject, e.g., a human or animal subject.

As used herein, the terms "oligonucleotide" and "polynucleotide" mean a polymer of linked nucleosides each of which can be independently modified or unmodified.

As used herein, an "RNAi agent" or "RNAi trigger" means a composition that contains an RNA or RNA-like (e.g., chemically modified RNA) oligonucleotide molecule that is capable of degrading or inhibiting translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to the mRNA being targeted. RNAi agents may be comprised of modified nucleotides and/or one or more non-phosphodiester linkages.

As used herein, the terms "silence," "reduce," "inhibit." "down-regulate," or "knockdown" when referring to expression of a given gene, mean that the expression of the gene, as measured by the level of RNA transcribed from the gene or the level of polypeptide, protein or protein subunit translated from the mRNA in a cell, group of cells, tissue, organ, or subject in which the gene is transcribed, is reduced when the cell, group of cells, tissue, organ, or subject is treated with oligomeric compounds, such as RNAi agents, described herein as compared to a second cell, group of cells, tissue, organ, or subject that has not or have not been so treated.

As used herein, the term "sequence" or "nucleotide sequence" mean a succession or order of nucleobases or nucleotides, described with a succession of letters using standard nomenclature.

As used herein, a "nucleotide base," or "nucleobase" is a heterocyclic pyrimidine or purine compound, which is a standard constituent of all nucleic acids, and includes the bases that form the nucleotides adenine (A), guanine (G), cytosine (C), thymine (T), and uracil (U). A nucleobase may further be modified to include, without limitation, universal bases, hydrophobic bases, promiscuous bases, size-expanded bases, and fluorinated bases.

As used herein, and unless otherwise indicated, the term "complementary," when used to describe a first nucleotide sequence (e.g., RNAi agent sense strand or targeted mRNA) in relation to a second nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or similar conditions in vitro)) and form a duplex or double helical structure under certain conditions with an oligonucleotide or polynucleotide including the second nucleotide sequence. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af are complementary to U (or T) and identical to A for the purposes of determining identity or complementarity.

As used herein, "perfectly complementary" or "fully complementary" means that all (100% o) of the bases in a contiguous sequence of a first polynucleotide will hybridize with the same number of bases in a contiguous sequence of a second polynucleotide. The contiguous sequence may comprise all or a part of a first or second nucleotide sequence.

As used herein, "partially complementary" means that in a hybridized pair of nucleobase sequences, at least 70%, but not all, of the bases in a contiguous sequence of a first polynucleotide will hybridize with the same number of bases in a contiguous sequence of a second polynucleotide.

As used herein, "substantially complementary" means that in a hybridized pair of nucleobase sequences, at least about 85%, but not all, of the bases in a contiguous sequence of a first polynucleotide will hybridize with the same number of bases in a contiguous sequence of a second polynucleotide. The terms "complementary," "fully complementary," and "substantially complementary" herein may be used with respect to the base matching between the sense strand and the antisense strand of a double-stranded RNAi agent, between the antisense strand of an RNAi agent and a sequence of a target mRNA, or between a single-stranded antisense oligonucleotide and a sequence of a target mRNA.

As used herein, the term "substantially identical" or "substantially identity" as applied to nucleic acid sequence means that a nucleic acid sequence comprises a sequence that has at least about 85% sequence identity or more, preferably at least 90%, at least 95%, or at least 99%, compared to a reference sequence. Percentage of sequence identity is determined by comparing two optimally aligned sequences over a comparison window. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity. The inventions disclosed herein encompasses nucleotide sequences substantially identical to those disclosed herein, e.g., in Tables 2, 3, and 4. In some embodiments, the sequences disclosed herein are exactly identical, or at least about 85%, 86%, 87%, 88%, 89%, 90%, 91%, 92%, 93%, 94%, 95%, 96%, 97%, 98%, or 99% percent identical to those disclosed herein, e.g., in Tables 1, 2, 3 and 4.

As used herein, the terms "treat," "treatment," and the like, mean the methods or steps taken to provide relief from or alleviation of the number, severity, and/or frequency of one or more symptoms of a disease or condition in a subject.

As used herein, the phrase "introducing into a cell," when referring to an oligomeric compound, means functionally delivering the oligomeric compound into a cell. The phrase "functional delivery," means that delivering the oligomeric compound to the cell in a manner that enables the oligomeric compound to have the expected biological activity, e.g., sequence-specific inhibition of gene expression.

Unless stated otherwise, use of the symbol ⁎ as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O. or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Described herein are RNAi agents for inhibiting expression of Hepatitis B Virus (HBV) (referred to herein as HBV RNAi agents or HBV RNAi triggers). Each HBV RNAi agent comprises a sense strand and an antisense strand. The sense strand and the antisense strand each can be 16 to 30 nucleotides in length. In some embodiments, the sense and antisense strands each can be 17 to 26 nucleotides in length. The sense and antisense strands can be either the same length or they can be different lengths. In some embodiments, the sense and antisense strands are each independently 17 to 26 nucleotides in length. In some embodiments, the sense and antisense strands are each independently 17-21 nucleotides in length. In some embodiments, both the sense and antisense strands are each 21-26 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, both the sense and antisense strands are each 26 nucleotides in length. In some embodiments, the RNAi agent sense and antisense strands are each independently 17, 18, 19, 20, 21, 22, 23, 24, 25, or 26 nucleotides in length. In some embodiments, a double-stranded RNAi agent has a duplex length of about 16, 17, 18, 19, 20, 21, 22, 23 or 24 nucleotides. This region of perfect or substantial complementarity between the sense strand and the antisense strand is typically 15-25 (e.g., 15, 16, 17, 18, 19, 20, 21, 22, 23, 24, or 25) nucleotides in length and occurs at or near the 5' end of the antisense strand (e.g., this region may be separated from the 5' end of the antisense strand by 0, 1, 2, 3, or 4 nucleotides that are not perfectly or substantially complementary).

The sense strand and antisense strand each contain a core stretch sequence that is 16 to 23 nucleobases in length. An antisense strand core stretch sequence is 100% (perfectly) complementary or at least about 85% (substantially) complementary to a nucleotide sequence (sometimes referred to, e.g., as a target sequence) present in the HBV mRNA target. A sense strand core stretch sequence is 100% (perfectly) complementary or at least about 85% (substantially) complementary to a core stretch sequence in the antisense strand, and thus the sense strand core stretch sequence is perfectly identical or at least about 85% identical to a nucleotide sequence (target sequence) present in the HBV mRNA target. A sense strand core stretch sequence can be the same length as a corresponding antisense core sequence or it can be a different length. In some embodiments, the antisense strand core stretch sequence is 16, 17, 18, 19, 20, 21, 22, or 23 nucleotides in length. In some embodiments, the sense strand core stretch sequence is 16, 17, 18, 19, 20, 21, 22, or 23 nucleotides in length.

Examples of sense and antisense strand nucleotide sequences used in forming HBV RNAi agents are provided in Tables 3 and 4. Examples of RNAi agent duplexes, that include the nucleotide sequences in Tables 3 and 4, are provided in Table 5.

The HBV RNAi agent sense and antisense strands anneal to form a duplex. A sense strand and an antisense strand of an HBV RNAi agent may be partially, substantially, or fully complementary to each other. Within the complementary duplex region, the sense strand core stretch sequence is at least about 85% complementary or 100% complementary to the antisense core stretch sequence. In some embodiments, the sense strand core stretch sequence contains a sequence of at least 16, at least 17, at least 18, at least 19, at least 20, or at least 21 nucleotides that is at least about 85% or 100% complementary to a corresponding 16, 17, 18, 19, 20, or 21 nucleotide sequence of the antisense strand core stretch sequence (i.e., the sense strand and antisense core stretch sequences of an HBV RNAi agent have a region of at least 16, at least 17, at least 18, at least 19, at least 20, or at least 21 nucleotides that is at least 85% base paired or 100% base paired).

In some embodiments, the antisense strand of an HBV RNAi agent disclosed herein differs by 0, 1, 2, or 3 nucleotides from any of the antisense strand sequences in Table 2 or Table 3. In some embodiments, the sense strand of an HBV RNAi agent disclosed herein differs by 0, 1, 2, or 3 nucleotides from any of the sense strand sequences in Table 2 or Table 4.

The length of the HBV RNAi agent sense and antisense strands described herein are independently 16 to 30 nucleotides in length. In some embodiments, the sense and antisense strands are independently 17 to 26 nucleotides in length. In some embodiments, the sense and antisense strands are 19-26 nucleotides in length. In some embodiments, the described RNAi agent sense and antisense strands are independently 17, 18, 19, 20, 21, 22, 23, 24, 25, or 26 nucleotides in length. The sense and antisense strands can be either the same length or they can be different lengths. In some embodiments, a sense strand and an antisense strand are each 26 nucleotides in length. In some embodiments, a sense strand is 23 nucleotides in length and an antisense strand is 21 nucleotides in length. In some embodiments, a sense strand is 22 nucleotides in length and an antisense strand is 21 nucleotides in length. In some embodiments, a sense strand is 21 nucleotides in length and an antisense strand is 21 nucleotides in length. In some embodiments, a sense strand is 19 nucleotides in length and an antisense strand is 21 nucleotides in length.

The sense strand and/or the antisense strand may optionally and independently contain an additional 1, 2, 3, 4, 5, or 6 nucleotides (extension) at the 3' end, the 5' end, or both the 3' and 5' ends of the core sequences. The antisense strand additional nucleotides, if present, may or may not be complementary to the corresponding sequence in an HBV mRNA. The sense strand additional nucleotides, if present, may or may not be identical to the corresponding sequence in an HBV mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch sequence nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an HBV RNAi agent has an antisense strand having a 3' extension and a sense strand having a 5' extension.

In some embodiments, an HBV RNAi agent comprises an antisense strand having a 3' extension of 1, 2, 3, 4, 5, or 6 nucleotides in length. In other embodiments, an HBV RNAi agent comprises an antisense strand having a 3' extension of 1, 2, or 3 nucleotides in length. In some embodiments, one or more of the antisense strand extension nucleotides comprise uracil or thymidine nucleotides or nucleotides which are complementary to a corresponding HBV mRNA sequence. In some embodiments, a 3' antisense strand extension includes or consists of, but is not limited to: AUA, UGCUU, CUG, UG, UGCC, CUGCC, CGU, CUU, UGCCUA, CUGCCU, UGCCU, UGAUU, GCCUAU, T, T, U, UU (each listed 5' to 3').

In some embodiments, the 3' end of the antisense strand may include additional abasic nucleosides (Ab). In some embodiments, Ab or AbAb may be added to the 3' end of the antisense strand.

In some embodiments, an HBV RNAi agent comprises an antisense strand having a 5' extension of 1, 2, 3, 4, or 5 nucleotides in length. In other embodiments, an HBV RNAi agent comprises an antisense strand having a 5' extension of 1 or 2 nucleotides in length. In some embodiments, one or more of the antisense strand extension nucleotides comprises uracil or thymidine nucleotides or nucleotides which are complementary to a corresponding HBV mRNA sequence. In some embodiments, the 5' antisense strand extension includes or consists of, but is no limited to, UA, TU, U, T, UU, T, CUC (each listed 5' to 3'). An antisense strand may have any of the 3' extensions described above in combination with any of the 5' antisense strand extensions described, if present.

In some embodiments, an HBV RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides which correspond to nucleotides in the HBV mRNA sequence. In some embodiments, the 3' sense strand extension includes or consists of, but is not limited to: T, UT, T, UU, UUT, TTT, or ITIT (each listed 5' to 3').

In some embodiments, the 3' end of the sense strand may include additional abasic nucleosides. In some embodiments, UUAb, UAb, or Ab may be added to the 3' end of the sense strand. In some embodiments, the one or more abasic nucleosides added to the 3' end of the sense strand may be inverted (invAb). In some embodiments, one or more inverted abasic nucleosides may be inserted between the targeting ligand and the nucleobase sequence of the sense strand of the RNAi agent. In some embodiments, the inclusion of one or more inverted abasic nucleosides at or near the terminal end or terminal ends of the sense strand of an RNAi agent may allow for enhanced activity or other desired properties of an RNAi agent.

In some embodiments, an HBV RNAi agent comprises a sense strand having a 5' extension of 1, 2, 3, 4, 5, or 6 nucleotides in length. In some embodiments, one or more of the sense strand extension nucleotides comprise uracil or adenosine nucleotides or nucleotides which correspond to nucleotides in the HBV mRNA sequence. In some embodiments, the sense strand 5' extension can be, but is not limited to: CA, AUAGGC, AUAGG, AUAG, AUA, A, AA, AC, GCA, GGCA, GGC, UAUCA, UAUC, UCA. UAU, U, UU (each listed 5' to 3'). A sense strand may have a 3' extension and/or a 5' extension.

In some embodiments, the 5' end of the sense strand may include an additional abasic nucleoside (Ab) or nucleosides (AbAb). In some embodiments, the one or more abasic nucleosides added to the 5' end of the sense strand may be inverted (invAb). In some embodiments, one or more inverted abasic nucleosides may be inserted between the targeting ligand and the nucleobase sequence of the sense strand of the RNAi agent. In some embodiments, the inclusion of one or more inverted abasic nucleosides at or near the terminal end or terminal ends of the sense strand of an RNAi agent may allow for enhanced activity or other desired properties of an RNAi agent.

Examples of nucleotide sequences used in forming HBV RNAi agents are provided in Tables 3 and 4. In some embodiments, an HBV RNAi agent antisense strand includes a nucleotide sequence of any of the sequences in Table 3. In some embodiments, an HBV RNAi agent antisense strand includes the sequence of nucleotides 1-17, 2-15, 2-17, 1-18, 2-18, 1-19, 2-19, 1-20, 2-20, 1-21, 2-21, 1-22, 2-22, 1-23, 2-23, 1-24, 2-24, 1-25, 2-25, 1-26, or 2-26 of any of the sequences in Table 3. In some embodiments, an HBV RNAi agent sense strand includes the nucleotide sequence of any of the sequences in Table 4. In some embodiments, an HBV RNAi agent sense strand includes the sequence of nucleotides 1-18, 1-19, 1-20, 1-21, 1-22, 1-23, 1-24, 1-25, 1-26, 2-19, 2-20, 2-21, 2-22, 2-23, 2-24, 2-25, 2-26, 3-20, 3-21, 3-22, 3-23, 3-24, 3-25, 3-26, 4-21, 4-22, 4-23, 4-24, 4-25, 4-26, 5-22, 5-23, 5-24, 5-25, 5-26, 6-23, 6-24, 6-25, 6-26, 7-24, 7-25, 7-25, 8-25, 8-26 of any of the sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a blunt end refers to an end of a double stranded RNAi agent in which the terminal nucleotides of the two annealed strands are complementary (form a complementary base-pair). In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e. do not form an overhang) but are not complementary (i.e. form a non-complementary pair). As used herein, an overhang is a stretch of one or more unpaired nucleotides at the end of one strand of a double stranded RNAi agent. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends.

A nucleotide base (or nucleobase) is a heterocyclic pyrimidine or purine compound which is a constituent of all nucleic acids and includes adenine (A), guanine (G), cytosine (C), thymine (T), and uracil (U). As used herein, the term "nucleotide" can include a modified nucleotide (such as, for example, a nucleotide mimic, abasic site (Ab), or a surrogate replacement moiety). Modified nucleotides, when used in various polynucleotide or oligonucleotide constructs, may preserve activity of the compound in cells while at the same time increasing the serum stability of these compounds, and can also minimize the possibility of activating interferon activity in humans upon administering of the polynucleotide or oligonucleotide construct.

In some embodiments, an HBV RNAi agent is prepared or provided as a salt, mixed salt, or a free-acid. In some embodiments, an HBV RNAi agent is prepared as a sodium salt. Such forms are within the scope of the inventions disclosed herein.

Modified Nucleotides

In some embodiments, an HBV RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides include, but are not limited to, deoxyribonucleotides, nucleotide mimics, abasic nucleotides (represented herein as Ab), 2'-modified nucleotides, 3' to 3' linkages (inverted) nucleotides (represented herein as invdN, invN, invn, invAb), non-natural base-comprising nucleotides, bridged nucleotides, peptide nucleic acids (PNAs), 2',3'-seco nucleotide mimics (unlocked nucleobase analogues, represented herein as $N_{UNA}$ or NUNA), locked nucleotides (represented herein as $N_{LNA}$ or NLNA), 3'-O-methoxy (2' internucleoside linked) nucleotides (represented herein as 3'-OMen), 2'-F-Arabino nucleotides (represented herein as NfANA or $Nf_{ANA}$), 5'-Me, 2'-fluoro nucleotide (represented herein as 5Me-Nf), morpholino nucleotides, vinyl phosphonate deoxyribonucleotides (represented herein as vpdN), vinyl phosphonate containing nucleotides, and cyclopropyl phosphonate containing nucleotides (cPrpN). 2'-modified nucleotides (i.e. a nucleotide with a group other than a hydroxyl group at the 2' position of the five-membered sugar ring) include, but are not limited to, 2'-O-methyl nucleotides (represented herein as a lower case 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxylethyl) nucleotides (represented herein as NM or 2'-MOE), 2'-amino nucleotides, and 2'-alkyl nucleotides. It is not necessary for all positions in a given compound to be uniformly modified. Conversely, more than one modification may be incorporated in a single HBV RNAi agent or even in a single nucleotide thereof. The HBV RNAi agent sense strands and antisense strands may be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides. As used herein, a sense strand wherein substantially all of the nucleotides present are modified nucleotides is a sense strand having two or fewer (i.e., 0, 1, or 2) nucleotides in the sense strand being ribonucleotides. As used herein, an antisense sense strand wherein substantially all of the nucleotides present are modified nucleotides is an antisense strand having two or fewer (i.e., 0, 1, or 2) nucleotides in the sense strand being ribonucleotides. In some embodiments, one or more nucleotides of an RNAi agent is a ribonucleotide.

Modified Internucleoside Linkages

In some embodiments, one or more nucleotides of an HBV RNAi agent are linked by non-standard linkages or backbones (i.e., modified internucleoside linkages or modified backbones). In some embodiments, a modified internucleoside linkage is a non-phosphate-containing covalent internucleoside linkage. Modified internucleoside linkages or backbones include, but are not limited to, 5'-phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkyl-phosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an HBV RNAi agent can contain 1, 2, 3, 4, 5, or 6 phosphorothioate linkages, an antisense strand of an HBV RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an HBV RNAi agent can contain 1, 2, 3, or 4 phosphorothioate linkages, an antisense strand of an HBV RNAi agent can contain 1, 2, 3, or 4 phosphorothioate linkages, or both the sense strand and the antisense strand independently can contain 1, 2, 3, or 4 phosphorothioate linkages.

In some embodiments, an HBV RNAi agent sense strand contains at least two phosphorothioate internucleoside linkages. In some embodiments, the at least two phosphorothioate internucleoside linkages are between the nucleotides at positions 1-3 from the 3' end of the sense strand. In some embodiments, the at least two phosphorothioate internucleoside linkages are between the nucleotides at positions 1-3, 2-4, 3-5, 4-6, 4-5, or 6-8 from the 5' end of the sense strand. In some embodiments, an HBV RNAi agent antisense strand contains four phosphorothioate internucleoside linkages. In some embodiments, the four phosphorothioate internucleoside linkages are between the nucleotides at positions 1-3 from the 5' end of the sense strand and between the nucleotides at positions 19-21, 20-22, 21-23, 22-24, 23-25, or 24-26 from the 5' end. In some embodiments, an HBV RNAi agent contains at least two phosphorothioate internucleoside linkages in the sense strand and three or four phosphorothioate internucleoside linkages in the antisense strand.

In some embodiments, an HBV RNAi agent contains one or more modified nucleotides and one or more modified internucleoside linkages. In some embodiments, a 2'-modified nucleoside is combined with modified internucleoside linkage.

HBV RNAi Agents

In some embodiments, the HBV RNAi agents disclosed herein target an HBV gene at or near the positions of the HBV genome shown in the following Table 1. In some embodiments, the antisense strand of an HBV RNAi agent disclosed herein includes a core stretch sequence that is fully, substantially, or at least partially complementary to a target HBV 19-mer sequence disclosed in Table 1.

TABLE 1

Example 19-mer HBV cDNA target sequences for HBV RNAi agents (taken from Hepatitis B virus (subtype ADW2), genotype A. complete genome GenBank AM282986.1 (SEQ ID NO: 1)).

| SEQ ID No. | HBV 19-mer Target Sequences (5'→3') | Genome Position of SEQ ID NO: 1 | Region of HBV Gene Targeted |
| --- | --- | --- | --- |
| 2 | GTGGTGGACTTCTCTCAAT | 256-274 | S ORF |
| 3 | TGGTGGACTTCTCTCAATT | 257-275 | S ORF |
| 4 | GGACTTCTCTCAATTTTCT | 261-279 | S ORF |
| 5 | GCTGTAGGCATAAATTGGT | 1780-1798 | X ORF |
| 6 | CTGTAGGCATAAATTGGTC | 1781-1799 | X ORF |

In some embodiments, an HBV RNAi agent includes an antisense strand wherein position 19 of the antisense strand (5'→3') is capable of forming a base pair with position 1 of a 19-mer target sequence disclosed in Table 1. In some embodiments, an HBV RNAi agent includes an antisense strand wherein position 1 of the antisense strand (5'3') is capable of forming a base pair with position 19 of the 19-mer target sequence disclosed in Table 1.

In some embodiments, an HBV RNAi agent includes an antisense strand wherein position 2 of the antisense strand (5'→3') is capable of forming a base pair with position 18 of the 19-mer target sequence disclosed in Table 1. In some embodiments, an HBV RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

In some embodiments, the HBV RNAi agents include core 19-mer nucleotide sequences shown in the following Table 2.

TABLE 2

HBV RNAi agent antisense strand and sense strand core stretch sequences (N = any nucleotide).

| SEQ ID NO: | Antisense Sequence (5'→3') (19-mer) | SEQ ID NO: | Sense Sequence (5'→3') (19-mer) | Genome Position of SEQ ID NO: 1 |
| --- | --- | --- | --- | --- |
| 7 | AUUGAGAGAAGUCCACCAC | 34 | GUGGUGGACUUCUCUCAAU | 256-274 |
| 8 | UUUGAGAGAAGUCCACCAC | 35 | GUGGUGGACUUCUCUCAAA | 256-274 |
| 9 | AUUGAGAGAAGUCCACCAN | 36 | NUGGUGGACUUCUCUCAAU | 256-274 |
| 10 | UUUGAGAGAAGUCCACCAN | 37 | NUGGUGGACUUCUCUCAAA | 256-274 |
| 11 | NUUGAGAGAAGUCCACCAN | 38 | NUGGUGGACUUCUCUCAAN | 256-274 |

TABLE 2-continued

HBV RNAi agent antisense strand and sense strand core stretch sequences (N = any nucleotide).

| SEQ ID NO: | Antisense Sequence (5'→3') (19-mer) | SEQ ID NO: | Sense Sequence (5'→3') (19-mer) | Genome Position of SEQ ID NO: 1 |
|---|---|---|---|---|
| 12 | AAUUGAGAGAAGUCCACCA | 39 | UGGUGGACUUCUCUCAAUU | 257-275 |
| 13 | UAUUGAGAGAAGUCCACCA | 40 | UGGUGGACUUCUCUCAAUA | 257-275 |
| 14 | AAUUGAGAGAAGUCCACCN | 41 | NGGUGGACUUCUCUCAAUU | 257-275 |
| 15 | UAUUGAGAGAAGUCCACCN | 42 | NGGUGGACUUCUCUCAAUA | 257-275 |
| 16 | NAUUGAGAGAAGUCCACCN | 43 | NGGUGGACUUCUCUCAAUN | 257-275 |
| 17 | AGAAAAUUGAGAGAAGUCC | 44 | GGACUUCUCUCAAUUUUCU | 261-279 |
| 18 | UGAAAAUUGAGAGAAGUCC | 45 | GGACUUCUCUCAAUUUUCA | 261-279 |
| 19 | AGAAAAUUGAGAGAAGUCN | 46 | NGACUUCUCUCAAUUUUCU | 261-279 |
| 20 | UGAAAAUUGAGAGAAGUCN | 47 | NGACUUCUCUCAAUUUUCA | 261-279 |
| 21 | NGAAAAUUGAGAGAAGUCN | 48 | NGACUUCUCUCAAUUUUCN | 261-279 |
| 22 | ACCAAUUUAUGCCUACAGC | 49 | GCUGUAGGCAUAAAUUGGU | 1780-1798 |
| 23 | UCCAAUUUAUGCCUACAGC | 50 | GCUGUAGGCAUAAAUUGGA | 1780-1798 |
| 24 | ACCAAUUUAUGCCUACAGN | 51 | NCUGUAGGCAUAAAUUGGU | 1780-1798 |
| 25 | UCCAAUUUAUGCCUACAGN | 52 | NCUGUAGGCAUAAAUUGGA | 1780-1798 |
| 26 | NCCAAUUUAUGCCUACAGN | 53 | NCUGUAGGCAUAAAUUGGN | 1780-1798 |
| 27 | GACCAAUUUAUGCCUACAG | 54 | CUGUAGGCAUAAAUUGGUC | 1781-1799 |
| 28 | AACCAAUUUAUGCCUACAG | 55 | CUGUAGGCAUAAAUUGGUU | 1781-1799 |
| 29 | UACCAAUUUAUGCCUACAG | 56 | CUGUAGGCAUAAAUUGGUA | 1781-1799 |
| 30 | GACCAAUUUAUGCCUACAN | 57 | NUGUAGGCAUAAAUUGGUC | 1781-1799 |
| 31 | AACCAAUUUAUGCCUACAN | 58 | NUGUAGGCAUAAAUUGGUU | 1781-1799 |
| 32 | UACCAAUUUAUGCCUACAN | 59 | NUGUAGGCAUAAAUUGGUA | 1781-1799 |
| 33 | NACCAAUUUAUGCCUACAN | 60 | NUGUAGGCAUAAAUUGGUN | 1781-1799 |

The HBV RNAi agent sense strands and antisense strands that comprise or consist of the nucleotide sequences in Table 2 can be modified nucleotides or unmodified nucleotides. In some embodiments, the HBV RNAi agents having the sense and antisense strand sequences that comprise or consist of the nucleotide sequences in Table 2 are all or substantially all modified nucleotides.

In some embodiments, the antisense strand of an HBV RNAi agent disclosed herein differs by 0, 1, 2, or 3 nucleotides from any of the antisense strand sequences in Table 2. In some embodiments, the sense strand of an HBV RNAi agent disclosed herein differs by 0, 1, 2, or 3 nucleotides from any of the sense strand sequences in Table 2.

Modified HBV RNAi agent antisense strand sequences, as well as their underlying unmodified sequences, are provided in Table 3. Modified HBV RNAi agent sense strands, as well as their underlying unmodified sequences, are provided in Table 4. In forming HBV RNAi agents, each of the nucleotides in each of the unmodified sequences listed in Tables 3 and 4 may be a modified nucleotide.

As used herein (including in Tables 3 and 4), the following notations are used to indicate modified nucleotides, targeting groups, and linking groups. As the person of ordinary skill in the art would readily understand, unless otherwise indicated by the sequence, that when present in an oligonucleotide, the monomers are mutually linked by 5'-3'-phosphodiester bonds:

A=adenosine-3'-phosphate;
C=cytidine-3'-phosphate;
G=guanosine-3'-phosphate;
U=uridine-3'-phosphate
n=any 2'-OMe modified nucleotide
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Nf=any 2'-fluoro modified nucleotide
Af=2'-fluoroadenosine-3'-phosphate Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dN=any 2'-deoxyribonucleotide
dT=2'-deoxythymidine-3'-phosphate
$N_{UNA}$=2',3'-seco nucleotide mimics (unlocked nucleobase analogs)
$N_{LNA}$=locked nucleotide
$Nf_{ANA}$=2'-F-Arabino nucleotide
NM=2'-methoxyethyl nucleotide
AM=2'-methoxyethyladenosine-3'-phosphate
AMs=2'-methoxyethyladenosine-3'-phosphorothioate
TM=2'-methoxyethylthymidine-3'-phosphate
TMs=2'-methoxyethylthymidine-3'-phosphorothioate
R=ribitol
(invdN)=any inverted deoxyribonucleotide (3'-3' linked nucleotide)
(invAb)=inverted (3'-3' linked) abasic deoxyribonucleotide, see Table 6
(invAb)s=inverted (3'-3' linked) abasic deoxyribonucleotide-5'-phosphorothioate, see Table 6
(invn)=any inverted 2'-OMe nucleotide (3'-3' linked nucleotide)
s=phosphorothioate linkage
vpdN=vinyl phosphonate deoxyribonucleotide
(5Me-Nf)=5'-Me, 2'-fluoro nucleotide
cPrp=cyclopropyl phosphonate, see Table 6
epTcPr=see Table 6
epTM=see Table 6

The person or ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Thus, for example, as shown above in the structure representation of AD05070, above, the "g" modified nucleotide on the terminal 3' end of the antisense strand of AM06606-AS has a hydroxyl group positioned at its 3' position. Unless expressly indicated otherwise herein, such understandings of the person of ordinary skill in the art are used when describing the HBV RNAi agents and compositions of HBV RNAi agents disclosed herein.

Targeting groups and linking groups include the following, for which their chemical structures are provided below in Table 6: (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s. Each sense strand and/or antisense strand can have any targeting groups or linking groups listed above, as well as other targeting or linking groups, conjugated to the 5' and/or 3' end of the sequence.

TABLE 3

HBV RNAi Agent antisense strand sequences.

| AS Strand ID | Modified sequence (5'→3') | SEQ ID NO. | Unmodified sequence (5'→3') | SEQ ID NO. |
| --- | --- | --- | --- | --- |
| AM03508-AS | usAfscCfaAfuUfuAfuGfcCfuAfcAfgGfccsusuAu | 61 | UACCAAUUUAUGCCUACAGGCCUUAU | 149 |
| AM04441-AS | usAfscCfaAfuUfuAfuGfcCfuAfcAfgGfcscsu | 62 | UACCAAUUUAUGCCUACAGGCCU | 150 |
| AM04442-AS | usAfscsCfaAfuUfuAfuGfcCfuAfcAfgGfccsu | 63 | UACCAAUUUAUGCCUACAGGCCU | 150 |
| AM04443-AS | usAfscsCfaAfuUfuAfuGfcCfuAfcAfgGfsc | 64 | UACCAAUUUAUGCCUACAGGC | 151 |
| AM04661-AS | usGfsugaAfgCfGfaaguGfcAfcacsusu | 65 | UGUGAAGCGAAGUGCACACUU | 152 |
| AM04768-AS | usAfscCfaAfuUfuAfuGfcCfuAfcAfgCfcsusccgc | 66 | UACCAAUUUAUGCCUACAGCCUCCGC | 153 |
| AM04769-AS | vpusAfscCfaAfuUfuAfuGfcCfuAfcAfgCfcsusccgc | 67 | UACCAAUUUAUGCCUACAGCCUCCGC | 153 |
| AM05011-AS | usAfscsCfaAfuUfuAfuGfcCfuAfcAfgusu | 68 | UACCAAUUUAUGCCUACAGUU | 154 |
| AM05012-AS | usAfscsCfaAfuUfuAfuGfcCfuAfcAfggsc | 69 | UACCAAUUUAUGCCUACAGGC | 151 |
| AM05013-AS | vpusAfscsCfaAfuUfuAfuGfcCfuAfcAfgGfsc | 70 | UACCAAUUUAUGCCUACAGGC | 151 |
| AM05014-AS | vpusAfscsCfaAfuUfuAfuGfcCfuAfcAfgusu | 71 | UACCAAUUUAUGCCUACAGUU | 154 |
| AM05052-AS | asUfsusGfaGfaGfaAfgUfcCfaCfcAfcGfsa | 72 | AUUGAGAGAAGUCCACCACGA | 155 |
| AM05053-AS | asUfsusGfaGfaGfaAfgUfcCfaCfcAfcgsa | 73 | AUUGAGAGAAGUCCACCACGA | 155 |
| AM05054-AS | asUfsusGfaGfaGfaAfgUfcCfaCfcAfcusu | 74 | AUUGAGAGAAGUCCACCACUU | 156 |
| AM05055-AS | vpusUfsusGfaGfaGfaAfgUfcCfaCfcAfcGfsa | 75 | UUUGAGAGAAGUCCACCACGA | 157 |
| AM05056-AS | asAfsusUfgAfgAfgAfaGfuCfcAfcCfaCfsg | 76 | AAUUGAGAGAAGUCCACCACG | 158 |
| AM05057-AS | asAfsusUfgAfgAfgAfaGfuCfcAfcCfacsg | 77 | AAUUGAGAGAAGUCCACCACG | 158 |
| AM05058-AS | asAfsusUfgAfgAfgAfaGfuCfcAfcCfausu | 78 | AAUUGAGAGAAGUCCACCAUU | 159 |

TABLE 3-continued

HBV RNAi Agent antisense strand sequences.

| AS Strand ID | Modified sequence (5'→3') | SEQ ID NO. | Unmodified sequence (5'→3') | SEQ ID NO. |
|---|---|---|---|---|
| AM05060-AS | vpusAfsusUfgAfgAfgAfaGfuCfcAfcCfaCfsg | 79 | UAUUGAGAGAAGUCCACCACG | 160 |
| AM05351-AS | usAfscsCfaAfuUfuAfuGfcCfuAfcAfgGfsu | 80 | UACCAAUUUAUGCCUACAGGU | 161 |
| AM05608-AS | usAfscCfaAfuUfuAfuGfcCfuAfcAfgsusu | 81 | UACCAAUUUAUGCCUACAGUU | 154 |
| AM05609-AS | usAfscsCfaAfuUfuAfuGfcCfuAfcAfgcsc | 82 | UACCAAUUUAUGCCUACAGCC | 162 |
| AM05610-AS | usAfscsCfaAfuUfuAfuGfcCfuAfcAfgccusu | 83 | UACCAAUUUAUGCCUACAGCCUU | 163 |
| AM05611-AS | usAfscsCfaAfuUfuAfuGfcCfuAfcAfgccusc | 84 | UACCAAUUUAUGCCUACAGCCUC | 164 |
| AM05612-AS | usAfscscaauUfuAfuGfcCfuacagcsc | 85 | UACCAAUUUAUGCCUACAGCC | 162 |
| AM05613-AS | usAfscscaauUfuAfuGfcCfuacagccusu | 86 | UACCAAUUUAUGCCUACAGCCUU | 163 |
| AM05614-AS | usAfscscaauUfuAfuGfcCfuacagccusc | 87 | UACCAAUUUAUGCCUACAGCCUC | 164 |
| AM05618-AS | asUfsusgagaGfaAfgUfcCfaccacusu | 88 | AUUGAGAGAAGUCCACCACUU | 156 |
| AM05621-AS | usUfsusGfaGfaGfaAfgUfcCfaCfcAfcusu | 89 | UUUGAGAGAAGUCCACCACUU | 165 |
| AM05623-AS | asUfsusGfaGfaGfaAfgUfcCfaCfcAfcggusu | 90 | AUUGAGAGAAGUCCACCACGGUU | 166 |
| AM05626-AS | asUfsusgagaGfaAfgUfcCfaccacggusu | 91 | AUUGAGAGAAGUCCACCACGGUU | 166 |
| AM05628-AS | asUfsusGfaGfaGfaAfgUfcCfaCfcAfcgagsu | 92 | AUUGAGAGAAGUCCACCACGAGU | 167 |
| AM05631-AS | usAfsusUfgAfgAfgAfaGfuCfcAfcCfaCfsg | 93 | UAUUGAGAGAAGUCCACCACG | 160 |
| AM05632-AS | usAfsusugagAfgAfaGfuCfcaccacsg | 94 | UAUUGAGAGAAGUCCACCACG | 160 |
| AM05633-AS | usAfsusUfgAfgAfgAfaGfuCfcAfcCfaCfgusu | 95 | UAUUGAGAGAAGUCCACCACGUU | 168 |
| AM05634-AS | usAfsusugagAfgAfaGfuCfcaccacgasg | 96 | UAUUGAGAGAAGUCCACCACGAG | 169 |
| AM05635-AS | usAfsusUfgAfgAfgAfaGfuCfcAfcCfaCfgasg | 97 | UAUUGAGAGAAGUCCACCACGAG | 169 |
| AM05637-AS | usAfsusUfgAfgAfgAfaGfuCfcAfcCfaCfgsa | 98 | UAUUGAGAGAAGUCCACCACGA | 170 |
| AM05638-AS | usAfsusugagAfgAfaGfuCfcaccacgsa | 99 | UAUUGAGAGAAGUCCACCACGA | 170 |
| AM05747-AS | asGfsasAfaAfuugagAfgAfaGfuCfcAfsc | 100 | AGAAAAUUGAGAGAAGUCCAC | 171 |
| AM05849-AS | usAfscsCfaAfuuuauGfcCfuAfcAfgusu | 101 | UACCAAUUUAUGCCUACAGUU | 154 |
| AM05850-AS | usAfscsCfaAfuuuauGfcCfuAfcAfgcsc | 102 | UACCAAUUUAUGCCUACAGCC | 162 |
| AM05851-AS | usAfscsCfaAfuuuauGfcCfuAfcAfgcusu | 103 | UACCAAUUUAUGCCUACAGCUU | 172 |
| AM05852-AS | usAfscsCfaAfuuuauGfcCfuAfcAfgccsu | 104 | UACCAAUUUAUGCCUACAGCCU | 173 |
| AM05853-AS | usAfscsCfaAfuuuauGfcCfuAfcAfgccusu | 105 | UACCAAUUUAUGCCUACAGCCUU | 163 |
| AM05854-AS | usAfscsCfaAfuuuauGfcCfuAfcAfgccusc | 106 | UACCAAUUUAUGCCUACAGCCUC | 164 |
| AM05855-AS | cPrpusAfscsCfaAfuUfuAfuGfcCfuAfcAfgusu | 107 | UACCAAUUUAUGCCUACAGUU | 154 |
| AM05860-AS | cPrpusAfsusUfgAfgAfgAfaGfuCfcAfcCfaCfsg | 108 | UAUUGAGAGAAGUCCACCACG | 160 |
| AM05862-AS | usAfsusUfgAfgagaaGfuCfcAfcCfausu | 109 | UAUUGAGAGAAGUCCACCAUU | 174 |
| AM05863-AS | usAfsusUfgAfgagaaGfuCfcAfcCfacsg | 110 | UAUUGAGAGAAGUCCACCACG | 160 |
| AM05864-AS | usAfsusUfgAfgagaaGfuCfcAfcCfacsusu | 111 | UAUUGAGAGAAGUCCACCACUU | 175 |
| AM05865-AS | usAfsusUfgAfgagaaGfuCfcAfcCfacsgsa | 112 | UAUUGAGAGAAGUCCACCACGA | 170 |
| AM05867-AS | vpusAfsusUfgAfgagaaGfuCfcAfcCfaCfsg | 113 | UAUUGAGAGAAGUCCACCACG | 160 |
| AM05873-AS | usUfsusGfaGfagaagUfcCfaCfcAfcusu | 114 | UUUGAGAGAAGUCCACCACUU | 165 |
| AM05874-AS | usUfsusGfaGfagaagUfcCfaCfcAfcgsa | 115 | UUUGAGAGAAGUCCACCACGA | 157 |
| AM05875-AS | usUfsusGfaGfagangUfcCfaCfcAfcgusu | 116 | UUUGAGAGAAGUCCACCACGUU | 176 |

TABLE 3-continued

HBV RNAi Agent antisense strand sequences.

| AS Strand ID | Modified sequence (5'→3') | SEQ ID NO. | Unmodified sequence (5'→3') | SEQ ID NO. |
|---|---|---|---|---|
| AM05876-AS | usUfsusGfaGfagaagUfcCfaCfcAfcgasg | 117 | UUUGAGAGAAGUCCACCACGAG | 177 |
| AM05877-AS | cPrpusUfsusGfaGfaGfaAfgUfcCfaCfcAfcusu | 118 | UUUGAGAGAAGUCCACCACUU | 165 |
| AM06074-AS | cPrpusAfsusUfgAfgagaaGfuCfcAfcCfacsusu | 119 | UAUUGAGAGAAGUCCACCACUU | 175 |
| AM06142-AS | usAfsusUfgAfgagaaGfuCfcAfcCfacusu | 120 | UAUUGAGAGAAGUCCACCACUU | 175 |
| AM06143-AS | usAfsusUfgAfgagaaGfuCfcAfcCfacgusu | 121 | UAUUGAGAGAAGUCCACCACGUU | 168 |
| AM06144-AS | usAfsusUfgAfgagaaGfuCfcAfcCfacuus(invAb) | 122 | UAUUGAGAGAAGUCCACCACUU | 175 |
| AM06145-AS | usAfsusUfgAfgagaaGfuCfcAfcCfacgasg | 123 | UAUUGAGAGAAGUCCACCACGAG | 169 |
| AM06222-AS | usAfsusUfgAfgAfgAfaGfuCfcAfcCfacusu | 124 | UAUUGAGAGAAGUCCACCACUU | 175 |
| AM06281-AS | asGfsasAfaAfuUfgAfgAfgAfaGfuCfcusu | 125 | AGAAAUUGAGAGAAGUCCUU | 178 |
| AM06282-AS | asGfsasAfaAfuUfgAfgAfgAfaGfuCfcasc | 126 | AGAAAUUGAGAGAAGUCCAC | 171 |
| AM06283-AS | asGfsasAfaAfuUfgAfgAfgAfaGfuCfcacusu | 127 | AGAAAUUGAGAGAAGUCCACUU | 179 |
| AM06284-AS | asGfsasAfaAfuUfgAfgAfgAfaGfuCfcacsc | 128 | AGAAAUUGAGAGAAGUCCACC | 180 |
| AM06285-AS | usGfsasAfaAfuUfgAfgAfgAfaGfuCfcusu | 129 | UGAAAUUGAGAGAAGUCCUU | 152 |
| AM06286-AS | usGfsasAfaAfuUfgAfgAfgAfaGfuCfcasc | 130 | UGAAAUUGAGAGAAGUCCAC | 181 |
| AM06299-AS | asCfscsAfaUfUfaUfgCfcUfaCfaGfcusu | 131 | ACCAAUUUAUGCCUACAGCUU | 182 |
| AM06300-AS | asCfscsAfaUfUfaUfgCfcUfaCfaGfccusu | 132 | ACCAAUUUAUGCCUACAGCCUU | 183 |
| AM06301-AS | asCfscsAfaUfUfaUfgCfcUfaCfaGfccusc | 133 | ACCAAUUUAUGCCUACAGCCUC | 184 |
| AM06302-AS | usCfscsAfaUfUfaUfgCfcUfaCfaGfcusu | 134 | UCCAAUUUAUGCCUACAGCUU | 185 |
| AM06303-AS | usCfscsAfaUfUfaUfgCfcUfaCfaGfccusu | 135 | UCCAAUUUAUGCCUACAGCCUU | 186 |
| AM06463-AS | cPrpusAfscsCfaAfuUfuAfuGfcCfuAfcAfgcsc | 136 | UACCAAUUUAUGCCUACAGCC | 162 |
| AM06464-AS | usAfscsCfaAfuUfuAfuGfcCfuAfcAfgscsc | 137 | UACCAAUUUAUGCCUACAGCC | 162 |
| AM06465-AS | cPrpusAfscsCfaAfuUfuAfuGfcCfuAfcAfgscsc | 138 | UACCAAUUUAUGCCUACAGCC | 162 |
| AM06604-AS | usAfscsCfaAfuUfuAfuGfcCfuAfcAfgcsu | 139 | UACCAAUUUAUGCCUACAGCU | 187 |
| AM06606-AS | usAfscsCfaAfuUfuAfuGfcCfuAfcAfgcsg | 140 | UACCAAUUUAUGCCUACAGCG | 188 |
| AM06608-AS | asAfscsCfaAfuUfuAfuGfcCfuAfcAfgcsc | 141 | AACCAAUUUAUGCCUACAGCC | 189 |
| AM06611-AS | usAfscsCfaAfuUfUfAfuGfcCfuAfcAfgusu | 142 | UACCAAUUUAUGCCUACAGUU | 154 |
| AM06612-AS | usAfscsCfaAfuUfuAfuGfcCfuAfcAfgCfsc | 143 | UACCAAUUUAUGCCUACAGCC | 162 |
| AM06614-AS | asCfscAfaUfuUfaUfgCfcUfaCfaGfcCfsu | 144 | ACCAAUUUAUGCCUACAGCCU | 190 |
| AM06616-AS | usCfscAfaUfuUfaUfgCfcUfaCfaGfcCfsu | 145 | UCCAAUUUAUGCCUACAGCCU | 191 |
| AM06618-AS | asCfscAfaUfuUfaUfgCfcUfaCfaGfccsg | 146 | ACCAAUUUAUGCCUACAGCCG | 192 |
| AM06620-AS | usCfscAfaUfuUfaUfgCfcUfaCfaGfccsg | 147 | UCCAAUUUAUGCCUACAGCCG | 193 |
| AM06751-AS | usAfscsCfaAfuUfuAfuGfcCfuAfcAfggsg | 148 | UACCAAUUUAUGCCUACAGGG | 194 |

TABLE 4

HBV RNAi agent sense strand sequences.

| Strand ID | Modified sequence (5'→3') | SEQ ID NO. | Unmodified sequence (5'→3') | SEQ ID NO. |
|---|---|---|---|---|
| AM04444-SS | (NAG25)uusgsccuguagGfCfAfuaaauugguaus(invdT) | 195 | UUGCCUGUAGGCAUAAAUUGGUAUT | 275 |
| AM04445-SS | (NAG25)uauausgsccuguagGfCfAfuaaauuggu(invdA) | 196 | UAUAUGCCUGUAGGCAUAAAUUGGUA | 276 |
| AM04767-SS | (NAG25)gcggagsgcuguagGfCfAfuaaauuggTM(invdA) | 197 | GCGGAGGCUGUAGGCAUAAAUUGGTA | 277 |
| AM05010-SS | (NAG25)scsuguagGfCfAfuaaauugguauus(invAb) | 198 | CUGUAGGCAUAAAUUGGUAUU | 278 |
| AM05015-SS | (NAG25)sgsccuguagGfCfAfuaaauuggas(invAb) | 199 | GCCUGUAGGCAUAAAUUGGUA | 279 |
| AM05016-SS | (NAG25)sgsccuguagGfCfAfuaaauuggus(invdA) | 200 | GCCUGUAGGCAUAAAUUGGUA | 279 |
| AM05017-SS | (NAG25)sgsccuguagGfCfAfuaaauugguAMs(invAb) | 201 | GCCUGUAGGCAUAAAUUGGUA | 279 |
| AM05018-SS | (NAG25)sgsccuguagGfCfAfuaaauuggTMAMs(invAb) | 202 | GCCUGUAGGCAUAAAUUGGTA | 280 |
| AM05019-SS | (NAG25)sasacuguagGfCfAfuaaauuggas(invAb) | 203 | AACUGUAGGCAUAAAUUGGUA | 281 |
| AM05034-SS | (NAG25)suscguggugGfAfCfuucucucaaus(invAb) | 204 | UCGUGGUGGACUUCUCUCAAU | 282 |
| AM05046-SS | (NAG25)sasaguggugGfAfCfuucucucaaus(invAb) | 205 | AAGUGGUGGACUUCUCUCAAU | 283 |
| AM05047-SS | (NAG25)suscguggugGfAfCfuucucucaAMTMs(invAb) | 206 | UCGUGGUGGACUUCUCUCAAT | 284 |
| AM05048-SS | (NAG25)scsguggugAfCfUfucucucaauus(invAb) | 207 | CGUGGUGGACUUCUCUCAAUU | 285 |
| AM05049-SS | (NAG25)sasaugguggAfCfUfucucucaauus(invAb) | 208 | AAUGGUGGACUUCUCUCAAUU | 286 |
| AM05050-SS | (NAG25)scsguggugAfCfUfucucucaaTMTMs(invAb) | 209 | CGUGGUGGACUUCUCUCAATT | 287 |
| AM05051-SS | (NAG25)sgsgacuucuCfUfCfaauuuucuaas(invAb) | 210 | GGACUUCUCUCAAUUUUCUAA | 288 |
| AM05063-SS | (NAG25)scsguggugAfCfUfucucucaauas(invAb) | 211 | CGUGGUGGACUUCUCUCAAUA | 289 |
| AM05064-SS | (NAG25)suscguggugGfAfCfuucucucaaas(invAb) | 212 | UCGUGGUGGACUUCUCUCAAA | 290 |
| AM05346-SS | (NAG31)sasccuguagGfCfAfuaaauuggas(invAb) | 213 | ACCUGUAGGCAUAAAUUGGUA | 291 |
| AM05347-SS | (NAG31)s(invAb)scuguagGfCfAfuaaauuggas(invAb) | 214 | CUGUAGGCAUAAAUUGGUA | 292 |
| AM05606-SS | (NAG25)s(invAb)scuguagGfCfAfuaaauuggas(invAb) | 215 | CUGUAGGCAUAAAUUGGUA | 292 |
| AM05607-SS | (NAG37)s(invAb)scuguagGfCfAfuaaauuggas(invAb) | 216 | CUGUAGGCAUAAAUUGGUA | 292 |
| AM05615-SS | (NAG25)s(invAb)sacuguagGfCfAfuaaauuggas(invAb) | 217 | ACUGUAGGCAUAAAUUGGUA | 293 |
| AM05616-SS | (NAG25)sgsgcuguagGfCfAfuaaatiuggas(invAb) | 218 | GGCUGUAGGCAUAAAUUGGUA | 294 |
| AM05617-SS | (NAG37)sasaguggugGfAfCfuucucucaaus(invAb) | 219 | AAGUGGUGGACUUCUCUCAAU | 283 |
| AM05620-SS | (NAG25)sasaguggugGfAfCfuucucucaaas(invAb) | 220 | AAGUGGUGGACUUCUCUCAAA | 295 |
| AM05622-SS | (NAG25)scscguggugGfAfCfuucucucaaus(invAb) | 221 | CCGUGGUGGACUUCUCUCAAU | 296 |
| AM05624-SS | (NAG25)s(invAb)sccguggugGfAfCfuucucucaaus(invAb) | 222 | CCGUGGUGGACUUCUCUCAAU | 296 |
| AM05627-SS | (NAG25)scsucguggugGfAfCfuucucucaaus(invAb) | 223 | CUCGUGGUGGACUUCUCUCAAU | 297 |
| AM05629-SS | (NAG25)s(invAb)sguggugGfAfCfuucucucaaus(invAb) | 224 | GUGGUGGACUUCUCUCAAU | 298 |
| AM05630-SS | (NAG25)s(invAb)sguggugGfAfCfuucucucaauusu(invAb) | 225 | GUGGUGGACUUCUCUCAAUU | 299 |
| AM05636-SS | (NAG25)suscguggugAfCfUfucucucaauus(invAb) | 226 | UCGUGGUGGACUUCUCUCAAUU | 300 |
| AM05639-SS | (NAG25)s(invAb)sugguggAfCfUfucucucaauus(invAb) | 227 | UGGUGGACUUCUCUCAAUU | 301 |
| AM05640-SS | (NAG37)s(invAb)sugguggAfCfUfucucucaauus(invAb) | 228 | UGGUGGACUUCUCUCAAUU | 301 |
| AM05746-SS | (NAG25)sgsuggacuuCfUfCfucaauuuucus(invAb) | 229 | GUGGACUUCUCUCAAUUUUCU | 302 |
| AM05856-SS | (NAG25)s(invAb)scuguagGfCfAfuaaauugguausu(invAb) | 230 | CUGUAGGCAUAAAUUGGUAUU | 278 |
| AM05857-SS | (NAG25)s(invAb)sgcuguagGfCfAfuaaauugguausu(invAb) | 231 | GCUGUAGGCAUAAAUUGGUAUU | 303 |

TABLE 4-continued

HBV RNAi agent sense strand sequences.

| Strand ID | Modified sequence (5'→3') | SEQ ID NO. | Unmodified sequence (5'→3') | SEQ ID NO. |
|---|---|---|---|---|
| AM05858-SS | (NAG25)s(invAb)sggcuguagGfCfAfuaaauuggguausu(invAb) | 232 | GGCUGUAGGCAUAAAUUGGUAUU | 304 |
| AM05859-SS | (NAG25)s(invAb)saacuguagGfCfAfuaaauuggguausu(invAb) | 233 | AACUGUAGGCAUAAAUUGGUAUU | 305 |
| AM05868-SS | (NAG25)s(invAb)uggugGAfCfUfucucucaauausu(invAb) | 234 | UGGUGGACUUCUCUCAAUAUU | 306 |
| AM05869-SS | (NAG25)s(invAb)sguggugAfCfUfucucucaauausu(invAb) | 235 | GUGGUGGACUUCUCUCAAUAUU | 307 |
| AM05870-SS | (NAG25)sasaugguggAfCfUfucucucaauausu(invAb) | 236 | AAUGGUGGACUUCUCUCAAUAUU | 308 |
| AM05871-SS | (NAG25)scsguggugAfCfUfucucucaauausu(invAb) | 237 | CGUGGUGGACUUCUCUCAAUAUU | 309 |
| AM05872-SS | (NAG31)scsguggugAfCfUfucucucaauas(invAb) | 238 | CGUGGUGGACUUCUCUCAAUA | 289 |
| AM05879-SS | (NAG25)s(invAb)saaguggugGfAfCfuucucucaaus(invAb) | 239 | AAGUGGUGGACUUCUCUCAAU | 283 |
| AM05880-SS | (NAG25)s(invAb)sguggugGfAfCfuucucucaaausu(invAb) | 240 | GUGGUGGACUUCUCUCAAAUU | 310 |
| AM05881-SS | (NAG25)s(invAb)scguggugGfAfCfuucucucaaausu(invAb) | 241 | CGUGGUGGACUUCUCUCAAAUU | 311 |
| AM05882-SS | (NAG25)sasaguggugGfAfCfuucucucaaausu(invAb) | 242 | AAGUGGUGGACUUCUCUCAAAUU | 312 |
| AM05883-SS | (NAG25)suscguggugGfAfCfuucucucaaausu(invAb) | 243 | UCGUGGUGGACUUCUCUCAAAUU | 313 |
| AM06146-SS | (NAG37)s(invAb)sguggugGAfCfUfucucucaauausu(invAb) | 244 | GUGGUGGACUUCUCUCAAUAUU | 307 |
| AM06147-SS | (NAG37)s(invAb)scgugguggAfCfUfucucucaauausu(invAb) | 245 | CGUGGUGGACUUCUCUCAAUAUU | 309 |
| AM06148-SS | (NAG37)s(invAb)scucgugguggAfCfUfucucucaauas(invAb) | 246 | CUCGUGGUGGACUUCUCUCAAUA | 314 |
| AM06149-SS | (NAG37)s(invAb)scucgugguggAfCfUfucucucaauausu(invAb) | 247 | CUCGUGGUGGACUUCUCUCAAUAUU | 315 |
| AM06150-SS | (NAG37)s(invAb)sggcuguagGfCfAfuaaauuggas(invAb) | 248 | GGCUGUAGGCAUAAAUUGGUA | 294 |
| AM06151-SS | (NAG37)s(invAb)sgaggcuguagGfCfAfuaaauuggguas(invAb) | 249 | GAGGCUGUAGGCAUAAAUUGGUA | 316 |
| AM06152-SS | (NAG37)s(invAb)sgaggcuguagGfCfAfuaaauuggguausu(invAb) | 250 | GAGGCUGUAGGCAUAAAUUGGUAUU | 317 |
| AM06287-SS | (NAG37)s(invAb)sggacuuCfUfCfucaauuucus(invAb) | 251 | GGACUUCUCUCAAUUUUCU | 318 |
| AM06288-SS | (NAG37)s(invAb)sguggacuuCfUfCfucaauuucus(invAb) | 252 | GUGGACUUCUCUCAAUUUUCU | 302 |
| AM06289-SS | (NAG37)s(invAb)sgguggacuuCfUfCfucaauuucus(invAb) | 253 | GGUGGACUUCUCUCAAUUUUCU | 319 |
| AM06290-SS | (NAG37)s(invAb)sggacuuCfUfCfucaauuucas(invAb) | 254 | GGACUUCUCUCAAUUUUCA | 320 |
| AM06291-SS | (NAG37)s(invAb)sguggacuuCfUfCfucaauuucas(invAb) | 255 | GUGGACUUCUCUCAAUUUUCA | 321 |
| AM06304-SS | (NAG37)s(invAb)sgcuguaGfGfCfauaaauuggus(invAb) | 256 | GCUGUAGGCAUAAAUUGGU | 322 |
| AM06305-SS | (NAG37)s(invAb)sggcuguaGfGfCfauaaauuggus(invAb) | 257 | GGCUGUAGGCAUAAAUUGGU | 323 |
| AM06306-SS | (NAG37)s(invAb)sgaggcuguaGfGfCfauaaauuggus(invAb) | 258 | GAGGCUGUAGGCAUAAAUUGGU | 324 |
| AM06307-SS | (NAG37)s(invAb)sgcuguaGfGfCfauaaauuggas(invAb) | 259 | GCUGUAGGCAUAAAUUGGA | 325 |
| AM06308-SS | (NAG37)s(invAb)sggcuguaGfGfCfauaaauuggas(invAb) | 260 | GGCUGUAGGCAUAAAUUGGA | 326 |
| AM06603-SS | (NAG37)s(invAb)sagcuguagGfCfAfuaaauugguas(invAb) | 261 | AGCUGUAGGCAUAAAUUGGUA | 327 |
| AM06605-SS | (NAG37)s(invAb)scgcuguagGfCfAfuaaauugguas(invAb) | 262 | CGCUGUAGGCAUAAAUUGGUA | 328 |
| AM06607-SS | (NAG37)s(invAb)sggcuguagGfCfAfuaaauugguus(invAb) | 263 | GGCUGUAGGCAUAAAUUGGUU | 329 |
| AM06609-SS | (NAG37)s(invAb)scuguagGfCfAfuaaauugguasuus(invAb) | 264 | CUGUAGGCAUAAAUUGGUAUU | 278 |
| AM06610-SS | (NAG37)s(invAb)scuGfuAfgGfCfAfuAfaAfUfgGfuasuus(invAb) | 265 | CUGUAGGCAUAAAUUGGUAUU | 278 |
| AM06613-SS | (NAG37)s(invAb)saggcuguaGfGfCfauaaauuggus(invAb) | 266 | AGGCUGUAGGCAUAAAUUGGU | 330 |
| AM06615-SS | (NAG37)s(invAb)saggcuguaGfGfCfauaaauuggas(invAb) | 267 | AGGCUGUAGGCAUAAAUUGGA | 331 |
| AM06617-SS | (NAG37)s(invAb)scggcuguaGfGfCfauaaauuggus(invAb) | 268 | CGGCUGUAGGCAUAAAUUGGU | 332 |

TABLE 4-continued

HBV RNAi agent sense strand sequences.

| Strand ID | Modified sequence (5'→3') | SEQ ID NO. | Unmodified sequence (5'→3') | SEQ ID NO. |
|---|---|---|---|---|
| AM06619-SS | (NAG37)s(invAb)scggcuguaGfGfCfauaaauuggas(invAb) | 269 | CGGCUGUAGGCAUAAAUUGGA | 333 |
| AM06750-SS | (NAG37)s(invAb)scccuguagGfCfAfuaaauugguas(invAb) | 270 | CCCUGUAGGCAUAAAUUGGUA | 334 |
| AM06752-SS | (NAG37)csgcuguagGfCfAfuaaauugguas(invAb) | 271 | CGCUGUAGGCAUAAAUUGGUA | 328 |
| AM06753-SS | (NAG37)csccuguagGfCfAfuaaauugguas(invAb) | 272 | CCCUGUAGGCAUAAAUUGGUA | 334 |
| AM06776-SS | (NAG25)s(invAb)sguggacuuCfUfCfucaauuuucus(invAb) | 273 | GUGGACUUCUCUCAAUUUUCU | 302 |
| AM06777-SS | (NAG25)s(invAb)scgcuguagGfCfAfuaaauugguas(invAb) | 274 | CGCUGUAGGCAUAAAUUGGUA | 328 |

The HBV RNAi agents described herein are formed by annealing an antisense strand with a sense strand. A sense strand containing a sequence listed in Table 4 can be hybridized to any antisense strand containing a sequence listed in Table 3, provided the two sequences have a region of at least about 85% complementarity over a contiguous 16, 17, 18, 19, 20, or 21 nucleotide sequence.

In some embodiments, the antisense strand of an HBV RNAi agent disclosed herein differs by 0, 1, 2, or 3 nucleotides from any of the antisense strand sequences in Table 3. In some embodiments, the sense strand of an HBV RNAi agent disclosed herein differs by 0, 1, 2, or 3 nucleotides from any of the sense strand sequences in Table 4.

In some embodiments, an HBV RNAi agent antisense strand comprises a nucleotide sequence of any of the sequences in Table 3. In some embodiments, an HBV RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, 2-24, 1-25, 2-25, 1-26, or 2-26 of any of the sequences in Table 3.

In some embodiments, an HBV RNAi agent sense strand comprises the nucleotide sequence of any of the sequences in Table 4. In some embodiments, an HBV RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, 4-24, 1-25, 2-25, 3-25, 4-25, 1-26, 2-26, 3-26, or 4-26 of any of the sequences in Table 4.

For the HBV RNAi agents disclosed herein, the nucleotide at position 1 of the antisense strand (from 5' end→3' end) can be perfectly complementary to an HBV gene, or can be non-complementary to an HBV gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, an HBV RNAi agent antisense strand comprises the sequence of nucleotides (from 5' end→3' end) 2-18 or 2-19 of any of the antisense strand sequences in Table 3. In some embodiments, an HBV RNAi sense strand comprises the sequence of nucleotides (from 5' end→3' end) 1-17 or 1-18 of any of the sense strand sequences in Table 4.

In some embodiments, an HBV RNAi agent includes (i) an antisense strand comprising the sequence of nucleotides (from 5' end→3' end) 2-18 or 2-19 of any of the antisense strand sequences in Table 3, and (ii) a sense strand comprising the sequence of nucleotides (from 5' end→3' end) 1-17 or 1-18 of any of the sense strand sequences in Table 4.

A sense strand containing a sequence listed in Table 4 can be hybridized to any antisense strand containing a sequence listed in Table 3 provided the two sequences have a region of at least about 85% complementarity over a contiguous 16, 17, 18, 19, 20, or 21 nucleotide sequence. Representative sequence pairings are exemplified by the Duplex ID Nos. shown in Table 5.

In some embodiments, an HBV RNAi agent comprises of any of the Duplex ID Nos. presented herein. In some embodiments, an HBV RNAi agent consists of any of the Duplex ID Nos. presented herein. In some embodiments, an HBV RNAi agent comprises the sense strand and/or the antisense strand nucleotide sequences of any of the Duplex ID Nos. presented herein. In some embodiments, an HBV RNAi agent comprises the sense strand and antisense strand nucleotide sequences of any of the Duplex ID Nos. presented herein and a targeting group and/or linking group wherein the targeting group and/or linking group is covalently linked (i.e. conjugated) to the sense strand or the antisense strand. In some embodiments, an HBV RNAi agent comprises the sense strand and antisense strand modified nucleotide sequences of any of the Duplex ID Nos. presented herein. In some embodiments, an HBV RNAi agent comprises the sense strand and antisense strand modified nucleotide sequences of any of the Duplex ID Nos. presented herein and a targeting group and/or linking group wherein the targeting group and/or linking group is covalently linked to the sense strand or the antisense strand.

In some embodiments, an HBV RNAi agent comprises an antisense strand and a sense strand having the nucleotide sequences of any of the antisense strand/sense strand duplexes of Table 5, and further comprises an asialoglycoprotein receptor ligand targeting group.

In some embodiments, an HBV RNAi agent comprises an antisense strand and a sense strand having the nucleotide sequences of any of the antisense strand and/or sense strand nucleotide sequences of any of the duplexes of Table 5, and further comprises a targeting group selected from the group consisting of (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s.

In some embodiments, an HBV RNAi agent comprises an antisense strand and a sense strand having the modified nucleotide sequences of any of the antisense strand and/or sense strand nucleotide sequences of any of the duplexes of Table 5.

In some embodiments, an HBV RNAi agent comprises an antisense strand and a sense strand having the modified nucleotide sequences of any of the antisense strand and/or sense strand nucleotide sequences of any of the duplexes of Table 5, and further comprises an asialoglycoprotein receptor ligand targeting group.

In some embodiments, an HBV RNAi agent comprises any of the duplexes of Table 5.

In some embodiments, an HBV RNAi agent consists of any of the duplexes of Table 5.

TABLE 5

Examples of HBV RNAi agent duplexes.

| Duplex ID | Antisense Strand ID | Sense Strand ID |
|---|---|---|
| AD03498 | AM03508-AS | AM04445-SS |
| AD03499 | AM04441-AS | AM04444-SS |
| AD03500 | AM04442-AS | AM04444-SS |
| AD03501 | AM04443-AS | AM04444-SS |
| AD03738 | AM04768-AS | AM04767-SS |
| AD03739 | AM04769-AS | AM04767-SS |
| AD03967 | AM04443-AS | AM05010-SS |
| AD03968 | AM05011-AS | AM05010-SS |
| AD03969 | AM04443-AS | AM05015-SS |
| AD03970 | AM05011-AS | AM05019-SS |
| AD03971 | AM05012-AS | AM05015-SS |
| AD03972 | AM04443-AS | AM05016-SS |
| AD03973 | AM04443-AS | AM05017-SS |
| AD03974 | AM04443-AS | AM05018-SS |
| AD03975 | AM05013-AS | AM05015-SS |
| AD03976 | AM05014-AS | AM05019-SS |
| AD03977 | AM05013-AS | AM05017-SS |
| AD03978 | AM05013-AS | AM04444-SS |
| AD04001 | AM05052-AS | AM05034-SS |
| AD04002 | AM05053-AS | AM05034-SS |
| AD04003 | AM05054-AS | AM05046-SS |
| AD04004 | AM05052-AS | AM05047-SS |
| AD04005 | AM05055-AS | AM05064-SS |
| AD04006 | AM05056-AS | AM05048-SS |
| AD04007 | AM05057-AS | AM05048-SS |
| AD04008 | AM05058-AS | AM05049-SS |
| AD04009 | AM05056-AS | AM05050-SS |
| AD04010 | AM05060-AS | AM05063-SS |
| AD04176 | AM05351-AS | AM05346-SS |
| AD04177 | AM04443-AS | AM05347-SS |
| AD04178 | AM05011-AS | AM05347-SS |
| AD04412 | AM05011-AS | AM05606-SS |
| AD04413 | AM05011-AS | AM05607-SS |
| AD04414 | AM05608-AS | AM05606-SS |
| AD04415 | AM05011-AS | AM05615-SS |
| AD04416 | AM05609-AS | AM05616-SS |
| AD04417 | AM05610-AS | AM05616-SS |
| AD04418 | AM05611-AS | AM05616-SS |
| AD04419 | AM05612-AS | AM05616-SS |
| AD04420 | AM05613-AS | AM05616-SS |
| AD04421 | AM05614-AS | AM05616-SS |
| AD04422 | AM05054-AS | AM05617-SS |
| AD04423 | AM05618-AS | AM05046-SS |
| AD04425 | AM05621-AS | AM05620-SS |
| AD04426 | AM05623-AS | AM05622-SS |
| AD04427 | AM05623-AS | AM05624-SS |
| AD04428 | AM05626-AS | AM05622-SS |
| AD04429 | AM05626-AS | AM05624-SS |
| AD04430 | AM05628-AS | AM05627-SS |
| AD04431 | AM05054-AS | AM05629-SS |
| AD04432 | AM05054-AS | AM05630-SS |
| AD04433 | AM05631-AS | AM05048-SS |

TABLE 5-continued

Examples of HBV RNAi agent duplexes.

| Duplex ID | Antisense Strand ID | Sense Strand ID |
|---|---|---|
| AD04434 | AM05632-AS | AM05048-SS |
| AD04435 | AM05633-AS | AM05048-SS |
| AD04436 | AM05635-AS | AM05048-SS |
| AD04437 | AM05634-AS | AM05048-SS |
| AD04438 | AM05637-AS | AM05636-SS |
| AD04439 | AM05638-AS | AM05636-SS |
| AD04440 | AM05058-AS | AM05639-SS |
| AD04441 | AM05057-AS | AM05639-SS |
| AD04442 | AM05057-AS | AM05640-SS |
| AD04511 | AM05747-AS | AM05746-SS |
| AD04570 | AM05011-AS | AM05856-SS |
| AD04571 | AM05849-AS | AM05856-SS |
| AD04572 | AM05850-AS | AM05856-SS |
| AD04573 | AM05851-AS | AM05857-SS |
| AD04574 | AM05852-AS | AM05857-SS |
| AD04575 | AM05853-AS | AM05858-SS |
| AD04576 | AM05854-AS | AM05858-SS |
| AD04577 | AM05011-AS | AM05859-SS |
| AD04578 | AM05850-AS | AM05858-SS |
| AD04579 | AM05014-AS | AM05347-SS |
| AD04580 | AM05855-AS | AM05347-SS |
| AD04581 | AM05860-AS | AM05063-SS |
| AD04583 | AM05862-AS | AM05868-SS |
| AD04584 | AM05863-AS | AM05868-SS |
| AD04585 | AM05864-AS | AM05869-SS |
| AD04586 | AM05865-AS | AM05869-SS |
| AD04587 | AM05862-AS | AM05870-SS |
| AD04588 | AM05863-AS | AM05871-SS |
| AD04590 | AM05867-AS | AM05063-SS |
| AD04591 | AM05860-AS | AM05872-SS |
| AD04592 | AM05054-AS | AM05879-SS |
| AD04593 | AM05873-AS | AM05880-SS |
| AD04594 | AM05874-AS | AM05880-SS |
| AD04595 | AM05875-AS | AM05881-SS |
| AD04596 | AM05876-AS | AM05881-SS |
| AD04597 | AM05873-AS | AM05882-SS |
| AD04598 | AM05874-AS | AM05883-SS |
| AD04599 | AM05877-AS | AM05620-SS |
| AD04734 | AM06074-AS | AM05869-SS |
| AD04771 | AM06142-AS | AM06146-SS |
| AD04772 | AM06143-AS | AM06147-SS |
| AD04773 | AM06144-AS | AM06146-SS |
| AD04774 | AM06145-AS | AM06148-SS |
| AD04775 | AM06145-AS | AM06149-SS |
| AD04776 | AM05850-AS | AM06150-SS |
| AD04777 | AM05854-AS | AM06151-SS |
| AD04778 | AM05854-AS | AM06152-SS |
| AD04822 | AM06222-AS | AM06146-SS |
| AD04823 | AM05609-AS | AM06150-SS |
| AD04871 | AM06281-AS | AM06287-SS |
| AD04872 | AM06282-AS | AM06288-SS |
| AD04873 | AM06283-AS | AM06288-SS |
| AD04874 | AM06284-AS | AM06289-SS |
| AD04875 | AM06285-AS | AM06290-SS |
| AD04876 | AM06286-AS | AM06291-SS |
| AD04881 | AM06299-AS | AM06304-SS |
| AD04882 | AM06300-AS | AM06305-SS |
| AD04883 | AM06301-AS | AM06306-SS |
| AD04884 | AM06302-AS | AM06307-SS |
| AD04885 | AM06303-AS | AM06308-SS |
| AD04962 | AM05864-AS | AM06146-SS |
| AD04963 | AM05855-AS | AM05607-SS |
| AD04981 | AM06463-AS | AM06150-SS |
| AD04982 | AM06464-AS | AM06150-SS |
| AD04983 | AM06465-AS | AM06150-SS |
| AD05069 | AM06604-AS | AM06603-SS |
| AD05070 | AM06606-AS | AM06605-SS |
| AD05071 | AM06608-AS | AM06607-SS |
| AD05072 | AM05011-AS | AM06609-SS |
| AD05073 | AM06611-AS | AM06610-SS |
| AD05074 | AM06612-AS | AM06150-SS |
| AD05075 | AM06614-AS | AM06613-SS |
| AD05076 | AM06616-AS | AM06615-SS |
| AD05077 | AM06618-AS | AM06617-SS |
| AD05078 | AM06620-AS | AM06619-SS |

TABLE 5-continued

Examples of HBV RNAi agent duplexes.

| Duplex ID | Antisense Strand ID | Sense Strand ID |
|---|---|---|
| AD05147 | AM06751-AS | AM06750-SS |
| AD05148 | AM06606-AS | AM06752-SS |
| AD05149 | AM06751-AS | AM06753-SS |
| AD05164 | AM06282-AS | AM06776-SS |
| AD05165 | AM06606-AS | AM06777-SS |

In some embodiments, an HBV RNAi agent is prepared or provided as a salt, mixed salt, or a free-acid. The RNAi agents described herein, upon delivery to a cell expressing an HBV gene, inhibit or knockdown expression of one or more HBV genes in vivo.

Targeting Groups, Linking Groups, and Delivery Vehicles

In some embodiments, an HBV RNAi agent is conjugated to one or more non-nucleotide groups including, but not limited to a targeting group, linking group, delivery polymer, or a delivery vehicle. The non-nucleotide group can enhance targeting, delivery or attachment of the RNAi agent. Examples of targeting groups and linking groups are provided in Table 6. The non-nucleotide group can be covalently linked to the 3' and/or 5' end of either the sense strand and/or the antisense strand. In some embodiments, an HBV RNAi agent contains a non-nucleotide group linked to the 3' and/or 5' end of the sense strand. In some embodiments, a non-nucleotide group is linked to the 5' end of an HBV RNAi agent sense strand. A non-nucleotide group may be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting groups or targeting moieties enhance the pharmacokinetic or biodistribution properties of a conjugate to which they are attached to improve cell-specific distribution and cell-specific uptake of the conjugate. A targeting group can be monovalent, divalent, trivalent, tetravalent, or have higher valency. Representative targeting groups include, without limitation, compounds with affinity to cell surface molecule, cell receptor ligands, hapten, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) groups. In some embodiments, a targeting group comprises a galactose derivative cluster.

The HBV RNAi agents described herein may be synthesized having a reactive group, such as an amine group, at the 5'-terminus. The reactive group may be used to subsequently attach a targeting moiety using methods typical in the art.

In some embodiments, a targeting group comprises an asialoglycoprotein receptor ligand. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoylgalactos-amine (see for example: Iobst, S. T. and Drickamer, K. *J.B.C.* 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945). Galactose derivatives have been used to target molecules to hepatocytes in vivo through their binding to the asialoglycoprotein receptor (ASGPr) expressed on the surface of hepatocytes. Binding of ASGPr ligands to the ASGPr(s) facilitates cell-specific targeting to hepatocytes and endocytosis of the molecule into hepatocytes. ASGPr ligands can be monomeric (e.g., having a single galactose derivative) or multimeric (e.g., having multiple galactose derivatives). The galactose derivative or galactose derivative cluster may be attached to the 3' or 5' end of the RNAi polynucleotide using methods known in the art. The preparation of targeting groups, such as galactose derivative clusters, is described in, for example, U.S. patent application Ser. Nos. 15/452,324 and 15/452,423, the contents of both of which are incorporated herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or tri-valent galactose derivative). In some embodiments, the galactose derivative cluster comprises N-acetyl-galactosamines. In some embodiments, the galactose derivative cluster comprises three N-acetyl-galactosamines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, for example, U.S. Pat. No. 5,885,968; Biessen et al. J. Med. Chem 1995 Vol. 39 p. 1538-1546). In some embodiments, the PEG spacer is a $PEG_3$ spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

In some embodiments, pharmaceutical compositions for delivering an HBV RNAi agent to a liver cell in vivo are described. Such pharmaceutical compositions can include, for example, an HBV RNAi agent conjugated to a galactose derivative cluster. In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

Targeting groups include, but are not limited to, (PAZ), (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30). (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s. Other targeting groups, including galactose cluster targeting ligands, are known in the art.

In some embodiments, a linking group is conjugated to the RNAi agent. The linking group facilitates covalent linkage of the agent to a targeting group or delivery polymer or delivery vehicle. The linking group can be linked to the 3' or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, include, but are not limited to: reactive groups such a primary amines and alkynes, alkyl groups, abasic nucleosides, ribitol (abasic ribose), and/or PEG groups.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

Any of the HBV RNAi agent nucleotide sequences listed in Tables 3 and 4, whether modified or unmodified, may contain 3' or 5' targeting group and/or linking group. Any of the HBV RNAi agent sequences listed in Table 3 and 4 which contain a 3' or 5' targeting group and/or linking group, may alternatively contain no 3' or 5' targeting group and/or linking group, or may contain a different 3' or 5' targeting group and/or linking group including, but not limited to, those depicted in Table 3. Any of the HBV RNAi agent duplexes listed in Table 5, whether modified or unmodified, may further comprise a targeting group and/or linking group, including, but not limited to, those depicted in Table 3, and the targeting group or linking group may be attached to the 3' or 5' terminus of either the sense strand or the antisense strand of the HBV RNAi agent duplex.

Examples of targeting groups and linking groups are provided in Table 6. Table 4 provides several embodiments of HBV RNAi agent sense strands having a targeting group or linking group linked to the 5' or 3' end.

TABLE 6

Structures representing various modified nucleotides, targeting groups, and linking groups.

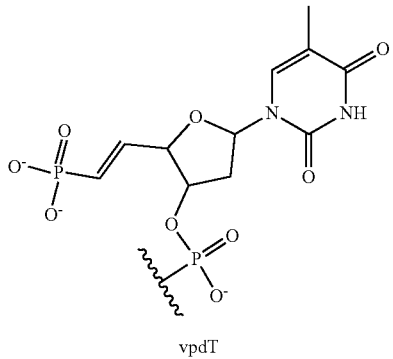 [SMILES: *P(=O)([O-])OC1CC(n2cc(C)c(=O)[nH]c2=O)OC1/C=C/P(=O)([O-])[O-]]

vpdT

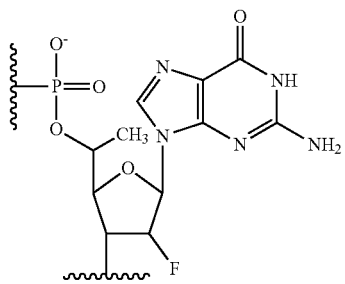

5Me-Gf

TABLE 6-continued
Structures representing various modified nucleotides, targeting groups, and linking groups.
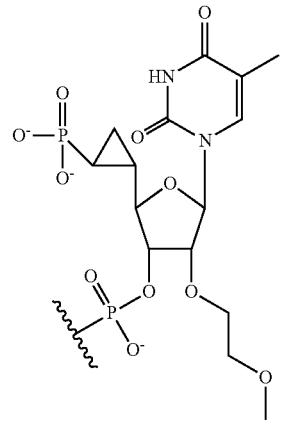
cPrpTM
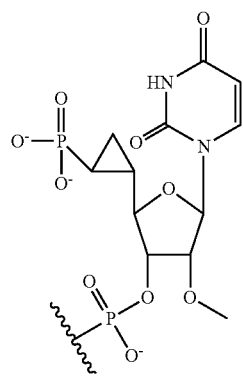
cPrpu
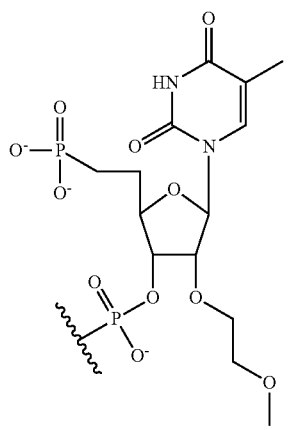
epTM TABLE 6-continued
Structures representing various modified nucleotides, targeting groups, and linking groups.
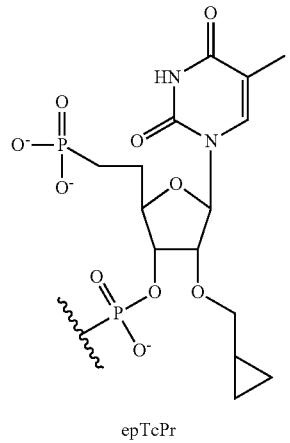 [SMILES: *P(=O)([O-])OC1C(CCP(=O)([O-])[O-])OC(n2cc(C)c(=O)[nH]c2=O)C1OCC1CC1]
epTcPr
When positioned internally on oligonucleotide:
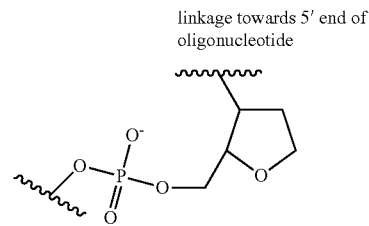
(invAb)
When positioned internally on oligonucleotide:
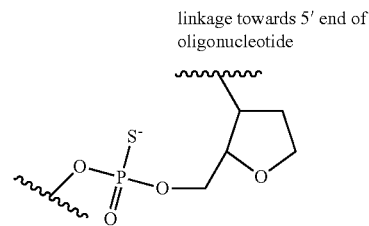
(invAb)s
When positioned at the 3' terminal end of oligonucleotide:
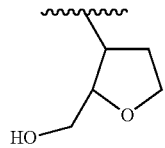
(invAb)

TABLE 6-continued
Structures representing various modified nucleotides, targeting groups, and linking groups.
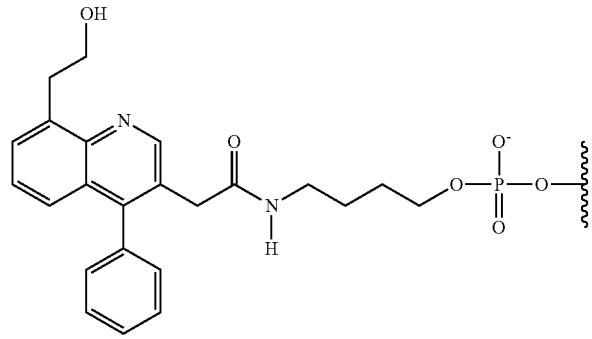
(PAZ)
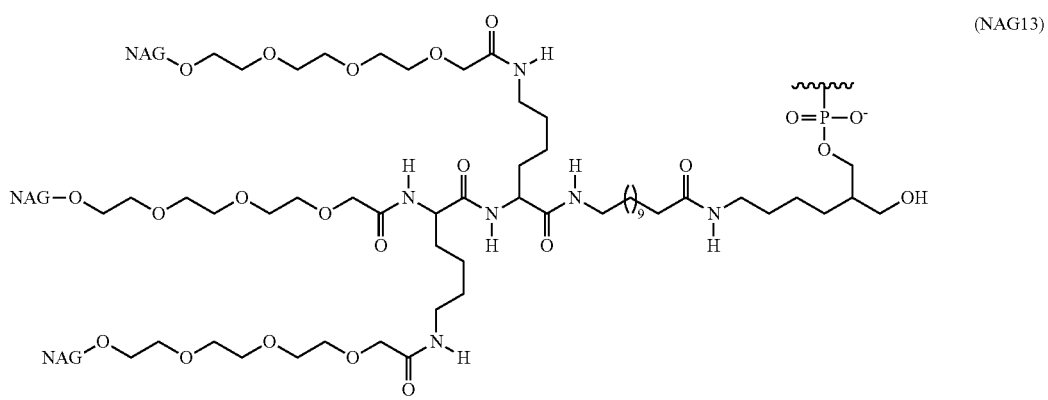
(NAG13)
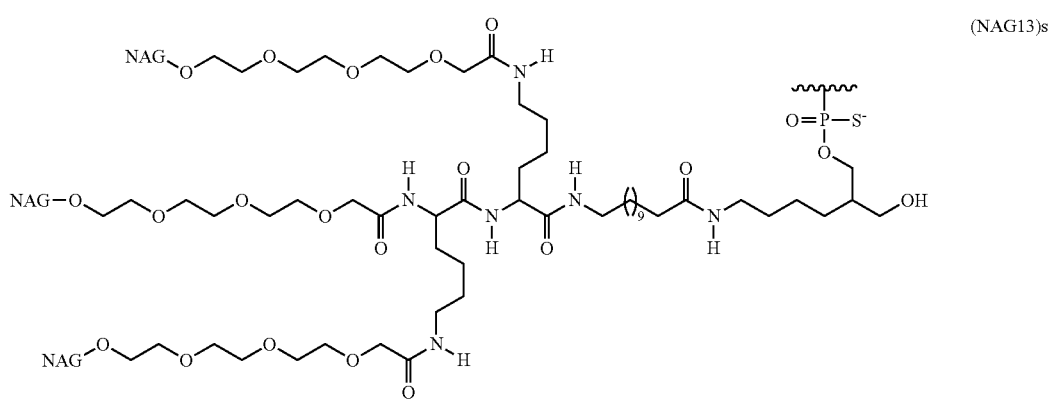
(NAG13)s TABLE 6-continued
Structures representing various modified nucleotides, targeting groups, and linking groups.
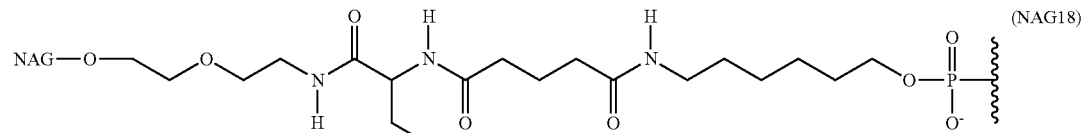
(NAG18)
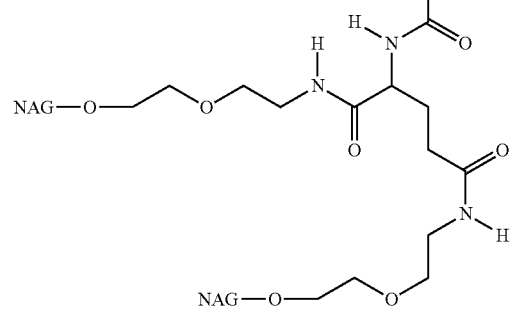
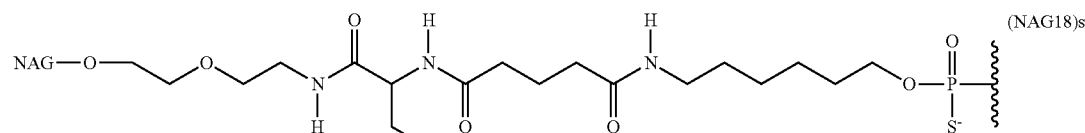
(NAG18)s
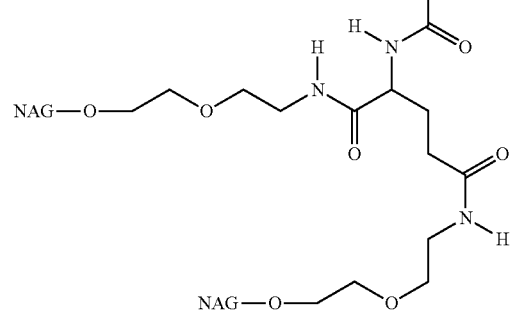
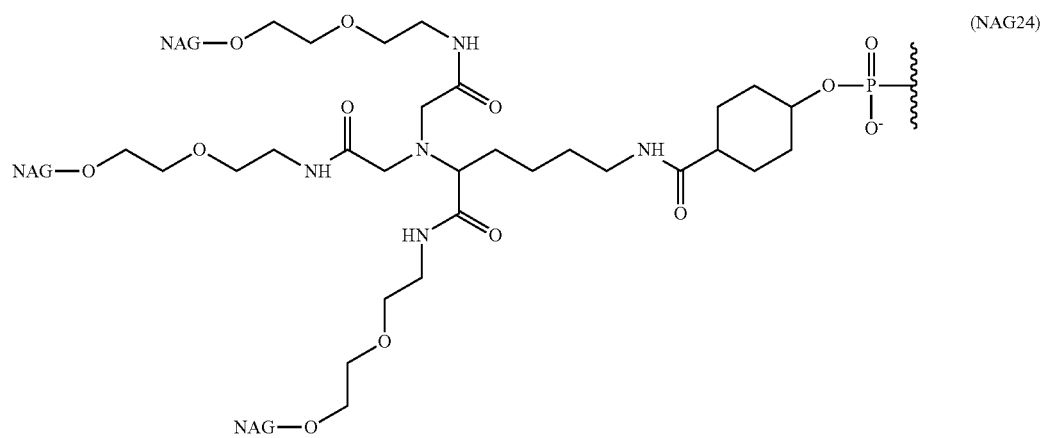
(NAG24)

TABLE 6-continued
Structures representing various modified nucleotides, targeting groups, and linking groups.
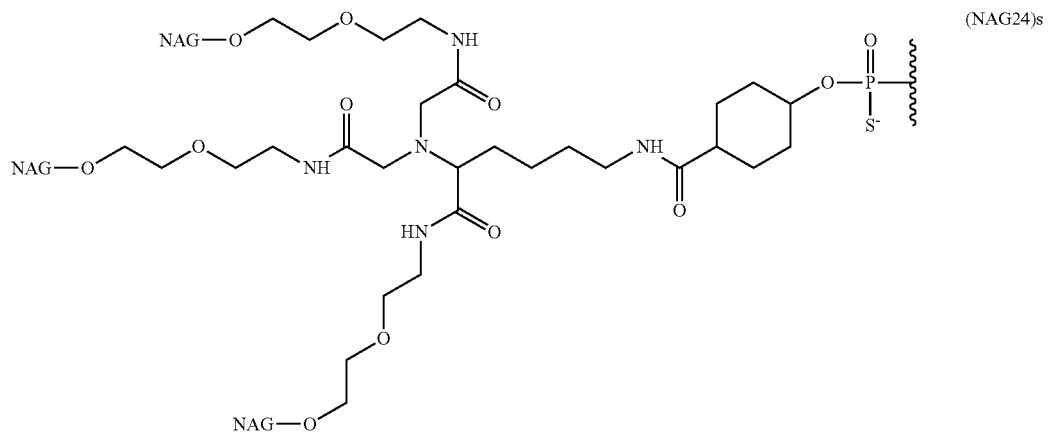
(NAG24)s
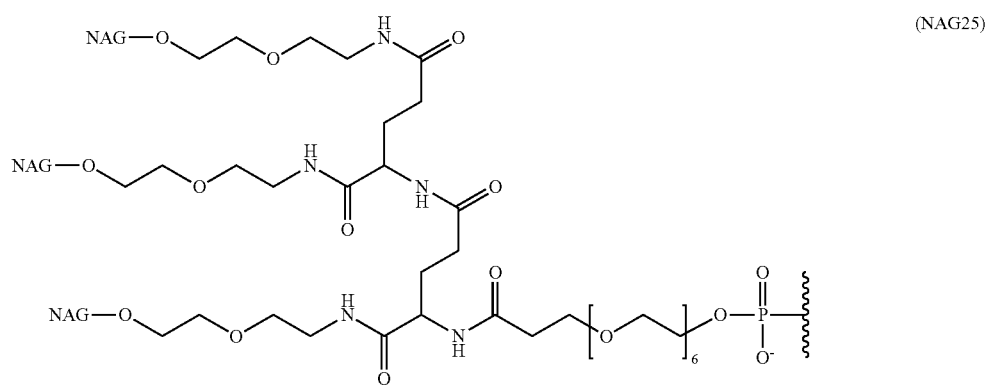
(NAG25)
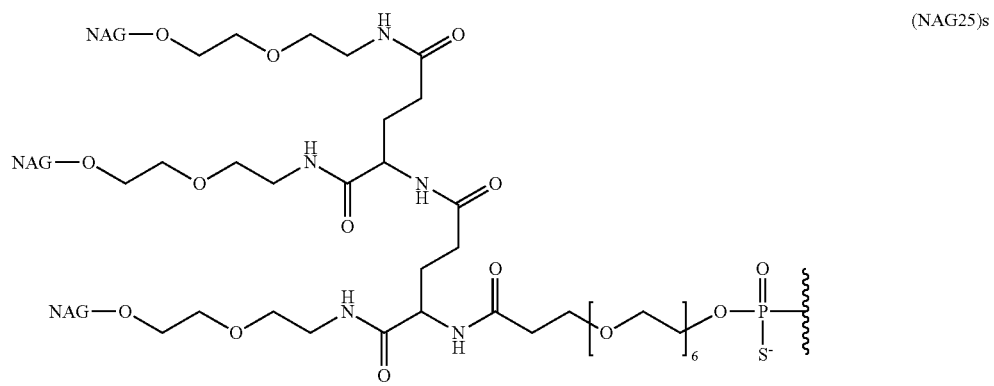
(NAG25)s
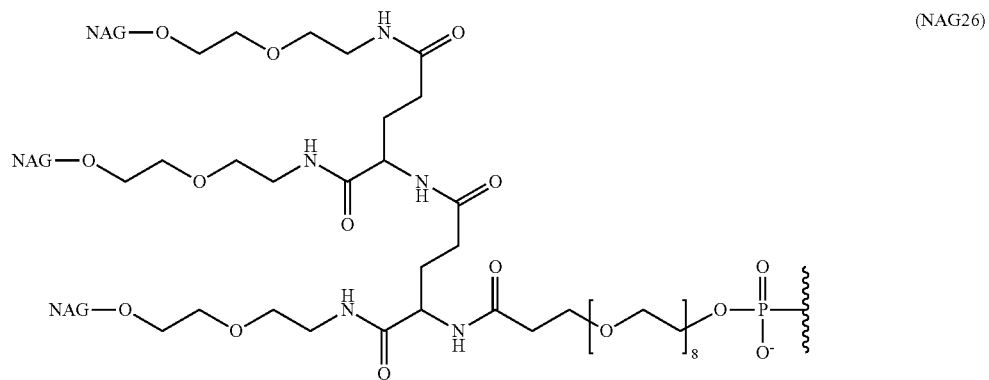
(NAG26)

TABLE 6-continued
Structures representing various modified nucleotides, targeting groups, and linking groups.
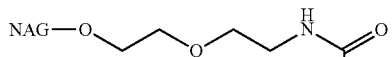
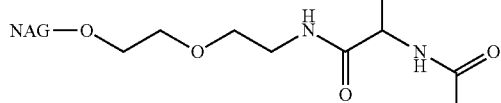
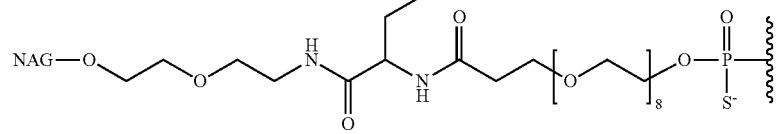
(NAG26)s
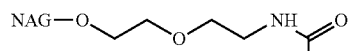
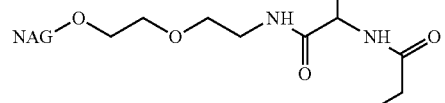
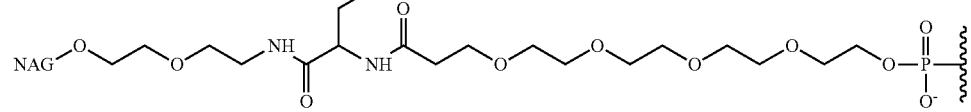
(NAG27)
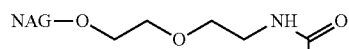
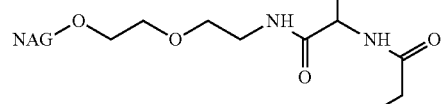
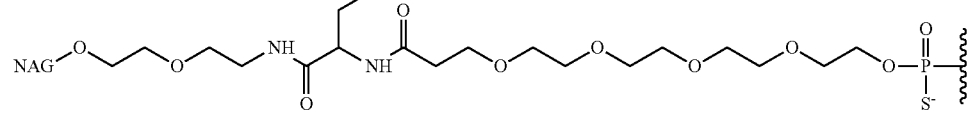
(NAG27)s
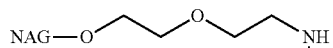
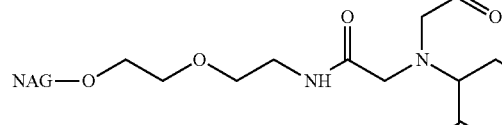
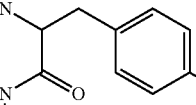
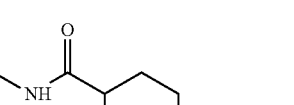
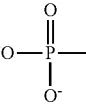
(NAG28)

TABLE 6-continued
Structures representing various modified nucleotides, targeting groups, and linking groups.
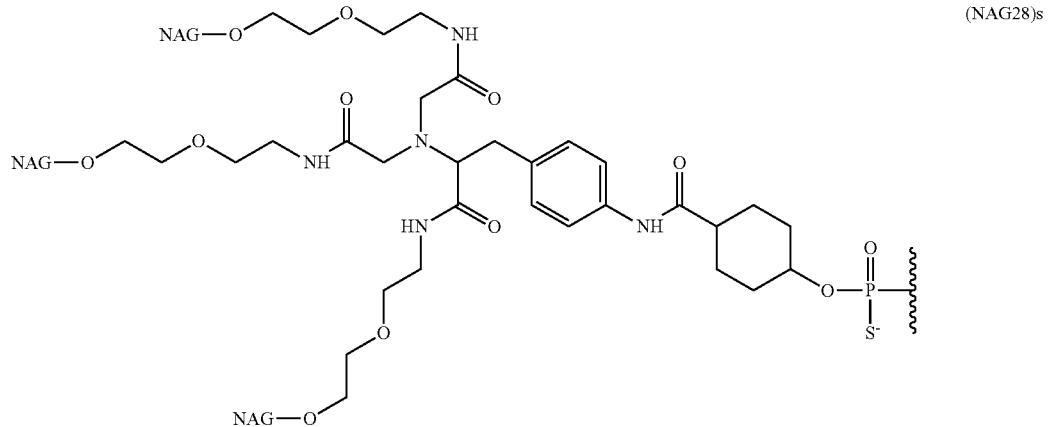
(NAG28)s
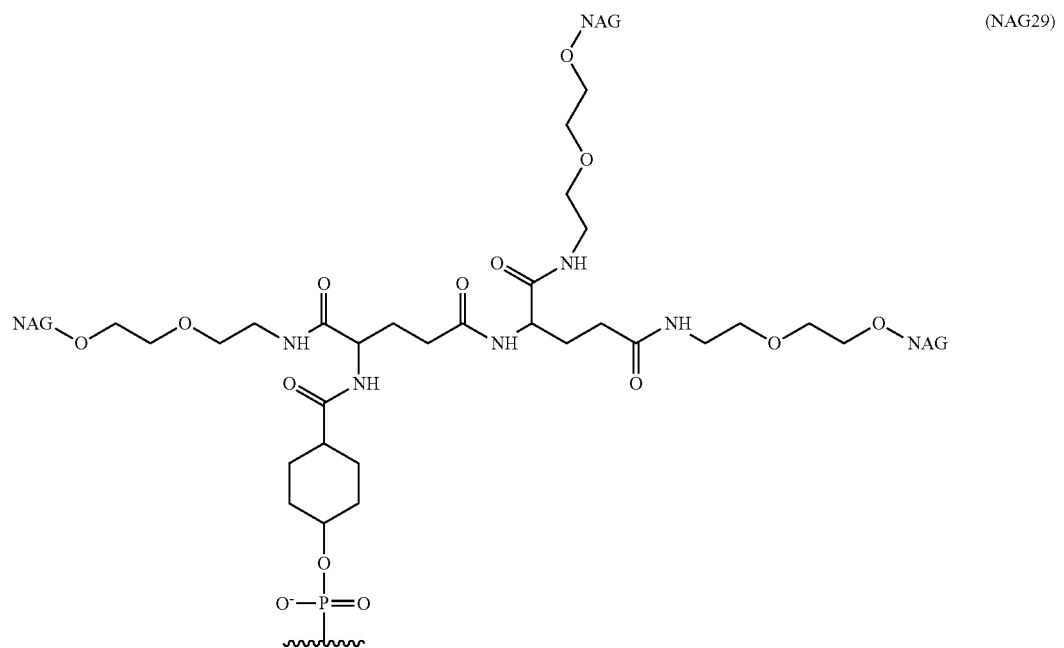
(NAG29)

TABLE 6-continued
Structures representing various modified nucleotides, targeting groups, and linking groups.
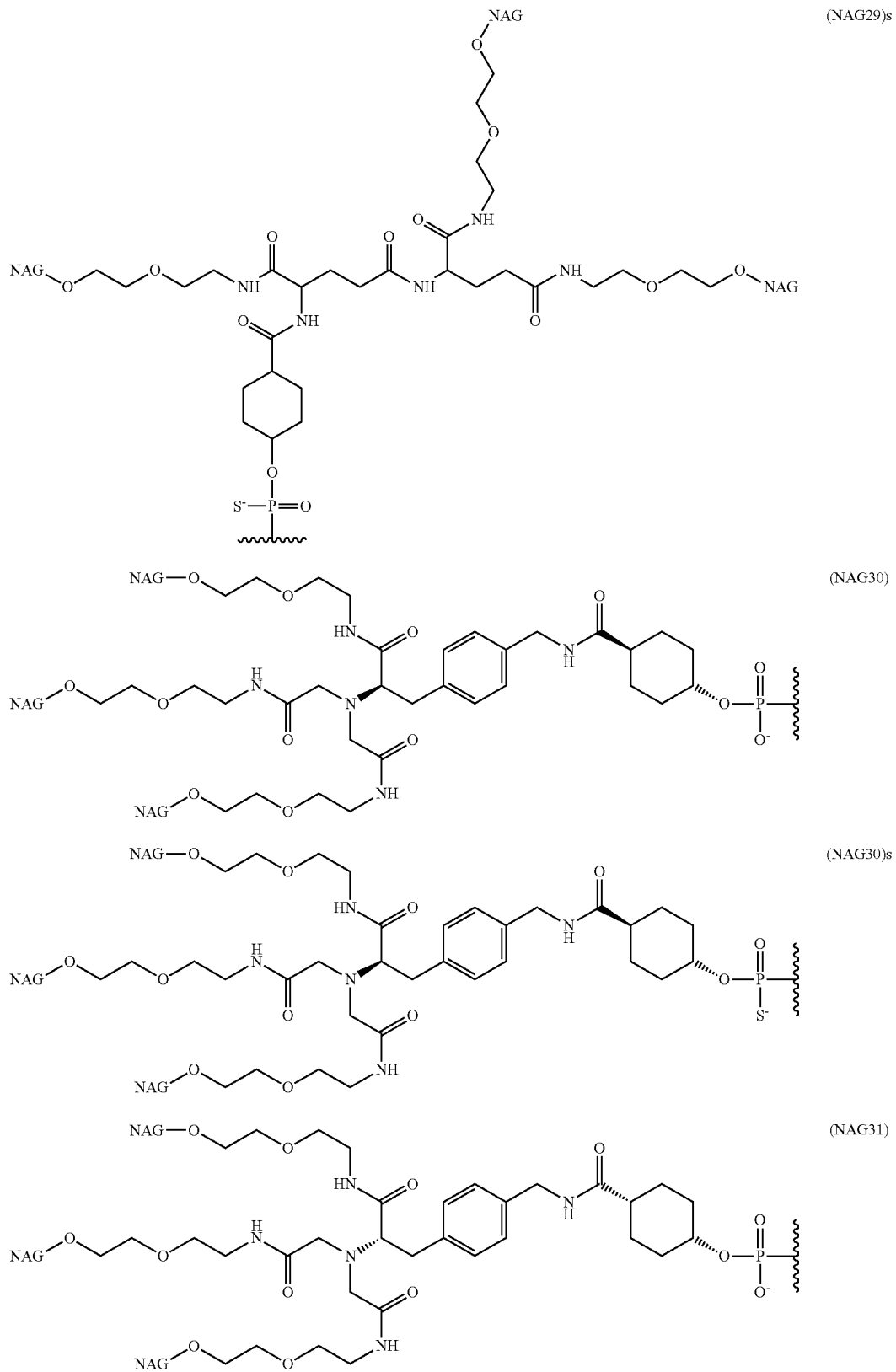

TABLE 6-continued
Structures representing various modified nucleotides, targeting groups, and linking groups.
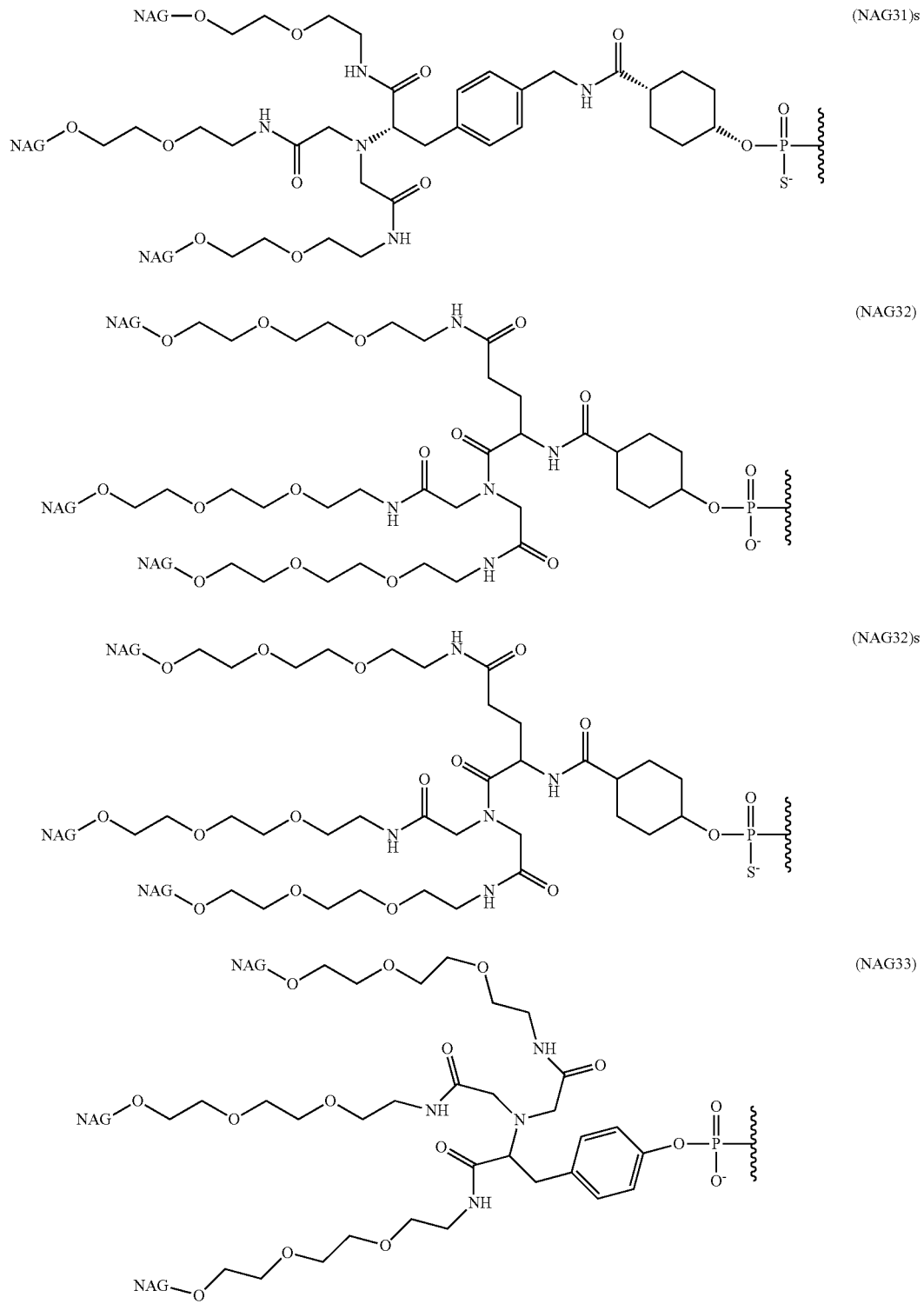

TABLE 6-continued
Structures representing various modified nucleotides, targeting groups, and linking groups.
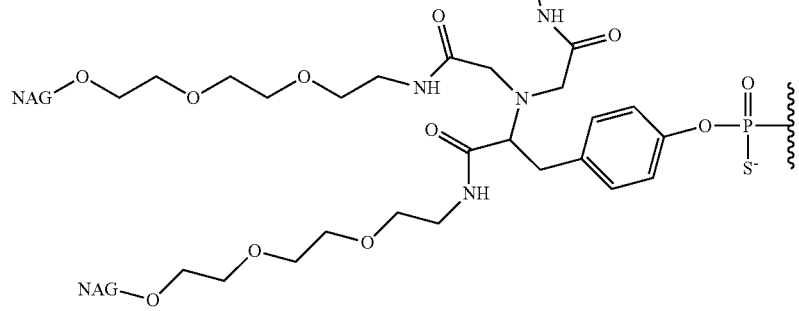
(NAG33)s
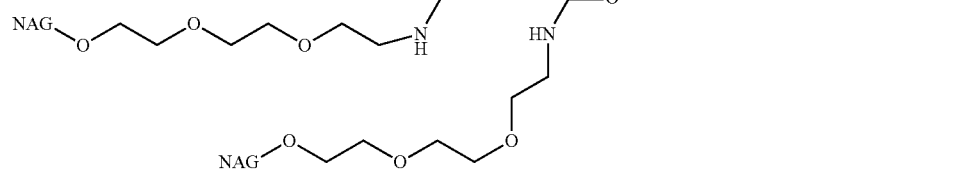
(NAG34)
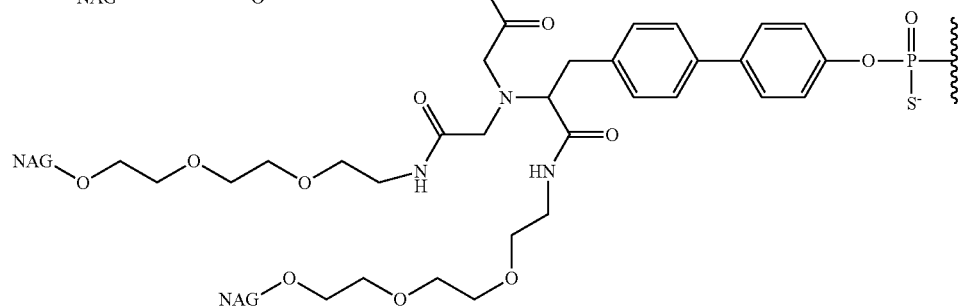
(NAG34)s
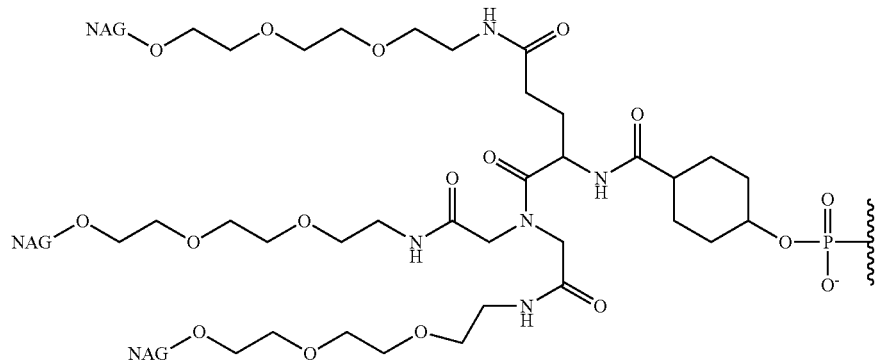
(NAG35)

TABLE 6-continued
Structures representing various modified nucleotides, targeting groups, and linking groups.
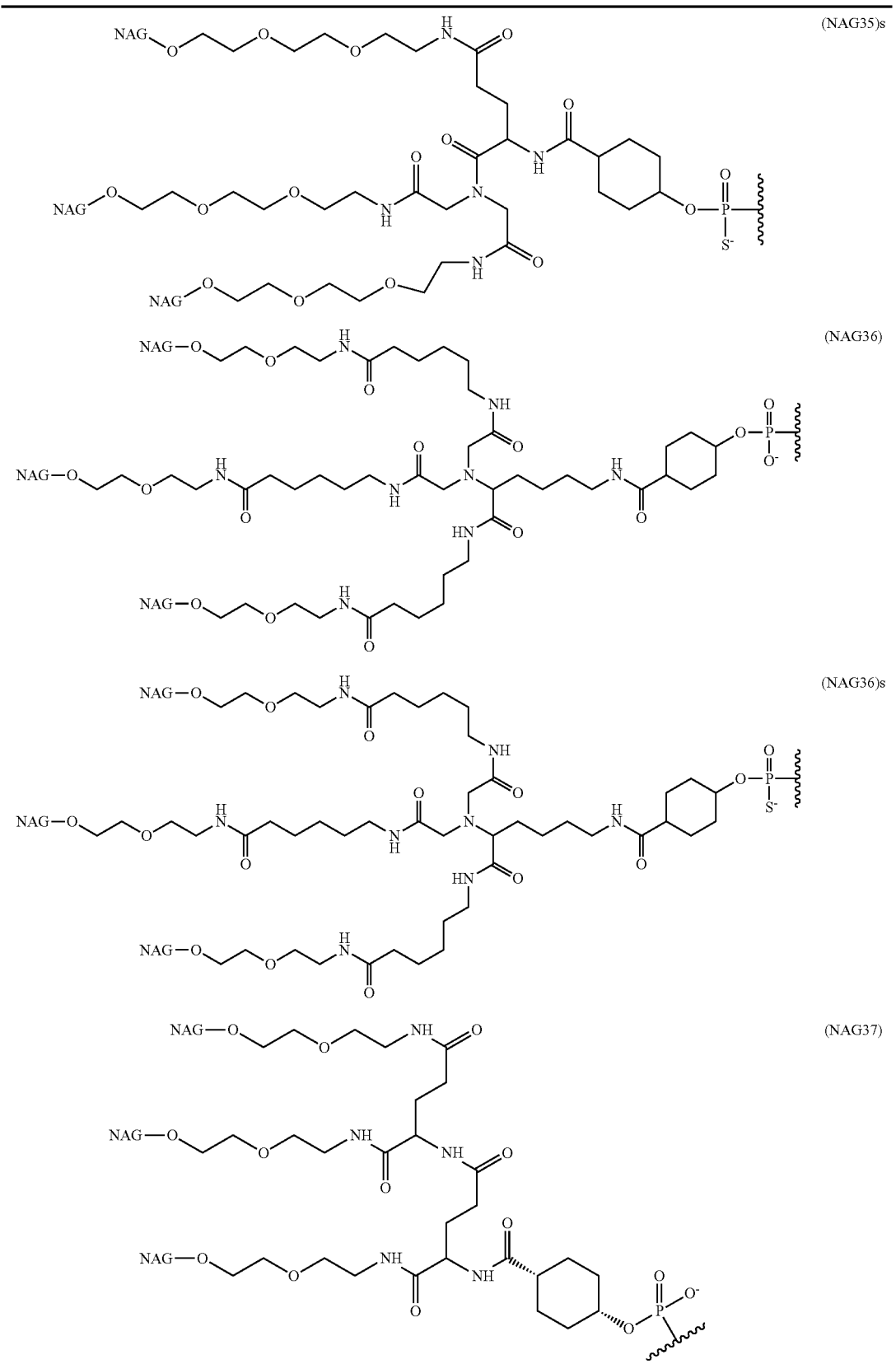
(NAG35)s
(NAG36)
(NAG36)s
(NAG37)

TABLE 6-continued
Structures representing various modified nucleotides, targeting groups, and linking groups.
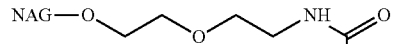
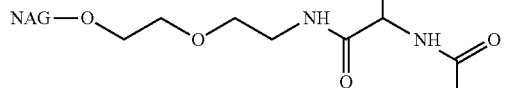
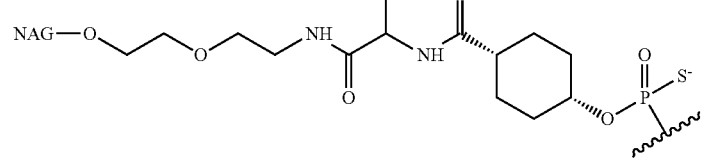
(NAG37)s
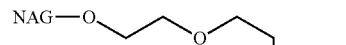
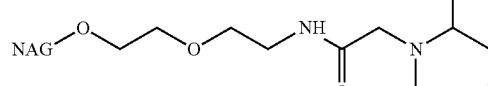
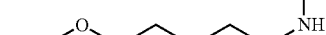
(NAG38)
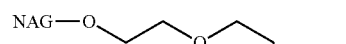
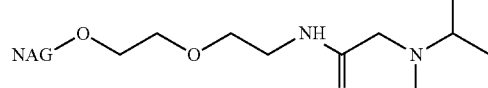
(NAG38)s
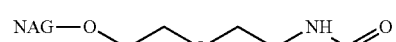
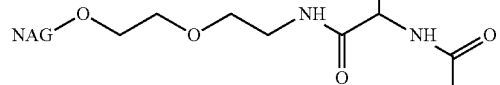
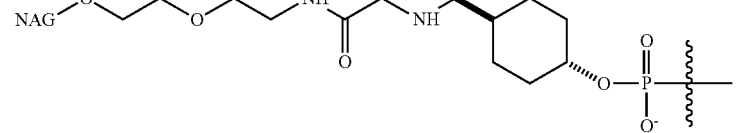
(NAG39)

TABLE 6-continued

Structures representing various modified nucleotides, targeting groups, and linking groups.

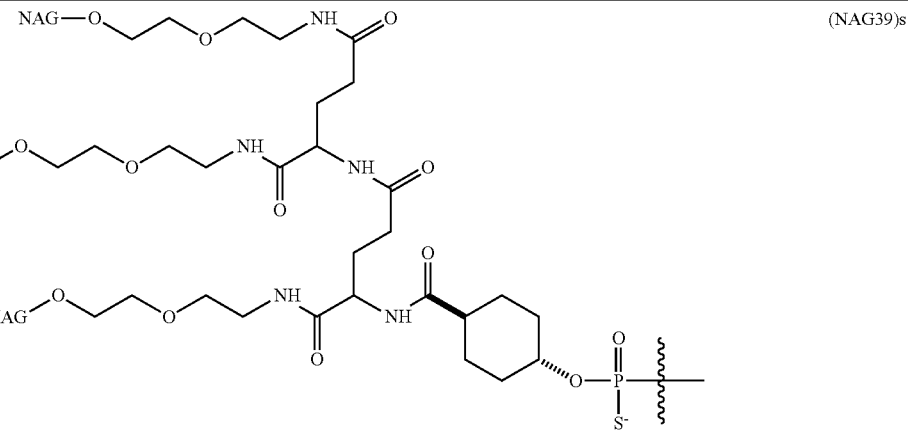

(NAG39)s

In each of the above structures in Table 6, NAG comprises an N-acetyl-galactosamine or another ASGPr ligand, as would be understood by a person of ordinary skill in the art to be attached in view of the structures above and description provided herein. For example, in some embodiments, NAG in the structures provided in Table 6 is represented by the following structure:

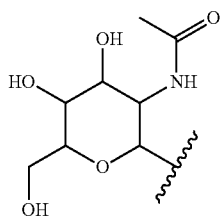

(N-acetyl-galactosamine)

Each (NAGx) may be attached to an HBV RNAi agent via a phosphate group (as in (NAG25), (NAG30), and (NAG31)), or a phosphorothioate group, (as is (NAG25)s, (NAG29)s, (NAG30)s, (NAG31)s, or (NAG37)s), or another linking group.

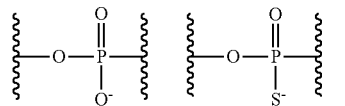

Phosphate group   Phosphorothioate group

Other linking groups known in the art may be use.

Delivery Vehicles

In some embodiments, a delivery vehicle may be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), or other delivery systems available in the art.

Pharmaceutical Compositions and Formulations

The HBV RNAi agents disclosed herein may be prepared as pharmaceutical compositions or formulations. In some embodiments, pharmaceutical compositions include at least one HBV RNAi agent. These pharmaceutical compositions are particularly useful in the inhibition of the expression of the target mRNA in a target cell, a group of cells, a tissue, or an organism. The pharmaceutical compositions can be used to treat a subject having a disease or disorder that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering an HBV RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions including an HBV RNAi agent, thereby forming a pharmaceutical formulation suitable for in vivo delivery to a human.

The pharmaceutical compositions that include an HBV RNAi agent and methods disclosed herein may decrease the level of the target mRNA in a cell, group of cells, group of cells, tissue, or subject, including: administering to the subject a therapeutically effective amount of a herein described HBV RNAi agent, thereby inhibiting the expression of a target mRNA in the subject.

In some embodiments, the described pharmaceutical compositions including an HBV RNAi agent are used for treating or managing clinical presentations associated with HBV infection. In some embodiments, a therapeutically or prophylactically effective amount of one or more of pharmaceutical compositions is administered to a subject in need of such treatment, prevention or management. In some embodiments, administration of any of the disclosed HBV RNAi agents can be used to decrease the number, severity, and/or frequency of symptoms of a disease in a subject.

The described pharmaceutical compositions including an HBV RNAi agent can be used to treat at least one symptom in a subject having a disease or disorder that would benefit from reduction or inhibition in expression of HBV mRNA. In some embodiments, the subject is administered a therapeutically effective amount of one or more pharmaceutical compositions including an HBV RNAi agent thereby treating the symptom. In other embodiments, the subject is administered a prophylactically effective amount of one or more HBV RNAi agents, thereby preventing the at least one symptom.

The route of administration is the path by which an HBV RNAi agent is brought into contact with the body. In general, methods of administering drugs and nucleic acids for treatment of a mammal are well known in the art and can be applied to administration of the compositions described herein. The HBV RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, there herein described pharmaceutical compositions via subcutaneous injection.

The pharmaceutical compositions including an HBV RNAi agent described herein can be delivered to a cell, group of cells, tumor, tissue, or subject using oligonucleotide delivery technologies known in the art. In general, any suitable method recognized in the art for delivering a nucleic acid molecule (in vitro or in vivo) can be adapted for use with a herein described compositions. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

Accordingly, in some embodiments, the herein described pharmaceutical compositions may comprise one or more pharmaceutically acceptable excipients. In some embodiments, the pharmaceutical compositions described herein can be formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical ingredient (API, therapeutic product, e.g., HBV RNAi agent) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The HBV RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic or preventive result.

Generally, an effective amount of an active compound will be in the range of from about 0.1 to about 100 mg/kg of body weight/day, e.g., from about 1.0 to about 50 mg/kg of body weight/day. In some embodiments, an effective amount of an active compound will be in the range of from about 0.25 to about 5 mg/kg of body weight per dose. In some embodiments, an effective amount of an active ingredient will be in the range of from about 0.5 to about 3 mg/kg of body weight per dose. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

For treatment of disease or for formation of a medicament or composition for treatment of a disease, the pharmaceutical compositions described herein including an HBV RNAi agent can be combined with an excipient or with a second therapeutic agent or treatment including, but not limited to: a second or other RNAi agent, a small molecule drug, an antibody, an antibody fragment, and/or a vaccine.

The described HBV RNAi agents, when added to pharmaceutically acceptable excipients or adjuvants, can be packaged into kits, containers, packs, or dispensers. The pharmaceutical compositions described herein may be packaged in pre-filled syringes or vials.

Methods of Treatment and Inhibition of Expression

The HBV RNAi agents disclosed herein can be used to treat a subject (e.g., a human or mammal) having a disease or disorder that would benefit from administration of the compound. In some embodiments, the RNAi agents disclosed herein can be used to treat a subject (e.g., a human) having a disease or disorder that would benefit from reduction or inhibition in expression of HBV mRNA. The subject is administered a therapeutically effective amount of any one or more RNAi agents. The subject can be a human, patient, or human patient. The subject may be an adult, adolescent, child, or infant. The described pharmaceutical compositions including an HBV RNAi agent can be used to provide methods for the therapeutic treatment of diseases. Such methods include administration of a pharmaceutical composition described herein to a human being or animal.

In some embodiments, the HBV RNAi agents described herein are used to treat a subject infected with HBV. In some embodiments, the described HBV RNAi agents are used to treat at least one symptom in a subject having a HBV infection. The subject is administered a therapeutically effective amount of any one or more of the described RNAi agents.

In some embodiments, the subject has both a HBV infection and a HDV infection. In some embodiments, the HBV RNAi agents described herein are used to treat a subject infected with both HBV and HDV. In some embodiments, the described HBV RNAi agents are used to treat at least one symptom in a subject having a HBV or a HDV infection. The subject is administered a therapeutically effective amount of any one or more of the described RNAi agents.

In some embodiments, the HBV RNAi agents are used to treat or manage a clinical presentation wherein a subject infected with HBV. The subject is administered a therapeutically or effective amount of one or more of the HBV RNAi agents or HBV RNAi agent-containing compositions described herein. In some embodiments, the method comprises administering a composition comprising an HBV RNAi agent described herein to a subject to be treated.

In some embodiments, the gene expression level and/or mRNA level of an HBV gene in a subject to whom a described HBV RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the HBV RNAi agent or to a subject not receiving the HBV RNAi agent. The gene expression level and/or mRNA level in the subject may be reduced in a cell, group of cells, and/or tissue of the subject. In some embodiments, the expressed protein level of an HBV gene in a subject to whom a described HBV RNAi agent has been administered is reduced by at least about 5%, 10%, 15%, 20%, 25%, 30%/a, 35%, 40%, 45%, 50%, 55%, 60%, 65%, 70%, 75%, 80%, 85%, 90%, 95%, 96%, 97%, 98%, 99%, or greater than 99% relative to the subject prior to being administered the HBV RNAi agent or to a subject not receiving the HBV RNAi agent. The protein level in the subject may be reduced in a cell, group of cells, tissue, blood, and/or other fluid of the subject. For example, in some embodiments, the amount or level of Hepatitis B surface antigen (HBsAg) in a subject to whom a described HBV RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the HBV RNAi agent or to a subject not receiving the HBV RNAi agent. In some embodiments, the amount or level of Hepatitis B e-antigen (HBeAg) in a subject to whom a described HBV RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the HBV RNAi agent or to a subject not receiving the HBV RNAi agent. In some embodiments, the amount or level of serum HBV DNA in a subject to whom a described HBV RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the HBV RNAi agent or to a subject not receiving the HBV RNAi agent. A reduction in the presence of serum HBV DNA, HBV gene expression, HBV mRNA, or HBV protein amounts or levels may be assessed by methods known in the art. Reduction or decrease in HBV mRNA amount or level, expressed protein amount or level, and/or serum HBV DNA amount or level, are collectively referred to herein as a reduction or decrease in HBV or inhibiting or reducing the expression of HBV.

Cells and Tissues and Non-Human Organisms

Cells, tissues, and non-human organisms that include at least one of the HBV RNAi agents described herein is contemplated. The cell, tissue, or non-human organism is made by delivering the RNAi agent to the cell, tissue, or non-human organism.

The above provided embodiments and items are now illustrated with the following, non-limiting examples.

EXAMPLES

Example 1. Synthesis of HBV RNAi Agents

HBV RNAi agent duplexes shown in Table 5 were synthesized in accordance with the following:
A. Synthesis.

The sense and antisense strands of the HBV RNAi agents were synthesized according to phosphoramidite technology on solid phase used in oligonucleotide synthesis. Depending on the scale, either a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, Pa., USA). All RNA and 2'-modified phosphoramidites were purchased from Thermo Fisher Scientific (Milwaukee, Wis., USA). Specifically, the following 2'-O-methyl phosphoramidites were used: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl amidites. The abasic (3'-O-dimethoxytrityl-2'-deoxyribose-5'-O-2-cyanoethyl-N,N-diisopropylamino) phosphoranidites were purchased from ChemGenes (Wilmington, Mass., USA). Targeting ligand containing phosphoramidites were dissolved in anhydrous dichloromethane or anhydrous acetonitrile (50 mM), while all other amidites were dissolved in anhydrous acetonitrile (50 mM) and molecular sieves (3 Å) were added. 5-Benzylthio-1H-tetrazole (BIT, 250 mM in acetonitrile) or 5-Ethylthio-1H-tetrazole (EIT, 250 mM in acetonitrile) was used as activator solution. Coupling times were 12 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, Mass., USA) in anhydrous Acetonitrile was employed.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5PW 131 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered DI water or 100 mM ammonium bicarbonate, pH 6.7 and 20% Acetonitrile.

D. Annealing.

Complementary strands were mixed by combining equimolar RNA solutions (sense and antisense) in 1× Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1× Phosphate-Buffered Saline. The solution absorbance at 260 nm was then multiplied by a conversion factor and the dilution factor to determine the duplex concentration. Unless otherwise stated, all conversion factor was 0.037 mg/(mL·cm). For some experiments, a conversion factor was calculated from an experimentally determined extinction coefficient.

Example 2 pHBV Modelmice

Six to eight-week-old female NOD.CB17-Prkdscid/Ncr-Crl (NOD-SCID) mice were transiently transfected in vivo with MC-HBV1.3 by hydrodynamic tail vein injection (Yang P L et al. "Hydrodynamic injection of viral DNA: a mouse model of acute hepatitis B virus infection," PNAS USA 2002 Vol. 99: p. 13825-13830), administered 30 to 45 days prior to administration of an HBV RNAi agent or control. MC-HBV1.3 is a plasmid-derived minicircle that contains the same terminally redundant human hepatitis B virus sequence HBV1.3 as in plasmid pHBV1.3 and in the HBV1.3.32 transgenic mice (GenBank accession # V01460) (Guidotti L G et al., "High-level hepatitis B virus replication in transgenic mice," J Virol 1995 Vol. 69, p 6158-6169.). 5 or 10 μg MC-HBV1.3 in Ringer's Solution in a total volume of 10% of the animal's body weight was injected into mice via tail vein to create pHBV model of chronic HBV infection. The solution was injected through a 27-gauge needle in 5-7 seconds as previously described (Zhang G et al., "High levels of foreign gene expression in hepatocytes after tail vein injection of naked plasmid DNA." Human Gene Therapy 1999 Vol. 10, p 1735-1737.). At pre-dose (either day 1 pre-dose, day −1, or day −2), Hepatitis B surface antigen (HBsAg) HBsAg expression levels in serum were measured by ELISA and the mice were grouped according to average HBsAg expression levels.

Analyses:

At various times, before and after administration of HBV RNAi agents, serum HBsAg, serum HBeAg, serum HBV DNA, or liver HBV RNA may be measured. HBV expression levels were normalized to pre-administration expression levels and to control mice injected with phosphate buffered saline ("PBS").

i) Serum Collection:

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C.

ii) Serum Hepatitis B Surface Antigen (HBsAg) Levels:

Serum was collected and diluted 10 to 8000-fold in PBS containing 5% nonfat dry milk. Secondary HBsAg standards diluted in the nonfat milk solution were prepared from serum of ICR mice (Harlan Sprague Dawley) that had been transfected with 10 μg HBsAg-expressing plasmid pRc/CMV-HBs (Aldevron, Fargo, N. Dak.). HBsAg levels were determined with a GS HBsAg EIA 3.0 kit (Bio-Rad Laboratories, Inc., Redmond, Wash.) as described by the manufacturer. Recombinant HBsAg protein, ayw subtype, also diluted in nonfat milk in PBS, was used as a primary standard (Aldevron).

HBsAg expression for each animal was normalized to the control group of mice injected with PBS in order to account for the non-treatment related decline in expression of MC-HBV1.3. First, the HBsAg level for each animal at a time point was divided by the pre-treatment level of expression in that animal in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal PBS control group.

iii) Serum Hepatitis B e-Antigen (HBeAg) Levels:

HBeAg analysis was performed with the HBeAg enzyme linked immunosorbent assay (ELISA) as described by the manufacturer (DiaSorin) using serum diluted 4- to 20-fold in 5% nonfat dry milk. The amount of antigen was determined in the linear range of the assay and quantitated against HBeAg protein standards (Fitzgerald Industries International, catalog #30-AH18, Acton, Mass.).

HBeAg expression for each animal was normalized to the control group of mice injected with PBS in order to account for the non-treatment related decline in expression of MC-HBV1.3. For evaluation of HBeAg in serum, HBeAg is analyzed from pooled group or subgroup serum samples. First, the HBeAg level for each pooled group or subgroup was divided by the pre-treatment level of expression in the same group or subgroup in order to determine the ratio of expression "normalized to pre-treatment". Expression at a specific time point was then normalized to the control group by dividing the "normalized to pre-treatment" ratio for a group or subgroup by the average "normalized to pre-treatment" ratio of all samples from the normal PBS control group.

iv) Serum HBVDNA Levels:

Equal volumes of serum from mice in a group or subgroup were pooled to a final volume of 100 μL. DNA was isolated from serum samples using the QIAamp MinElute Virus Spin Kit (Qiagen, Valencia, Calif.) following the manufacturer's instructions. Sterile 0.9% saline was added to each sample to a final volume of 200 μL. Serum samples were added to tubes containing buffer and protease. Carrier RNA was added to aid in the isolation of small amounts of DNA. 1 ng of pHCR/UbC-SEAP plasmid DNA (Wooddell C I, et al. "Long-term RNA interference from optimized siRNA expression constructs in adult mice." *Biochem Biophys Res Commun* (2005) 334, 117-127) was added as a recovery control. After incubating 15 min at 56° C., nucleic acids were precipitated from the lysates with ethanol and the entire solution applied to a column. After washing, the samples were eluted into a volume of 50 μL Buffer AVE.

The number of copies of HBV genomes in DNA isolated from the pHBV mouse model serum was determined by qPCR. Plasmid pSEAP-HBV353-777, encoding a short segment of the HBV genome within the S gene (bases 353-777 of GenBank accession # V01460), was used to create a six log standard curve. Samples with recovery of DNA below 2 standard deviations from the average, based on detection of pHCRlUbC-SEAP were omitted. TaqMan chemistry-based primers and probes with fluor/ZEN/IBFQ are utilized.

qPCR assays were performed on a 7500 Fast or StepOne Plus Real-Time PCR system (Life Technologies). For evaluation of HBV DNA in serum, DNA was isolated from singlet or duplicate purification steps from pooled group serum samples. Quantitations of HBV DNA and recovery control plasmid were determined by qPCR reactions performed in triplicate. The probes to quantitate HBV and pHCR/UbC-SEAP were included in each reaction.

Example 3. HBV RNAi Agents in pHBV Model Mice

The pHBV mouse model described in Example 2, above, was used. At day 1, each mouse was administered a single subcutaneous injection of 200 μl containing 2 mg/kg (mpk) of an HBV RNAi agent formulated in phosphate buffered saline ("PBS"), or 200 μl of phosphate buffered saline without an HBV RNAi agent, to be used as a control. Each of the HBV RNAi agents included N-acetyl-galactosamine targeting ligands conjugated to the 5'-terminal end of the sense strand, as shown in Tables 4 and 5. The HBV RNAi agents tested included those having the duplex numbers shown in Table 7, below. The injections were performed between the skin and muscle (i.e. subcutaneous injections) into the loose skin over the neck and shoulder area. Three (3) mice in each group were tested (n=3).

Serum was collected on day 8, day 15, day 22, and day 29, and serum Hepatitis B surface antigen (HBsAg) levels were determined pursuant to the procedure set forth in Example 2, above. Data from the experiment is shown in the following Table:

TABLE 7

Average HBsAg levels normalized to pre-treatment and PBS control in pHBV mice following administration of HBV RNAi agents from Example 3 (standard deviation reflected as (+/−)).

| Group | Day 8 | Day 15 | Day 22 | Day 29 |
|---|---|---|---|---|
| PBS | 1.000 ± 0.185 | 1.000 ± 0.288 | 1.000 ± 0.540 | 1.000 ± 0.326 |
| AD04178 | 0.164 ± 0.043 | 0.206 ± 0.044 | 0.293 ± 0.050 | 0.348 ± 0.099 |
| AD04579 | 0.083 ± 0.028 | 0.099 ± 0.022 | 0.112 ± 0.022 | 0.138 ± 0.056 |
| AD04580 | 0.048 ± 0.007 | 0.073 ± 0.012 | 0.085 ± 0.012 | 0.126 ± 0.014 |
| AD04570 | 0.241 ± 0.076 | 0.294 ± 0.071 | 0.276 ± 0.068 | 0.474 ± 0.092 |
| AD04572 | 0.190 ± 0.040 | 0.279 ± 0.011 | 0.323 ± 0.049 | 0.441 ± 0.046 |
| AD04573 | 0.333 ± 0.143 | 0.505 ± 0.106 | 0.361 ± 0.060 | 0.444 ± 0.068 |
| AD04574 | 0.291 ± 0.032 | 0.650 ± 0.056 | 0.388 ± 0.048 | 0.485 ± 0.070 |
| AD04575 | 0.397 ± 0.189 | 0.514 ± 0.234 | 0.574 ± 0.204 | 0.689 ± 0.207 |
| AD04419 | 0.262 ± 0.038 | 0.174 ± 0.042 | 0.258 ± 0.064 | 0.311 ± 0.089 |
| AD04578 | 0.210 ± 0.056 | 0.235 ± 0.033 | 0.298 ± 0.035 | 0.336 ± 0.049 |

RNAi agents AD04178, AD04579, AD04580, AD04570, AD04572, AD04573, AD04574, AD04575, AD04419, and AD04578 were each designed to have antisense strand sequences at least partially complementary to the X open reading frame at positions 1781-1789 of the HBV genome shown in Tables 1 and 2, above. Each of the HBV RNAi agents showed substantial reduction in HBsAg as compared to the PBS control across all measured time points. For example, AD04580 showed greater than 95% reduction in s-antigen levels at day 8 (0.048±0.007 HBsAg level) when normalized to pre-treatment and PBS control.

Additionally, serum HBV DNA levels were determined for the PBS, AD04579, and AD04580 groups from serum samples collected on days 8, 15, 22, 29, 36, 43 and 50, pursuant to the procedure set forth in Example 2, above. Serum from each group was pooled and then DNA was isolated from the serum in duplicate isolations. Data are presented in the following Table:

TABLE 8

Average Serum HBV DNA levels normalized to pre-treatment and PBS control in pHBV mice following administration of HBV RNAi agents from Example 3 (standard deviation reflected as (+/−)).

| Group | Day 8 | Day 15 | Day 22 | Day 29 |
|---|---|---|---|---|
| PBS | 1.0000 ± 0.1185 | 1.0000 ± 0.0591 | 1.0000 ± 0.0322 | 1.0000 ± 0.0597 |
| AD04579 | 0.1541 ± 0.0070 | 0.1776 ± 0.0027 | 0.1810 ± 0.0450 | 0.3738 ± 0.0302 |
| AD04580 | 0.0921 ± 0.0253 | 0.0869 ± 0.0117 | 0.1444 ± 0.0755 | 0.0950 ± 0.0026 |

| Group | Day 36 | Day 43 | Day 50 |
|---|---|---|---|
| PBS | 1.0000 ± 0.1625 | 1.0000 ± 0.0055 | 1.0000 ± 0.1484 |
| AD04579 | 0.9670 ± 0.1247 | 0.7643 ± 0.1334 | 0.6299 ± 0.1319 |
| AD04580 | 0.4949 ± 0.0096 | 0.4350 ± 0.0344 | 0.6819 ± 0.0266 |

The data in Table 8 indicate that both RNAi agents examined provided a substantial reduction in HBV DNA levels compared to the PBS group, with AD04580 achieving slightly greater than 1 log knockdown at nadir (e.g., 0.0869±0.0117 average serum DNA level at day 15).

Example 4. HBV RNAi Agents in pHBV Model Mice

The pHBV mouse model described in Example 2, above, was used. At day 1, each mouse was given a single subcutaneous administration of 200 μl containing 2 mg/kg (mpk) of an HBV RNAi agent formulated in phosphate buffered saline, or 200 μl of phosphate buffered saline without an HBV RNAi agent to be used as a control. Each of the HBV RNAi agents included N-acetyl-galactosamine targeting ligands conjugated to the 5'-terminal end of the sense strand, as shown in Tables 4 and 5. The HBV RNAi agents administered included those listed in Table 9, below. The injections were performed between the skin and muscle (i.e. subcutaneous injections) into the loose skin over the neck and shoulder area. Three (3) mice in each group were tested (n=3).

Serum was collected on day 8, day 15, day 22, and day 29, and serum Hepatitis B surface antigen (HBsAg) levels were determined pursuant to the procedure set forth in Example 2, above. Data from the experiment is shown in the following Table:

TABLE 9

Average HBsAg levels normalized to pre-treatment and PBS control in pHBV mice following administration of HBV RNAi agents from Example 4 (standard deviation reflected as (+/−)).

| Group | Day 8 | Day 15 | Day 22 | Day 29 |
| --- | --- | --- | --- | --- |
| PBS | 1.000 ± 0.085 | 1.000 ± 0.235 | 1.000 ± 0.171 | 1.000 ± 0.099 |
| AD04010 | 0.229 ± 0.141 | 0.165 ± 0.091 | 0.142 ± 0.085 | 0.116 ± 0.076 |
| AD04581 | 0.379 ± 0.042 | 0.221 ± 0.066 | 0.135 ± 0.040 | 0.112 ± 0.050 |
| AD04591 | 0.285 ± 0.101 | 0.145 ± 0.064 | 0.086 ± 0.024 | 0.081 ± 0.026 |
| AD04434 | 0.295 ± 0.041 | 0.191 ± 0.008 | 0.147 ± 0.016 | 0.187 ± 0.049 |
| AD04583 | 0.488 ± 0.018 | 0.545 ± 0.037 | 0.511 ± 0.086 | 0.663 ± 0.112 |
| AD04584 | 0.392 ± 0.136 | 0.337 ± 0.073 | 0.364 ± 0.075 | 0.515 ± 0.155 |
| AD04585 | 0.099 ± 0.016 | 0.042 ± 0.014 | 0.030 ± 0.009 | 0.044 ± 0.014 |
| AD04586 | 0.222 ± 0.056 | 0.107 ± 0.034 | 0.074 ± 0.016 | 0.106 ± 0.039 |
| AD04588 | 0.255 ± 0.065 | 0.205 ± 0.021 | 0.185 ± 0.021 | 0.207 ± 0.024 |
| AD04438 | 0.265 ± 0.106 | 0.113 ± 0.045 | 0.091 ± 0.031 | 0.130 ± 0.038 |

RNAi agents AD04010, AD04581, AD04591, AD04434, AD04583, AD04584, AD04585, AD04586, AD04588, and AD04438 were designed to have antisense strand sequences that are at least partially complementary to the S open reading frame at positions 257-275 of the HBV genome, as shown in Tables 1 and 2. The HBV RNAi agents shown in Table 9, directly above, each showed substantial reduction in HBsAg as compared to the PBS control across all measured time points. For example, AD04585 exhibited approximately a 90% reduction of HBsAg at day 8, a 95% reduction at day 15, a 97% reduction at day 22, and a 95% reduction at day 29.

Additionally, serum HBV DNA levels were determined for the PBS, AD04585 groups from serum samples collected on days 8, 15, 22, 29, 36, 43 and 50, pursuant to the procedure set forth in Example 2, above. Serum from each group was pooled and then DNA was isolated from the serum in duplicate isolations. Data are presented in the following Table:

TABLE 10

Average Serum HBV DNA levels normalized to pre-treatment and PBS control in pHBV mice following administration of HBV RNAi agents from Example 4 (standard deviation reflected as (+/−)).

| Group | Day 8 | Day 15 | Day 22 | Day 29 |
| --- | --- | --- | --- | --- |
| PBS | 1.000 ± 0.248 | 1.000 ± 0.089 | 1.000 ± 0.195 | 1.000 ± 0.180 |
| AD04585 | 0.901 ± 0.183 | 0.225 ± 0.003 | 0.187 ± 0.023 | 0.191 ± 0.004 |

| Group | Day 36 | Day 43 | Day 50 |
| --- | --- | --- | --- |
| PBS | 1.000 ± 0.018 | 1.000 ± 0.033 | 1.000 ± 0.778 |
| AD04585 | 0.209 ± 0.017 | 0.171 ± 0.019 | 0.305 ± 0.010 |

The data in Table 10 indicate that HBV RNAi agent AD04585 provided a reduction in HBV DNA levels compared to the PBS group.

Example 5. Dose Response and Combinations of HBV RNAi Agents in pHBV Model Mice

The pHBV mouse model described in Example 2, above, was used. The mice were divided into various groups including those set forth in Table 11, below, and the mice were given 200 μl subcutaneous injections pursuant to the dosing regimen set forth in Table 11:

TABLE 11

Dosing groups of pHBV mice for Example 5.

| Group | RNAi Agent and Dose | Dosing Regimen |
|---|---|---|
| A | PBS (no RNAi agent) | Single injection on day 1 |
| B | 3.0 mg/kg AD04585 | Single injection on day 1 |
| C | 3.0 mg/kg AD04585 | Injection on day 1, day 8, and day 15 (i.e., three weekly injections) |
| D | 3.0 mg/kg AD04580 | Single injection on day 1 |
| E | 3.0 mg/kg AD04580 | Injection on day 1, day 8, and day 15 (i.e., three weekly injections) |
| F | 1.0 mg/kg AD4585 + 1.0 mg/kg AD04580 | Injection on day 1, and another injection on day 22 |
| G | 1.0 mg/kg AD4585 + 1.0 mg/kg AD04580 | Injection on day 1, day 8, day 15, and day 43 |
| H | 1.5 mg/kg AD4585 + 1.5 mg/kg AD04580 | Injection on day 1, day 22, and day 43 |
| I | 1.5 mg/kg AD4585 + 1.5 mg/kg AD04580 | Injection on day 1, day 8, day 15, and day 43 |

Each mouse was given a subcutaneous administration of 200 µl containing the amount of HBV RNAi agent(s) formulated in phosphate buffered saline, or 200 µl of phosphate buffered saline without an HBV RNAi agent, as set forth in Table 11. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected on day 8, day 15, day 22, day 29, day 36, day 43, day 50, and day 57, and serum Hepatitis B surface antigen (HBsAg) levels were determined pursuant to the procedure set forth in Example 2, above. Data from the experiment is shown in the following Table:

HBV RNAi agents AD04580 and AD04585 each individually showed a reduction in HBsAg as compared to the PBS control across all measured time points. Furthermore, combination treatment of AD04585 and AD04580, which as noted in the Examples above target different regions of the HBV genome, also showed reduction in HBsAg as compared to the PBS control across all measured time points.

Additionally, serum HBV DNA levels were determined for each of the groups in Table 11 from serum samples collected on days 8, 15, 22, 29, and 36, pursuant to the procedure set forth in Example 2, above. Serum from each group was pooled and then DNA was isolated from the serum in duplicate reactions. Data are presented in the following Table:

TABLE 12

Average HBsAg levels normalized to pre-treatment and PBS control in pHBV mice following administration of HBV RNAi agents from Example 5 (standard deviation reflected as (+/−)).

| Group | Day 8 | Day 15 | Day 22 | Day 29 |
|---|---|---|---|---|
| A | 1.000 ± 0.162 | 1.000 ± 0.138 | 1.000 ± 0.083 | 1.000 ± 0.204 |
| B | 0.060 ± 0.015 | 0.010 ± 0.003 | 0.006 ± 0.002 | 0.007 ± 0.002 |
| C | 0.087 ± 0.014 | 0.004 ± 0.001 | 0.001 ± 0.0003 | 0.0002 ± 0.0001 |
| D | 0.026 ± 0.009 | 0.035 ± 0.013 | 0.037 ± 0.014 | 0.046 ± 0.006 |
| E | 0.023 ± 0.005 | 0.002 ± 0.001 | 0.001 ± 0.0003 | 0.001 ± 0.0004 |
| F | 0.063 ± 0.046 | 0.083 ± 0.051 | 0.086 ± 0.016 | 0.027 ± 0.006 |
| G | 0.062 ± 0.011 | 0.022 ± 0.008 | 0.009 ± 0.003 | 0.008 ± 0.002 |
| H | 0.055 ± 0.015 | 0.062 ± 0.002 | 0.072 ± 0.013 | 0.011 ± 0.001 |
| I | 0.031 ± 0.006 | 0.008 ± 0.001 | 0.003 ± 0.0004 | 0.003 ± 0.0003 |

| Group | Day 36 | Day 43 | Day 50 | Day 57 |
|---|---|---|---|---|
| A | 1.000 ± 0.211 | 1.000 ± 0.189 | 1.000 ± 0.179 | 1.000 ± 0.062 |
| B | 0.013 ± 0.005 | 0.027 ± 0.004 | 0.026 ± 0.004 | 0.057 ± 0.012 |
| C | 0.001 ± 0.0002 | 0.002 ± 0.001 | 0.008 ± 0.004 | 0.020 ± 0.015 |
| D | 0.116 ± 0.019 | 0.214 ± 0.056 | 0.263 ± 0.046 | 0.404 ± 0.030 |
| E | 0.003 ± 0.0001 | 0.007 ± 0.001 | 0.012 ± 0.002 | 0.033 ± 0.011 |
| F | 0.029 ± 0.003 | 0.065 ± 0.005 | 0.064 ± 0.004 | 0.161 ± 0.033 |
| G | 0.014 ± 0.008 | 0.039 ± 0.011 | 0.018 ± 0.008 | 0.046 ± 0.008 |
| H | 0.017 ± 0.005 | 0.039 ± 0.008 | 0.007 ± 0.001 | 0.013 ± 0.003 |
| I | 0.007 ± 0.001 | 0.020 ± 0.002 | 0.005 ± 0.001 | 0.011 ± 0.002 |

TABLE 13

Average Serum HBV DNA levels normalized to pre-treatment and PBS control in pHBV mice following administration of HBV RNAi agents from Example 5 (standard deviation reflected as (+/−)).

| Group | Day 8 | Day 15 | Day 22 | Day 29 | Day 36 |
|---|---|---|---|---|---|
| A | 1.000 ± 0.063 | 1.000 ± 0.059 | 1.000 ± 0.372 | 1.000 ± 0.237 | 1.000 ± 0.024 |
| B | 0.267 ± 0.003 | 0.043 ± 0.016 | 0.038 ± 0.008 | 0.044 ± 0.004 | 0.046 ± 0.007 |
| C | 0.236 ± 0.016 | 0.023 ± 0.001 | 0.004 ± 0.001 | 0.002 ± 0.000 | 0.003 ± 0.000 |
| D | 0.058 ± 0.016 | 0.085 ± 0.017 | 0.252 ± 0.071 | 0.217 ± 0.009 | 0.319 ± 0.034 |
| E | 0.056 ± 0.002 | 0.0009 ± 0.0004 | 0.0005 ± 0.0002 | 0.003 ± 0.002 | 0.002 ± 0.000 |
| F | 0.298 ± 0.013 | 0.351 ± 0.032 | 0.823 ± 0.127 | 0.217 ± 0.007 | 0.122 ± 0.004 |
| G | 0.276 ± 0.035 | 0.112 ± 0.020 | 0.061 ± 0.002 | 0.073 ± 0.002 | 0.047 ± 0.006 |
| H | 0.232 ± 0.012 | 0.213 ± 0.028 | 0.403 ± 0.047 | 0.079 ± 0.005 | 0.056 ± 0.003 |
| I | 0.092 ± 0.026 | 0.055 ± 0.000 | 0.002 ± 0.003 | 0.010 ± 0.004 | 0.021 ± 0.007 |

The data in Table 13 indicate that the RNAi agents examined, both individually and in combination, provided a reduction in HBV DNA levels compared to the PBS group. Re-dosing or increasing the dose amount yielded additional HBV DNA reductions.

Example 6. HBV RNAi Agents in pHBV Mice: Dose Response and Combination Studies

The pHBV mouse model described in Example 2, above, was used. Mice were divided into various groups as set forth in Table 14, below, and each mouse was administered a single 200 μl subcutaneous injection pursuant to the dosing regimen set forth in Table 14:

TABLE 14

Dosing groups of pHBV mice for Example 6.

| Group | RNAi Agent and Dose | Dosing Regimen |
|---|---|---|
| A | PBS (no RNAi agent) | Single injection on day 1 |
| B | 4.0 mg/kg AD04981 | Single injection on day 1 |
| C | 1.0 mg/kg AD04981 | Single injection on day 1 |
| D | 2.0 mg/kg AD04981 | Single injection on day 1 |
| E | 1.0 mg/kg AD04963 | Single injection on day 1 |
| F | 2.0 mg/kg AD04963 | Single injection on day 1 |
| G | 3.0 mg/kg AD04872 | Single injection on day 1 |
| H | 3.0 mg/kg AD04872 + 1.0 mg/kg AD04981 | Single injection on day 1 |
| I | 3.0 mg/kg AD04872 + 1.0 mg/kg AD04963 | Single injection on day 1 |
| J | 3.0 mg/kg AD04872 + 2.0 mg/kg AD04981 | Single injection on day 1 |

Each mouse was given a subcutaneous administration of 200 μl containing the amount of HBV RNAi agent(s) formulated in phosphate buffered saline, or 200 μl of phosphate buffered saline without an HBV RNAi agent, as set forth in Table 14. Each of the HBV RNAi agents included N-acetyl-galactosamine targeting ligands conjugated to the 5′-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected on day −1 prior to administration, and then on day 8, day 15, day 22, day 29, and day 36, and serum HBsAg levels were determined pursuant to the procedure set forth in Example 2, above. Data from the experiment is shown in the following Table 15, with Average HBsAg reflecting the normalized average value of HBsAg:

TABLE 15

Average HBsAg levels normalized to pre-treatment and PBS control in pHBV mice following administration of HBV RNAi agents from Example 6 (standard deviation reflected as (+/−)).

| Group | Day 8 | Day 15 | Day 22 |
|---|---|---|---|
| A | 1.000 ± 0.068 | 1.000 ± 0.183 | 1.000 ± 0.181 |
| B | 0.085 ± 0.020 | 0.068 ± 0.005 | 0.089 ± 0.014 |
| C | 0.283 ± 0.039 | 0.343 ± 0.055 | 0.436 ± 0.004 |
| D | 0.161 ± 0.052 | 0.137 ± 0.036 | 0.190 ± 0.068 |
| E | 0.182 ± 0.040 | 0.233 ± 0.023 | 0.436 ± 0.029 |
| F | 0.078 ± 0.024 | 0.093 ± 0.015 | 0.167 ± 0.028 |
| G | 0.066 ± 0.030 | 0.013 ± 0.002 | 0.010 ± 0.002 |
| H | 0.033 ± 0.012 | 0.016 ± 0.005 | 0.020 ± 0.005 |
| I | 0.040 ± 0.011 | 0.028 ± 0.003 | 0.032 ± 0.007 |
| J | 0.035 ± 0.010 | 0.019 ± 0.002 | 0.021 ± 0.001 |

| Group | Day 29 | Day 36 |
|---|---|---|
| A | 1.000 ± 0.032 | 1.000 ± 0.141 |
| B | 0.148 ± 0.016 | 0.194 ± 0.047 |
| C | 0.622 ± 0.041 | 0.741 ± 0.132 |
| D | 0.234 ± 0.055 | 0.280 ± 0.071 |
| E | 0.623 ± 0.116 | 0.782 ± 0.114 |
| F | 0.259 ± 0.014 | 0.368 ± 0.068 |
| G | 0.010 ± 0.003 | 0.009 ± 0.004 |
| H | 0.022 ± 0.005 | 0.024 ± 0.009 |
| I | 0.065 ± 0.014 | 0.087 ± 0.015 |
| J | 0.031 ± 0.0001 | 0.044 ± 0.002 |

The HBV RNAi agents tested showed a reduction in HBsAg as compared to the PBS control across all measured time points. Furthermore, combination treatment of AD04872 (which includes an antisense strand sequence that is at least partially complementary to the S ORF at positions 261-279 of the HBV genome, as shown in Tables 1 and 2) and either AD04981 or AD04963 (both of which include antisense strand sequences that are at least partially complementary to the X ORF at positions 1781-1799 of the HBV genome, as shown in Tables 1 and 2), which are shown in Groups H, I, and J of Example 6, illustrate that combination treatment of two RNAi agents targeting, one which targets in the S ORF, and the other which targets in the X ORF of the HBV genome, similarly showed reduction in HBsAg compared to the PBS control across all measured time points.

Additionally, Serum Hepatitis B e-antigen (HBeAg) levels were also assessed. Samples from the mice in each respective group were first pooled, and the resulting serum samples were assayed in singlet. Data from the experiment is shown in the following Table:

TABLE 16

Average HBeAg levels normalized to pre-treatment and PBS control in pHBV mice following administration of HBV RNAi agents from Example 6.

| Group | Day 8 | Day 15 | Day 22 | Day 29 | Day 36 |
|---|---|---|---|---|---|
| A | 1.000 | 1.000 | 1.000 | 0.183 | 1.000 |
| B | 0.138 | 0.180 | 0.274 | 0.005 | 0.089 |
| C | 0.316 | 0.376 | 0.588 | 0.055 | 0.436 |
| D | 0.167 | 0.250 | 0.262 | 0.036 | 0.190 |
| E | 0.301 | 0.327 | 0.447 | 0.023 | 0.436 |
| F | 0.167 | 0.172 | 0.305 | 0.015 | 0.167 |
| G | 0.275 | 0.135 | 0.158 | 0.002 | 0.010 |
| H | 0.080 | 0.053 | 0.094 | 0.005 | 0.020 |
| I | 0.165 | 0.124 | 0.185 | 0.003 | 0.032 |
| J | 0.120 | 0.057 | 0.101 | 0.002 | 0.021 |

As shown in Table 16, the combination AD04872 (which targets the S ORF of the HBV genome) with either AD04981 or AD04963 (both of which target the X ORF of the HBV genome), showed a further reduction in HBeAg levels relative to administering AD04872 alone.

Example 7. HBV RNAi Agents in pHBV Mice: Additional Dose Response and Combination Studies The pHBV mouse model described in Example 2, above, was used. Mice were divided into various groups as set forth in Table 17, below, and each mouse was administered a single 200 µl subcutaneous injection pursuant to the dosing regimen set forth in Table 17:

TABLE 17

Dosing groups of pHBV mice for Example 7.

| Group | RNAi Agent and Dose | Dosing Regimen |
|---|---|---|
| A | PBS (no RNAi agent) | Single injection on day 1 |
| B | 4.0 mg/kg AD04776 | Single injection on day 1 |
| C | 1.0 mg/kg AD04982 | Single injection on day 1 |
| D | 2.0 mg/kg AD04982 | Single injection on day 1 |
| E | 1.0 mg/kg AD04776 | Single injection on day 1 |
| F | 2.0 mg/kg AD04776 | Single injection on day 1 |
| G | 3.0 mg/kg AD04872 | Single injection on day 1 |
| H | 3.0 mg/kg AD04872 + 1.0 mg/kg AD04982 | Single injection on day 1 |
| I | 3.0 mg/kg AD04872 + 2.0 mg/kg AD04982 | Single injection on day 1 |

Each mouse was given a subcutaneous administration of 200 pd containing the amount of HBV RNAi agent(s) formulated in phosphate buffered saline, or 200 µl of phosphate buffered saline without an HBV RNAi agent, as set forth in Table 17. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Four (4) mice in each group were tested on day −1 and day 8 (n=4), and then one mouse per group was euthanized for histological evaluation. Three (3) mice in each group were tested at day 22 and day 29 (n=3).

Serum was collected on day −1 prior to administration, and then on day 8, day 15, day 22, and day 29, and serum Hepatitis B surface antigen (HBsAg) levels were determined pursuant to the procedure set forth in Example 2, above. Data from the experiment is shown in the following Table 18:

TABLE 18

Average HBsAg levels normalized to pre-treatment (day −1) and PBS control in pHBV mice following administration of HBV RNAi agents from Example 7 (standard deviation reflected as (+/−)).

| Group | Day 8 | Day 15 | Day 22 | Day 29 |
|---|---|---|---|---|
| A | 1.000 ± 0.347 | 1.000 ± 0.278 | 1.000 ± 0.194 | 1.000 ± 0.318 |
| B | 0.117 ± 0.069 | 0.085 ± 0.039 | 0.148 ± 0.045 | 0.198 ± 0.049 |
| C | 0.519 ± 0.058 | 0.375 ± 0.012 | 0.422 ± 0.046 | 0.525 ± 0.037 |
| D | 0.342 ± 0.062 | 0.255 ± 0.046 | 0.272 ± 0.122 | 0.314 ± 0.068 |
| E | 0.279 ± 0.057 | 0.245 ± 0.032 | 0.374 ± 0.121 | 0.304 ± 0.035 |
| F | 0.224 ± 0.018 | 0.161 ± 0.009 | 0.310 ± 0.016 | 0.482 ± 0.053 |
| G | 0.029 ± 0.010 | 0.005 ± 0.001 | 0.004 ± 0.001 | 0.006 ± 0.001 |
| H | 0.016 ± 0.005 | 0.004 ± 0.001 | 0.010 ± 0.006 | 0.015 ± 0.008 |
| I | 0.026 ± 0.012 | 0.008 ± 0.001 | 0.010 ± 0.002 | 0.015 ± 0.005 |

The HBV RNAi agents tested showed a reduction in HBsAg as compared to the PBS control across all measured time points.

Additionally, Serum Hepatitis B e-antigen (HBeAg) levels were also assessed. Samples from the mice in each respective group were first pooled, and the resulting serum samples were assayed in singlet. Data from the experiment is shown in the following Table:

TABLE 19

Average HBeAg levels normalized to pre-treatment and PBS control in pHBV mice following administration of HBV RNAi agents from Example 7.

| Group | Day 8 | Day 15 | Day 22 | Day 29 | Day 36 |
|---|---|---|---|---|---|
| A | 1.000 | 1.000 | 1.000 | 1.000 | 1.000 |
| B | 0.193 | 0.213 | 0.260 | 0.307 | 0.464 |
| C | 0.471 | 0.424 | 0.562 | 0.513 | 0.705 |
| D | 0.335 | 0.310 | 0.411 | 0.442 | 0.500 |
| E | 0.381 | 0.368 | 0.355 | 0.564 | 0.483 |
| F | 0.275 | 0.255 | 0.370 | 0.495 | 0.449 |
| G | 0.323 | 0.218 | 0.205 | 0.250 | 0.190 |
| H | 0.124 | 0.102 | 0.099 | 0.156 | 0.156 |
| I | 0.081 | 0.059 | 0.045 | 0.063 | 0.086 |

TABLE 19-1

Average HBeAg fold knockdown normalized to pre-treatment and PBS control in pHBV mice following administration of HBV RNAi agents from Example 7.

| Group | Day 8 (Fold KD) | Day 15 (Fold KD) | Day 22 (Fold KD) | Day 29 (Fold KD) | Day 36 (Fold KD) |
|---|---|---|---|---|---|
| A | 1.0 | 1.0 | 1.0 | 1.0 | 1.0 |
| B | 5.2 | 4.7 | 3.8 | 3.3 | 2.2 |
| C | 2.1 | 2.4 | 1.8 | 2.0 | 1.4 |
| D | 3.0 | 3.2 | 2.4 | 2.3 | 2.0 |
| E | 2.6 | 2.7 | 2.8 | 1.8 | 2.1 |
| F | 3.6 | 3.9 | 2.7 | 2.0 | 2.2 |
| G | 3.1 | 4.6 | 4.9 | 4.0 | 5.3 |
| H | 8.1 | 9.8 | 10.1 | 6.4 | 6.4 |
| I | 12.3 | 17.0 | 22.3 | 15.7 | 11.6 |

Table 19-1 reflects the fold knockdown ratio of HBeAg compared to control, which is calculated as normalized HBeAg level of the control (PBS) group/normalized HBeAg level of the respected RNAi agent(s) group (i.e., 1.000/HBeAg level). The data in Table 19-1 indicate that the combination of AD04872 (which, as noted above, includes an antisense strand sequence that is at least partially complementary to the S ORF at positions 261-279 of the HBV genome) with AD04982 (which includes an antisense strand sequence that is at least partially complementary to the X ORF at positions 1781-1799 of the HBV genome), showed a further reduction in HBeAg levels relative to administering the individual RNAi agents alone (See, e.g., Tables 19 and 19-1 for Groups H and I). Further, the data from this Example also show that the combination of AD04872 with AD04982 resulted in fold decrease of HBeAg greater than the sum of the fold decrease of HBeAg in AD04872 and AD04982 administered individually. For example, Group I (which is the administration of 3.0 mg/kg AD04872+2.0 mg/kg AD04982) resulted in a fold decrease of HBeAg at day 15 of 17.0, which is greater than the sum of the fold decrease for Group G (3.0 mg/kg AD04872) of 4.6 plus the fold decrease for Group D (2.0 mg/kg AD04982) of 3.2.

Further, serum HBV DNA levels were determined for each of the groups in Table 17 from serum samples collected on days −1, 8, 15, 22, 29, and 36, pursuant to the procedure set forth in Example 2, above. Serum HBV DNA was isolated from each animal at each time point. Data are presented in the following Table:

TABLE 20

Average Serum HBV DNA levels normalized to pre-treatment and PBS control in pHBV mice following administration of HBV RNAi agents from Example 7 (standard deviation reflected as (+/−)).

| Group | Day 8 | Day 15 | Day 22 | Day 29 | Day 36 |
|---|---|---|---|---|---|
| A | 1.000 ± 0.493 | 1.000 ± 0.358 | 1.000 ± 0.424 | 1.000 ± 0.387 | 1.000 ± 0.326 |
| B | 0.224 ± 0.150 | 0.263 ± 0.185 | 0.335 ± 0.204 | 0.449 ± 0.108 | 0.603 ± 0.068 |
| C | 0.358 ± 0.207 | 0.428 ± 0.073 | 0.433 ± 0.220 | 0.474 ± 0.090 | 0.509 ± 0.163 |
| D | 0.516 ± 0.163 | 0.523 ± 0.264 | 0.244 ± 0.123 | 0.241 ± 0.085 | 0.543 ± 0.079 |
| E | 0.601 ± 0.388 | 0.319 ± 0.125 | 0.279 ± 0.138 | 0.506 ± 0.525 | 0.444 ± 0.407 |
| F | 0.363 ± 0.128 | 0.374 ± 0.197 | 0.275 ± 0.146 | 0.385 ± 0.141 | 0.721 ± 0.043 |
| G | 0.071 ± 0.032 | 0.022 ± 0.009 | 0.015 ± 0.015 | 0.025 ± 0.005 | 0.058 ± 0.030 |
| H | 0.069 ± 0.070 | 0.018 ± 0.014 | 0.019 ± 0.020 | 0.022 ± 0.001 | 0.047 ± 0.021 |
| I | 0.044 ± 0.024 | 0.033 ± 0.016 | 0.017 ± 0.012 | 0.022 ± 0.014 | 0.058 ± 0.051 |

The data in Table 20 indicate that the RNAi agents examined, both individually and in combination, provided a reduction in HBV DNA levels compared to the PBS group, and further show that the combination of AD04872 (which targets the S ORF) and AD04982 (which targets the X ORF) reduces serum HBV DNA to a similar degree as an equal amount of AD04872 alone.

Example 8. HBV RNAi Agents in pHBV Mice: Further Dose Response and Combination Studies The pHBV mouse model described in Example 2, above, was used. Mice were divided into various groups as set forth in Table 21, below, and each mouse was administered a single 200 µl subcutaneous injection pursuant to the dosing regimen set forth in Table 21:

TABLE 21

Dosing groups of pHBV mice for Example 8.

| Group | RNAi Agent and Dose | Dosing Regimen | Number of Animals (n) |
|---|---|---|---|
| 1 | PBS (no RNAi agent) | Single injection on day 1 | 4 |
| 2A | 4.0 mg/kg AD04872 + 1.0 mg/kg AD05070 | Single injection on day 1 | 4 |
| 2B | 4.0 mg/kg AD04872 + 1.0 mg/kg AD05070 | Single injection on day 1 | 4 |
| 3A | 3.3 mg/kg AD04872 + 1.7 mg/kg AD05070 | Single injection on day 1 | 4 |
| 3B | 3.3 mg/kg AD04872 + 1.7 mg/kg AD05070 | Single injection on day 1 | 4 |
| 4A | 3.2 mg/kg AD04872 + 0.8 mg/kg AD05070 | Single injection on day 1 | 4 |
| 4B | 3.2 mg/kg AD04872 + 0.8 mg/kg AD05070 | Single injection on day 1 | 4 |
| 5A | 2.7 mg/kg AD04872 + 1.3 mg/kg AD05070 | Single injection on day 1 | 4 |
| 5B | 2.7 mg/kg AD04872 + 1.3 mg/kg AD05070 | Single injection on day 1 | 4 |
| 6A | 4.0 mg/kg AD05070 | Single injection on day 1 | 4 |
| 6B | 4.0 mg/kg AD05070 | Single injection on day 1 | 4 |
| 7A | 1.7 mg/kg AD05070 | Single injection on day 1 | 4 |
| 7B | 1.7 mg/kg AD05070 | Single injection on day 1 | 4 |
| 8A | 0.8 mg/kg AD05070 | Single injection on day 1 | 4 |
| 8B | 0.8 mg/kg AD05070 | Single injection on day 1 | 4 |
| 9 | 1.7 mg/kg AD05148 | Single injection on day 1 | 4 |
| 10 | 2.7 mg/kg AD04872 | Single injection on day 1 | 3 |
| 11 | 1.7 mg/kg AD05147 | Single injection on day 1 | 3 |
| 12 | 4.0 mg/kg AD04872 | Single injection on day 1 | 3 |
| 13 | 1.7 mg/kg AD05149 | Single injection on day 1 | 3 |

Additionally, the mice are scheduled to be euthanized pursuant to the following schedule:

Day 11: Euthanize 2 mice from groups 2A, 3A, 4A, 5A, 6A, 7A and 8A, and euthanize one mouse from group 9.

Day 14: Euthanize 2 mice from groups 2A, 3A, 4A, 5A, 6A, 7A, and 8A.

Day 21: Euthanize 2 mice from groups 2B, 3B, 4B, 5B, 6B, 7B, and 8B.

Day 28: Euthanize 2 mice from groups 1, 2B, 3B, 4B, 5B, 6B, 7B, and 8B, and all mice (4) from groups 10 and 12.

Each mouse was given a subcutaneous administration of 200 µl containing the amount of HBV RNAi agent(s)

formulated in phosphate buffered saline, or 200 μl of phosphate buffered saline without an HBV RNAi agent, as set forth in Table 21. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. As shown in Table 14 above, four (4) mice in each group were tested (n=4), except for groups 10, 11, 12 and 13, in which three mice were tested (n=3).

Serum was collected on day −1 prior to administration, and on days 8, 14, 21 and 28, and serum Hepatitis B surface antigen (HBsAg) levels were determined pursuant to the procedure set forth in Example 2, above. Data from the experiment is shown in the following Table:

TABLE 22

Average HBsAg levels normalized to pre-treatment and PBS control in pHBV mice following administration of HBV RNAi agents from Example 8 (standard deviation reflected as (+/−)).

| Group Number | Day 8 | Day 14 | Day 21 | Day 28 |
|---|---|---|---|---|
| 1 | 1.000 ± 0.089 | 1.000 ± 0.087 | 1.000 ± 0.132 | 1.000 ± 0.138 |
| 2A | 0.009 ± 0.003 | 0.005 ± 0.001 | | |
| 2B | 0.006 ± 0.003 | 0.002 ± 0.001 | 0.004 ± 0.001 | 0.005 ± 0.001 |
| 3A | 0.032 ± 0.021 | 0.009 ± 0.004 | | |
| 3B | 0.028 ± 0.027 | 0.008 ± 0.006 | 0.012 ± 0.005 | 0.015 ± 0.005 |
| 4A | 0.036 ± 0.020 | 0.012 ± 0.006 | | |
| 4B | 0.029 ± 0.025 | 0.010 ± 0.008 | 0.015 ± 0.005 | 0.022 ± 0.004 |
| 5A | 0.027 ± 0.014 | 0.008 ± 0.002 | | |
| 5B | 0.027 ± 0.013 | 0.007 ± 0.003 | 0.019 ± 0.004 | 0.031 ± 0.005 |
| 6A | 0.058 ± 0.035 | 0.069 ± 0.039 | | |
| 6B | 0.117 ± 0.058 | 0.079 ± 0.047 | 0.145 ± 0.082 | 0.135 ± 0.061 |
| 7A | 0.189 ± 0.100 | 0.084 ± 0.029 | | |
| 7B | 0.099 ± 0.010 | 0.147 ± 0.025 | 0.267 ± 0.048 | 0.345 ± 0.063 |
| 8A | 0.355 ± 0.099 | 0.366 ± 0.069 | | |
| 8B | 0.271 ± 0.058 | 0.334 ± 0.060 | 0.464 ± 0.055 | 0.624 ± 0.053 |
| 9 | 0.239 ± 0.148 | 0.179 ± 0.127 | 0.309 ± 0.213 | 0.345 ± 0.225 |
| 10 | 0.018 ± 0.009 | 0.005 ± 0.003 | 0.005 ± 0.002 | 0.007 ± 0.003 |
| 11 | 0.129 ± 0.068 | 0.138 ± 0.060 | 0.239 ± 0.092 | 0.315 ± 0.119 |
| 12 | 0.033 ± 0.022 | 0.002 ± 0.001 | 0.002 ± 0.001 | 0.002 ± 0.0004 |
| 13 | 0.200 ± 0.093 | 0.239 ± 0.114 | 0.367 ± 0.123 | 0.477 ± 0.125 |

The HBV RNAi agents tested, both alone and in combination, showed a substantial reduction in HBsAg as compared to the PBS control across all measured time points.

Example 9. RNAi Agent Delivery

The pHBV mouse model described in Example 2, above, was used. At day 1, each mouse was administered a single subcutaneous injection of 200 μl containing 10 mg/kg (mpk) of an HBV RNAi agent formulated in phosphate buffered saline, or 200 μl of phosphate buffered saline without an HBV RNAi agent, to be used as a control. The HBV RNAi agents tested included those having the duplex numbers shown in Table 23, below, which each included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected prior to administration, and then on day 8, day 15, day 22, and day 29, and serum Hepatitis B surface antigen (HBsAg) levels were determined pursuant to the procedure set forth in Example 2, above. Data from the experiment is shown in the following Table:

TABLE 23

Average HBsAg levels normalized to pre-treatment and PBS control in pHBV mice following administration of HBV RNAi agents from Example 9 (standard deviation reflected as (+/−)).

| RNAi agent | HBsAg in serum at nadir (norm. fraction) | % KD at nadir | Day of nadir |
|---|---|---|---|
| PBS | 1.000 | N/A | N/A |
| AD03498 | 0.087 ± 0.016 | 91.3% | 8 |
| AD03499 | 0.069 ± 0.011 | 93.1% | 15 |
| AD03500 | 0.095 ± 0.031 | 90.5% | 8 |
| AD03501 | 0.046 ± 0.020 | 95.4% | 15 |

Each of the HBV RNAi agents shown in Table 23, above, included an antisense strand sequence that is at least partially complementary to the X ORF at positions 1781-1799 of the HBV genome. Each of the RNAi agents showed a significant knockdown compared to PBS control.

Example 10. HBV RNAi Agents in pHBV Mice: Further Combination Studies

The pHBV mouse model described in Example 2, above, was used. Mice were divided into various groups as set forth in Table 24, below, and each mouse was administered a single 200 μl subcutaneous injection pursuant to the dosing regimen set forth in Table 24:

TABLE 24

Dosing groups of pHBV mice for Example 10.

| Group | RNAi Agent and Dose | Dosing Regimen |
|---|---|---|
| A | PBS Group I (no RNAi agent) | Single injection on day 1 and day 22 |
| B | PBS Group II (no RNAi agent) | Single injection on day 1 and day 22 |
| C | 3.0 mg/kg AD04585 | Single injection on day 1, day 22, day 50, and day 64 |
| D | 3.0 mg/kg AD04771 | Single injection on day 1 and day 22 |
| E | 3.0 mg/kg AD04580 | Single injection on day 1, day 22, day 50, and day 64 |
| F | 3.0 mg/kg AD04776 | Single injection on day 1 and day 22 |
| G | 1.5 mg/kg AD04585 + 1.5 mg/kg AD04580 | Single injection on day 1, day 22, day 50, and day 64 |
| H | 1.5 mg/kg AD04771 + 1.5 mg/kg AD04776 | Single injection on day 1 and day 22 |
| I | 2.0 mg/kg AD04771 + 1.0 mg/kg AD04776 | Single injection on day 1 and day 22 |
| J | 2.25 mg/kg AD04771 + 0.75 mg/kg AD04776 | Single injection on day 1 and day 22 |

Each mouse was given a subcutaneous administration of 200 μl containing the amount of HBV RNAi agent(s) formulated in phosphate buffered saline, or 200 μl of phosphate buffered saline without an HBV RNAi agent, as set forth in Table 24. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected prior to administration, and then on day −1, day 8, day 15, day 22, day 29, day 36, day 43, day 50, day 57, and day 64. Serum Hepatitis B surface antigen (HBsAg) levels were determined pursuant to the procedure set forth in Example 2, above. Data from the experiment is shown in the following:

TABLE 25

Average HBsAg levels normalized to pre-treatment and PBS control (Group A used as control) in pHBV mice following administration of HBV RNAi agents from Example 10 (standard deviation reflected as (+/−)).

| Group | Day 8 | Day 15 | Day 22 |
|---|---|---|---|
| A | 1.000 ± 0.146 | 1.000 ± 0.095 | 1.000 ± 0.202 |
| B | 0.931 ± 0.161 | 1.091 ± 0.156 | 1.132 ± 0.259 |
| C | 0.071 ± 0.050 | 0.031 ± 0.022 | 0.024 ± 0.013 |
| D | 0.134 ± 0.035 | 0.130 ± 0.024 | 0.119 ± 0.028 |
| E | 0.015 ± 0.001 | 0.041 ± 0.012 | 0.087 ± 0.015 |
| F | 0.197 ± 0.081 | 0.308 ± 0.138 | 0.476 ± 0.156 |
| G | 0.029 ± 0.015 | 0.069 ± 0.029 | 0.094 ± 0.016 |
| H | 0.191 ± 0.057 | 0.315 ± 0.094 | 0.420 ± 0.126 |
| I | 0.153 ± 0.050 | 0.194 ± 0.076 | 0.233 ± 0.116 |
| J | 0.155 ± 0.059 | 0.177 ± 0.067 | 0.316 ± 0.117 |

| Group | Day 29 | Day 36 | Day 43 |
|---|---|---|---|
| A | 1.000 ± 0.182 | 1.000 ± 0.287 | 1.000 ± 0.298 |
| B | 1.417 ± 0.414 | 1.166 ± 0.248 | |
| C | 0.007 ± 0.005 | 0.004 ± 0.003 | 0.006 ± 0.001 |
| D | 0.048 ± 0.023 | 0.036 ± 0.020 | 0.052 ± 0.027 |
| E | 0.014 ± 0.006 | 0.021 ± 0.011 | 0.026 ± 0.011 |
| F | 0.246 ± 0.081 | 0.244 ± 0.097 | 0.179 ± 0.061 |
| G | 0.023 ± 0.009 | 0.027 ± 0.009 | 0.037 ± 0.013 |
| H | 0.200 ± 0.080 | 0.185 ± 0.081 | 0.194 ± 0.055 |
| I | 0.141 ± 0.082 | 0.133 ± 0.051 | 0.151 ± 0.082 |
| J | 0.133 ± 0.064 | 0.102 ± 0.039 | 0.129 ± 0.050 |

| Group | Day 50 | Day 57 | Day 64 |
|---|---|---|---|
| A | 1.000 ± 0.296 | 1.000 ± 0.394 | 1.000 ± 0.395 |
| B | | | |
| C | 0.015 ± 0.0001 | 0.002 ± 0.001 | 0.004 ± 0.001 |
| D | | | |
| E | 0.052 ± 0.015 | 0.009 ± 0.002 | 0.018 ± 0.007 |
| F | | | |
| G | 0.076 ± 0.020 | 0.012 ± 0.003 | 0.020 ± 0.007 |
| H | | | |
| I | | | |
| J | | | |

HBV RNAi agents AD04585 and AD04771 were designed to have antisense strand sequences that are at least partially complementary to the S open reading frame at positions 257-275 of the HBV genome, as shown in Tables 1 and 2. HBV RNAi agents AD04580 and AD04776 were designed to have antisense strand sequences that are at least partially complementary to the X open reading frame at positions 1781-1799 of the HBV genome, as shown in Tables 1 and 2 The HBV RNAi agents tested, both alone and in combination, showed a reduction in HBsAg as compared to the PBS control across all measured time points. Each subsequent dose further reduced the nadir of HBsAg reduction.

Additionally, serum HBV DNA levels were determined for Group C (3.0 mg/kg AD04585), Group E (3.0 mg/kg AD04580), and Group G (1.5 mg/kg AD04585+1.5 mg/kg AD04580) in Table 24, from serum samples collected on days −1, 8, 15, 22, 29, and 36, 43 and 50 pursuant to the procedure set forth in Example 2, above. Serum HBV DNA was isolated for each animal at each of these time points. Data are presented in the following Table:

TABLE 26

Average Serum HBV DNA levels normalized to pre-treatment and PBS controls (both PBS groups A and B) in pHBV mice following administration of HBV RNAi agents from Example 10 (standard deviation reflected as (+/−)).

| Group | Day 8 | Day 15 | Day 22 | Day 29 |
|---|---|---|---|---|
| A/B (PBS) | 1.000 ± 0.316 | 1.000 ± 0.427 | 1.000 ± 0.428 | 1.000 ± 0.475 |
| C | 0.172 ± 0.151 | 0.142 ± 0.079 | 0.252 ± 0.132 | 0.072 ± 0.086 |
| E | 0.024 ± 0.015 | 0.042 ± 0.037 | 0.449 ± 0.184 | 0.053 ± 0.048 |
| G | 0.093 ± 0.053 | 0.083 ± 0.037 | 0.370 ± 0.153 | 0.211 ± 0.060 |

| Group | Day 36 | Day 43 | Day 50 |
|---|---|---|---|
| A/B (PBS) | 1.000 ± 0.623 | 1.000 ± 0.532 | 1.000 ± 0.532 |
| C | 0.044 ± 0.020 | 0.104 ± 0.033 | 0.156 ± 0.016 |
| E | 0.012 ± 0.004 | 0.061 ± 0.031 | 0.161 ± 0.019 |
| G | 0.048 ± 0.022 | 0.147 ± 0.010 | 0.295 ± 0.041 |

The data in Table 26 indicate that the HBV RNAi agents examined, both individually and in combination, provided a reduction in HBV DNA levels compared to the PBS group.

Example 11. HBV RNAi Agents in pHBV Mice: Combination Studies

The pHBV mouse model described in Example 2, above, was used. Mice were divided into various groups as set forth in Table 27, below, and each mouse was administered a single 200 μl subcutaneous injection pursuant to the dosing regimen set forth in Table 27:

TABLE 27

Dosing groups of pHBV mice for Example 11.

| Group | RNAi Agent and Dose | Dosing Regimen |
|---|---|---|
| A | PBS (no RNAi agent) | Single injection on day 1 |
| B | 3.0 mg/kg AD04962 | Single injection on day 1 |
| C | 3.0 mg/kg AD04963 | Single injection on day 1 |
| D | 1.5 mg/kg AD04962 + 1.5 mg/kg AD04963 | Single injection on day 1 |
| E | 2.0 mg/kg AD04962 + 1.0 mg/kg AD04963 | Single injection on day 1 |
| F | 2.25 mg/kg AD04962 + 0.75 mg/kg AD04963 | Single injection on day 1 |
| G | 1.5 mg/kg AD04962 + 1.5 mg/kg AD04963 | Single injection on day 1 |
| H | 3.0 mg/kg AD04962 + 3.0 mg/kg AD04963 | Single injection on day 1 |
| I | 1.5 mg/kg AD04962 + 1.5 mg/kg AD04963 | Single injection on day 1 |
| J | 4.5 mg/kg AD04962 + 4.5 mg/kg AD04963 | Single injection on day 1 |
| K | 3.0 mg/kg AD04872 | Single injection on day 1 |
| L | 3.0 mg/kg AD04882 | Single injection on day 1 |
| M | 3.0 mg/kg AD04885 | Single injection on day 1 |

Each mouse was given a subcutaneous administration of 200 μl containing the amount of HBV agent(s) formulated in phosphate buffered saline, or 200 μl of phosphate buffered saline without an HBV RNAi agent, as set forth in Table 24.

Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected on day −1 prior to administration, and then on day 8, day 15, day 22, day 29, and day 36 (except for Group L (AD04882) and Group M (AD04885), and serum Hepatitis B surface antigen (HBsAg) levels were determined pursuant to the procedure set forth in Example 2, above. Data from the experiment is shown in the following Table:

TABLE 28

Average HBsAg normalized to pre-treatment and PBS control in pHBV mice following administration of HBV RNAi agents from Example 11 (standard deviation reflected as (+/−)).

| Group | Day 8 | Day 15 | Day 22 |
|---|---|---|---|
| A | 1.000 ± 0.048 | 1.000 ± 0.144 | 1.000 ± 0.083 |
| B | 0.125 ± 0.025 | 0.083 ± 0.014 | 0.063 ± 0.016 |
| C | 0.019 ± 0.005 | 0.035 ± 0.008 | 0.052 ± 0.009 |
| D | 0.054 ± 0.013 | 0.079 ± 0.009 | 0.108 ± 0.021 |
| E | 0.099 ± 0.025 | 0.098 ± 0.053 | 0.142 ± 0.050 |
| F | 0.070 ± 0.015 | 0.103 ± 0.036 | 0.140 ± 0.020 |
| G | 0.041 ± 0.021 | 0.012 ± 0.008 | 0.021 ± 0.013 |
| H | 0.020 ± 0.006 | 0.044 ± 0.010 | 0.062 ± 0.019 |
| I | 0.077 ± 0.017 | 0.019 ± 0.004 | 0.004 ± 0.001 |
| J | 0.012 ± 0.002 | 0.021 ± 0.001 | 0.032 ± 0.002 |
| K | 0.045 ± 0.014 | 0.013 ± 0.005 | 0.008 ± 0.005 |
| L | 0.106 ± 0.020 | 0.176 ± 0.044 | 0.215 ± 0.082 |
| M | 0.275 ± 0.029 | 0.378 ± 0.080 | 0.572 ± 0.043 |

| Group | Day 29 | Day 36 |
|---|---|---|
| A | 1.000 ± 0.209 | 1.000 ± 0.270 |
| B | 0.079 ± 0.020 | 0.096 ± 0.007 |
| C | 0.087 ± 0.014 | 0.164 ± 0.026 |
| D | 0.176 ± 0.014 | 0.292 ± 0.030 |
| E | 0.223 ± 0.082 | 0.373 ± 0.150 |
| F | 0.213 ± 0.020 | 0.328 ± 0.034 |
| G | 0.031 ± 0.013 | 0.078 ± 0.064 |
| H | 0.97 ± 0.028 | 0.160 ± 0.060 |
| I | 0.008 ± 0.001 | 0.002 ± 0.0003 |
| J | 0.044 ± 0.008 | 0.069 ± 0.009 |
| K | 0.011 ± 0.007 | 0.011 ± 0.009 |
| L | 0.299 ± 0.009 | |
| M | 0.792 ± 0.057 | |

RNAi agent AD04962 was designed to have an antisense strand sequence that is at least partially complementary to the S open reading frame at positions 257-275 of the HBV genome, as shown in Tables 1 and 2. RNAi agent AD04872 was designed to have an antisense strand sequence that is at least partially complementary to the S open reading frame at positions 261-279 of the HBV genome, as shown in Tables 1 and 2. RNAi agent AD04963 was designed to have an antisense strand sequence that is at least partially complementary to the X open reading frame at positions 1781-1799 of the HBV genome, as shown in Tables 1 and 2. RNAi agents AD04882 and AD04885 were designed to have antisense strand sequences that are at least partially complementary to the X open reading frame at positions 1780-1798 of the HBV genome, as shown in Tables 1 and 2. The HBV RNAi agents shown in Table 9, directly above, each showed a reduction in HBsAg as compared to the PBS control across all measured timepoints, both individually and in combination. Re-dosing yielded additional HBsAg reduction.

Additionally, Serum Hepatitis B e-antigen (HBeAg) levels were also assessed for all groups except Groups L and M. Samples from the mice in each respective group were first pooled, and the resulting serum samples were assayed in singlet. Data from the experiment is shown in the following Table:

TABLE 29

Average HBeAg levels normalized to pre-treatment and PBS control in pHBV mice following administration of HBV RNAi agents from Example 11.

| Group | Day 8 | Day 22 | Day 29 | Day 36 |
|---|---|---|---|---|
| A | 1.000 | 1.000 | 1.000 | 1.000 |
| B | 0.425 | 0.291 | 0.371 | 0.365 |
| C | 0.152 | 0.170 | 0.328 | 0.356 |
| D | 0.266 | 0.249 | 0.456 | 0.440 |
| E | 0.278 | 0.295 | 0.589 | 0.561 |
| F | 0.306 | 0.291 | 0.718 | 0.522 |
| G | 0.183 | 0.138 | 0.291 | 0.249 |
| H | 0.091 | 0.131 | 0.315 | 0.238 |
| I | 0.183 | 0.052 | 0.069 | 0.036 |
| J | 0.089 | 0.114 | 0.190 | 0.236 |
| K | 0.458 | 0.172 | 0.322 | 0.207 |

Further, serum HBV DNA levels were determined for each of the groups in Table 27 from serum samples collected on days 8, 15, 22, and 29, pursuant to the procedure set forth in Example 2, above. Serum HBV DNA was isolated from each animal at each time point. Data are presented in the following Table:

TABLE 30

Average Serum HBV DNA levels normalized to pre-treatment and PBS control in pHBV mice following administration of HBV RNAi agents from Example 7 (standard deviation reflected as (+/−)).

| Group | Day 8 | Day 15 | Day 22 | Day 29 |
|---|---|---|---|---|
| A | 1.000 ± 0.232 | 1.000 ± 0.463 | 1.000 ± 0.272 | 1.000 ± 0.205 |
| B | 0.577 ± 0.219 | 0.222 ± 0.064 | 0.196 ± 0.055 | 0.261 ± 0.117 |
| C | 0.165 ± 0.051 | 0.070 ± 0.042 | 0.142 ± 0.105 | 0.228 ± 0.174 |
| D | 0.343 ± 0.125 | 0.307 ± 0.091 | 0.300 ± 0.092 | 0.356 ± 0.032 |
| E | 0.262 ± 0.033 | 0.216 ± 0.018 | 0.227 ± 0.028 | 0.279 ± 0.090 |
| F | 0.320 ± 0.134 | 0.332 ± 0.208 | 0.344 ± 0.209 | 0.338 ± 0.211 |
| G | 0.231 ± 0.036 | 0.034 ± 0.024 | 0.069 ± 0.039 | 0.077 ± 0.020 |
| H | 0.229 ± 0.101 | 0.155 ± 0.121 | 0.148 ± 0.079 | 0.215 ± 0.035 |
| I | 0.281 ± 0.129 | 0.109 ± 0.071 | 0.023 ± 0.019 | 0.011 ± 0.009 |
| J | 0.078 ± 0.050 | 0.061 ± 0.020 | 0.074 ± 0.029 | 0.056 ± 0.030 |
| K | 0.314 ± 0.064 | 0.119 ± 0.043 | 0.076 ± 0.067 | 0.078 ± 0.095 |
| L | 0.295 ± 0.077 | 0.305 ± 0.101 | 0.213 ± 0.088 | 0.186 ± 0.084 |
| M | 0.515 ± 0.247 | 0.505 ± 0.293 | 0.488 ± 0.318 | 0.478 ± 0.267 |

The data in Table 30 indicate that the RNAi agents examined, both individually and in combination, provided a reduction in HBV DNA levels compared to the PBS group. Re-dosing yielded addition reduction of HBV DNA.

Example 12. HBV RNAi Agents in pHBV Mice

The pHBV mouse model described in Example 2, above, was used. Mice were divided into various groups as set forth in Table 31, below, and each mouse was administered a single 200 μl subcutaneous injection pursuant to the dosing regimen set forth in Table 31:

TABLE 31

Dosing groups of pHBV mice for Example 12.

| Group | RNAi Agent and Dose | Dosing Regimen |
|---|---|---|
| A | PBS (no RNAi agent) | Single injection on day 1 |
| B | 2.0 mg/kg AD04871 | Single injection on day 1 |
| C | 2.0 mg/kg AD04872 | Single injection on day 1 |
| D | 2.0 mg/kg AD04874 | Single injection on day 1 |
| E | 2.0 mg/kg AD04875 | Single injection on day 1 |
| F | 2.0 mg/kg AD04876 | Single injection on day 1 |
| G | 2.0 mg/kg AD04881 | Single injection on day 1 |
| H | 2.0 mg/kg AD04883 | Single injection on day 1 |
| I | 2.0 mg/kg AD04884 | Single injection on day 1 |

Each mouse was given a subcutaneous administration of 200 μl containing the amount of HBV RNAi agent formulated in phosphate buffered saline, or 200 μl of phosphate buffered saline without an HBV RNAi agent, as set forth in Table 24. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected prior to administration, and then on day 8, day 15, and day 22. Group A (PBS), Group B (2.0 mg/kg AD04871), Group C (2.0 mg/kg AD04872), Group D (2.0 mg/kg AD04874), Group E (2.0 mg/kg AD04875), and Group F (2.0 mg/kg AD04876) also had serum collected on day 29, day 36, day 43, and day 50. Serum Hepatitis B surface antigen (HBsAg) levels were determined pursuant to the procedure set forth in Example 2, above. Data from the experiment is shown in the following Table:

TABLE 32

Average HBsAg normalized to pre-treatment and PBS control in pHBV mice following administration of HBV RNAi agents from Example 12 (standard deviation reflected as (+/−)).

| Group | Day 8 | Day 15 | Day 22 | Day 29 |
|---|---|---|---|---|
| A | 1.000 ± 0.132 | 1.000 ± 0.089 | 1.000 ± 0.080 | 1.000 ± 0.098 |
| B | 0.102 ± 0.034 | 0.041 ± 0.021 | 0.049 ± 0.033 | 0.048 ± 0.031 |
| C | 0.153 ± 0.064 | 0.064 ± 0.032 | 0.063 ± 0.034 | 0.042 ± 0.017 |
| D | 0.123 ± 0.022 | 0.049 ± 0.017 | 0.039 ± 0.010 | 0.023 ± 0.001 |
| E | 0.190 ± 0.075 | 0.094 ± 0.038 | 0.107 ± 0.061 | 0.081 ± 0.051 |
| F | 0.190 ± 0.031 | 0.076 ± 0.035 | 0.084 ± 0.038 | 0.049 ± 0.024 |
| G | 0.159 ± 0.047 | 0.216 ± 0.057 | 0.235 ± 0.151 | |
| H | 0.508 ± 0.078 | 0.666 ± 0.131 | 0.543 ± 0.048 | |
| I | 0.279 ± 0.087 | 0.357 ± 0.078 | 0.614 ± 0.156 | |

| Group | Day 36 | Day 43 | Day 50 |
|---|---|---|---|
| A | 1.000 ± 0.065 | 1.000 ± 0.242 | 1.000 ± 0.224 |
| B | 0.054 ± 0.038 | 0.064 ± 0.030 | 0.092 ± 0.025 |
| C | 0.049 ± 0.017 | 0.054 ± 0.015 | 0.085 ± 0.010 |
| D | 0.037 ± 0.004 | 0.037 ± 0.010 | 0.065 ± 0.012 |
| E | 0.126 ± 0.077 | 0.125 ± 0.063 | 0.170 ± 0.079 |
| F | 0.089 ± 0.044 | 0.082 ± 0.034 | 0.115 ± 0.028 |
| G | | | |
| H | | | |
| I | | | |

HBV RNAi agents AD04871, AD04872, AD04874, AD04875, and AD04876 were each designed to have antisense strand sequences that are at least partially complementary to the S open reading frame at positions 261-279 of the HBV genome, as shown in Tables 1 and 2. Each of these HBV RNAi agents should a substantial reduction in HBsAg compared to PBS control. For example, a single 2 mg/kg dose of each of AD04871 (Group B), AD04872 (Group C) and AD04874 (Group D), and AD04876 (Group F), exhibited a greater than 90% reduction in HBsAg for each of the timepoints measured from day 15 through day 43 compared to control. HBV RNAi agents AD04881, AD04883, AD04884 were each designed to have antisense strand sequences that are at least partially complementary to the X open reading frame at positions 1780-1798 of the HBV genome, as shown in Tables 1 and 2.

Example 13. Dose Response and Combinations of HBV RNAi Agents in X Region Knockout Model Mice As an alternative means in assessing the effects of the combination of an RNAi agent that includes an antisense strand sequence that is at least partially complementary to a region located in the S ORF of an HBV mRNA, and a second RNAi agent that includes an antisense strand sequence that is at least partially complementary to a region located in the X ORF of an HBV mRNA, a plasmid was generated that included the HBV genome with a knockout of the binding site for HBV RNAi agents that target positions 1780 and 1781, as shown in Tables 1 and 2 (hereinafter referred to as X Region Knockout mice). This model was generated by mutating ten (10) bases in the pHBV1.3 plasmid within the binding site of these RNAi agents. The remainder of the HBV mRNA, including the S-region, remained functional. Thus, in this HBV mouse model, inclusion of an HBV RNAi agent having an antisense strand that targets positions 1780 and 1781 of the HBV genome disclosed herein is expected to be ineffective in silencing expression.

The mice were divided into various groups including those set forth in Table 33, below, and the mice were given 200 pd subcutaneous injections pursuant to the dosing regimen set forth in the following Table:

TABLE 33

Dosing groups of X Region Knockout mice for Example 13.

| Group | RNAi Agent and Dose | Dosing Regimen | Number of Animals (n) |
|---|---|---|---|
| 1 | PBS (no RNAi agent) | Single injection on day 1 | 4 |
| 2 | 2.0 mg/kg AD04585 + 1.0 mg/kg AD04963 | Single injection on day 1 | 4 |
| 3 | 2.0 mg/kg AD04872 + 1.0 mg/kg AD04963 | Single injection on day 1 | 4 |
| 4 | 2.5 mg/kg AD04585 + 0.5 mg/kg AD04963 | Single injection on day 1 | 4 |
| 5 | 2.5 mg/kg AD04872 + 0.5 mg/kg AD04963 | Single injection on day 1 | 4 |
| 6 | 3.0 mg/kg AD04963 | Single injection on day 15 | 1 |

Each mouse was given a subcutaneous administration of 200 µl containing the amount of HBV RNAi agent(s) formulated in phosphate buffered saline, or 200 µl of phosphate buffered saline without an HBV RNAi agent, as set forth in Table 33. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected on day 5, day 8, day 15, day 22, and day 29 and serum Hepatitis B surface antigen (HBsAg) levels were determined pursuant to the procedure set forth in Example 2, above. Serum was also collected for Groups 1 through 5 on days 36 and 43. Data from the experiment is shown in the following Table 34:

TABLE 34

Average HBsAg normalized to pre-treatment and PBS control in X Region Knockout mice following administration of HBV RNAi agents from Example 13 (standard deviation reflected as (+/−)).

| Group | Day 8 | Day 15 | Day 22 |
|---|---|---|---|
| 1 | 1.000 ± 0.186 | 1.000 ± 0.165 | 1.000 ± 0.132 |
| 2 | 0.061 ± 0.034 | 0.041 ± 0.035 | 0.030 ± 0.015 |
| 3 | 0.020 ± 0.011 | 0.007 ± 0.003 | 0.003 ± 0.002 |
| 4 | 0.063 ± 0.039 | 0.022 ± 0.011 | 0.029 ± 0.013 |
| 5 | 0.027 ± 0.014 | 0.003 ± 0.003 | 0.001 ± 0.001 |
| 6 | 0.948 | 1.360 | 1.652 |

| Group | Day 29 | Day 36 | Day 43 |
|---|---|---|---|
| 1 | 1.000 ± 0.059 | 1.000 ± 0.044 | 1.000 ± 0.045 |
| 2 | 0.051 ± 0.029 | 0.062 ± 0.029 | |
| 3 | 0.004 ± 0.003 | 0.008 ± 0.003 | 0.018 ± 0.007 |
| 4 | 0.040 ± 0.022 | 0.061 ± 0.030 | |
| 5 | 0.002 ± 0.001 | 0.003 ± 0.002 | 0.014 ± 0.006 |
| 6 | 1.831 | | |

As expected, Group 6, which was a single dose of 3.0 mg/kg of HBV RNAi agent AD04963 and includes an antisense strand that is at least partially complementary to the X open reading frame at positions 1781-1799 of the HBV genome, was unable to provide knockdown of HBsAg. Additionally, each of Groups 2 through 5 provided substantial knockdown of HBsAg compared to PBS control, with both Group 3 and Group 5 exhibiting a greater than 2 log reduction in HBsAg at nadir (day 22).

Example 14. Dose Response and Combinations of HBV RNAi Agents in X Region Knockout Model Mice The X Region Knockout mouse model described in Example 13, above, was used. Mice were divided into various groups including those set forth in Table 31, below, and each mouse was administered a single 200 µl subcutaneous injection pursuant to the dosing regimen set forth in Table 35:

TABLE 35

Dosing groups of X Region Knockout mice for Example 14.

| Group | RNAi Agent and Dose | Dosing Regimen |
|---|---|---|
| 1 | PBS (no RNAi agent) | Single injection on day 1 |
| 2 | 2.0 mg/kg AD04872 | Single injection on day 1 |
| 3 | 2.0 mg/kg AD04872 + 0.7 mg/kg AD05070 | Single injection on day 1 |
| 4 | 2.0 mg/kg AD04872 + 1.0 mg/kg AD05070 | Single injection on day 1 |
| 5 | 2.0 mg/kg AD04872 + 2.0 mg/kg AD05070 | Single injection on day 1 |

Each mouse was given a subcutaneous administration of 200 µl containing the amount of HBV RNAi agent(s) formulated in phosphate buffered saline, or 200 µl of phosphate buffered saline without an HBV RNAi agent, as set forth in Table 35. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group shown in Table 35 were tested (n=3).

Serum was collected on day 1 (pre-dose), day 8, day 15, day 22, and day 29, and serum Hepatitis B surface antigen (HBsAg) levels were determined pursuant to the procedure set forth in Example 2, above. Data from the experiment is shown in the following Table:

TABLE 36

Average HBsAg levels normalized to pre-treatment and PBS control in X Region Knockout mice from Example 14.

| Group | Day 8 | Day 15 | Day 22 | Day 29 |
|---|---|---|---|---|
| 1 | 1.000 ± 0.120 | 1.000 ± 0.255 | 1.000 ± 0.224 | 1.000 ± 0.143 |
| 2 | 0.104 ± 0.104 | 0.009 ± 0.009 | 0.005 ± 0.004 | 0.005 ± 0.003 |

TABLE 36-continued

Average HBsAg levels normalized to pre-treatment and
PBS control in X Region Knockout mice from Example 14.

| Group | Day 8 | Day 15 | Day 22 | Day 29 |
|---|---|---|---|---|
| 3 | 0.076 ± 0.041 | 0.010 ± 0.009 | 0.006 ± 0.005 | 0.005 ± 0.005 |
| 4 | 0.036 ± 0.008 | 0.002 ± 0.001 | 0.001 ± 0.001 | 0.002 ± 0.001 |
| 5 | 0.019 ± 0.017 | 0.003 ± 0.002 | 0.003 ± 0.001 | 0.004 ± 0.000 |

Table 36 shows that HBV RNAi agent AD04872 administered alone, and the combination of AD04872 (which includes an antisense strand that is at least partially complementary to the S open reading from at positions 261-279 of the HBV genome) and AD05070 (which includes an antisense strand that is at least partially complementary to the X open reading frame at positions 1781-1799 of the HBV genome), provided significant knockdown of HBsAg compared to PBS control across each of the time points measured. Addition of 0.7 mg/kg to 2 mg/kg HBV RNAi agent AD05070 for which there was a mutated target site in this X Region Knockout model did not diminish the activity of the 2 mg/kg HBV RNAi agent AD04872.

Additionally, serum HBV DNA levels were determined from serum samples collected on days 8, 15, and 22 pursuant to the procedure set forth in Example 2, above. Serum from each group was pooled and then DNA was isolated from the serum in singlet. Data are presented in the following Table:

TABLE 37

Average Serum HBV DNA levels normalized to pre-treatment
and PBS controls in X Region Knockout mice following administration
of HBV RNAi agents from Example 14 (standard deviation
reflected as (+/−)).

| Group | Day 8 | Day 15 | Day 22 |
|---|---|---|---|
| 1 | 1.000 ± 0.007 | 1.000 ± 0.011 | 1.000 ± 0.066 |
| 2 | 0.225 ± 0.019 | 0.022 ± 0.001 | 0.036 ± 0.001 |
| 3 | 0.151 ± 0.002 | 0.029 ± 0.001 | 0.042 ± 0.003 |
| 4 | 0.140 ± 0.006 | 0.016 ± 0.000 | 0.018 ± 0.000 |
| 5 | 0.069 ± 0.002 | 0.018 ± 0.003 | 0.043 ± 0.002 |

Addition of 0.7 mg/kg to 2 mg/kg HBV RNAi agent AD05070 for which there was a mutated target site in this X Region Knockout model did not diminish the activity of the 2 mg/kg HBV RNAi agent AD04872.

Example 15. HBV RNAi Agents in pHBV Mice

The pHBV mouse model described in Example 2, above, was used. Mice were divided into various groups including those set forth in Table 38, below, and each mouse was administered a single 200 µl subcutaneous injection pursuant to the dosing regimen set forth in Table 38:

TABLE 38

Dosing groups of pHBV mice for Example 15.

| Group | RNAi Agent and Dose | Dosing Regimen |
|---|---|---|
| 1 | PBS (no RNAi agent) | Single injection on day 1 |
| 2 | 2.0 mg/kg AD04776 | Single injection on day 1 |
| 3 | 2.0 mg/kg AD05069 | Single injection on day 1 |
| 4 | 2.0 mg/kg AD05070 | Single injection on day 1 |
| 5 | 2.0 mg/kg AD05071 | Single injection on day 1 |
| 6 | 2.0 mg/kg AD05073 | Single injection on day 1 |
| 7 | 2.0 mg/kg AD05074 | Single injection on day 1 |
| 8 | 2.0 mg/kg AD05075 | Single injection on day 1 |
| 9 | 2.0 mg/kg AD05076 | Single injection on day 1 |
| 10 | 2.0 mg/kg AD05077 | Single injection on day 1 |
| 11 | 2.0 mg/kg AD05078 | Single injection on day 1 |
| 12 | 3.0 mg/kg AD04872 + 1.0 mg/kg AD04776 | Single injection on day 1 |
| 13 | 3.0 mg/kg AD04872 + 1.0 mg/kg AD05069 | Single injection on day 1 |
| 14 | 3.0 mg/kg AD04872 + 1.0 mg/kg AD05070 | Single injection on day 1 |
| 15 | 3.0 mg/kg AD04872 + 1.0 mg/kg AD05071 | Single injection on day 1 |
| 16 | 3.0 mg/kg AD04872 + 1.0 mg/kg AD05073 | Single injection on day 1 |
| 17 | 3.0 mg/kg AD04872 + 1.0 mg/kg AD05074 | Single injection on day 1 |
| 18 | 3.0 mg/kg AD04872 + 1.0 mg/kg AD05075 | Single injection on day 1 |
| 19 | 3.0 mg/kg AD04872 + 1.0 mg/kg AD05076 | Single injection on day 1 |
| 20 | 3.0 mg/kg AD04872 + 1.0 mg/kg AD05077 | Single injection on day 1 |
| 21 | 3.0 mg/kg AD04872 + 1.0 mg/kg AD05078 | Single injection on day 1 |

Each mouse was given a subcutaneous administration of 200 µl containing the amount of HBV RNAi agent(s) formulated in phosphate buffered saline, or 200 µl of phosphate buffered saline without an HBV RNAi agent, as set forth in Table 38. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected on day −1 prior to administration, and then on day 8, day 15, day 22, day 29, day 36, day 43, and day 50. Serum Hepatitis B surface antigen (HBsAg) levels were determined pursuant to the procedure set forth in Example 2, above. Data from the experiment is shown in the following Table 39, with Average HBsAg reflecting the normalized average value of HBsAg:

TABLE 39

Average HBsAg normalized to pre-treatment and PBS control in pHBV mice following administration of HBV RNAi agents from Example 15.

| Group | Day 8 | Day 15 | Day 22 | Day 29 |
|---|---|---|---|---|
| 1 | 1.000 ± 0.119 | 1.000 ± 0.047 | 1.000 ± 0.080 | 1.000 ± 0.027 |
| 2 | 0.339 ± 0.076 | 0.414 ± 0.126 | 0.385 ± 0.067 | 0.450 ± 0.075 |
| 3 | 0.240 ± 0.096 | 0.361 ± 0.078 | 0.446 ± 0.073 | 0.508 ± 0.114 |
| 4 | 0.081 ± 0.026 | 0.127 ± 0.031 | 0.223 ± 0.057 | 0.330 ± 0.112 |
| 5 | 0.452 ± 0.020 | 0.431 ± 0.126 | 0.373 ± 0.079 | 0.383 ± 0.080 |
| 6 | 0.375 ± 0.181 | 0.632 ± 0.192 | 0.463 ± 0.117 | 0.567 ± 0.159 |
| 7 | 0.325 ± 0.032 | 0.438 ± 0.125 | 0.393 ± 0.056 | 0.443 ± 0.096 |
| 8 | 0.155 ± 0.031 | 0.322 ± 0.019 | 0.333 ± 0.077 | 0.463 ± 0.043 |
| 9 | 0.245 ± 0.063 | 0.467 ± 0.090 | 0.477 ± 0.045 | 0.562 ± 0.049 |
| 10 | 0.120 ± 0.062 | 0.173 ± 0.029 | 0.289 ± 0.019 | 0.331 ± 0.042 |
| 11 | 0.128 ± 0.042 | 0.172 ± 0.046 | 0.179 ± 0.015 | 0.215 ± 0.049 |
| 12 | 0.040 ± 0.015 | 0.014 ± 0.004 | 0.014 ± 0.006 | 0.015 ± 0.004 |
| 13 | 0.050 ± 0.020 | 0.015 ± 0.011 | 0.017 ± 0.008 | 0.022 ± 0.009 |
| 14 | 0.020 ± 0.011 | 0.011 ± 0.006 | 0.015 ± 0.006 | 0.023 ± 0.004 |
| 15 | 0.043 ± 0.005 | 0.013 ± 0.005 | 0.010 ± 0.002 | 0.011 ± 0.004 |
| 16 | 0.021 ± 0.017 | 0.008 ± 0.004 | 0.012 ± 0.003 | 0.011 ± 0.001 |
| 17 | 0.032 ± 0.011 | 0.009 ± 0.003 | 0.007 ± 0.002 | 0.008 ± 0.0003 |
| 18 | 0.023 ± 0.014 | 0.010 ± 0.006 | 0.009 ± 0.006 | 0.009 ± 0.004 |
| 19 | 0.025 ± 0.006 | 0.010 ± 0.004 | 0.009 ± 0.002 | 0.010 ± 0.003 |
| 20 | 0.061 ± 0.013 | 0.027 ± 0.006 | 0.020 ± 0.003 | 0.029 ± 0.006 |
| 21 | 0.061 ± 0.050 | 0.013 ± 0.010 | 0.012 ± 0.005 | 0.018 ± 0.006 |

| Group | Day 36 | Day 43 | Day 50 |
|---|---|---|---|
| 1 | 1.000 ± 0.031 | 1.000 ± 0.114 | 1.000 ± 0.112 |
| 2 | 0.617 ± 0.116 | 0.643 ± 0.154 | 0.665 ± 0.199 |
| 3 | 0.638 ± 0.067 | 0.743 ± 0.015 | 0.792 ± 0.115 |
| 4 | 0.472 ± 0.121 | 0.515 ± 0.126 | 0.689 ± 0.167 |
| 5 | 0.591 ± 0.159 | 0.604 ± 0.086 | 0.709 ± 0.115 |
| 6 | 0.717 ± 0.136 | 0.686 ± 0.194 | 0.781 ± 0.301 |
| 7 | 0.586 ± 0.069 | 0.775 ± 0.143 | 0.747 ± 0.095 |
| 8 | 0.666 ± 0.066 | 0.803 ± 0.096 | 0.856 ± 0.180 |
| 9 | 0.801 ± 0.047 | 0.667 ± 0.055 | 0.765 ± 0.208 |
| 10 | 0.640 ± 0.059 | 0.667 ± 0.034 | 0.742 ± 0.133 |
| 11 | 0.429 ± 0.063 | 0.383 ± 0.005 | 0.497 ± 0.060 |
| 12 | 0.037 ± 0.013 | 0.044 ± 0.012 | 0.056 ± 0.014 |
| 13 | 0.046 ± 0.011 | 0.055 ± 0.010 | 0.070 ± 0.010 |
| 14 | 0.054 ± 0.016 | 0.070 ± 0.018 | 0.096 ± 0.012 |
| 15 | 0.029 ± 0.011 | 0.032 ± 0.015 | 0.051 ± 0.020 |
| 16 | 0.033 ± 0.005 | 0.038 ± 0.007 | 0.062 ± 0.004 |
| 17 | 0.021 ± 0.002 | 0.031 ± 0.004 | 0.061 ± 0.005 |
| 18 | 0.034 ± 0.014 | 0.047 ± 0.016 | 0.079 ± 0.017 |
| 19 | 0.028 ± 0.005 | 0.037 ± 0.006 | 0.060 ± 0.011 |
| 20 | 0.070 ± 0.009 | 0.063 ± 0.018 | 0.097 ± 0.018 |
| 21 | 0.040 ± 0.012 | 0.066 ± 0.007 | 0.120 ± 0.036 |

RNAi agents AD04776, AD05069, AD05070, AD05071, AD05073, and AD05074 were each designed to have an antisense strand sequence that is at least partially complementary to the X open reading frame at positions 1781-1799 of the HBV genome, as shown in Tables 1 and 2. RNAi agents AD05075, AD05076, AD05077, and AD05078 were each designed to have antisense strand sequences that are at least partially complementary to the X open reading frame at positions 1780-1798 of the HBV genome, as shown in Tables 1 and 2.

Table 39 shows that HBV RNAi agents AD04776, AD05069, AD05070, AD05071, AD05073, and AD05074 administered alone or their combination with AD04872 (which includes an antisense strand that is at least partially complementary to the S open reading from at positions 261-279 of the HBV genome) provided significant knockdown of HBsAg compared to PBS control across each of the time points measured.

Example 16. HBV RNAi Agents in pHBV Mice: Dose Response and Combination Studies

The pHBV mouse model described in Example 2, above, was used. Mice were divided into various groups as set forth in Table 40, below, and each mouse was administered a single 200 μl subcutaneous injection pursuant to the dosing regimen set forth in Table 40:

TABLE 40

Dosing groups of pHBV mice for Example 16.

| Group | RNAi Agent and Dose | Dosing Regimen |
|---|---|---|
| 1 | PBS (no RNAi agent) | Single injection on day 1 |
| 2 | 3.2 mg/kg AD04872 | Single injection on day 1 |
| 3 | 3.2 mg/kg AD04872 | Single injection on day 1 and day 22 |
| 4 | 3.0 mg/kg AD04872 + 0.8 mg/kg AD05070 | Single injection on day 1 |
| 5 | 3.0 mg/kg AD04872 + 0.8 mg/kg AD05070 | Single injection on day 1 and day 22 |
| 6 | 3.0 mg/kg AD04872 + 1.0 mg/kg AD05070 | Single injection on day 1 |
| 7 | 3.0 mg/kg AD04872 + 1.0 mg/kg AD05070 | Single injection on day 1 and day 22 |
| 8 | 2.7 mg/kg AD04872 + 1.3 mg/kg AD05070 | Single injection on day 1 |

TABLE 40-continued

Dosing groups of pHBV mice for Example 16.

| Group | RNAi Agent and Dose | Dosing Regimen |
|---|---|---|
| 9 | 2.7 mg/kg AD04872 + 1.3 mg/kg AD05070 | Single injection on day 1 and day 22 |
| 10 | 2.0 mg/kg AD04872 + 2.0 mg/kg AD04776 | Single injection on day 1 and day 22 |
| 11 | 0.8 mg/kg AD05070 | Single injection on day 1 and day 22 |
| 12 | 1.3 mg/kg AD05070 | Single injection on day 1 and day 22 |

Each mouse was given a subcutaneous administration of 200 µl containing the amount of HBV RNAi agent(s) formulated in phosphate buffered saline, or 200 µl of phosphate buffered saline without an HBV RNAi agent, as set forth in Table 40. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Six (6) mice in each group were tested (n=6).

Serum was collected prior to administration, and then on day 8, day 15, day 22, and day 29, and serum Hepatitis B surface antigen (HBsAg) levels were determined pursuant to the procedure set forth in Example 2, above. Data from the experiment is shown in the following Table 41:

TABLE 41

Average HBsAg levels normalized to pre-treatment and PBS control in pHBV mice following administration of HBV RNAi agents from Example 16 (standard deviation reflected as (+/−)).

| Group | Day 8 | Day 15 | Day 22 | Day 29 |
|---|---|---|---|---|
| 1 | 1.000 ± 0.117 | 1.000 ± 0.213 | 1.000 ± 0.169 | 1.000 ± 0.130 |
| 2 | 0.050 ± 0.018 | 0.015 ± 0.007 | 0.011 ± 0.005 | 0.009 ± 0.006 |
| 3 | 0.051 ± 0.037 | 0.014 ± 0.011 | 0.010 ± 0.006 | 0.002 ± 0.001 |
| 4 | 0.029 ± 0.018 | 0.010 ± 0.006 | 0.011 ± 0.006 | 0.010 ± 0.005 |
| 5 | 0.022 ± 0.003 | 0.007 ± 0.001 | 0.009 ± 0.003 | 0.001 ± 0.001 |
| 6 | 0.027 ± 0.012 | 0.007 ± 0.004 | 0.008 ± 0.005 | 0.011 ± 0.005 |
| 7 | 0.028 ± 0.012 | 0.010 ± 0.005 | 0.009 ± 0.005 | 0.001 ± 0.000 |
| 8 | 0.033 ± 0.016 | 0.016 ± 0.008 | 0.020 ± 0.009 | 0.021 ± 0.011 |
| 9 | 0.034 ± 0.025 | 0.015 ± 0.011 | 0.018 ± 0.013 | 0.003 ± 0.002 |
| 10 | 0.038 ± 0.021 | 0.015 ± 0.005 | 0.019 ± 0.004 | 0.003 ± 0.001 |
| 11 | 0.446 ± 0.143 | 0.376 ± 0.120 | 0.474 ± 0.149 | 0.338 ± 0.123 |
| 12 | 0.307 ± 0.111 | 0.257 ± 0.122 | 0.236 ± 0.057 | 0.138 ± 0.031 |

The HBV RNAi agents tested, both individually and in combination, showed a reduction in HBsAg as compared to the PBS control across all measured time points. HBsAg expression was further reduced in all groups that were re-dosed on day 22.

Additionally, Serum Hepatitis B e-antigen (HBeAg) levels were also assessed. For the day 8 measurement, the serum samples for all six mice in each group were pooled, and the resulting samples were assayed in singlet. For the day −1, day 15, day 22, and day 29 measurements, the six mice from each group were paired within each group and their respective serum samples were pooled, forming three subgroups for each group. The serum samples for each of the three subgroups for each group were then assayed. Data from the experiment is shown in the following Table 42:

TABLE 42

Average HBeAg levels normalized to pre-treatment and PBS control in pHBV mice following administration of HBV RNAi agents from Example 16 (standard deviation for days 15, 22, and 29 reflected as (+/−)).

| Group | Day 8 | Day 15 | Day 22 | Day 29 |
|---|---|---|---|---|
| 1 | 1.000 | 1.000 ± 0.011 | 1.000 ± 0.170 | 1.000 ± 0.173 |
| 2 | 0.510 | 0.308 ± 0.031 | 0.217 ± 0.021 | 0.226 ± 0.035 |
| 3 | 0.488 | 0.301 ± 0.065 | 0.283 ± 0.081 | 0.147 ± 0.030 |
| 4 | 0.213 | 0.216 ± 0.067 | 0.192 ± 0.029 | 0.141 ± 0.048 |
| 5 | 0.192 | 0.211 ± 0.053 | 0.216 ± 0.088 | 0.047 ± 0.016 |
| 6 | 0.176 | 0.163 ± 0.022 | 0.238 ± 0.069 | 0.117 ± 0.011 |
| 7 | 0.165 | 0.175 ± 0.046 | 0.215 ± 0.061 | 0.028 ± 0.012 |
| 8 | 0.128 | 0.166 ± 0.065 | 0.386 ± 0.284 | 0.167 ± 0.118 |
| 9 | 0.172 | 0.171 ± 0.037 | 0.244 ± 0.052 | 0.032 ± 0.010 |
| 10 | 0.180 | 0.211 ± 0.012 | 0.283 ± 0.034 | 0.034 ± 0.001 |
| 11 | 0.634 | 0.594 ± 0.082 | 0.840 ± 0.152 | 0.271 ± 0.029 |
| 12 | 0.486 | 0.441 ± 0.066 | 0.804 ± 0.096 | 0.214 ± 0.039 |

The HBV RNAi agents tested, both individually and in combination, showed a reduction in HBeAg as compared to the saline control across all measured time points. HBeAg expression was further reduced in all groups that were re-dosed on day 22.

Further, serum HBV DNA levels were determined for each of the groups in Table 40 from serum samples collected on days −1, 8, 15, and 22, pursuant to the procedure set forth in Example 2, above. Serum from each pair of mice was pooled and then DNA was isolated from each serum pool in a single isolation. Data are presented in the following Table:

TABLE 43

Average Serum HBV DNA levels normalized to pre-treatment and PBS control in pHBV mice following administration of HBV RNAi agents from Example 16 (standard deviation reflected as (+/−)).

| Group | Day 8 | Day 15 | Day 22 |
|---|---|---|---|
| 1 | 1.000 ± 0.122 | 1.000 ± 0.299 | 1.000 ± 0.241 |
| 2 | 0.312 ± 0.016 | 0.126 ± 0.008 | 0.087 ± 0.018 |
| 3 | 0.264 ± 0.065 | 0.081 ± 0.023 | 0.073 ± 0.028 |
| 4 | 0.321 ± 0.254 | 0.120 ± 0.066 | 0.134 ± 0.101 |
| 5 | 0.319 ± 0.081 | 0.108 ± 0.038 | 0.098 ± 0.051 |
| 6 | 0.260 ± 0.095 | 0.068 ± 0.010 | 0.076 ± 0.031 |
| 7 | 0.170 ± 0.028 | 0.082 ± 0.013 | 0.062 ± 0.018 |

TABLE 43-continued

Average Serum HBV DNA levels normalized to pre-treatment and PBS control in pHBV mice following administration of HBV RNAi agents from Example 16 (standard deviation reflected as (+/−)).

| Group | Day 8 | Day 15 | Day 22 |
|---|---|---|---|
| 8 | 0.188 ± 0.020 | 0.192 ± 0.160 | 0.307 ± 0.309 |
| 9 | 0.242 ± 0.003 | 0.100 ± 0.042 | 0.075 ± 0.028 |
| 10 | 0.322 ± 0.028 | 0.159 ± 0.025 | 0.086 ± 0.016 |
| 11 | 1.124 ± 0.142 | 0.742 ± 0.127 | 0.807 ± 0.192 |
| 12 | 1.004 ± 0.144 | 0.541 ± 0.340 | 0.569 ± 0.060 |

The HBV RNAi agents tested, both individually and in combination, showed a reduction in serum HBV DNA as compared to the saline control across all measured time points except in groups 11 and 12 that had no reduction in serum HBV DNA at Day 8.

Example 17. HBV RNAi Agents in in pHBV Mice

The pHBV mouse model described in Example 2, above, was used. Mice were divided into various groups as set forth in Table 44, below, and each mouse was administered a single 200 μl subcutaneous injection pursuant to the dosing regimen set forth in Table 44:

TABLE 44

Dosing groups of pHBV mice for Example 17.

| Group | RNAi Agent and Dose | Dosing Regimen |
|---|---|---|
| 1 | PBS (no RNAi agent) | Single injection on day 1 |
| 2 | 5 mg/kg AD04585 + 1 mg/kg AD04963 | Single injection on day 1 |
| 3 | 5 mg/kg AD04872 + 1 mg/kg AD04963 | Single injection on day 1 |
| 4 | 5 mg/kg AD04585 + 1 mg/kg AD04963 | Single injection on day 1 and day 8 |
| 5 | 5 mg/kg AD04872 + 1 mg/kg AD04963 | Single injection on day 1 and day 8 |
| 6 | 2.5 mg/kg AD04585 + 0.5 mg/kg AD04963 | Single injection on day 1 |
| 7 | 2.0 mg/kg AD04585 + 1.0 mg/kg AD04963 | Single injection on day 1 |
| 8 | 2.5 mg/kg AD04872 + 0.5 mg/kg AD04963 | Single injection on day 1 |
| 9 | 2.0 mg/kg AD04872 + 1.0 mg/kg AD04963 | Single injection on day 1 |
| 10 | 5 mg/kg AD04872 + 1 mg/kg AD04981 | Single injection on day 1 |
| 11 | 2.5 mg/kg AD04872 + 0.5 mg/kg AD04981 | Single injection on day 1 and day 8 |
| 12 | 2.5 mg/kg AD04872 + 0.5 mg/kg AD04981 | Single injection on day 1 |
| 13 | 2 mg/kg AD04872 + 1 mg/kg AD04981 | Single injection on day 1 |
| 14 | 2.5 mg/kg AD04585 + 0.5 mg/kg AD04981 | Single injection on day 1 |
| 15 | 2 mg/kg AD04585 + 1 mg/kg AD04981 | Single injection on day 1 |
| 16 | 0.5 mg/kg AD04981 | Single injection on day 1 |

Each mouse was given a subcutaneous administration of 200 μl containing the amount of HBV RNAi agent(s) formulated in phosphate buffered saline, or 200 μl of phosphate buffered saline without an HBV RNAi agent, as set forth in Table 44. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area. Three (3) mice in each group were tested (n=3).

Serum was collected prior to administration, and then on day 8, day 14, day 21, and day 29 and day 36, and serum Hepatitis B surface antigen (HBsAg) levels were determined pursuant to the procedure set forth in Example 2, above. Data from the experiment is shown in the following Table 45:

TABLE 45

Average HBsAg levels normalized to pre-treatment and PBS control in pHBV mice following administration of HBV RNAi agents from Example 17 (standard deviation reflected as (+/−)).

| Group | Day 8 | Day 14 | Day 21 | Day 29 | Day 36 |
|---|---|---|---|---|---|
| 1 | 1.000 ± 0.068 | 1.000 ± 0.125 | 1.000 ± 0.152 | 1.000 ± 0.110 | 1.000 ± 0.225 |
| 2 | 0.058 ± 0.033 | 0.059 ± 0.022 | 0.085 ± 0.023 | 0.158 ± 0.021 | |
| 3 | 0.025 ± 0.009 | 0.014 ± 0.006 | 0.015 ± 0.008 | 0.026 ± 0.015 | 0.049 ± 0.019 |
| 4 | 0.032 ± 0.007 | 0.005 ± 0.001 | 0.006 ± 0.002 | 0.014 ± 0.002 | |
| 5 | 0.024 ± 0.009 | 0.003 ± 0.001 | 0.001 ± 0.0004 | 0.001 ± 0.0005 | 0.004 ± 0.0004 |
| 6 | 0.063 ± 0.020 | 0.077 ± 0.013 | 0.131 ± 0.011 | 0.214 ± 0.026 | |
| 7 | 0.041 ± 0.018 | 0.059 ± 0.017 | 0.091 ± 0.016 | 0.140 ± 0.045 | |
| 8 | 0.070 ± 0.008 | 0.046 ± 0.016 | 0.043 ± 0.009 | 0.055 ± 0.012 | 0.081 ± 0.010 |
| 9 | 0.043 ± 0.006 | 0.027 ± 0.003 | 0.064 ± 0.017 | 0.064 ± 0.014 | 0.108 ± 0.026 |
| 10 | 0.015 ± 0.008 | 0.005 ± 0.003 | 0.005 ± 0.003 | 0.005 ± 0.003 | 0.009 ± 0.004 |
| 11 | 0.047 ± 0.014 | 0.005 ± 0.003 | 0.003 ± 0.002 | 0.003 ± 0.003 | 0.005 ± 0.003 |
| 12 | 0.062 ± 0.006 | 0.025 ± 0.007 | 0.027 ± 0.005 | 0.033 ± 0.005 | 0.060 ± 0.014 |
| 13 | 0.092 ± 0.029 | 0.050 ± 0.021 | 0.050 ± 0.022 | 0.054 ± 0.0019 | 0.094 ± 0.027 |
| 14 | 0.310 ± 0.180 | 0.056 ± 0.010 | 0.081 ± 0.010 | 0.112 ± 0.0018 | |
| 15 | 0.304 ± 0.044 | 0.083 ± 0.021 | 0.115 ± 0.013 | 0.165 ± 0.025 | |
| 16 | 1.667 ± 0.217 | 0.416 ± 0.163 | 0.341 ± 0.179 | 0.511 ± 0.0011 | 0.634 ± 0.005 |

The HBV RNAi agent combinations tested showed a reduction in HBsAg as compared to the saline control across all measured time points. Combinations containing AD04872 showed greater reductions than the equivalent combinations with AD04585 in place of AD04872.

Additionally, serum HBV DNA levels were determined for serum samples collected on days 8, 14, 21, and 29 pursuant to the procedure set forth in Example 2, above. Serum HBV DNA was isolated from each animal at each time point. Data are presented in the following Table 46:

TABLE 46

Average Serum HBV DNA levels normalized to pre-treatment and PBS control in pHBV mice following administration of HBV RNAi agents from Example 17 (standard deviation reflected as (+/−)).

| Group | Day 8 | Day 14 | Day 21 | Day 29 |
|---|---|---|---|---|
| 1 | 1.000 ± 0.280 | 1.000 ± 0.269 | 1.000 ± 0.418 | 1.000 ± 0.383 |
| 2 | 0.136 ± 0.068 | 0.192 ± 0.071 | 0.173 ± 0.032 | 0.292 ± 0.039 |
| 3 | 0.097 ± 0.034 | 0.068 ± 0.016 | 0.076 ± 0.034 | 0.131 ± 0.061 |
| 4 | 0.061 ± 0.039 | 0.002 ± 0.001 | 0.003 ± 0.001 | 0.019 ± 0.013 |
| 5 | 0.068 ± 0.025 | 0.003 ± 0.002 | 0.0009 ± 0.0003 | 0.0009 ± 0.0003 |
| 6 | 0.354 ± 0.299 | 0.345 ± 0.187 | 0.522 ± 0.234 | 0.509 ± 0.106 |
| 7 | 0.103 ± 0.064 | 0.291 ± 0.025 | 0.203 ± 0.043 | 0.203 ± 0.015 |
| 8 | 0.336 ± 0.142 | 0.185 ± 0.071 | 0.183 ± 0.065 | 0.162 ± 0.064 |
| 9 | 0.198 ± 0.055 | 0.093 ± 0.023 | 0.118 ± 0.054 | 0.143 ± 0.032 |
| 10 | 0.122 ± 0.071 | 0.024 ± 0.026 | 0.023 ± 0.020 | 0.014 ± 0.017 |
| 11 | 0.160 ± 0.069 | 0.016 ± 0.023 | 0.003 ± 0.001 | 0.005 ± 0.004 |
| 12 | 0.158 ± 0.039 | 0.120 ± 0.044 | 0.100 ± 0.049 | 0.091 ± 0.034 |
| 13 | 0.190 ± 0.038 | 0.169 ± 0.025 | 0.066 ± 0.015 | 0.081 ± 0.015 |
| 14 | 0.434 ± 0.136 | 0.318 ± 0.104 | 0.144 ± 0.094 | 0.240 ± 0.029 |
| 15 | 0.358 ± 0.185 | 0.287 ± 0.108 | 0.279 ± 0.080 | 0.303 ± 0.038 |
| 16 | 0.713 ± 0.085 | 0.674 ± 0.140 | 0.496 ± 0.128 | 0.590 ± 0.093 |

The HBV RNAi agent combinations tested showed a reduction in serum HBV DNA as compared to the saline control across all measured time points. Combinations containing AD04872 showed greater reductions than the equivalent combinations with AD04585 in place of AD04872. These greater reductions were observed at Day 22 and Day 29.

Example 18. HBV RNAi Agents in a HBV-Infected Humanized Mouse Model

For this study, Male FRG® (genotype Fah −/−/Rag2−/−/Il2rg −/− triple knockout mice on a C57BL/6 background (Yecuris) were transplanted with human hepatocytes when they were 1-2 months old. The human hepatocytes were allowed to repopulate the liver for approximately 6 months with periodic NTBC treatment to discourage growth of mouse hepatocytes. At 9 months of age the mice were given an intravenous inoculation of $4 \times 10^8$ genomes/kg HBV genotype C, which infected the human hepatocytes. After 2-3 months, serum HBV DNA levels reached a plateau indicating the human hepatocytes were maximally infected (mouse hepatocytes cannot be infected by HBV). Mice were one year old at the start of treatment with HBV RNAi agents, thus nearing the end of their life span.

Pre-treatment serum samples were taken on day −10 and day −3. Beginning on day 1, each mouse was administered an oral daily gavage with 0.01 mg/kg Entecavir dissolved in water to inhibit HBV replication. Daily dosing of Entecavir continued until the day mice were euthanized. Entecavir administration was expected to reduce serum HBV DNA in chronically infected human patients, but not reduce HBsAg.

Mice were divided into various groups including those set forth in Table 47, below:

TABLE 47

Dosing groups of HBV-infected FRG humanized model mice for Example 18.

| Group | RNAi Agent and Dose | Dosing Regimen | Terminal Day |
|---|---|---|---|
| A- mouse 1 | PBS (no RNAi agent) | Single injection on day 1 | Euthanized day 21 (unhealthy animal) |
| A- mouse 2 | PBS (no RNAi agent) | Single injection on day 1 and day 29 | Euthanized day 36 |
| B- mouse 1 | 4.0 mg/kg AD04872 + 2.0 mg/kg AD05070 | Single injection on day 1 and day 29 | Euthanized day 36 |
| B- mouse 2 | 4.0 mg/kg AD04872 + 2.0 mg/kg AD05070 | Single injection on day 1 and day 29 | Euthanized day 40 |
| C- mouse 1 | 4.5 mg/kg AD04872 + 1.5 mg/kg AD05070 | Single injection on day 1 | Euthanized day 15 |
| C- mouse 2 | 4.5 mg/kg AD04872 + 1.5 mg/kg AD05070 | Single injection on day 1 and day 29 | Euthanized day 36 |
| C- mouse 3 | 4.5 mg/kg AD04872 + 1.5 mg/kg AD05070 | Single injection on day 1 and day 29 | Euthanized day 40 |

Each mouse was also given a subcutaneous administration of 100 μl per 20 grams body weight containing the amount of HBV RNAi agent(s) formulated in phosphate buffered saline, or an equal volume of phosphate buffered saline without an HBV RNAi agent, on day 1 and on day 29 (if still alive on day 29), pursuant to the schedule as set forth in Table 47, directly above. Each of the HBV RNAi agents included N-acetyl-galactosamine targeting ligands conjugated to the 5'-terminal end of the sense strand, as shown in Tables 4 and 5. The injections were performed between the skin and muscle (i.e. subcutaneous injections) into the loose skin over the neck and shoulder area.

Serum was collected on day 8, day 15, day 22, day 29, day 36, and day 40 and serum Hepatitis B surface antigen (HBsAg) levels were determined pursuant to the procedure set forth in Example 2, above. Data from the experiment is shown in the following Table:

TABLE 48

Average HBsAg levels normalized to pre-treatment (day −3) for each individual HBV-infected humanized FRG model mouse from Example 18.

| Group | Day 8 | Day 15 | Day 22 | Day 29 | Day 36 | Day 40 |
|---|---|---|---|---|---|---|
| A-1 | 0.830 | 0.828 | 0.932 | 0.858 | 1.107 | |
| A-2 | 1.303 | 1.328 | | | | |
| B-1 | 0.548 | 0.314 | 0.272 | 0.207 | 0.138 | |
| B-2 | 0.592 | 0.337 | 0.243 | 0.215 | 0.160 | 0.175 |
| C-1 | 0.643 | 0.460 | 0.415 | 0.251 | 0.164 | |
| C-2 | 0.353 | 0.228 | 0.182 | 0.172 | 0.224 | 0.216 |
| C-3 | 0.814 | 0.674 | | | | |

Additionally, serum HBV DNA levels were determined from serum samples collected on days −10, −3, 8, 15, 22, 29, 36, and 40, pursuant to the procedure set forth in Example 2, above. Data are presented in the following Table 49:

TABLE 49

Serum HBV DNA levels normalized to the average of pre-treatment day −10 and day −3 for each HBV-infected FRG humanized mouse following administration of HBV RNAi agents from Example 14.

| Group | Day −10 | Day −3 | Day 8 | Day 15 | Day 22 | Day 29 | Day 36 | Day 40 |
|---|---|---|---|---|---|---|---|---|
| A-1 | 0.883 | 1.117 | 0.072 | 0.038 | 0.015 | 0.027 | 0.060 | |
| A-2 | 1.070 | 0.930 | 0.130 | 0.075 | | | | |
| B-1 | 1.538 | 0.462 | 0.032 | 0.017 | 0.011 | 0.006 | 0.010 | |
| B-2 | 1.350 | 0.650 | 0.042 | 0.018 | 0.012 | 0.007 | 0.008 | 0.007 |
| C-1 | 1.348 | 0.652 | 0.041 | 0.020 | 0.016 | 0.005 | 0.004 | |
| C-2 | 1.030 | 0.970 | 0.031 | 0.015 | 0.006 | 0.011 | 0.008 | 0.008 |

As expected, administration of Entecavir reduced viral replication in both the absence and presence of HBV RNAi agents.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A composition comprising an RNAi agent for inhibiting expression of a Hepatitis B Virus (HBV) gene, wherein the RNAi agent comprises:
an antisense strand comprising a nucleotide sequence of any one of the following: SEQ ID NO:100, SEQ ID NO:126, SEQ ID NO:127, SEQ ID NO:128, SEQ ID NO:171, SEQ ID NO:179, and SEQ ID NO:180, and
a sense strand comprising a nucleotide sequence of any one of the following: SEQ ID NO:229, SEQ ID NO:252, SEQ ID NO:253, SEQ ID NO:273, SEQ ID NO:302, and SEQ ID NO:319.

2. The composition of claim 1, wherein at least one nucleotide of the sense strand, the antisense strand, or both the sense strand and the antisense strand of the RNAi agent is a modified nucleotide, has a modified internucleoside linkage, or is both a modified nucleotide and has a modified internucleoside linkage.

3. The composition of claim 2, wherein all or substantially all of the nucleotides in both the sense strand and the antisense strand of the RNAi agent are modified nucleotides.

4. The composition of claim 1, wherein the RNAi agent further comprises a targeting ligand that is conjugated to the RNAi agent.

5. The composition of claim 4, wherein the targeting ligand comprises N-acetyl-galactosamine.

6. The composition of claim 5, wherein the targeting ligand is (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), or (NAG39)s.

7. The composition of claim 6, wherein the targeting ligand is (NAG25), (NAG25)s, (NAG31), (NAG31)s, (NAG37), or (NAG37)s.

8. The composition of claim 5, wherein the targeting ligand is conjugated to the sense strand of the RNAi agent.

9. The composition of claim 6, wherein the targeting ligand is conjugated to the sense strand of the RNAi agent.

10. The composition of claim 8, wherein the targeting ligand is conjugated to the 5' terminal end of the sense strand of the RNAi agent.

11. The composition of claim 7, wherein the targeting ligand is conjugated to the 5' terminal end of the sense strand of the RNAi agent.

12. The composition of claim 1, further comprising a pharmaceutically acceptable excipient.

13. The composition of claim 1, wherein the RNAi agent is conjugated to a targeting ligand that includes N-acetyl-galactosamine and has the duplex structure of AD04511 (SEQ ID NO:100 and SEQ ID NO:229), AD04872 (SEQ ID NO:126 and SEQ ID NO:252), AD04873 (SEQ ID NO:127 and SEQ ID NO:252), AD04874 (SEQ ID NO:128 and SEQ ID NO:253), or AD05164 (SEQ ID NO:126 and SEQ ID NO:273).

14. The composition of claim 1, wherein the composition comprises:
(a) a first RNAi agent comprising:
an antisense strand comprising a nucleotide sequence of any one of the following: SEQ ID NO:100, SEQ ID NO:126, SEQ ID NO:127, SEQ ID NO:128, SEQ ID NO:171, SEQ ID NO:179, and SEQ ID NO:180, and
a sense strand comprising a nucleotide sequence of any one of the following: SEQ ID NO:229, SEQ ID NO:252, SEQ ID NO:253, SEQ ID NO:273, SEQ ID NO:302, and SEQ ID NO:319; and
(b) a second RNAi agent comprising:
an antisense strand comprising a nucleotide sequence of any one of the following: SEQ ID NO:140 and SEQ ID NO:188, and
a sense strand comprising a nucleotide sequence of any one of the following: SEQ ID NO:262, SEQ ID NO:271, SEQ ID NO:274, and SEQ ID NO:328.

15. The composition of claim 14, wherein the first RNAi agent and the second RNAi agent are each independently conjugated to a targeting ligand that includes N-acetyl-galactosamine, and the first RNAi agent has the duplex structure of AD04872 (SEQ ID NO:126 and SEQ ID NO:252) and the second RNAi agent has the duplex structure of AD05070 (SEQ ID NO:140 and SEQ ID NO:262).

16. The composition of claim 14, wherein the composition further comprises one or more additional therapeutics.

17. The composition of claim 15, wherein the ratio of the first RNAi agent duplex (AD04872) to the second RNAi agent duplex (AD05070) in the composition is between about 1:2 to about 5:1.

18. The composition of claim 17, wherein the ratio of the first RNAi agent duplex (AD04872) to the second RNAi agent duplex (AD05070) in the composition is about 2:1.

19. The composition of claim 17, wherein the ratio of the first RNAi agent duplex (AD04872) to the second RNAi agent duplex (AD05070) in the composition is about 3:1.

20. The composition of claim 17, wherein the ratio of the first RNAi agent duplex (AD04872) to the second RNAi agent duplex (AD05070) in the composition is about 4:1.

21. A method for inhibiting expression of a Hepatitis B Virus (HBV) gene in a subject that has an HBV infection, the method comprising administering to the subject an effective amount of the composition of claim 1 to inhibit an HBV gene.

22. The method of claim 21, wherein administering the composition further treats a disease, disorder, or condition associated with the HBV infection in the subject.

23. The method of claim 21, wherein the composition comprises a first RNAi agent and a second RNAi agent, wherein the first RNAi agent and the second RNAi agent are each independently conjugated to a targeting ligand that includes N-acetyl-galactosamine, and the first RNAi agent has the duplex structure of AD04872 (SEQ ID NO:126 and SEQ ID NO:252) and the second RNAi agent has the duplex structure of AD05070 (SEQ ID NO:140 and SEQ ID NO:262).

24. The method of claim 23, wherein administering the composition further treats a disease, disorder, or condition associated with the HBV infection in the subject.

25. The method of claim 23, wherein the effective amount of the composition is sufficient to reduce the level of HBsAg, HBeAg, and/or serum HBV DNA, in a subject by at least about 40% relative to the subject's respective expression level prior to administration of the composition.

26. The method of claim 24, wherein the disease, disorder, or condition associated with the HBV infection is a chronic liver disease or disorder, liver inflammation, a fibrotic condition, a proliferative disorder, hepatocellular carcinoma, a Hepatitis D virus infection, or an acute HBV infection.

27. The method of claim 23, wherein the effective amount of the first RNAi agent duplex is between about 0.5 mg/kg and about 5 mg/kg, and the effective amount of the second RNAi agent duplex is between about 0.5 mg/kg and about 5 mg/kg.

28. An RNAi agent for inhibiting expression of a Hepatitis B Virus (HBV) gene, wherein the RNAi agent has a duplex structure comprising a sense strand and an antisense strand that is identical or substantially identical to the respective sense strand and antisense strand in a duplex structure selected from the group consisting of: AD04511 (SEQ ID NO:100 and SEQ ID NO:229), AD04872 (SEQ ID NO:126 and SEQ ID NO:252), AD04873 (SEQ ID NO:127 and SEQ ID NO:252), AD04874 (SEQ ID NO:128 and SEQ ID NO:253), and AD05164 (SEQ ID NO:126 and SEQ ID NO:273).

29. The RNAi agent of claim 28, wherein the RNAi agent comprises at least one overhang.

30. The RNAi agent of claim 29, wherein the RNAi agent comprises an overhang at the 3' end of the antisense strand.

31. The RNAi agent of claim 30, wherein the RNAi agent further comprises an overhang at the 3' end of the sense strand.

32. The RNAi agent of claim 28, wherein the RNAi agent comprises one or two blunt ends.

33. The RNAi agent of claim 28, wherein the RNAi agent comprises one or two frayed ends.

34. The RNAi agent of claim 28, wherein the sense strand comprises at least one inverted abasic nucleoside.

35. The method of claim 21, wherein the effective amount of the composition is subcutaneously or intravenously administered.

36. The method of claim 21, further comprising administering to the subject one or more additional therapeutics.

37. The method of claim 36, wherein the one or more additional therapeutics comprises an antiviral agent.

38. The method of claim 36, wherein the one or more additional therapeutics comprises lamivudine, tenofovir, tenofovir alafenamide, tenofovir disoproxil, or entecavir.

39. The method of claim 23, wherein the effective amount of the composition is subcutaneously or intravenously administered.

40. The method of claim 23, further comprising administering to the subject one or more additional therapeutics.

41. The method of claim 40, wherein the one or more additional therapeutics comprises an antiviral agent.

42. The method of claim 40, wherein the one or more additional therapeutics comprises lamivudine, tenofovir, tenofovir alafenamide, tenofovir disoproxil, or entecavir.

43. The method of claim 24, wherein the disease, disorder, or condition associated with the HBV infection is a chronic liver disease or disorder.

44. The method of claim 24, wherein the disease, disorder, or condition associated with the HBV infection is liver inflammation.

45. The method of claim 24, wherein the disease, disorder, or condition associated with the HBV infection is a fibrotic condition.

46. The method of claim 24, wherein the disease, disorder, or condition associated with the HBV infection is a proliferative disorder.

47. The method of claim 24, wherein the disease, disorder, or condition associated with the HBV infection is hepatocellular carcinoma.

48. The method of claim 24, wherein the disease, disorder, or condition associated with the HBV infection is a Hepatitis D virus infection.

49. The method of claim 24, wherein the disease, disorder, or condition associated with the HBV infection is an acute HBV infection.

50. The composition of claim 1, comprising a first RNAi agent and a second RNAi agent, wherein the first RNAi agent and the second RNAi agent are each independently conjugated to a targeting ligand that includes N-acetyl-galactosamine, and wherein the first RNAi agent has the duplex structure of AD04872 (SEQ ID NO: 126 and SEQ ID NO:252), and wherein the second RNAi agent has the duplex structure of AD04776 (SEQ ID NO: 102 and SEQ ID NO: 248).

51. The composition of claim 50, wherein the ratio of the first RNAi agent duplex (AD04872) to the second RNAi agent duplex (AD04776) in the composition is between about 1:2 to about 5:1.

52. The composition of claim 50, wherein the ratio of the first RNAi agent duplex (AD04872) to the second RNAi agent duplex (AD04776) in the composition is about 2:1.

53. The composition of claim 50, wherein the ratio of the first RNAi agent duplex (AD04872) to the second RNAi agent duplex (AD04776) in the composition is about 3:1.

54. The composition of claim 50, wherein the ratio of the first RNAi agent duplex (AD04872) to the second RNAi agent duplex (AD04776) in the composition is about 4:1.

55. The composition of claim 1, comprising a first RNAi agent and a second RNAi agent, wherein the first RNAi agent and the second RNAi agent are each independently conjugated to a targeting ligand that includes N-acetyl-galactosamine, and wherein the first RNAi agent has the duplex structure of AD04872 (SEQ ID NO: 126 and SEQ ID NO:252), and wherein the second RNAi agent has the duplex structure of AD04982 (SEQ ID NO: 137 and SEQ ID NO: 248).

56. The composition of claim 55, wherein the ratio of the first RNAi agent duplex (AD04872) to the second RNAi agent duplex (AD04982) in the composition is between about 1:2 to about 5:1.

57. The composition of claim 55, wherein the ratio of the first RNAi agent duplex (AD04872) to the second RNAi agent duplex (AD04982) in the composition is about 2:1.

58. The composition of claim 55, wherein the ratio of the first RNAi agent duplex (AD04872) to the second RNAi agent duplex (AD04982) in the composition is about 3:1.

59. The composition of claim 55, wherein the ratio of the first RNAi agent duplex (AD04872) to the second RNAi agent duplex (AD04982) in the composition is about 4:1.

60. The method of claim 21, wherein the composition comprises a first RNAi agent and a second RNAi agent, wherein the first RNAi agent and the second RNAi agent are each independently conjugated to a targeting ligand that includes N-acetyl-galactosamine, and wherein the first RNAi agent has the duplex structure of AD04872 (SEQ ID NO: 126 and SEQ ID NO: 252), and wherein the second RNAi agent has the duplex structure of AD04776 (SEQ ID NO: 102 and SEQ ID NO: 248).

61. The method of claim 60, wherein the effective amount of the composition is sufficient to reduce the level of HBsAg, HBeAg, and/or serum HBV DNA, in a subject by at least about 40% relative to the subject's respective expression level prior to administration of the composition.

62. The method of claim 60, wherein the disease, disorder, or condition associated with the HBV infection is a chronic liver disease or disorder, liver inflammation, a fibrotic condition, a proliferative disorder, hepatocellular carcinoma, a Hepatitis D virus infection, or an acute HBV infection.

63. The method of claim 60, wherein the effective amount of the first RNAi agent duplex is between about 0.5 mg/kg and about 5 mg/kg, and the effective amount of the second RNAi agent duplex is between about 0.5 mg/kg and about 5 mg/kg.

64. The method of claim 21, wherein the composition comprises a first RNAi agent and a second RNAi agent, wherein the first RNAi agent and the second RNAi agent are each independently conjugated to a targeting ligand that includes N-acetyl-galactosamine, and wherein the first RNAi agent has the duplex structure of AD04872 (SEQ ID NO: 126 and SEQ ID NO:252), and wherein the second RNAi agent has the duplex structure of AD04982 (SEQ ID NO: 137 and SEQ ID NO: 248).

65. The method of claim 64, wherein the effective amount of the composition is sufficient to reduce the level of HBsAg, HBeAg, and/or serum HBV DNA, in a subject by at least about 40% relative to the subject's respective expression level prior to administration of the composition.

66. The method of claim 64, wherein the disease, disorder, or condition associated with the HBV infection is a chronic liver disease or disorder, liver inflammation, a fibrotic condition, a proliferative disorder, hepatocellular carcinoma, a Hepatitis D virus infection, or an acute HBV infection.

67. The method of claim 64, wherein the effective amount of the first RNAi agent duplex is between about 0.5 mg/kg and about 5 mg/kg, and the effective amount of the second RNAi agent duplex is between about 0.5 mg/kg and about 5 mg/kg.

* * * * *

SEQUENCE LISTING

<160> NUMBER OF SEQ ID NOS: 334

<210> SEQ ID NO 1
<211> LENGTH: 3221
<212> TYPE: DNA
<213> ORGANISM: Artificial sequence
<220> FEATURE:
<223> OTHER INFORMATION: Hepatitis B virus (subtype ADW2), genotype A, complete gene (AM282986.1)

<400> SEQUENCE: 1

```
ttccactgcc ttccaccaag ctctgcagga tcccaaagtc aggggtctgt attttcctgc      60
tggtggctcc agttcaggaa cagtaaaccc tgctccgaat attgcctctc acatctcgtc     120
aatctccgcg aggactgggg accctgtgac gaatatggag aacatcacat caggattcct     180
aggacccctg ctcgtgttac aggcggggtt tttcttgttg acaagaatcc tcacaatacc     240
gcagagtcta gactcgtggt ggacttctct caattttcta gggggatcac ccgtgtgtct     300
```

```
tggccaaaat tcgcagtccc caacctccaa tcactcacca acctcctgtc ctccaatttg     360
tcctggttat cgctggatgt gtctgcggcg ttttatcata ttcctcttca tcctgctgct     420
atgcctcatc ttcttgttgg ttcttctgga ttatcaaggt atgttgcccg tttgtcctct     480
aattccagga acaacaacaa ccagtacggg accatgcaaa acctgcacga ctcctgctca     540
aggcaactct atgtttccct catgttgctg tacaaaacct tcggatggaa attgcacctg     600
tattcccatc ccatcgtctt gggctttcgc aaaatacctaa tgggagtggg cctcagtccg    660
tttctcttgg ctcagtttac tagtgccatt tgttcagtgg ttcgtagggc tttcccccac     720
tgtttggctt tcagctatat ggatgatgtg gtattggggg ccaagtctgt acagcatcgt     780
gagtcccttt ataccgctgt taccaattt cttttgtctc tgggtataca tttaaacccct    840
aacaaaacaa aaagatgggg ttattccta aacttcatgg gttacataat ggaagttgg      900
ggaacgttgc cacaggatca tattgtacaa aagatcaaac actgttttag aaaacttcct    960
gttaacaggc ctattgattg gaaagtatgt caaagaattg tgggtctttt gggctttgct   1020
gctccattta cacaatgtgg atatcctgcc ttaatgcctt tgtatgcctg tatacaagct   1080
aaacaggctt tcactttctc gccaacttac aaggcctttc taagtaaaca gtacatgaac   1140
ctttaccccg ttgctcggca acggcctggt ctgtgccaag tgtttgctga cgcaaccccc   1200
actggctggg gcttggccat aggccatcag cgcatgcgtg aacctttgt ggctcctctg    1260
ccgatccata ctgcggaact cctagccgct tgttttgctc gcagccggtc tggggcaaag   1320
ctcatcggaa ctgacaattc tgtcgtcctc tcgcggaaat atacatcgtt tccatggctg   1380
ctaggttgta ctgccaactg gatccttcgc gggacgtcct tgtttacgt cccgtcggcg    1440
ctgaatcccg cggacgaccc ctctcggggc cgcttgggac tctctcgtcc ccttctccgt   1500
ctgccgttcc agccgaccac ggggcgcacc tctctttacg cggtctcccc gtctgtgcct   1560
tctcatctgc cggtccgtgt gcacttcgct tcacctctgc acgttgcatg gagaccaccg   1620
tgaacgccca tcagatcctg cccaaggtct tacataagag gactcttgga ctcccagcaa   1680
tgtcaacgac cgaccttgag gcctacttca agactgtgt gtttaaggac tgggaggagc    1740
tgggggagga gattaggtta aaggtctttg tattaggagg ctgtaggcat aaattggtct   1800
gcgcaccagc accatgcaac ttttcacct ctgcctaatc atctcttgta catgtcccac    1860
tgttcaagcc tccaagctgt gccttgggtg gctttgggc atggacattg acccttataa    1920
agaatttgga gctactgtgg agttactctc gttttgcct tctgactttt tccttccgt     1980
cagagatctc ctagacaccg cctcagctct gtatcgggaa gccttagagt ctcctgagca   2040
ttgctcacct caccatactg cactcaggca agcaattctc tgctgggggg aattgatgac   2100
tctagctacc tgggtgggta ataatttgga agatccagca tccagggatc tagtagtcaa   2160
ttatgttaat actaacatgg gtttaaagat caggcaacta ttgtggtttc atatatcttg   2220
ccttactttt ggaagagaga ctgtacttga atatttggtc tctttcggag tgtggattcg   2280
cactcctcca gcctatagac caccaaatgc ccctatctta tcaacacttc cggaaactac   2340
tgttgttaga cgacgggacc gaggcaggtc ccctagaaga agaactccct cgcctcgcag   2400
acgcagatct caatcgccgc gtcgcagaag atctcaatct cgggaatctc aatgttagta   2460
ttccttggac tcataaggtg ggaaacttta ctgggcttta ttcctctaca gtacctatct   2520
ttaatcctga atggcaaact ccttcctttc ctaagattca tttacaagag gacattatta   2580
ataggtgtca acaatttgtg ggccctctca ctgtaaatga aaagagaaga ttgaaattaa   2640
ttatgcctgc tagattctat cctacccaca ctaaatattt gcccttagac aaaggaatta   2700
```

```
aaccttatta tccagatcag gtagttaatc attacttcaa aaccagacat tatttacata    2760
ctctttggaa ggctggtatt ctatataaga gggaaaccac acgtagcgca tcattttgcg    2820
ggtcaccata ttcttgggaa caagagctac agcatgggag gttggtcatc gaaacctcgc    2880
aaaggcatgg ggacgaatct ttctgttccc aaccctctgg gattctttcc cgatcatcag    2940
ttggaccctg cattcggagc caactcaaac aatccagatt gggacttcaa ccccatcaag    3000
gaccactggc cagcagccaa ccaggtagga gtgggagcat tcgggccagg gttcaccccT    3060
ccacacggcg gtgttttggg gtggagccct caggctcagg gcatattgac cacagtgtca    3120
acaattcctc ctcctgcctc caccaatcgg cagtcaggaa ggcagcctac tcccatctct    3180
ccacctctaa gagacagtca tcctcaggcc atgcagtgga a                       3221
```

<210> SEQ ID NO 2
<211> LENGTH: 19
<212> TYPE: DNA
<213> ORGANISM: Artificial sequence
<220> FEATURE:
<223> OTHER INFORMATION: HBV cDNA target sequence

<400> SEQUENCE: 2
gtggtggact tctctcaat                                                  19

<210> SEQ ID NO 3
<211> LENGTH: 19
<212> TYPE: DNA
<213> ORGANISM: Artificial sequence
<220> FEATURE:
<223> OTHER INFORMATION: HBV cDNA target sequence

<400> SEQUENCE: 3
tggtggactt ctctcaatt                                                  19

<210> SEQ ID NO 4
<211> LENGTH: 19
<212> TYPE: DNA
<213> ORGANISM: Artificial sequence
<220> FEATURE:
<223> OTHER INFORMATION: HBV cDNA target sequence

<400> SEQUENCE: 4
ggacttctct caattttct                                                  19

<210> SEQ ID NO 5
<211> LENGTH: 19
<212> TYPE: DNA
<213> ORGANISM: Artificial sequence
<220> FEATURE:
<223> OTHER INFORMATION: HBV cDNA target sequence

<400> SEQUENCE: 5
gctgtaggca taaattggt                                                  19

<210> SEQ ID NO 6
<211> LENGTH: 19
<212> TYPE: DNA
<213> ORGANISM: Artificial sequence
<220> FEATURE:
<223> OTHER INFORMATION: HBV cDNA target sequence

<400> SEQUENCE: 6
ctgtaggcat aaattggtc                                                  19

```
<210> SEQ ID NO 7
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 7
auugagagaa guccaccac                                                   19

<210> SEQ ID NO 8
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 8
uuugagagaa guccaccac                                                   19

<210> SEQ ID NO 9
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 9
auugagagaa guccaccan                                                   19

<210> SEQ ID NO 10
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 10
uuugagagaa guccaccan                                                   19

<210> SEQ ID NO 11
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 1, 19
<223> OTHER INFORMATION: n = any nucleotide

<400> SEQUENCE: 11
nuugagagaa guccaccan                                                   19

<210> SEQ ID NO 12
```

```
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 12
aauugagaga aguccacca                                                   19

<210> SEQ ID NO 13
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 13
uauugagaga aguccacca                                                   19

<210> SEQ ID NO 14
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 14
aauugagaga aguccaccn                                                   19

<210> SEQ ID NO 15
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 15
uauugagaga aguccaccn                                                   19

<210> SEQ ID NO 16
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 1, 19
<223> OTHER INFORMATION: n = any nucleotide

<400> SEQUENCE: 16
nauugagaga aguccaccn                                                   19

<210> SEQ ID NO 17
<211> LENGTH: 19
<212> TYPE: RNA
```

```
<213> ORGANISM: Artificial sequence
<220> FEATURE:
<223> OTHER INFORMATION: HBV RNAi agent antisense strand core stretch
      sequence

<400> SEQUENCE: 17
agaaaauuga gagaagucc                                                 19

<210> SEQ ID NO 18
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 18
ugaaaauuga gagaagucc                                                 19

<210> SEQ ID NO 19
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 19
agaaaauuga gagaagucn                                                 19

<210> SEQ ID NO 20
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 20
ugaaaauuga gagaagucn                                                 19

<210> SEQ ID NO 21
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 1, 19
<223> OTHER INFORMATION: n = any nucleotide

<400> SEQUENCE: 21
ngaaaauuga gagaagucn                                                 19

<210> SEQ ID NO 22
<211> LENGTH: 19
<212> TYPE: RNA
<213> ORGANISM: Artificial sequence
<220> FEATURE:
```

```
<223> OTHER INFORMATION: HBV RNAi agent antisense strand core stretch
      sequence

<400> SEQUENCE: 22
accaauuuau gccuacagc                                                    19

<210> SEQ ID NO 23
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 23
uccaauuuau gccuacagc                                                    19

<210> SEQ ID NO 24
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 24
accaauuuau gccuacagn                                                    19

<210> SEQ ID NO 25
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 25
uccaauuuau gccuacagn                                                    19

<210> SEQ ID NO 26
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 1,19
<223> OTHER INFORMATION: n = any nucleotide

<400> SEQUENCE: 26
nccaauuuau gccuacagn                                                    19

<210> SEQ ID NO 27
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
```

<400> SEQUENCE: 27
gaccaauuua ugccuacag                                                  19

<210> SEQ ID NO 28
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 28
aaccaauuua ugccuacag                                                  19

<210> SEQ ID NO 29
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence

<400> SEQUENCE: 29
uaccaauuua ugccuacag                                                  19

<210> SEQ ID NO 30
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 30
gaccaauuua ugccuacan                                                  19

<210> SEQ ID NO 31
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 31
aaccaauuua ugccuacan                                                  19

<210> SEQ ID NO 32
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 19
<223> OTHER INFORMATION: n = any nucleotide

<400> SEQUENCE: 32
uaccaauuua ugccuacan                                                    19

<210> SEQ ID NO 33
<211> LENGTH: 19
<212> TYPE: RNA
<213> ORGANISM: Artificial sequence
<220> FEATURE:
<223> OTHER INFORMATION: HBV RNAi agent antisense strand core stretch
      sequence
<220> FEATURE:
<221> NAME/KEY: modified_base
<222> LOCATION: 1, 19
<223> OTHER INFORMATION: n = any nucleotide

<400> SEQUENCE: 33
naccaauuua ugccuacan                                                    19

<210> SEQ ID NO 34
<211> LENGTH: 19
<212> TYPE: DNA
<213> ORGANISM: Artificial sequence
<220> FEATURE:
<223> OTHER INFORMATION: HBV RNAi agent sense strand core stretch
      sequence

<400> SEQUENCE: 34
gugguggacu ucucucaau                                                    19

<210> SEQ ID NO 35
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 35
gugguggacu ucucucaaa                                                    19

<210> SEQ ID NO 36
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 36
nugguggacu ucucucaau                                                    19

<210> SEQ ID NO 37
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 37
nugguggacu ucucucaaa                                                    19

<210> SEQ ID NO 38
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1, 19
<223> OTHER INFORMATION: n = any nucleotide

<400> SEQUENCE: 38
nugguggacu ucucucaan                                                19

<210> SEQ ID NO 39
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 39
ugguggacuu cucucaauu                                                19

<210> SEQ ID NO 40
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 40
ugguggacuu cucucaaua                                                19

<210> SEQ ID NO 41
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 41
ngguggacuu cucucaauu                                                19

<210> SEQ ID NO 42
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 42
ngguggacuu cucucaaua                                                19

```
<210> SEQ ID NO 43
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1, 19
<223> OTHER INFORMATION: n = any nucleotide

<400> SEQUENCE: 43
ngguggacuu cucucaaun                                                  19

<210> SEQ ID NO 44
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 44
ggacuucucu caauuuucu                                                  19

<210> SEQ ID NO 45
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 45
ggacuucucu caauuuuca                                                  19

<210> SEQ ID NO 46
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 46
ngacuucucu caauuuucu                                                  19

<210> SEQ ID NO 47
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 47
ngacuucucu caauuuuca                                                  19

<210> SEQ ID NO 48
<211> LENGTH: 19
```

```
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1, 19
<223> OTHER INFORMATION: n = any nucleotide

<400> SEQUENCE: 48
ngacuucucu caauuuucn                                           19

<210> SEQ ID NO 49
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 49
gcuguaggca uaaauuggu                                           19

<210> SEQ ID NO 50
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 50
gcuguaggca uaaauugga                                           19

<210> SEQ ID NO 51
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 51
ncuguaggca uaaauuggu                                           19

<210> SEQ ID NO 52
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 52
ncuguaggca uaaauugga                                           19

<210> SEQ ID NO 53
<211> LENGTH: 19
<212> TYPE: RNA
<213> ORGANISM: Artificial sequence
```

```
<220> FEATURE:
<223> OTHER INFORMATION: HBV RNAi agent sense strand core stretch
      sequence
<220> FEATURE:
<221> NAME/KEY: modified_base
<222> LOCATION: 1, 19
<223> OTHER INFORMATION: n = any nucleotide

<400> SEQUENCE: 53
ncuguaggca uaaauuggn                                                  19

<210> SEQ ID NO 54
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 54
cuguaggcau aaauugguc                                                  19

<210> SEQ ID NO 55
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 55
cuguaggcau aaauugguu                                                  19

<210> SEQ ID NO 56
<211> LENGTH: 19
<212> TYPE: RNA
<213> ORGANISM: Artificial sequence
<220> FEATURE:
<223> OTHER INFORMATION: HBV RNAi agent sense strand core stretch
      sequence

<400> SEQUENCE: 56
cuguaggcau aaauuggua                                                  19

<210> SEQ ID NO 57
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 57
nuguaggcau aaauugguc                                                  19

<210> SEQ ID NO 58
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
```

<223> OTHER INFORMATION: n = any nucleotide

<400> SEQUENCE: 58
nuguaggcau aaauugguu                                               19

<210> SEQ ID NO 59
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1
<223> OTHER INFORMATION: n = any nucleotide

<400> SEQUENCE: 59
nuguaggcau aaauuggua                                               19

<210> SEQ ID NO 60
<211> LENGTH: 19
<212> TYPE: RNA
<213> ORGANISM: Artificial sequence
<220> FEATURE:
<223> OTHER INFORMATION: HBV RNAi agent sense strand core stretch
      sequence
<220> FEATURE:
<221> NAME/KEY: modified_base
<222> LOCATION: 1, 19
<223> OTHER INFORMATION: n = any nucleotide

<400> SEQUENCE: 60
nuguaggcau aaauuggun                                               19

<210> SEQ ID NO 61
<211> LENGTH: 26
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 61
uaccaauuua ugccuacagg ccuuau                                       26

<210> SEQ ID NO 62
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 62
uaccaauuua ugccuacagg ccu                                          23

<210> SEQ ID NO 63
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 63
uaccaauuua ugccuacagg ccu                                          23

<210> SEQ ID NO 64
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 64
uaccaauuua ugccuacagg c                                       21

<210> SEQ ID NO 65
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 65
ugugaagcga agugcacacu u                                       21

<210> SEQ ID NO 66
<211> LENGTH: 26
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 66
uaccaauuua ugccuacagc cuccgc                                  26

<210> SEQ ID NO 67
<211> LENGTH: 26
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 67
uaccaauuua ugccuacagc cuccgc                                  26

<210> SEQ ID NO 68
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 68
uaccaauuua ugccuacagu u                                       21

<210> SEQ ID NO 69
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 69
uaccaauuua ugccuacagg c                                       21

```
<210> SEQ ID NO 70
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 70
uaccaauuua ugccuacagg c                                            21

<210> SEQ ID NO 71
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 71
uaccaauuua ugccuacagu u                                            21

<210> SEQ ID NO 72
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 72
auugagagaa guccaccacg a                                            21

<210> SEQ ID NO 73
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 73
auugagagaa guccaccacg a                                            21

<210> SEQ ID NO 74
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 74
auugagagaa guccaccacu u                                            21

<210> SEQ ID NO 75
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 75
uuugagagaa guccaccacg a                                            21

<210> SEQ ID NO 76
```

```
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 76
aauugagaga aguccaccac g                                                  21

<210> SEQ ID NO 77
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 77
aauugagaga aguccaccac g                                                  21

<210> SEQ ID NO 78
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 78
aauugagaga aguccaccau u                                                  21

<210> SEQ ID NO 79
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 79
uauugagaga aguccaccac g                                                  21

<210> SEQ ID NO 80
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 80
uaccaauuua ugccuacagg u                                                  21

<210> SEQ ID NO 81
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 81
uaccaauuua ugccuacagu u                                                  21

<210> SEQ ID NO 82
<211> LENGTH: 21
```

<212> TYPE: RNA
<213> ORGANIZM: Artificial sequence
<220> FEATURE:
<223> OTHER INFORMATION: HBV RNAi Agent antisense strand modified
      sequence

<400> SEQUENCE: 82
uaccaauuua ugccuacagc c                                              21

<210> SEQ ID NO 83
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 83
uaccaauuua ugccuacagc cuu                                            23

<210> SEQ ID NO 84
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 84
uaccaauuua ugccuacagc cuc                                            23

<210> SEQ ID NO 85
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 85
uaccaauuua ugccuacagc c                                              21

<210> SEQ ID NO 86
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 86
uaccaauuua ugccuacagc cuu                                            23

<210> SEQ ID NO 87
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 87
uaccaauuua ugccuacagc cuc                                            23

<210> SEQ ID NO 88
<211> LENGTH: 21
<212> TYPE: RNA

<213> ORGANISM: Artificial sequence
<220> FEATURE:
<223> OTHER INFORMATION: HBV RNAi Agent antisense strand modified
<220> FEATURE:
<223> OTHER INFORMATION: HBV RNAi Agent antisense strand modified
      sequence

<400> SEQUENCE: 94
uauugagaga aguccaccac g                                              21

<210> SEQ ID NO 95
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 95
uauugagaga aguccaccac guu                                            23

<210> SEQ ID NO 96
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 96
uauugagaga aguccaccac gag                                            23

<210> SEQ ID NO 97
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 97
uauugagaga aguccaccac gag                                            23

<210> SEQ ID NO 98
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 98
uauugagaga aguccaccac ga                                             22

<210> SEQ ID NO 99
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 99
uauugagaga aguccaccac ga                                             22

<210> SEQ ID NO 100
<211> LENGTH: 21
<212> TYPE: RNA
<213> ORGANISM: Artificial sequence
<220> FEATURE:

```
<223> OTHER INFORMATION: HBV RNAi Agent antisense strand modified
      sequence

<400> SEQUENCE: 100
agaaaauuga gagaagucca c                                              21

<210> SEQ ID NO 101
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 101
uaccaauuua ugccuacagu u                                              21

<210> SEQ ID NO 102
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 102
uaccaauuua ugccuacagc c                                              21

<210> SEQ ID NO 103
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 103
uaccaauuua ugccuacagc uu                                             22

<210> SEQ ID NO 104
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 104
uaccaauuua ugccuacagc cu                                             22

<210> SEQ ID NO 105
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 105
uaccaauuua ugccuacagc cuu                                            23

<210> SEQ ID NO 106
<211> LENGTH: 23
<212> TYPE: RNA
<213> ORGANISM: Artificial sequence
<220> FEATURE:
<223> OTHER INFORMATION: HBV RNAi Agent antisense strand modified
``` sequence

<400> SEQUENCE: 106
uaccaauuua ugccuacagc cuc                                               23

<210> SEQ ID NO 107
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 107
uaccaauuua ugccuacagu u                                                 21

<210> SEQ ID NO 108
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 108
uauugagaga aguccaccac g                                                 21

<210> SEQ ID NO 109
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 109
uauugagaga aguccaccau u                                                 21

<210> SEQ ID NO 110
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 110
uauugagaga aguccaccac g                                                 21

<210> SEQ ID NO 111
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 111
uauugagaga aguccaccac uu                                                22

<210> SEQ ID NO 112
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

```
<400> SEQUENCE: 112
uauugagaga aguccaccac ga                                        22

<210> SEQ ID NO 113
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 113
uauugagaga aguccaccac g                                         21

<210> SEQ ID NO 114
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 114
uuugagagaa guccaccacu u                                         21

<210> SEQ ID NO 115
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 115
uuugagagaa guccaccacg a                                         21

<210> SEQ ID NO 116
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 116
uuugagagaa guccaccacg uu                                        22

<210> SEQ ID NO 117
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 117
uuugagagaa guccaccacg ag                                        22

<210> SEQ ID NO 118
<211> LENGTH: 21
<212> TYPE: RNA
<213> ORGANISM: Artificial sequence
<220> FEATURE:
<223> OTHER INFORMATION: HBV RNAi Agent antisense strand modified
      sequence
```

```
<400> SEQUENCE: 118
uuugagagaa guccaccacu u                                              21

<210> SEQ ID NO 119
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 119
uauugagaga aguccaccac uu                                             22

<210> SEQ ID NO 120
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 120
uauugagaga aguccaccac uu                                             22

<210> SEQ ID NO 121
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 121
uauugagaga aguccaccac guu                                            23

<210> SEQ ID NO 122
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 122
uauugagaga aguccaccac uu                                             22

<210> SEQ ID NO 123
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 123
uauugagaga aguccaccac gag                                            23

<210> SEQ ID NO 124
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 124
```

```
uauugagaga aguccaccac uu                                          22

<210> SEQ ID NO 125
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 125
agaaaauuga gagaaguccu u                                           21

<210> SEQ ID NO 126
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 126
agaaaauuga gagaagucca c                                           21

<210> SEQ ID NO 127
<211> LENGTH: 23
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 127
agaaaauuga gagaagucca cuu                                         23

<210> SEQ ID NO 128
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 128
agaaaauuga gagaagucca cc                                          22

<210> SEQ ID NO 129
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 129
ugaaaauuga gagaaguccu u                                           21

<210> SEQ ID NO 130
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 130
```
ugaaaauuga gagaagucca c                                              21

<210> SEQ ID NO 131
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 131
accaauuuau gccuacagcu u                                              21

<210> SEQ ID NO 132
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 132
accaauuuau gccuacagcc uu                                             22

<210> SEQ ID NO 133
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 133
accaauuuau gccuacagcc uc                                             22

<210> SEQ ID NO 134
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 134
uccaauuuau gccuacagcu u                                              21

<210> SEQ ID NO 135
<211> LENGTH: 22
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 135
uccaauuuau gccuacagcc uu                                             22

<210> SEQ ID NO 136
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 136
uaccaauuua ugccuacagc c                                              21

<210> SEQ ID NO 137
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 137
uaccaauuua ugccuacagc c                                              21

<210> SEQ ID NO 138
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 138
uaccaauuua ugccuacagc c                                              21

<210> SEQ ID NO 139
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 139
uaccaauuua ugccuacagc u                                              21

<210> SEQ ID NO 140
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 140
uaccaauuua ugccuacagc g                                              21

<210> SEQ ID NO 141
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 141
aaccaauuua ugccuacagc c                                              21

<210> SEQ ID NO 142
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 142
uaccaauuua ugccuacagu u                                              21

<210> SEQ ID NO 143
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 143
uaccaauuua ugccuacagc c                                           21

<210> SEQ ID NO 144
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 144
accaauuuau gccuacagcc u                                           21

<210> SEQ ID NO 145
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 145
uccaauuuau gccuacagcc u                                           21

<210> SEQ ID NO 146
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 146
accaauuuau gccuacagcc g                                           21

<210> SEQ ID NO 147
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 147
uccaauuuau gccuacagcc g                                           21

<210> SEQ ID NO 148
<211> LENGTH: 21
<212> TYPE: RNA
<213> ORGANISM: Artificial sequence
<220> FEATURE:
<223> OTHER INFORMATION: HBV RNAi Agent antisense strand modified
      sequence

<400> SEQUENCE: 148
uaccaauuua ugccuacagg g                                           21

```
<210> SEQ ID NO 149
<211> LENGTH: 26
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 149
uaccaauuua ugccuacagg ccuuau                                      26

<210> SEQ ID NO 150
<211> LENGTH: 23
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 150
uaccaauuua ugccuacagg ccu                                         23

<210> SEQ ID NO 151
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 151
uaccaauuua ugccuacagg c                                           21

<210> SEQ ID NO 152
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 152
ugugaagcga agugcacacu u                                           21

<210> SEQ ID NO 153
<211> LENGTH: 26
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 153
uaccaauuua ugccuacagc cuccgc                                      26

<210> SEQ ID NO 154
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 154
uaccaauuua ugccuacagu u                                           21

<210> SEQ ID NO 155
```

```
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 155
auugagagaa guccaccacg a                                              21

<210> SEQ ID NO 156
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 156
auugagagaa guccaccacu u                                              21

<210> SEQ ID NO 157
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 157
uuugagagaa guccaccacg a                                              21

<210> SEQ ID NO 158
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 158
aauugagaga aguccaccac g                                              21

<210> SEQ ID NO 159
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 159
aauugagaga aguccaccau u                                              21

<210> SEQ ID NO 160
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 160
uauugagaga aguccaccac g                                              21

<210> SEQ ID NO 161
<211> LENGTH: 21
```

```
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 161
uaccaauuua ugccuacagg u                                              21

<210> SEQ ID NO 162
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 162
uaccaauuua ugccuacagc c                                              21

<210> SEQ ID NO 163
<211> LENGTH: 23
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 163
uaccaauuua ugccuacagc cuu                                            23

<210> SEQ ID NO 164
<211> LENGTH: 23
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 164
uaccaauuua ugccuacagc cuc                                            23

<210> SEQ ID NO 165
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 165
uuugagagaa guccaccacu u                                              21

<210> SEQ ID NO 166
<211> LENGTH: 23
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 166
auugagagaa guccaccacg guu                                            23

<210> SEQ ID NO 167
<211> LENGTH: 23
<212> TYPE: RNA
```

```
<213> ORGANISM: Artificial sequence
<220> FEATURE:
<223> OTHER INFORMATION: HBV RNAi Agent antisense strand unmodified
      sequence

<400> SEQUENCE: 167
auugagagaa guccaccacg agu                                          23

<210> SEQ ID NO 168
<211> LENGTH: 23
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 168
uauugagaga aguccaccac guu                                          23

<210> SEQ ID NO 169
<211> LENGTH: 23
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 169
uauugagaga aguccaccac gag                                          23

<210> SEQ ID NO 170
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 170
uauugagaga aguccaccac ga                                           22

<210> SEQ ID NO 171
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 171
agaaaauuga gagaagucca c                                            21

<210> SEQ ID NO 172
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 172
uaccaauuua ugccuacagc uu                                           22

<210> SEQ ID NO 173
<211> LENGTH: 22
<212> TYPE: RNA
<213> ORGANISM: Artificial sequence
```

```
<220> FEATURE:
<223> OTHER INFORMATION: HBV RNAi Agent antisense strand unmodified
      sequence

<400> SEQUENCE: 173
uaccaauuua ugccuacagc cu                                           22

<210> SEQ ID NO 174
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 174
uauugagaga aguccaccau u                                            21

<210> SEQ ID NO 175
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 175
uauugagaga aguccaccac uu                                           22

<210> SEQ ID NO 176
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 176
uuugagagaa guccaccacg uu                                           22

<210> SEQ ID NO 177
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 177
uuugagagaa guccaccacg ag                                           22

<210> SEQ ID NO 178
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 178
agaaaauuga gagaaguccu u                                            21

<210> SEQ ID NO 179
<211> LENGTH: 23
<212> TYPE: RNA
<213> ORGANISM: Artificial sequence
<220> FEATURE:
```

<223> OTHER INFORMATION: HBV RNAi Agent antisense strand unmodified
      sequence

<400> SEQUENCE: 179
agaaaauuga gagaagucca cuu                                              23

<210> SEQ ID NO 180
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 180
agaaaauuga gagaagucca cc                                               22

<210> SEQ ID NO 181
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 181
ugaaaauuga gagaagucca c                                                21

<210> SEQ ID NO 182
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 182
accaauuuau gccuacagcu u                                                21

<210> SEQ ID NO 183
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 183
accaauuuau gccuacagcc uu                                               22

<210> SEQ ID NO 184
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 184
accaauuuau gccuacagcc uc                                               22

<210> SEQ ID NO 185
<211> LENGTH: 21
<212> TYPE: RNA
<213> ORGANISM: Artificial sequence
<220> FEATURE:
<223> OTHER INFORMATION: HBV RNAi Agent antisense strand unmodified -continued

<400> SEQUENCE: 185
uccaauuuau gccuacagcu u    21

<210> SEQ ID NO 186
<211> LENGTH: 22
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 186
uccaauuuau gccuacagcc uu    22

<210> SEQ ID NO 187
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 187
uaccaauuua ugccuacagc u    21

<210> SEQ ID NO 188
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 188
uaccaauuua ugccuacagc g    21

<210> SEQ ID NO 189
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 189
aaccaauuua ugccuacagc c    21

<210> SEQ ID NO 190
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 190
accaauuuau gccuacagcc u    21

<210> SEQ ID NO 191
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 191
uccaauuuau gccuacagcc u                                              21

<210> SEQ ID NO 192
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 192
accaauuuau gccuacagcc g                                              21

<210> SEQ ID NO 193
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 193
uccaauuuau gccuacagcc g                                              21

<210> SEQ ID NO 194
<211> LENGTH: 21
<212> TYPE: RNA
<213> ORGANISM: Artificial sequence
<220> FEATURE:
<223> OTHER INFORMATION: HBV RNAi Agent antisense strand unmodified
      sequence

<400> SEQUENCE: 194
uaccaauuua ugccuacagg g                                              21

<210> SEQ ID NO 195
<211> LENGTH: 25
<212> TYPE: DNA
<213> ORGANISM: Artificial sequence
<220> FEATURE:
<223> OTHER INFORMATION: HBV RNAi Agent sense strand modified sequence

<400> SEQUENCE: 195
uugccuguag gcauaaauug guaut                                          25

<210> SEQ ID NO 196
<211> LENGTH: 26
<212> TYPE: RNA
<213> ORGANISM: Artificial sequence
<220> FEATURE:
<223> OTHER INFORMATION: HBV RNAi Agent sense strand modified sequence

<400> SEQUENCE: 196
uauaugccug uaggcauaaa uuggua                                         26

<210> SEQ ID NO 197
<211> LENGTH: 26
<212> TYPE: DNA
<213> ORGANISM: Artificial sequence
<220> FEATURE:
<223> OTHER INFORMATION: HBV RNAi Agent sense strand modified sequence

<400> SEQUENCE: 197
gcggaggcug uaggcauaaa uuggta                                         26

<210> SEQ ID NO 198
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 198
cuguaggcau aaauugguau u                                              21

<210> SEQ ID NO 199
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 199
gccuguaggc auaaauuggu a                                              21

<210> SEQ ID NO 200
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 200
gccuguaggc auaaauuggu a                                              21

<210> SEQ ID NO 201
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 201
gccuguaggc auaaauuggu a                                              21

<210> SEQ ID NO 202
<211> LENGTH: 21
<212> TYPE: DNA
<213> ORGANISM: Artificial sequence
<220> FEATURE:
<223> OTHER INFORMATION: HBV RNAi Agent sense strand modified sequence

<400> SEQUENCE: 202
gccuguaggc auaaauuggt a                                              21

<210> SEQ ID NO 203
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 203
aacuguaggc auaaauuggu a                                              21

<210> SEQ ID NO 204
<211> LENGTH: 21
<212> TYPE: RNA
<213> ORGANISM: Artificial sequence
<220> FEATURE:

<223> OTHER INFORMATION: HBV RNAi Agent sense strand modified sequence

<400> SEQUENCE: 204
ucguggugga cuucucucaa u 21

<210> SEQ ID NO 205
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 205
aaguggugga cuucucucaa u 21

<210> SEQ ID NO 206
<211> LENGTH: 21
<212> TYPE: DNA
<213> ORGANISM: Artificial sequence
<220> FEATURE:
<223> OTHER INFORMATION: HBV RNAi Agent sense strand modified sequence

<400> SEQUENCE: 206
ucguggugga cuucucucaa t 21

<210> SEQ ID NO 207
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 207
cgugguggac uucucucaau u 21

<210> SEQ ID NO 208
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 208
aaugguggac uucucucaau u 21

<210> SEQ ID NO 209
<211> LENGTH: 21
<212> TYPE: DNA
<213> ORGANISM: Artificial sequence
<220> FEATURE:
<223> OTHER INFORMATION: HBV RNAi Agent sense strand modified sequence

<400> SEQUENCE: 209
cgugguggac uucucucaat t 21

<210> SEQ ID NO 210
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 210
ggacuucucu caauuuucua a 21

```
<210> SEQ ID NO 211
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 211
cgugguggac uucucucaau a                                              21

<210> SEQ ID NO 212
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 212
ucguggugga cuucucucaa a                                              21

<210> SEQ ID NO 213
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 213
accuguaggc auaaauuggu a                                              21

<210> SEQ ID NO 214
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 214
cuguaggcau aaauuggua                                                 19

<210> SEQ ID NO 215
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 215
cuguaggcau aaauuggua                                                 19

<210> SEQ ID NO 216
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 216
cuguaggcau aaauuggua                                                 19

<210> SEQ ID NO 217
<211> LENGTH: 20
<212> TYPE: RNA
<213> ORGANISM: Artificial sequence
<220> FEATURE:
<223> OTHER INFORMATION: HBV RNAi Agent sense strand modified sequence
```

```
<400> SEQUENCE: 217
acuguaggca uaaauuggua                                                      20

<210> SEQ ID NO 218
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 218
ggcuguaggc auaaauuggu a                                                    21

<210> SEQ ID NO 219
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 219
aaguggugga cuucucucaa u                                                    21

<210> SEQ ID NO 220
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 220
aaguggugga cuucucucaa a                                                    21

<210> SEQ ID NO 221
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 221
ccguggugga cuucucucaa u                                                    21

<210> SEQ ID NO 222
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 222
ccguggugga cuucucucaa u                                                    21

<210> SEQ ID NO 223
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 223
cucguggugg acuucucuca au                                                   22

<210> SEQ ID NO 224
<211> LENGTH: 19
```

```
<212> TYPE: RNA
<213> ORGANISM: Artificial sequence
<220> FEATURE:
<223> OTHER INFORMATION: HBV RNAi Agent sense strand modified sequence

<400> SEQUENCE: 224
gugguggacu ucucucaau                                                    19

<210> SEQ ID NO 225
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 225
gugguggacu ucucucaauu u                                                 21

<210> SEQ ID NO 226
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 226
ucguggugga cuucucucaa uu                                                22

<210> SEQ ID NO 227
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 227
ugguggacuu cucucaauu                                                    19

<210> SEQ ID NO 228
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 228
ugguggacuu cucucaauu                                                    19

<210> SEQ ID NO 229
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 229
guggacuucu cucaauuuuc u                                                 21

<210> SEQ ID NO 230
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 230
```
cguuaggcau aaauuggauau u                                             21

<210> SEQ ID NO 231
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 231
gcuguaggca uaaauuggua uu                                             22

<210> SEQ ID NO 232
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 232
ggcuguaggc auaaauuggu auu                                            23

<210> SEQ ID NO 233
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 233
aacuguaggc auaaauuggu auu                                            23

<210> SEQ ID NO 234
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 234
ugguggacuu cucucaauau u                                              21

<210> SEQ ID NO 235
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 235
gugguggacu ucucucaaua uu                                             22

<210> SEQ ID NO 236
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 236
aaugguggac uucucucaau auu                                            23

<210> SEQ ID NO 237
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 237
cgugguggac uucucucaau auu 23

<210> SEQ ID NO 238
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 238
cgugguggac uucucucaau a 21

<210> SEQ ID NO 239
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 239
aaguggugga cuucucucaa u 21

<210> SEQ ID NO 240
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 240
gugguggacu ucucucaaau u 21

<210> SEQ ID NO 241
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 241
cgugguggac uucucucaaa uu 22

<210> SEQ ID NO 242
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 242
aaguggugga cuucucucaa auu 23

<210> SEQ ID NO 243
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 243 ucgugugga cuucucucaa auu 23

```
<210> SEQ ID NO 244
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 244
gugguggacu ucucucaaua uu                                              22

<210> SEQ ID NO 245
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 245
cgugguggac uucucucaau auu                                             23

<210> SEQ ID NO 246
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 246
cucguggugg acuucucuca aua                                             23

<210> SEQ ID NO 247
<211> LENGTH: 25
<212> TYPE: RNA
<213> ORGANISM: Artificial sequence
<220> FEATURE:
<223> OTHER INFORMATION: HBV RNAi Agent sense strand modified sequence

<400> SEQUENCE: 247
cucguggugg acuucucuca auauu                                           25

<210> SEQ ID NO 248
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 248
ggcuguaggc auaaauuggu a                                               21

<210> SEQ ID NO 249
<211> LENGTH: 23
<212> TYPE: RNA
<213> ORGANISM: Artificial sequence
<220> FEATURE:
<223> OTHER INFORMATION: HBV RNAi Agent sense strand modified sequence

<400> SEQUENCE: 249
gaggcuguag gcauaaauug gua                                             23

<210> SEQ ID NO 250
<211> LENGTH: 25
<212> TYPE: RNA
<213> ORGANISM: Artificial sequence
<220> FEATURE:
<223> OTHER INFORMATION: HBV RNAi Agent sense strand modified sequence
```

-continued

<400> SEQUENCE: 250
gaggcuguag gcauaaauug guauu                                              25

<210> SEQ ID NO 251
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 251
ggacuucucu caauuuucu                                                     19

<210> SEQ ID NO 252
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 252
guggacuucu cucaauuuuc u                                                  21

<210> SEQ ID NO 253
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 253
gguggacuuc ucucaauuuu cu                                                 22

<210> SEQ ID NO 254
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 254
ggacuucucu caauuuuca                                                     19

<210> SEQ ID NO 255
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 255
ggacuucucu caauuuuca                                                     19

<210> SEQ ID NO 256
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 256
gcuguaggca uaaauuggu                                                     19

<210> SEQ ID NO 257

```
<211> LENGTH: 20
<212> TYPE: RNA
<213> ORGANISM: Artificial sequence
<220> FEATURE:
<223> OTHER INFORMATION: HBV RNAi Agent sense strand modified sequence

<400> SEQUENCE: 257
ggcuguaggc auaaauuggu                                                    20

<210> SEQ ID NO 258
<211> LENGTH: 22
<212> TYPE: RNA
<213> ORGANISM: Artificial sequence
<220> FEATURE:
<223> OTHER INFORMATION: HBV RNAi Agent sense strand modified sequence

<400> SEQUENCE: 258
gaggcuguag gcauaaauug gu                                                 22

<210> SEQ ID NO 259
<211> LENGTH: 19
<212> TYPE: RNA
<213> ORGANISM: Artificial sequence
<220> FEATURE:
<223> OTHER INFORMATION: HBV RNAi Agent sense strand modified sequence

<400> SEQUENCE: 259
gcuguaggca uaaauugga                                                     19

<210> SEQ ID NO 260
<211> LENGTH: 20
<212> TYPE: RNA
<213> ORGANISM: Artificial sequence
<220> FEATURE:
<223> OTHER INFORMATION: HBV RNAi Agent sense strand modified sequence

<400> SEQUENCE: 260
ggcuguaggc auaaauugga                                                    20

<210> SEQ ID NO 261
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 261
agcuguaggc auaaauuggu a                                                  21

<210> SEQ ID NO 262
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 262
cgcuguaggc auaaauuggu a                                                  21

<210> SEQ ID NO 263
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 263
```
ggcuguaggc auaaauuggu u                                              21

<210> SEQ ID NO 264
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 264 cguaggcau aaauugguau u                                               21

<210> SEQ ID NO 265
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 265 cguaggcau aaauugguau u                                               21

<210> SEQ ID NO 266
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 266
aggcuguagg cauaaauugg u                                              21

<210> SEQ ID NO 267
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 267
aggcuguagg cauaaauugg a                                              21

<210> SEQ ID NO 268
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 268
cggcuguagg cauaaauugg u                                              21

<210> SEQ ID NO 269
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 269
cggcuguagg cauaaauugg a                                              21

<210> SEQ ID NO 270
<211> LENGTH: 21
<212> TYPE: RNA

<213> ORGANISM: Artificial sequence
<220> FEATURE:
<223> OTHER INFORMATION: HBV RNAi Agent sense strand modified sequence

<400> SEQUENCE: 270
cccuguaggc auaaauuggu a                                              21

<210> SEQ ID NO 271
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 271
cgcuguaggc auaaauuggu a                                              21

<210> SEQ ID NO 272
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 272
cccuguaggc auaaauuggu a                                              21

<210> SEQ ID NO 273
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 273
guggacuucu cucaauuuuc u                                              21

<210> SEQ ID NO 274
<211> LENGTH: 21
<212> TYPE: RNA
<213> ORGANISM: Artificial sequence
<220> FEATURE:
<223> OTHER INFORMATION: HBV RNAi Agent sense strand modified sequence

<400> SEQUENCE: 274
cgcuguaggc auaaauuggu a                                              21

<210> SEQ ID NO 275
<211> LENGTH: 25
<212> TYPE: DNA
<213> ORGANISM: Artificial sequence
<220> FEATURE:
<223> OTHER INFORMATION: HBV RNAi Agent sense strand unmodified sequence

<400> SEQUENCE: 275
uugccuguag gcauaaauug guaut                                          25

<210> SEQ ID NO 276
<211> LENGTH: 26
<212> TYPE: RNA
<213> ORGANISM: Artificial sequence
<220> FEATURE:
<223> OTHER INFORMATION: HBV RNAi Agent sense strand unmodified sequence

<400> SEQUENCE: 276
uauaugccug uaggcauaaa uuggua                                         26

<210> SEQ ID NO 277
<211> LENGTH: 26
<212> TYPE: DNA
<213> ORGANISM: Artificial sequence
<220> FEATURE:
<223> OTHER INFORMATION: HBV RNAi Agent sense strand unmodified sequence

<400> SEQUENCE: 277
gcggaggcug uaggcauaaa uuggta                                      26

<210> SEQ ID NO 278
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 278
cuguaggcau aaauugguau u                                           21

<210> SEQ ID NO 279
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 279
gccuguaggc auaaauuggu a                                           21

<210> SEQ ID NO 280
<211> LENGTH: 21
<212> TYPE: DNA
<213> ORGANISM: Artificial sequence
<220> FEATURE:
<223> OTHER INFORMATION: HBV RNAi Agent sense strand unmodified sequence

<400> SEQUENCE: 280
gccuguaggc auaaauuggt a                                           21

<210> SEQ ID NO 281
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 281
aacuguaggc auaaauuggu a                                           21

<210> SEQ ID NO 282
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 282
ucguggugga cuucucucaa u                                           21

<210> SEQ ID NO 283
<211> LENGTH: 21
<212> TYPE: RNA
<213> ORGANISM: Artificial sequence
<220> FEATURE:

<223> OTHER INFORMATION: HBV RNAi Agent sense strand unmodified sequence

<400> SEQUENCE: 283
aaguggugga cuucucucaa u                                              21

<210> SEQ ID NO 284
<211> LENGTH: 21
<212> TYPE: DNA
<213> ORGANISM: Artificial sequence
<220> FEATURE:
<223> OTHER INFORMATION: HBV RNAi Agent sense strand unmodified sequence

<400> SEQUENCE: 284
ucguggugga cuucucucaa t                                              21

<210> SEQ ID NO 285
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 285
cgugguggac uucucucaau u                                              21

<210> SEQ ID NO 286
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 286
aaugguggac uucucucaau u                                              21

<210> SEQ ID NO 287
<211> LENGTH: 21
<212> TYPE: DNA
<213> ORGANISM: Artificial sequence
<220> FEATURE:
<223> OTHER INFORMATION: HBV RNAi Agent sense strand unmodified sequence

<400> SEQUENCE: 287
cgugguggac uucucucaat t                                              21

<210> SEQ ID NO 288
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 288
ggacuucucu caauuuucua a                                              21

<210> SEQ ID NO 289
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 289
cgugguggac uucucucaau a                                              21

<210> SEQ ID NO 290
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 290
ucguggugga cuucucucaa a 21

<210> SEQ ID NO 291
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 291
accuguaggc auaaauuggu a 21

<210> SEQ ID NO 292
<211> LENGTH: 19
<212> TYPE: RNA
<213> ORGANISM: Artificial sequence
<220> FEATURE:
<223> OTHER INFORMATION: HBV RNAi Agent sense strand unmodified sequence

<400> SEQUENCE: 292
cuguaggcau aaauuggua 19

<210> SEQ ID NO 293
<211> LENGTH: 20
<212> TYPE: RNA
<213> ORGANISM: Artificial sequence
<220> FEATURE:
<223> OTHER INFORMATION: HBV RNAi Agent sense strand unmodified sequence

<400> SEQUENCE: 293
acuguaggca uaaauuggua 20

<210> SEQ ID NO 294
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 294
ggcuguaggc auaaauuggu a 21

<210> SEQ ID NO 295
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 295
aaguggugga cuucucucaa a 21

<210> SEQ ID NO 296
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 296
ccguggugga cuucucucaa u					21

<210> SEQ ID NO 297
<211> LENGTH: 22
<212> TYPE: RNA
<213> ORGANISM: Artificial sequence
<220> FEATURE:
<223> OTHER INFORMATION: HBV RNAi Agent sense strand unmodified sequence

<400> SEQUENCE: 297
cucguggugg acuucucuca au					22

<210> SEQ ID NO 298
<211> LENGTH: 19
<212> TYPE: RNA
<213> ORGANISM: Artificial sequence
<220> FEATURE:
<223> OTHER INFORMATION: HBV RNAi Agent sense strand unmodified sequence

<400> SEQUENCE: 298
gugguggacu ucucucaau					19

<210> SEQ ID NO 299
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 299
gugguggacu ucucucaauu u					21

<210> SEQ ID NO 300
<211> LENGTH: 22
<212> TYPE: RNA
<213> ORGANISM: Artificial sequence
<220> FEATURE:
<223> OTHER INFORMATION: HBV RNAi Agent sense strand unmodified sequence

<400> SEQUENCE: 300
ucguggugga cuucucucaa uu					22

<210> SEQ ID NO 301
<211> LENGTH: 19
<212> TYPE: RNA
<213> ORGANISM: Artificial sequence
<220> FEATURE:
<223> OTHER INFORMATION: HBV RNAi Agent sense strand unmodified sequence

<400> SEQUENCE: 301
ugguggacuu cucucaauu					19

<210> SEQ ID NO 302
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 302
guggacuucu cucaauuuuc u					21

<210> SEQ ID NO 303
<211> LENGTH: 22

<212> TYPE: RNA
<213> ORGANISM: Artificial sequence
<220> FEATURE:
<223> OTHER INFORMATION: HBV RNAi Agent sense strand unmodified sequence

<400> SEQUENCE: 303
gcuguaggca uaaauuggua uu                                            22

<210> SEQ ID NO 304
<211> LENGTH: 23
<212> TYPE: RNA
<213> ORGANISM: Artificial sequence
<220> FEATURE:
<223> OTHER INFORMATION: HBV RNAi Agent sense strand unmodified sequence

<400> SEQUENCE: 304
ggcuguaggc auaaauuggu auu                                           23

<210> SEQ ID NO 305
<211> LENGTH: 23
<212> TYPE: RNA
<213> ORGANISM: Artificial sequence
<220> FEATURE:
<223> OTHER INFORMATION: HBV RNAi Agent sense strand unmodified sequence

<400> SEQUENCE: 305
aacuguaggc auaaauuggu auu                                           23

<210> SEQ ID NO 306
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 306
ugguggacuu cucucaauau u                                             21

<210> SEQ ID NO 307
<211> LENGTH: 22
<212> TYPE: RNA
<213> ORGANISM: Artificial sequence
<220> FEATURE:
<223> OTHER INFORMATION: HBV RNAi Agent sense strand unmodified sequence

<400> SEQUENCE: 307
gugguggacu ucucucaaua uu                                            22

<210> SEQ ID NO 308
<211> LENGTH: 23
<212> TYPE: RNA
<213> ORGANISM: Artificial sequence
<220> FEATURE:
<223> OTHER INFORMATION: HBV RNAi Agent sense strand unmodified sequence

<400> SEQUENCE: 308
aaugguggac uucucucaau auu                                           23

<210> SEQ ID NO 309
<211> LENGTH: 23
<212> TYPE: RNA
<213> ORGANISM: Artificial sequence
<220> FEATURE:
<223> OTHER INFORMATION: HBV RNAi Agent sense strand unmodified sequence

<400> SEQUENCE: 309
cgugguggac uucucucaau auu                                             23

<210> SEQ ID NO 310
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 310
gugguggacu ucucucaaau u                                               21

<210> SEQ ID NO 311
<211> LENGTH: 22
<212> TYPE: RNA
<213> ORGANISM: Artificial sequence
<220> FEATURE:
<223> OTHER INFORMATION: HBV RNAi Agent sense strand unmodified sequence

<400> SEQUENCE: 311
cgugguggac uucucucaaa uu                                              22

<210> SEQ ID NO 312
<211> LENGTH: 23
<212> TYPE: RNA
<213> ORGANISM: Artificial sequence
<220> FEATURE:
<223> OTHER INFORMATION: HBV RNAi Agent sense strand unmodified sequence

<400> SEQUENCE: 312
aaguggugga cuucucucaa auu                                             23

<210> SEQ ID NO 313
<211> LENGTH: 23
<212> TYPE: RNA
<213> ORGANISM: Artificial sequence
<220> FEATURE:
<223> OTHER INFORMATION: HBV RNAi Agent sense strand unmodified sequence

<400> SEQUENCE: 313
ucguggugga cuucucucaa auu                                             23

<210> SEQ ID NO 314
<211> LENGTH: 23
<212> TYPE: RNA
<213> ORGANISM: Artificial sequence
<220> FEATURE:
<223> OTHER INFORMATION: HBV RNAi Agent sense strand unmodified sequence

<400> SEQUENCE: 314
cucguggugg acuucucuca aua                                             23

<210> SEQ ID NO 315
<211> LENGTH: 25
<212> TYPE: RNA
<213> ORGANISM: Artificial sequence
<220> FEATURE:
<223> OTHER INFORMATION: HBV RNAi Agent sense strand unmodified sequence

<400> SEQUENCE: 315
cucguggugg acuucucuca auauu                                           25

<210> SEQ ID NO 316
<211> LENGTH: 23
<212> TYPE: RNA
<213> ORGANISM: Artificial sequence

```
<220> FEATURE:
<223> OTHER INFORMATION: HBV RNAi Agent sense strand unmodified sequence

<400> SEQUENCE: 316
gaggcuguag gcauaaauug gua                                              23

<210> SEQ ID NO 317
<211> LENGTH: 25
<212> TYPE: RNA
<213> ORGANISM: Artificial sequence
<220> FEATURE:
<223> OTHER INFORMATION: HBV RNAi Agent sense strand unmodified sequence

<400> SEQUENCE: 317
gaggcuguag gcauaaauug guauu                                            25

<210> SEQ ID NO 318
<211> LENGTH: 19
<212> TYPE: RNA
<213> ORGANISM: Artificial sequence
<220> FEATURE:
<223> OTHER INFORMATION: HBV RNAi Agent sense strand unmodified sequence

<400> SEQUENCE: 318
ggacuucucu caauuuucu                                                   19

<210> SEQ ID NO 319
<211> LENGTH: 22
<212> TYPE: RNA
<213> ORGANISM: Artificial sequence
<220> FEATURE:
<223> OTHER INFORMATION: HBV RNAi Agent sense strand unmodified sequence

<400> SEQUENCE: 319
gguggacuuc ucucaauuuu cu                                               22

<210> SEQ ID NO 320
<211> LENGTH: 19
<212> TYPE: RNA
<213> ORGANISM: Artificial sequence
<220> FEATURE:
<223> OTHER INFORMATION: HBV RNAi Agent sense strand unmodified sequence

<400> SEQUENCE: 320
ggacuucucu caauuuuca                                                   19

<210> SEQ ID NO 321
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 321
guggacuucu cucaauuuuc a                                                21

<210> SEQ ID NO 322
<211> LENGTH: 19
<212> TYPE: RNA
<213> ORGANISM: Artificial sequence
<220> FEATURE:
<223> OTHER INFORMATION: HBV RNAi Agent sense strand unmodified sequence

<400> SEQUENCE: 322
gcuguaggca uaaauuggu                                                   19
```

<210> SEQ ID NO 323
<211> LENGTH: 20
<212> TYPE: RNA
<213> ORGANISM: Artificial sequence
<220> FEATURE:
<223> OTHER INFORMATION: HBV RNAi Agent sense strand unmodified sequence

<400> SEQUENCE: 323
ggcuguaggc auaaauuggu                                               20

<210> SEQ ID NO 324
<211> LENGTH: 22
<212> TYPE: RNA
<213> ORGANISM: Artificial sequence
<220> FEATURE:
<223> OTHER INFORMATION: HBV RNAi Agent sense strand unmodified sequence

<400> SEQUENCE: 324
gaggcuguag gcauaaauug gu                                            22

<210> SEQ ID NO 325
<211> LENGTH: 19
<212> TYPE: RNA
<213> ORGANISM: Artificial sequence
<220> FEATURE:
<223> OTHER INFORMATION: HBV RNAi Agent sense strand unmodified sequence

<400> SEQUENCE: 325
gcuguaggca uaaauugga                                                19

<210> SEQ ID NO 326
<211> LENGTH: 20
<212> TYPE: RNA
<213> ORGANISM: Artificial sequence
<220> FEATURE:
<223> OTHER INFORMATION: HBV RNAi Agent sense strand unmodified sequence

<400> SEQUENCE: 326
ggcuguaggc auaaauugga                                               20

<210> SEQ ID NO 327
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 327
agcuguaggc auaaauuggu a                                             21

<210> SEQ ID NO 328
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 328
cgcuguaggc auaaauuggu a                                             21

<210> SEQ ID NO 329
<211> LENGTH: 21
<212> TYPE: RNA
<213> ORGANISM: Artificial sequence
<220> FEATURE:
<223> OTHER INFORMATION: HBV RNAi Agent sense strand unmodified sequence

```
<400> SEQUENCE: 329
ggcuguaggc auaaauuggu u                                              21

<210> SEQ ID NO 330
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 330
aggcuguagg cauaaauugg u                                              21

<210> SEQ ID NO 331
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 331
aggcuguagg cauaaauugg a                                              21

<210> SEQ ID NO 332
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 332
cggcuguagg cauaaauugg u                                              21

<210> SEQ ID NO 333
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 333
cggcuguagg cauaaauugg a                                              21

<210> SEQ ID NO 334
<211> LENGTH: 21
<212> TYPE: RNA
<213> ORGANISM: Artificial sequence
<220> FEATURE:
<223> OTHER INFORMATION: HBV RNAi Agent sense strand unmodified sequence

<400> SEQUENCE: 334
cccuguaggc auaaauuggu a                                              21
```